（12）United States Patent
Kyrpides et al.

US011692184B2

(10) Patent No.: US 11,692,184 B2
(45) Date of Patent: Jul. 4, 2023

(54) THERMOSTABLE RNA-GUIDED ENDONUCLEASES AND METHODS OF USE THEREOF

(71) Applicant: The Regents of the University of California, Oakland, CA (US)

(72) Inventors: Nikos C. Kyrpides, Berkeley, CA (US); Jennifer A. Doudna, Berkeley, CA (US); Lucas Benjamin Harrington, Berkeley, CA (US); David Paez-Espino, Walnut Creek, CA (US)

(73) Assignee: The regents of the university of california, Oakland, CA (US)

( * ) Notice: Subject to any disclaimer, the term of this patent is extended or adjusted under 35 U.S.C. 154(b) by 642 days.

(21) Appl. No.: 16/604,946

(22) PCT Filed: May 15, 2018

(86) PCT No.: PCT/US2018/032832
§ 371 (c)(1),
(2) Date: Oct. 11, 2019

(87) PCT Pub. No.: WO2018/213351
PCT Pub. Date: Nov. 22, 2018

(65) Prior Publication Data
US 2020/0392472 A1 Dec. 17, 2020

Related U.S. Application Data

(60) Provisional application No. 62/507,123, filed on May 16, 2017.

(51) Int. Cl.
*C12N 9/22* (2006.01)
*C12N 15/113* (2010.01)

(52) U.S. Cl.
CPC .............. *C12N 9/22* (2013.01); *C12N 15/113* (2013.01); *C07K 2319/00* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| 8,889,418 B2 | 11/2014 | Zhang et al. |
| 2016/0177278 A1* | 6/2016 | Wolfe ................. C12N 9/22 |
| | | 435/199 |

FOREIGN PATENT DOCUMENTS

| WO | WO 2013/176772 | 11/2013 |
| WO | WO 2015/071474 | 5/2015 |
| WO | WO 2015/089277 | 6/2015 |
| WO | WO 2016/198361 | 12/2016 |
| WO | WO 2016/205759 | 12/2016 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Nishimasu, et al.; "Crystal Structure of Cas9 in Complex with Guide RNA and Target DNA,"; Cell; vol. 156, No. 5, pp. 935-949 (Feb. 27, 2014).

* cited by examiner

*Primary Examiner* — Richard G Hutson
(74) *Attorney, Agent, or Firm* — Bozicevic Field & Francis, LLP; Paula A. Borden; Mandar A. Joshi

(57) ABSTRACT

The present disclosure provides RNA-guided endonucleases, nucleic acids encoding same, and compositions comprising same. The present disclosure provides ribonucleoprotein complexes comprising: an RNA-guided endonuclease of the present disclosure; and a guide RNA. The present disclosure provides methods of modifying a target nucleic acid, using an RNA-guided endonuclease of the present disclosure and a guide RNA.

16 Claims, 28 Drawing Sheets
Specification includes a Sequence Listing.

| Cas9 from: | Length (aa) | Max host growth temperature |
|---|---|---|
| Fno | 1,629 | 37°C |
| Sth (3) | 1,388 | 42°C |
| Spy | 1,368 | 37°C |
| Sau | 1,053 | 37°C |
| Nme | 1,082 | 37°C |
| Geo st. | 1,087 | 68°C |
| Geo LC300 | 1,087 | 72°C |

Figure 1 | GeoCas9 is a thermostable Cas9 homolog

Figure 2 | PAM identification and engineering of GeoCas9

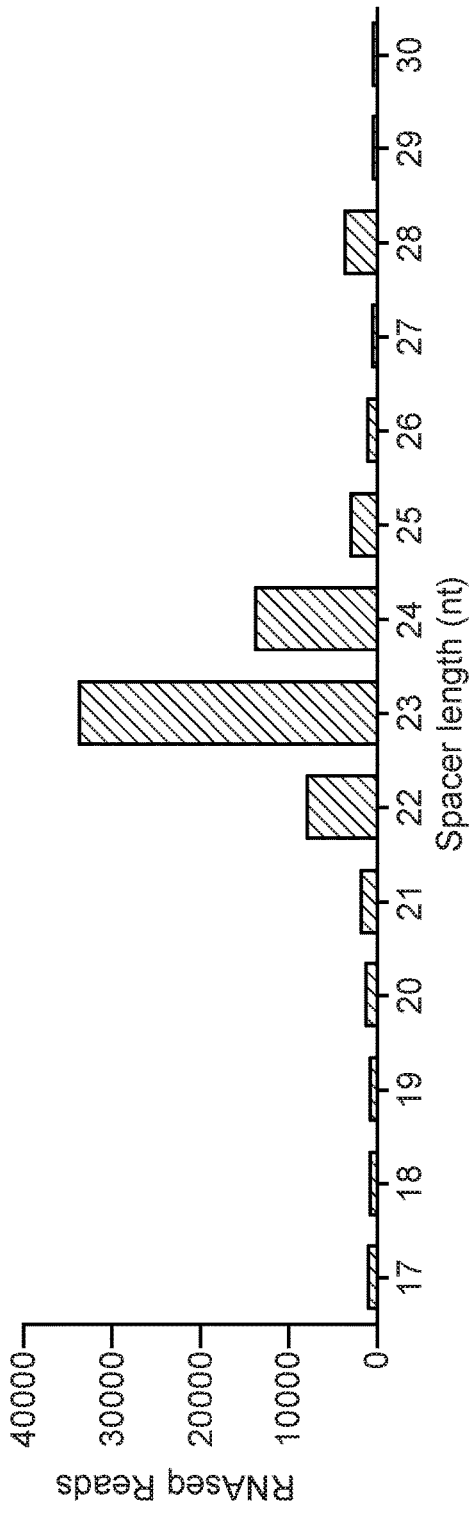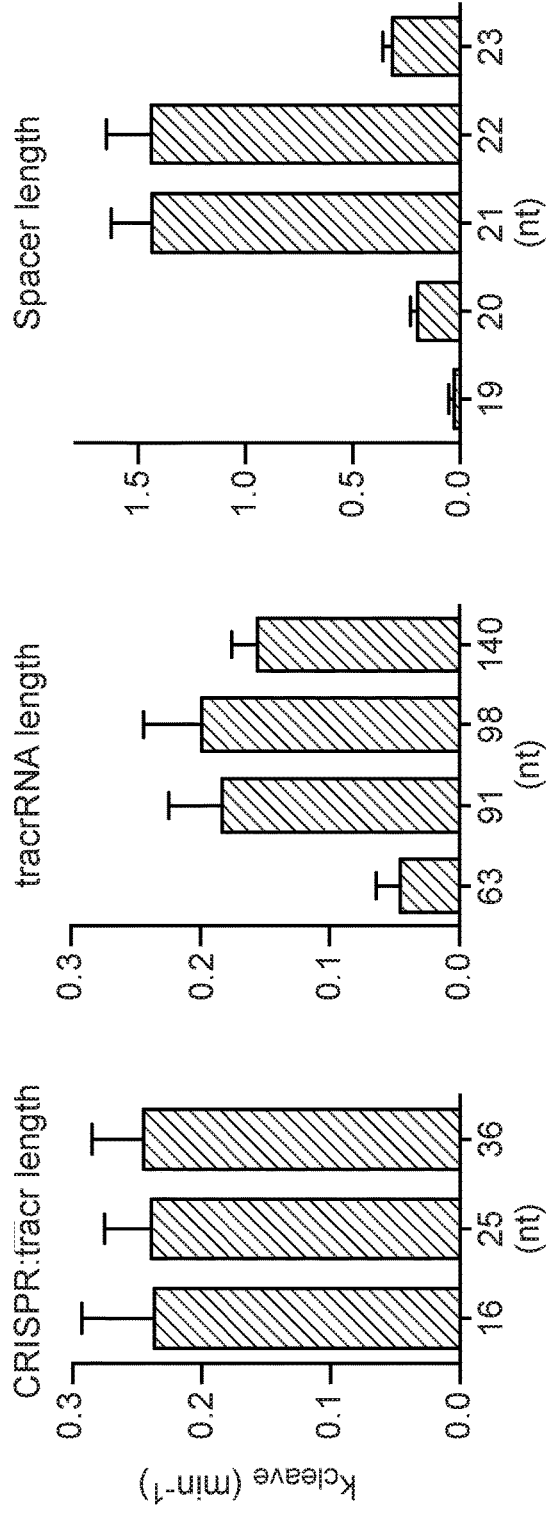
FIG. 3B
FIG. 3C

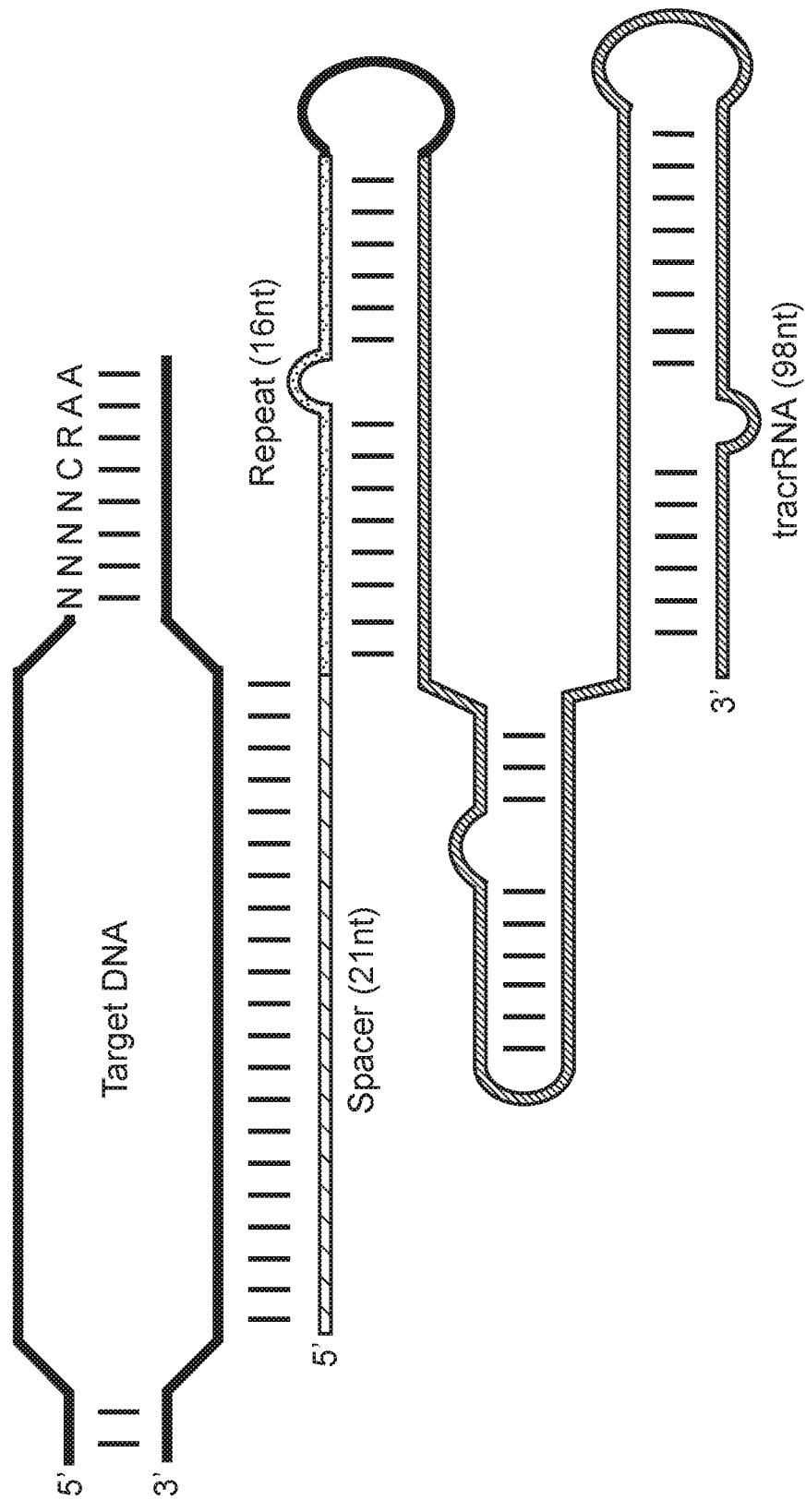
Figure 3 | RNAseq from Geobacillus stearothermophilus and engineering of GeoCas9 sgRNA FIG. 4A
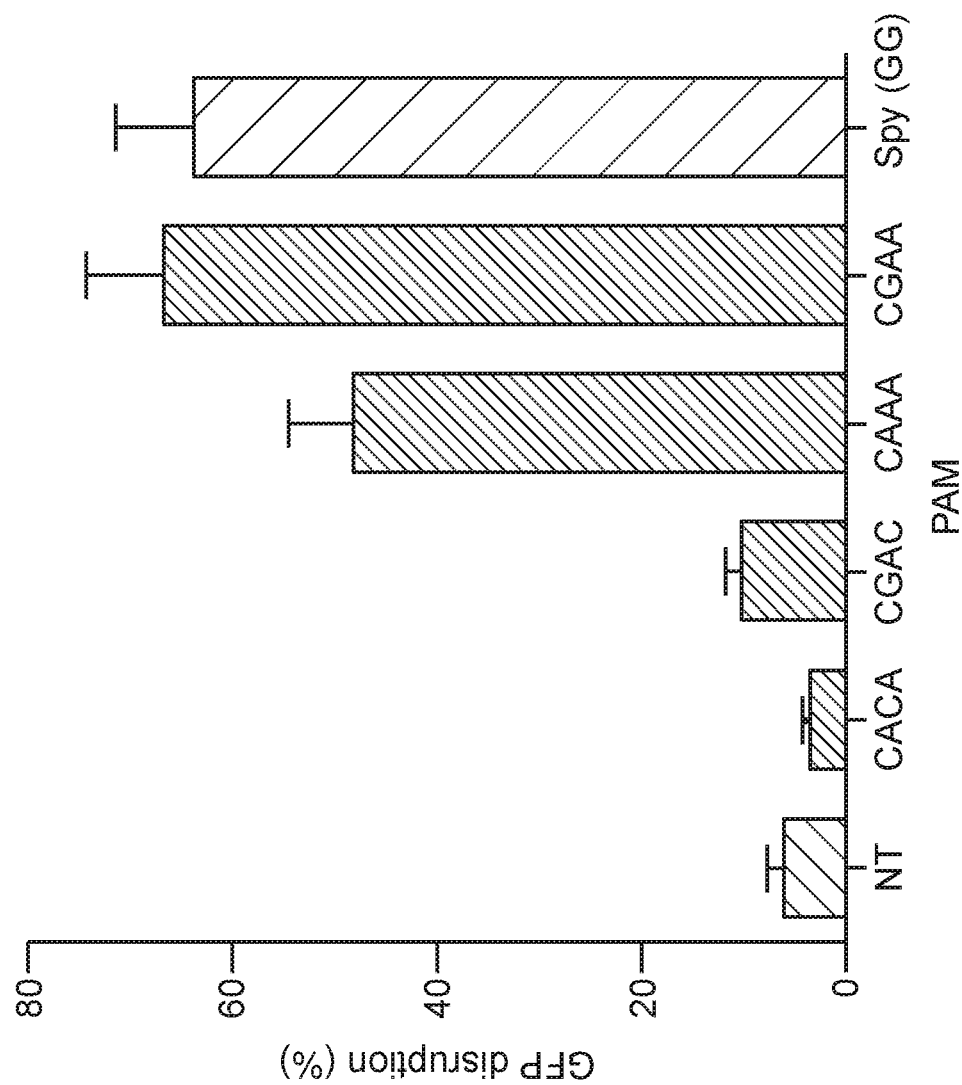
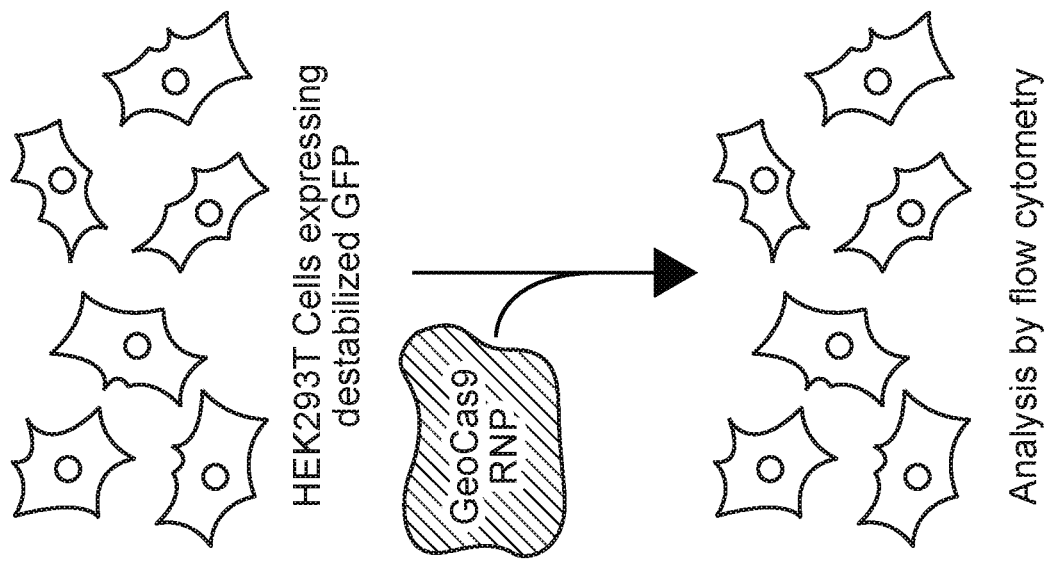

Figure 4 | Genome editing in HEK293 cells using GeoCas9

Figure 5 | Thermostability of GeoCas9 and longevity in human plasma

FIG. 6

GeoCas9:
MRYKIGLDIGITSVGWAVMNLDIPRIEDLGVRIFDRAENPQTGESLALPRRLARSARRRLR
RRKHRLERIRRLVIREGILTKEELDKLFEEKHEIDVWQLRVEALDRKLNNDELARVLLHLA
KRRGFKSNRKSERSNKENSTMLKHIEENRAILSSYRTVGEMIVKDPKFALHKRNKGENYT
NTIARDDLEREIRLIFSKQREFGNMSCTEEFENEYITIWASQRPVASKDDIEKKVGFCTFEP
KEKRAPKATYTFQSFIAWEHINKLRLISPSGARGLTDEERRLLYEQAFQKNKITYHDIRTLL
HLPDDTYFKGIVYDRGESRKQNENIRFLELDAYHQIRKAVDKVYGKGKSSSFLPIDFDTFG
YALTLFKDDADIHSYLRNEYEQNGKRMPNLANKVYDNELIEELLNLSFTKFGHLSLKALRS
ILPYMEQGEVYSSACERAGYTFTGPKKKQKTMLLPNIPPIANPVVMRALTQARKVVNAIIK
KYGSPVSIHIELARDLSQTFDERRKTKKEQDENRKKNETAIRQLMEYGLTLNPTGHDIVKF
KLWSEQNGRCAYSLQPIEIERLLEPGYVEVDHVIPYSRSLDDSYTNKVLVLTRENREKGNR
IPAEYLGVGTERWQQFETFVLTNKQFSKKKRDRLLRLHYDENEETEFKNRNLNDTRYISR
FFANFIREHLKFAESDDKQKVYTVNGRVTAHLRSRWEFNKNREESDLHHAVDAVIVACT
TPSDIAKVTAFYQRREQNKELAKKTEPHFPQPWPHFADELRARLSKHPKESIKALNLGNY
DDQKLESLQPVFVSRMPKRSVTGAAHQETLRRYVGIDERSGKIQTVVKTKLSEIKLDASGH
FPMYGKESDPRTYEAIRQRLLEHNNDPKKAFQEPLYKPKKNGEPGPVIRTVKIIDTKNQVI
PLNDGKTVAYNSNIVRVDVFEKDGKYYCVPVYTMDIMKGILPNKAIEPNKPYSEWKEMTE
DYTFRFSLYPNDLIRIELPREKTVKTAAGEEINVKDVFVYYKTIDSANGGLELISHDHRFSL
RGVGSRTLKRFEKYQVDVLGNIYKVRGEKRVGLASSAHSKPGKTIRPLQSTRD*
    (SEQ ID NO: 1)

FIG. 7

GeoCas9 PAM variant (highlighted is exchanged region):
MRYKIGLDIGITSVGWAVMNLDIPRIEDLGVRIFDRAENPQTGESLALPRRLARSARRRLR
RRKHRLERIRRLVIREGILTKEELDKLFEEKHEIDVWQLRVEALDRKLNNDELARVLLHLA
KRRGFKSNRKSERSNKENSTMLKHIEENRAILSSYRTVGEMIVKDPKFALHKRNKGENYT
NTIARDDLEREIRLIFSKQREFGNMSCTEEFENEYITIWASQRPVASKDDIEKKVGFCTFEP
KEKRAPKATYTFQSFIAWEHINKLRLISPSGARGLTDEERRLLYEQAFQKNKITYHDIRTLL
HLPDDTYFKGIVYDRGESRKQNENIRFLELDAYHQIRKAVDKVYGKGKSSSFLPIDFDTFG
YALTLFKDDADIHSYLRNEYEQNGKRMPNLANKVYDNELIEELLNLSFTKFGHLSLKALRS
ILPYMEQGEVYSSACERAGYTFTGPKKKQKTMLLPNIPPIANPVVMRALTQARKVVNAIIK
KYGSPVSIHIELARDLSQTFDERRKTKKEQDENRKKNETAIRQLMEYGLTLNPTGHDIVKF
KLWSEQNGRCAYSLQPIEIERLLEPGYVEVDHVIPYSRSLDDSYTNKVLVLTRENREKGNR
IPAEYLGVGTERWQQFETFVLTNKQFSKKKRDRLLRLHYDENEETEFKNRNLNDTRYISR
FFANFIREHLKFAESDDKQKVYTVNGRVTAHLRSRWEFNKNREESDLHHAVDAVIVACT
TPSDIAKVTAFYQRREQNKELAKKTEPHFPQPWPHFADELRARLSKHPKESIKALNLGNY
DDQKLESLQPVFVSRMPKRSVTGAAHQETLRRYVGIDERSGKIQTVVKTKLSEIKLDASGH
FPMYGKESDPRTYEAIRQRLLEHNNDPKKAFQEPLYKPKKNGEPGPVIRTVKIIDTKNQVI
PLNDGKTVAYNSNIVRVDVFEKDGKYYCVPVYTMDIMKGILPNKAIEPNKPYSEWKEMTE
DYTFRFSLYPNDLIRIELPREKIIKTAGGEEIKIKDLFAYYKTIHSGTAGLELVSHDCSFSLSG
VGSRTLKRFEKYQVDVLGNIYKVRGEKRVGLASSAHSKTGETIRPLQSTRD*
 (SEQ ID NO: 2)

FIG. 8

GeoLC300:
MRYKIGLDIGITSVGWAVINLDIPRIEDLGVRIFDRAENPQTGESLALPRRLARSARRR
LRRRKHRLERIRRLIIREGILTKEELDKLFEEKHEIDVWQLRVEALDRKLNNDELARVL
LHLAKRRGFKSNRKSERSNKENSTMLKHIEENRAILSSYRTVGEMIVKDPKFALHKRNK
GENYTNTIARDDLEREIRLIFSKQREFGNMSCTEEFENEYIAIWASQRPVASKDDIEKK
VGFCTFEPKEKRAPKATYTFQSFIAWEHINKLRLISPSGTRGLTDEERRLLYEQAFQKN
KITYHDIRTLLHLPDDTYFKGIVYDRGESRKQNENIRFLELDAYHQIRKAVDKVYGKGK
SSSFLPIDFDTFGYALTLFKDDADIRSYLRNEYEQNGKRMPNLANKVYDNELIEELLNL
SFTKFGHLSLKALRSILPYMEQGEVYSSACERAGYTFTGPKKKQKTMLLPNIPPIANPV
VMRALTQARKVVNAIIKKYGSPVSIHIELARDLSQTFDERRKTKKEQDENRKKNETAIR
QLMEYGLTLNPTGHDIVKFKLWSEQNGRCAYSLQPIEIERLLEPGYTEVDHVIPYSRSL
DDSYTNKVLVLTKENREKGNRIPAEYLGVGTERWQQFETFVLTNKQFSKKKRDRLLRLH
YDENEETEFKNRNLNDTRYISRFFANFIREHLKFAESDDKQKVYTVNGRVTAHLRSRWE
FNKNREESDLHHAVDAVIVACTTPSDIAKVTAFYQRREQNKELAKKTEPHFPQPWPHFA
DELRARLSKHPKESIKALNLGNYDDQKLESLQPVFVSRMPKRSVTGAAHQETLRRYVGI
DERSGKIQTVVKTKLSEIKLDASGHFPMYGKESDPRTYEAIRQRLLEHNNDPKKAFQEP
LYKPKKNGEPGPVIRTVKIIDTKNQVIPLNDGKTVAYNSNIVRVDVFEKDGKYYCVPVY
TMDIMKGILPNKAIEPNKPYSEWKEMTEDYTFRFSLYPNDLIRIELPREKIIKTAGGEE
IKIKDLFAYYKTIHSGTAGLELVSHDCSFSLSGVGSRTLKRFEKYQVDVLGNIYKVRGE
KRVGLASSAHSKTGETIRPLQSTRD*
    (SEQ ID NO: 3)

FIG. 10A

*G. stearothermophilus*

Geobacillus stearothermophilus plasmid pGS18

```
5' ----------UUGUCGCUGUUCCUCCGGCGUGAUGUCCAG---------- 3'
              ||||||||||||||||||||||||||||
3' ACCAGACGTTCACAGCGACAAGGAGGCCGCACTACAGGTCGGTAGCTTAC 5'
   |||||||||                              |||||||||
5' TGGTCTGCAAGTGTCGCTGTTCCTCCGGCGTGATGTCCAGCCATCGAATG
```

GU568037 Deep-sea thermophilic phage D6E

```
5' ----------UUCUUUCUGCGCACAUCCGUUCCGCGAAUC---------- 3'
              || ||||| |||||||||| |||||||||
3' GTAGGAGTGTAAAAAGAGGCGTGTAGGCAGGGCGCTTAGTAGCGATTTT 5'
   |||||||||                              |||||||||
5' CATCCTCACATTTTTCTCCGCACATCCGTCCCGCGAATCATCGCTAAAA 3'

5' ----------CUUCAUUUAUUGCACUAUUGCGACAGAAGG---------- 3'
              |||||||||| ||||||| ||||| |
3' GGCAGTCGGCGAAGTAAATAACGCAATAACGCCGTCTTTCCCTAGTTTCA 5'
   |||||||||                              |||||||||
5' CCGTCAGCCGCTTCATTTATTGCGTTATTGCGGCAGAAAGGGATCAAAGT
```

FIG. 10B

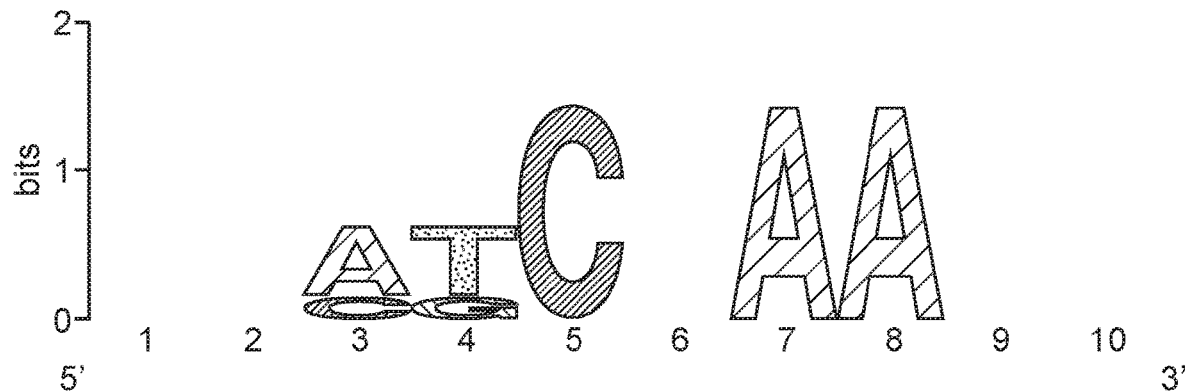

GU568037 Deep-sea thermophilic phage D6E

```
5' -----------AGUUUUUAGGCCGUAGCGGCUCGAAUACGG------------ 3'
              |||||||||||||||||||||||||||||
3' CTGTCGCACGTCAAAAATCCGGCATCGCCGAGCTTATGCCGTCTCTTTGT 5'
   ||||||||||                                |||||||||
5' GACAGCGTGCAGTTTTTAGGCCGTAGCGGCTCGAATACGGCAGAGAAACA 3'v

5' -----------GGUCGGCCAGCCGAUCAGCACGCACACGGA------------ 3'
              |||||||||||||||||||||||||| ||
3' TACTGTAACAGCAGCCGGTCGGCTAGTCGTGCGTGTGGCTCCTTCTTTTC 5'
   ||||||||||                                |||||||||
5' ATGACATTGTCGTCGGCCAGCCGATCAGCACGCACACCGAGGAAGAAAAG
```

KJ159566 Geobacillus phage GBK2

```
5' -----------UGCCCAUGCGACGGCAUGCUCCUUCAUUUC------------ 3'
              |||||||||  |||||||||||  |||||||||
3' CCACTCCGGGACGGGTACGTTGCCGTACGAGAAAGTAAAGTTTTCGCTAA 5'
   ||||||||||                                |||||||||
5' GGTGAGGCCCTGCCCATGCAACGGCATGCTCTTTCATTTCAAAAGCGATT 3'
```

FIG. 10C (Cont.)

DQ453159 Geobacillus virus E2

```
5'     ----------CGGACUGAUACCCAACACAACAAAGGAGGC---------- 3'
                 ||||||||||||||||||||||||||||||
3' ACAAGGTCCGGCCTGACTATGGGTTGTGTTGTTTCCTCCGCAAACTTTTT 5'
   |||||||||                              |||||||||
5' TGTTCCAGGCCGGACTGATACCCAACACAACAAAGGAGGCGTTTGAAAAA 3'

5'     ----------UUCCCUCGCUGAUUUCUCCGCGUGCGAAUUG---------- 3'
                 ||||||||||||||||||||||||||||||
3' CGAGATATAACAGGGAGCGACTAAAGAGGCGCACGCTTAACTAGCCGTTGA 5'
   |||||||||                              |||||||||
5' GCTCTATATTGTCCCTCGCTGATTTCTCCGCGTGCGAATTGATCGGCAACT 3'

5'     ----------UCGGAGUGACGUUGUUCGGCCUGCGACGAG---------- 3'
                | ||||||||||||||||||||| |||||
3' CGGTGGGGTAAACCTCACTGCAACAAGCCGGACGTTGCTCTGTCCGTTGC 5'
   |||||||||                              ||||||||||
5' GCCACCCCATTTGGAGTGACGTTGTTCGGCCTGCAACGAGACAGGCAACG 3'

5'     -----------AGUUUUUAGGCCGUAGCGGCUCGAAUACGG---------- 3'
                 ||||||||||||||||||||||||||| |
3' CTGTCGCATGTCAAAAATCCGGCATCGCCGAGCTTATTGCTTCCTTTTCG 5'
   |||||||||                              |||||||||
5' GACAGCGTACAGTTTTTAGGCCGTAGCGGCTCGAATAACGAAGGAAAAGC
```

FIG. 10D

FIG. 11

| Name | Sequence (DNA)<br>(tracrRNA: 3' of gaaa tetraloop) | tracrRNA length | Figure | SEQ ID NO. |
|---|---|---|---|---|
| 16nt cr:tracr sgRNA | ggCTGTAAGCGGATGCCATATGGTCATAGTTCCCCTGAgaaaTCAGGGTTACTATGATAAGGGCTTTCTGCCTAAGGCAGACTGACCCGCGGCGTTGGGGATCGCCTGTCGCCCGCTTTTGGCGGGCATTCCCCATCCTT | 98 | 3c | 56 |
| 25nt cr:tracr sgRNA | ggCTGTAAGCGGATGCCATATGGTCATAGTTCCCCTGAGATTATCGCgaaaATGATCTCAGGGTTACTATGATAAGGGCTTTCTGCCTAAGGCAGACTGACCCGCGGCGTTGGGGATCGCCTGTCGCCCGCTTTTGGCGGGCATTCCCCATCCTT | 104 | 3c | 57 |
| 36nt cr:tracr sgRNA | ggCTGTAAGCGGATGCCATATGGTCATAGTTCCCCTGAGATTATCGCTGTGGTATAATgaaaATACCACAGCAATGATCTCAGGGTTACTATGATAAGGGCTTTCTGCCTAAGGCAGACTGACCCGCGGCGTTGGGGATCGCCTGTCGCCCGCTTTTGGCGGGCATTCCCCATCCTT | 115 | 3c | 58 |
| 63nt tracrRNA sgRNA | ggCTGTAAGCGGATGCCATATGGTCATAGTTCCCCTGAgaaaTCAGGGTTACTATGATAAGGGCTTTCTGCCTAAGGCAGACTGACCCGCGGCGTTGGGGATCGC | 63 | 3c | 59 |
| 91nt tracrRNA sgRNA | ggCTGTAAGCGGATGCCATATGGTCATAGTTCCCCTGAgaaaTCAGGGTTACTATGATAAGGGCTTTCTGCCTAAGGCAGACTGACCCGCGGCGTTGGGGATCGCCTGTCGCCCGCTTTTGGCGGGCATTCCC | 91 | 3c | 60 |

FIG. 11 (Cont.)

| Name | Sequence (DNA) (tracrRNA: 3' of gaaa tetraloop) | tracrRNA length | Figure | SEQ ID NO. |
|---|---|---|---|---|
| 98nt tracrRNA sgRNA | ggCTGTAAGCGGATGCCATATGGTCATAGTTCCCCTGAgaaaTCAGGGTTACTATGATAAGGGCTTTCTGCCTAAGGCAGACTGACCCGCGGCGTTGGGGATCGCCTGTCGCCCGCTTTTGGCGGGCATTCCCCATCCTT | 98 | 3c | 61 |
| 140nt tracrRNA sgRNA | ggCTGTAAGCGGATGCCATATGGTCATAGTTCCCCTGAgaaaTCAGGGTTACTATGATAAGGGCTTTCTGCCTAAGGCAGACTGACCCGCGGCGTTGGGGATCGCCTGTCGCCCGCTTTTGGCGGGCATTCCCCATCCTTGCGCAAACTCAGACCTTGGCGGAAAACGCTAAGGTCTTTTTT | 140 | 3c | 62 |
| 19nt spacer sgRNA | ggTGTAAGCGGATGCCATATGGTCATAGTTCCCCTGAgaaaTCAGGGTTACTATGATAAGGGCTTTCTGCCTAAGGCAGACTGACCCGCGGCGTTGGGGATCGCCTGTCGCCCGCTTTTGGCGGGCATTCCCCATCCTT | 98 | 3c | 63 |
| 20nt spacer sgRNA | ggCTGTAAGCGGATGCCATATGGTCATAGTTCCCCTGAgaaaTCAGGGTTACTATGATAAGGGCTTTCTGCCTAAGGCAGACTGACCCGCGGCGTTGGGGATCGCCTGTCGCCCGCTTTTGGCGGGCATTCCCCATCCTT | 98 | 3c | 64 |
| 21nt spacer sgRNA | ggTCTGTAAGCGGATGCCATATGGTCATAGTTCCCCTGAgaaaTCAGGGTTACTATGATAAGGGCTTTCTGCCTAAGGCAGACTGACCCGCGGCGTTGGGGATCGCCTGTCGCCCGCTTTTGGCGGGCATTCCCCATCCTT | 98 | 3c | 65 |

FIG. 11 (Cont.)

| Name | Sequence (DNA)<br>(tracrRNA: 3' of gaaa tetraloop) | tracrRNA length | Figure | SEQ ID NO. |
|---|---|---|---|---|
| 22nt spacer sgRNA | ggGTCTGTAAGCGGATGCCATATGGT<br>CATAGTTCCCCTGAgaaaTCAGGGTT<br>ACTATGATAAGGGCTTTCTGCCTAAG<br>GCAGACTGACCCGCGGCGTTGGGG<br>ATCGCCTGTCGCCCGCTTTTGGCGG<br>GCATTCCCCATCCTT | 98 | 4a, 4b, 4c | 66 |
| Geo NT | GGTCTGTAAGCGGATGCCATATGGT<br>CATAGTTCCCCTGAgaaaTCAGGGTT<br>ACTATGATAAGGGCTTTCTGCCTAAG<br>GCAGACTGACCCGCGGCGTTGGGG<br>ATCGCCTGTCGCCCGCTTTTGGCGG<br>GCATTCCCCATCCTT | 98 | 4a | 67 |
| Geo CACA PAM, GFP targeting | gGAGCTGGACGGCGACGTAAAGTCA<br>TAGTTCCCCTGAgaaaTCAGGGTTAC<br>TATGATAAGGGCTTTCTGCCTAAGG<br>CAGACTGACCCGCGGCGTTGGGGA<br>TCGCCTGTCGCCCGCTTTTGGCGGG<br>CATTCCCCATCCTT | 98 | 4a | 68 |
| Geo CGAC PAM, GFP targeting | GGAGCGCACCATCTTCTTCAGTCAT<br>AGTTCCCCTGAgaaaTCAGGGTTACT<br>ATGATAAGGGCTTTCTGCCTAAGGC<br>AGACTGACCCGCGGCGTTGGGGAT<br>CGCCTGTCGCCCGCTTTTGGCGGG<br>CATTCCCCATCCTT | 98 | 4a | 69 |
| Geo CAAA PAM, GFP targeting | ggCCTGAGCACCCAGTCCGCCCGTC<br>ATAGTTCCCCTGAgaaaTCAGGGTTA<br>CTATGATAAGGGCTTTCTGCCTAAG<br>GCAGACTGACCCGCGGCGTTGGGG<br>ATCGCCTGTCGCCCGCTTTTGGCGG<br>GCATTCCCCATCCTT | 98 | 4a | 70 |

FIG. 11 (Cont.)

| Name | Sequence (DNA) (tracrRNA: 3' of gaaa tetraloop) | tracrRNA length | Figure | SEQ ID NO. |
|---|---|---|---|---|
| Geo CGAA PAM, GFP targeting | ggTGCGGTTCACCAGGGTGTCGGTC ATAGTTCCCCTGAgaaaTCAGGGTTA CTATGATAAGGGCTTTCTGCCTAAG GCAGACTGACCCGCGGCGTTGGGG ATCGCCTGTCGCCCGCTTTTGGCGG GCATTCCCCATCCTT | 98 | 4b | 71 |
| Geo AAVS1 21nt | CAAATGAAAGGAGTGAGAGGTGTCA TAGTTCCCCTGAgaaaTCAGGGTTAC TATGATAAGGGCTTTCTGCCTAAGG CAGACTGACCCGCGGCGTTGGGGA TCGCCTGTCGCCCGCTTTTGGCGGG CATTCCCCATCCTT | 21 | 4b | 72 |
| Geo AAVS1 22nt | CCAAATGAAAGGAGTGAGAGGTGTC ATAGTTCCCCTGAgaaaTCAGGGTTA CTATGATAAGGGCTTTCTGCCTAAG GCAGACTGACCCGCGGCGTTGGGG ATCGCCTGTCGCCCGCTTTTGGCGG GCATTCCCCATCCTT | 22 | 4b | 73 |
| Spy AAVS1 20nt | GTGGCTAAAGCCAGGGAGACGTTTT AGAGCTAGAAATAGCAAGTTAAAATA AGGCTAGTCCGTTATCAACTTGAAAA AGTGGCACCGAGTCGGTGCTTTTTT T | 67 | 4b | 74 |
| Geo AAVS1 21nt | GACTCCAATGCGGAAGAGAGTGTCA TAGTTCCCCTGAgaaaTCAGGGTTAC TATGATAAGGGCTTTCTGCCTAAGG CAGACTGACCCGCGGCGTTGGGGA TCGCCTGTCGCCCGCTTTTGGCGGG CATTCCCCATCCTT | 98 | 4b | 75 |

FIG. 11 (Cont.)

| Name | Sequence (DNA)<br>(tracrRNA: 3' of gaaa tetraloop) | tracrRNA length | Figure | SEQ ID NO. |
|---|---|---|---|---|
| Geo AAVS1 22nt | GCGACTCCAATGCGGAAGAGAGTGT<br>CATAGTTCCCCTGAgaaaTCAGGGTT<br>ACTATGATAAGGGCTTTCTGCCTAAG<br>GCAGACTGACCCGCGGCGTTGGGG<br>ATCGCCTGTCGCCCGCTTTTGGCGG<br>GCATTCCCCATCCTT | 98 | 4b | 76 |
| Spy AAVS1 20nt | gACTCCAATGCGGAAGAGAGTGTTTT<br>AGAGCTAGAAATAGCAAGTTAAAATA<br>AGGCTAGTCCGTTATCAACTTGAAAA<br>AGTGGCACCGAGTCGGTGCTTTTTT<br>T | 67 | 4b | 77 |
| Geo DNMT1 21nt | gGCAGCTGAGGCAGGTGCCTGCTGT<br>CATAGTTCCCCTGAgaaaTCAGGGTT<br>ACTATGATAAGGGCTTTCTGCCTAAG<br>GCAGACTGACCCGCGGCGTTGGGG<br>ATCGCCTGTCGCCCGCTTTTGGCGG<br>GCATTCCCCATCCTT | 98 | 4c | 78 |
| Spy NT | ggCTGTAAGCGGATGCCATATGGTTT<br>TAGAGCTAGAAATAGCAAGTTAAAAT<br>AAGGCTAGTCCGTTATCAACTTGAAA<br>AAGTGGCACCGAGTCGGTGCTTTTT<br>TT | 67 | 4c | 79 |
| Spy DNMT1 20nt | gAGTACGTTAATGTTTCCTGAGTTTT<br>AGAGCTAGAAATAGCAAGTTAAAATA<br>AGGCTAGTCCGTTATCAACTTGAAAA<br>AGTGGCACCGAGTCGGTGCTTTTTT<br>T | 67 | 4c | 80 |

FIG. 12

| Primers | | | |
|---|---|---|---|
| Name | Sequence | Figure | SEQ ID NO. |
| AAVS1 Amplification 1 F | GGGTGGAGGGGACAGATAAAAGTAC | 4b | 81 |
| AAVS1 Amplification 1 R | ACGTGATGTCCTCTGAGCGGATC | 4b | 82 |
| AAVS1 Amplification 2 F | TCCACCAACGCCGACGGTATCAG | 4b | 83 |
| AAVS1 Amplification 2 R | GCAGAAGCCAGTAGAGCTCAAAGTGGTC | 4b | 84 |
| DNMT1 Amplification F | CCTCACACAACAGCTTCATGTCAGC | 4c | 85 |
| DNMT1 Amplification R | GCCAAAGCCCGAGAGAGTGCC | 4c | 86 |

| DNA substrates | | | |
|---|---|---|---|
| Name | Sequence | Figure | SEQ ID NO. |
| CAAA PAM target | TCACGGTCACAGCTGATGGTGTAAGCGGATGCCATATGTGGGCAAACTGCCCGCTT | 2b | 87 |
| | AAGCGGGCAGTTTGCCCACATATGGCATCCGCTTACACCATCAGCTGTGACCGTGA | | 88 |
| GAAA PAM target | TCACGGTCACAGCTGATGGTGTAAGCGGATGCCATATGTGGGGAAACTGCCCGCTT | 2b | 89 |
| | AAGCGGGCAGTTTCCCCACATATGGCATCCGCTTACACCATCAGCTGTGACCGTGA | | 90 |
| CGAA PAM target | TCACGGTCACAGCTGATGGTGTAAGCGGATGCCATATGTGGGCGAACTGCCCGCTT | 2b | 91 |
| | AAGCGGGCAGTTCGCCCACATATGGCATCCGCTTACACCATCAGCTGTGACCGTGA | | 92 |
| GCAA PAM target | TCACGGTCACAGCTGATGGTGTAAGCGGATGCCATATGTGGGGCAACTGCCCGCTT | 2b | 93 |
| | AAGCGGGCAGTTGCCCCACATATGGCATCCGCTTACACCATCAGCTGTGACCGTGA | | 94 |

FIG. 12 (Cont.)

| DNA substrates | | | |
|---|---|---|---|
| Name | Sequence | Figure | SEQ ID NO. |
| CTAA PAM target | TCACGGTCACAGCTGATGGTGTAAGCGGA TGCCATATGTGGGCTAACTGCCCGCTT | 2b | 95 |
| | AAGCGGGCAGTTAGCCCACATATGGCATC CGCTTACACCATCAGCTGTGACCGTGA | | 96 |
| GAAG PAM target | TCACGGTCACAGCTGATGGTGTAAGCGGA TGCCATATGTGGGGAAGCTGCCCGCTT | 2b | 97 |
| | AAGCGGGCAGCTTCCCCACATATGGCATC CGCTTACACCATCAGCTGTGACCGTGA | | 98 |
| Geo pUC Target | TCACGGTCACAGCTGGTCTGTAAGCGGAT GCCATATGTGGGCAAACTGCCCGCTT | 3c | 99 |
| | AAGCGGGCAGTTTGCCCACATATGGCATC CGCTTACAGACCAGCTGTGACCGTGA | | 100 |

FIG. 13

| Gene ID | Locus Tag | Genome | cas9 Length (bp) | Scaffold Length (bp) | Isolation | Temp. Range |
|---|---|---|---|---|---|---|
| Reference | | | | | | |
| 2555743823 | M1GAS476_0830 | Streptococcus pyogenes M1 476 | 4107 | 1831079 | Isolated from yogurt in France | Thermophile |
| Thermophiles | | | | | | |
| 2514224873 | IALB_3034 | Ignavibacterium album Mat9-16, JCM 16511 | 5067 | 3658997 | Hot spring, Yumata, Nagano, Japan | Mesophile 30-55 (45) |
| 2523804957 | LrCIT5draft1_00026 | Lactobacillus reuteri Y2 (LrCIT5draft1) | 4149 | 99160 | Porcine gastrointestinal tract | Thermophile 37-43 |
| 2512376689 | Sinf_1255 | Streptococcus infantarius infantarius CJ18 | 4128 | 1988420 | local camel milk market in Mandera, Kenya | Thermophile |
| 637593069 | str0657 | Streptococcus thermophilus CNRZ1066 | 3387 | 1796226 | Deteriorated canned food | Thermophile 45 |
| 2625842855 | Ga007665 0_11717 | Streptococcus thermophilus CNRZ1066 (re-annotation) | 3387 | 1796226 | Commercial yogurt in 1974 in the United Kingdom | Thermophile 45 |
| 2626024641 | Ga007677 4_11723 | Streptococcus thermophilus LMG 18311 (re-annotation) | 3369 | 1796846 | Isolated from yogurt in France | Thermophile 45 |

FIG. 13 (Cont.)

| 637591093 | stu0657 | Streptococcus thermophilus LMG 18311 | 3369 | 1796846 | Commercial yogurt in 1974 in the United Kingdom | Thermophile 45 |

| Gene ID | Locus Tag | Genome | cas9 Length (bp) | Scaffold Length (bp) | Isolation | Temp. Range |
|---|---|---|---|---|---|---|
| 2526045052 | H596DRAFT_02636 | Rubritepida flocculans DSM 14296 | 3363 | 75156 | Hot spring | Thermophile 50 |
| 2610904261 | Ga0054994_10813 | Geobacillus stearothermophilus 1518, ATCC 7953 | 3264 | 15737 | Hot spring | Thermophile 30-75 (55) |
| 2526196768 | GbsDRAFT_02642 | Geobacillus stearothermophilus ATCC7953 (Draft 1) | 3264 | 20875 | Deteriorated canned food | Thermophile 30-75 (55) |
| 2526046077 | H596DRAFT_03661 | Rubritepida flocculans DSM 14296 | 3153 | 12433 | Hot spring | Thermophile 50 |
| 2520605854 | F563DRAFT_01965 | Elioraea tepidiphila DSM 17972 | 3105 | 148130 |  | 50 |
| 2550090243 | OUUDRAFT_01763 | Campylobacter jejuni jejuni ATCC 33560 | 2955 | 229725 | Bovine feces | Thermophile 30-50 |

FIG. 14

| DNA that Encodes Spacer Sequences | SEQ ID NO. |
| --- | --- |
| CCTCACTCGCAACAGTTTCCACCATGTCC | 101 |
| AAGGCTTATGATTACTTAGTTGATTTATGG | 102 |
| CGCAGTATGCATTTACACGAAAACCAGAAG | 103 |
| ATCGATAATCGCCAATAACGCAAATCCTA | 104 |
| CAGCGATAAAGCTATAATTCATCAGTTAGT | 105 |
| CGTTGGTGAGGGACATAACCGAAGCGCTG | 106 |
| CAAAGACATGAGAATGCTGGCGCAGGTGAT | 107 |
| ACAAATGATAGACGGGGACTACAGACATAA | 108 |
| AACAATGATTTTCCCTACGCCGGTGGTAA | 109 |
| AAATATGAAACTCTGACATCTTCAAATCAG | 110 |
| TGCCCATGCGACGGCATGCTCCTTCATTTC | 111 |
| GCTTTTTTATCCACCTTGGCCGGCTGTGGG | 112 |
| ATTTCCAGCAGTCTTTTGACGACAAACTG | 113 |
| AGTTTTTAGGCCGTAGCGGCTCGAATACGG | 114 |
| ATGTCTTTAGTCTCATTGGTGCCGTATGGT | 115 |
| TGTTCTTGACTTCTACAGTCAACAAATAAA | 116 |
| ACTGTTCCCCTTGAACTGAGTGACGCCTT | 117 |
| GGTCGGCCAGCCGATCAGCACGCACACGGA | 118 |
| GTTGAGCAAGTAGAAAGGCGATGGAGGTT | 119 |
| TCACACCCCTTTTTTGTCTGTCGCCGCTCA | 120 |
| CATGAATCGAAAGGCCGTTTTTATACATAA | 121 |
| TTCCCTCGCTGATTTCTCCGCGTGCGAATTG | 122 |
| TAAATACGTCAACATCTACGTGGATATGGAA | 123 |
| CCGGGGCCTTTTTGTTATGGCCGATGGTAT | 124 |
| TCAGTCTCGACCCAGAGGGGACAGTCAAGGA | 125 |
| CGGACTGATACCCAACACAACAAAGGAGGC | 126 |
| TCGGAGTGACGTTGTTCGGCCTGCGACGAG | 127 |
| TCCGCCTGAAGCTCCGTATGTAGCGGATAG | 128 |
| TTGAACAGGCATAGGGAGGGACTAAATGA | 129 |
| AAGTGACGTAAGATAAAGACCGAAATCAG | 130 |
| CGCATCCAGGGCTCGCCCTATATCCCAAGG | 131 |
| TTGCTCCGACTATCCGAAATCAAGCGATAC | 132 |

THERMOSTABLE RNA-GUIDED ENDONUCLEASES AND METHODS OF USE THEREOF

CROSS-REFERENCE

This application is a national stage filing under 35 U.S.C. § 371 of PCT/US2018/032832, filed May 15, 2018, which claims the benefit of U.S. Provisional Patent Application No. 62/507,123, filed May 16, 2017, which applications are incorporated herein by reference in their entirety.

STATEMENT REGARDING FEDERALLY SPONSORED RESEARCH

This invention was made with government support under Grant No. 1244557 awarded by the National Science Foundation. The government has certain rights in the invention.

INCORPORATION BY REFERENCE OF SEQUENCE LISTING PROVIDED AS A TEXT FILE

A Sequence Listing is provided herewith as a text file, "BERK-357WO_SeqList_ST25.txt" created on May 15, 2018 and having a size of 77 KB. The contents of the text file are incorporated by reference herein in their entirety.

INTRODUCTION

CRISPR-Cas systems include Cas proteins, which are involved in acquisition, targeting and cleavage of foreign DNA or RNA, and a guide RNA(s), which includes a segment that binds Cas proteins and a segment that binds to a target nucleic acid. For example, Class 2 CRISPR-Cas systems comprise a single Cas protein bound to a guide RNA, where the Cas protein binds to and cleaves a targeted nucleic acid. The programmable nature of these systems has facilitated their use as a versatile technology for use in modification of target nucleic acid.

There is a need in the art for additional CRISPR-Cas systems with desirable properties such as thermostability.

SUMMARY

The present disclosure provides RNA-guided endonucleases, nucleic acids encoding same, and compositions comprising same. The present disclosure provides ribonucleoprotein complexes comprising: an RNA-guided endonuclease of the present disclosure; and a guide RNA. The present disclosure provides methods of modifying a target nucleic acid, using an RNA-guided endonuclease of the present disclosure and a guide RNA.

BRIEF DESCRIPTION OF THE DRAWINGS

FIG. 3A-3C depict small RNA-seq and sgRNA engineering for GeoCas9.

FIG. 4A-4C depict GeoCas9 editing in mammalian cells.

FIG. 6 provides an amino acid sequence of a *Geobacillus stearothermophilus* RNA-guided endonuclease.

FIG. 7 provides an amino acid sequence of a GeoCas9 with a heterologous protospacer adjacent motif (PAM)-interacting domain.

FIG. 8 provides an amino acid sequence of a GeoLC300 RNA-guided endonuclease.

FIG. 10A-10D provides targets used to generate logos in FIGS. 2B and 2C.

FIG. 11 provides Table 1: Guide RNAs used in various Figures.

FIG. 12 provides Table 2: Primers and DNA substrates used in various Figures.

FIG. 13 provides Table 3: Candidate Thermophiles.

FIG. 14 provides Table 4: Spacer sequences in *Geobacillus* sp. LC300, complete genome.

DEFINITIONS

Figures 1A, 1B:
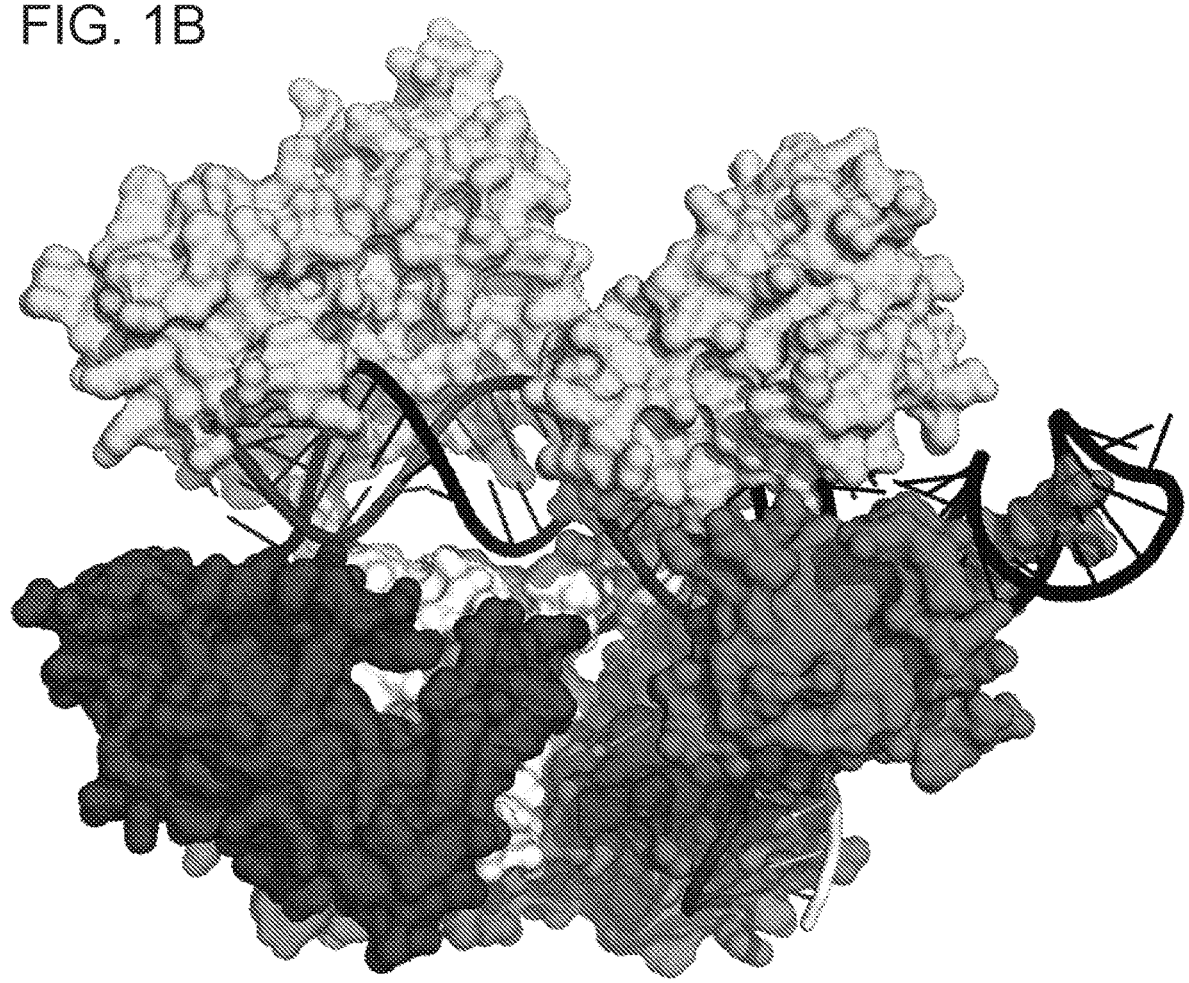
FIG. 1A-1E depict various features of *Geobacillus stearothermophilus* RNA-guided endonuclease ("GeoCas9").
Figure 1C:
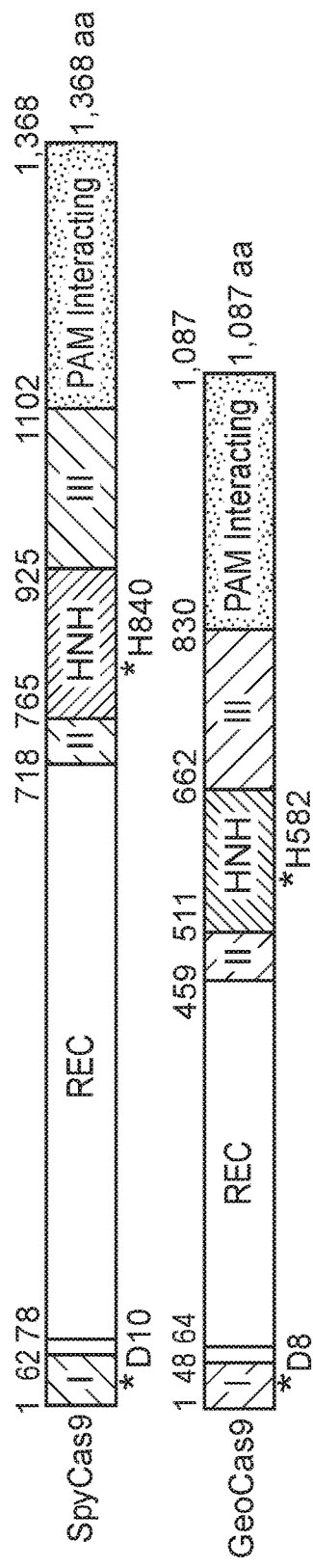

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine (A) pairing with thymidine (T), adenine (A) pairing with uracil (U), and guanine (G) pairing with cytosine (C) [DNA, RNA]. In addition, for hybridization between two RNA molecules (e.g., dsRNA), and for hybridization of a DNA molecule with an RNA molecule (e.g., when a DNA target nucleic acid base pairs with a guide RNA, etc.): guanine (G) can also base pair with uracil (U). For example, G/U base-pairing is at least partially responsible for the degeneracy (i.e., redundancy) of the genetic code in the context of tRNA anti-codon base-pairing with codons in mRNA. Thus, in the context of this disclosure, a guanine (G) (e.g., of dsRNA duplex of a guide RNA molecule; of a guide RNA base pairing with a target nucleic acid, etc.) is considered complementary to both a uracil (U) and to an adenine (A). For example, when a G/U base-pair can be made at a given nucleotide position of a dsRNA duplex of a guide RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. For hybridizations between nucleic acids with short stretches of complementarity (e.g. complementarity over 35 or less, 30 or less, 25 or less, 22 or less, 20 or less, or 18 or less nucleotides) the position of mismatches can become important (see Sambrook et al., supra, 11.7-11.8). Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more). Temperature, wash solution salt concentration, and other conditions may be adjusted as necessary according to factors such as length of the region of complementation and the degree of complementation.

It is understood that the sequence of a polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a bulge, a loop structure or hairpin structure, etc.). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Example methods include BLAST programs (basic local alignment search tools) and PowerBLAST programs (Altschul et al., J. Mol. Biol., 1990, 215, 403-410; Zhang and Madden, Genome Res., 1997, 7, 649-656), the Gap program (Wisconsin Sequence Analysis Package, Version 8 for Unix, Genetics Computer Group, University Research Park, Madison Wis.), e.g., using default settings, which uses the algorithm of Smith and Waterman (Adv. Appl. Math., 1981, 2, 482-489), and the like.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to an RNA-binding domain of a polypeptide, binding to a target nucleic acid, and the like) refers to a non-covalent interaction between macromolecules (e.g., between a protein and a nucleic acid; between a GeoCas protein/guide RNA complex and a target nucleic acid; and the like). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant ($K_D$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_D$.

By "binding domain" it is meant a protein domain that is able to bind non-covalently to another molecule. A binding domain can bind to, for example, a DNA molecule (a DNA-binding domain), an RNA molecule (an RNA-binding domain) and/or a protein molecule (a protein-binding domain). In the case of a protein having a protein-binding domain, it can in some cases bind to itself (to form homodimers, homotrimers, etc.) and/or it can bind to one or more regions of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various convenient methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

A DNA sequence that "encodes" a particular RNA is a DNA nucleotide sequence that is transcribed into RNA. A DNA polynucleotide may encode an RNA (mRNA) that is translated into protein (and therefore the DNA and the mRNA both encode the protein), or a DNA polynucleotide may encode an RNA that is not translated into protein (e.g. tRNA, rRNA, microRNA (miRNA), a "non-coding" RNA (ncRNA), a guide RNA, etc.).

A "protein coding sequence" or a sequence that encodes a particular protein or polypeptide, is a nucleotide sequence that is transcribed into mRNA (in the case of DNA) and is translated (in the case of mRNA) into a polypeptide in vitro or in vivo when placed under the control of appropriate regulatory sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., guide RNA) or a coding sequence (e.g., RNA-guided endonuclease, GeoCas9 polypeptide, GeoCas9 fusion polypeptide, and the like) and/or regulate translation of an encoded polypeptide.

As used herein, a "promoter" or a "promoter sequence" is a DNA regulatory region capable of binding RNA polymerase and initiating transcription of a downstream (3' direction) coding or non-coding sequence. For purposes of the present disclosure, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive expression by the various vectors of the present disclosure.

The term "naturally-occurring" or "unmodified" or "wild type" as used herein as applied to a nucleic acid, a polypeptide, a cell, or an organism, refers to a nucleic acid, polypeptide, cell, or organism that is found in nature. For example, a polypeptide or polynucleotide sequence that is present in an organism that can be isolated from a source in nature is naturally occurring.

The term "fusion" as used herein as applied to a nucleic acid or polypeptide refers to two components that are defined by structures derived from different sources. For example, where "fusion" is used in the context of a fusion polypeptide (e.g., a fusion GeoCas9 protein), the fusion polypeptide includes amino acid sequences that are derived from different polypeptides. A fusion polypeptide may comprise either modified or naturally-occurring polypeptide sequences (e.g., a first amino acid sequence from a modified or unmodified GeoCas9 protein; and a second amino acid sequence from a modified or unmodified protein other than a GeoCas9 protein, etc.). Similarly, "fusion" in the context of a polynucleotide encoding a fusion polypeptide includes nucleotide sequences derived from different coding regions (e.g., a first nucleotide sequence encoding a modified or unmodified GeoCas9 protein; and a second nucleotide sequence encoding a polypeptide other than a GeoCas9 protein).

The term "fusion polypeptide" refers to a polypeptide which is made by the combination (i.e., "fusion") of two otherwise separated segments of amino acid sequence, usually through human intervention.

"Heterologous," as used herein, means a nucleotide or polypeptide sequence that is not found in the native nucleic acid or protein, respectively. For example, in some cases, in a variant GeoCas9 protein of the present disclosure, a portion of naturally-occurring GeoCas9 polypeptide (or a variant thereof) may be fused to a heterologous polypeptide (i.e. an amino acid sequence from a protein other than a Cas9 from *Geobacillus stearothermophilus* or an amino acid sequence from another organism). As another example, a fusion GeoCas9 polypeptide can comprise all or a portion of a naturally-occurring GeoCas9 polypeptide (or variant thereof) fused to a heterologous polypeptide, i.e., a polypeptide from a protein other than a Cas9 from *Geobacillus stearothermophilus* or a polypeptide from another organism. The heterologous polypeptide may exhibit an activity (e.g., enzymatic activity) that will also be exhibited by the variant GeoCas9 protein or the fusion GeoCas9 protein (e.g., biotin ligase activity; nuclear localization; etc.). A heterologous nucleic acid sequence may be linked to a naturally-occurring nucleic acid sequence (or a variant thereof) (e.g., by genetic engineering) to generate a chimeric nucleotide sequence encoding a chimeric polypeptide (a fusion protein).

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences"). Alternatively, DNA sequences encoding RNA (e.g., guide RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. An example of such a case is a DNA (a recombinant) encoding a wild-type protein where the DNA sequence is codon optimized for expression of the protein in a cell (e.g., a eukaryotic cell) in which the protein is not naturally found (e.g., expression of a CRISPR/Cas RNA-guided polypeptide such as GeoCas9 (e.g., wild-type GeoCas9; variant GeoCas9; variant GeoCas9 comprising a heterologous PI domain; fusion GeoCas9; etc.) in a eukaryotic cell). A codon-optimized DNA can therefore be recombinant and non-naturally occurring while the protein encoded by the DNA may have a wild type amino acid sequence.

Thus, the term "recombinant" polypeptide does not necessarily refer to a polypeptide whose amino acid sequence does not naturally occur. Instead, a "recombinant" polypeptide is encoded by a recombinant non-naturally occurring DNA sequence, but the amino acid sequence of the polypeptide can be naturally occurring ("wild type") or non-naturally occurring (e.g., a variant, a mutant, etc.). Thus, a "recombinant" polypeptide is the result of human intervention, but may have a naturally occurring amino acid sequence.

A "vector" or "expression vector" is a replicon, such as plasmid, phage, virus, artificial chromosome, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence (or the coding sequence can also be said to be operably linked to the promoter) if the promoter affects its transcription or expression.

The terms "recombinant expression vector," or "DNA construct" are used interchangeably herein to refer to a DNA molecule comprising a vector and an insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A cell has been "genetically modified" or "transformed" or "transfected" by exogenous DNA or exogenous RNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al. Adv Drug Deliv Rev. 2012 Sep. 13. pii: 50169-409X(12)00283-9. doi: 10.1016/j.addr.2012.09.023), and the like.

The choice of method of genetic modification is generally dependent on the type of cell being transformed and the circumstances under which the transformation is taking place (e.g., in vitro, ex vivo, or in vivo). A general discussion of these methods can be found in Ausubel, et al., Short Protocols in Molecular Biology, 3rd ed., Wiley & Sons, 1995.

A "target nucleic acid" as used herein is a polynucleotide (e.g., DNA such as genomic DNA) that includes a site ("target site" or "target sequence") targeted by an RNA-guided endonuclease polypeptide (e.g., wild-type GeoCas9; variant GeoCas9; variant GeoCas9 comprising a heterologous PI domain; fusion GeoCas9; etc.). The target sequence is the sequence to which the guide sequence of a subject GeoCas9 guide RNA (e.g., a dual GeoCas9 guide RNA or a single-molecule GeoCas9 guide RNA) will hybridize. For example, the target site (or target sequence) 5'-GAG-CAUAUC-3' within a target nucleic acid is targeted by (or is bound by, or hybridizes with, or is complementary to) the sequence 5'-GAUAUGCUC-3'. Suitable hybridization conditions include physiological conditions normally present in a cell. For a double stranded target nucleic acid, the strand of the target nucleic acid that is complementary to and hybridizes with the guide RNA is referred to as the "complementary strand" or "target strand"; while the strand of the target nucleic acid that is complementary to the "target strand" (and is therefore not complementary to the guide RNA) is referred to as the "non-target strand" or "non-complementary strand."

By "cleavage" it is meant the breakage of the covalent backbone of a target nucleic acid molecule (e.g., RNA, DNA). Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events.

"Nuclease" and "endonuclease" are used interchangeably herein to mean an enzyme which possesses catalytic activity for nucleic acid cleavage (e.g., ribonuclease activity (ribonucleic acid cleavage), deoxyribonuclease activity (deoxyribonucleic acid cleavage), etc.).

By "cleavage domain" or "active domain" or "nuclease domain" of a nuclease it is meant the polypeptide sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide.

The term "stem cell" is used herein to refer to a cell (e.g., plant stem cell, vertebrate stem cell) that has the ability both to self-renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells (described below) can differentiate into lineage-restricted progenitor cells (e.g., mesodermal stem cells), which in turn can differentiate into cells that are further restricted (e.g., neuron progenitors), which can differentiate into end-stage cells (i.e., terminally differentiated cells, e.g., neurons, cardiomyocytes, etc.), which play a characteristic role in a certain tissue type, and may or may not retain the capacity to proliferate further. Stem cells may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to multiple differentiated progeny.

Stem cells of interest include pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ectoderm, mesoderm, or endoderm tissues in a living organism.

Pluripotent stem cells of plants are capable of giving rise to all cell types of the plant (e.g., cells of the root, stem, leaves, etc.).

PSCs of animals can be derived in a number of different ways. For example, embryonic stem cells (ESCs) are derived from the inner cell mass of an embryo (Thomson et. al, Science. 1998 Nov. 6; 282(5391):1145-7) whereas induced pluripotent stem cells (iPSCs) are derived from somatic cells (Takahashi et. al, Cell. 2007 Nov. 30; 131(5): 861-72; Takahashi et. al, Nat Protoc. 2007; 2(12):3081-9; Yu et. al, Science. 2007 Dec. 21; 318(5858):1917-20. Epub 2007 Nov. 20). Because the term PSC refers to pluripotent stem cells regardless of their derivation, the term PSC encompasses the terms ESC and iPSC, as well as the term embryonic germ stem cells (EGSC), which are another example of a PSC. PSCs may be in the form of an established cell line, they may be obtained directly from primary embryonic tissue, or they may be derived from a somatic cell. PSCs can be target cells of the methods described herein.

By "embryonic stem cell" (ESC) is meant a PSC that was isolated from an embryo, typically from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells may be obtained from any mammalian species, e.g. human, equine, bovine, porcine, canine, feline, rodent, e.g. mice, rats, hamster, primate, etc. (Thomson et al. (1998) Science 282:1145; Thomson et al. (1995) Proc. Natl. Acad. Sci USA 92:7844; Thomson et al. (1996) Biol. Reprod. 55:254; Shamblott et al., Proc. Natl. Acad. Sci. USA 95:13726, 1998). In culture, ESCs typically grow as flat colonies with large nucleo-cytoplasmic ratios, defined borders and prominent nucleoli. In addition, ESCs express SSEA-3, SSEA-4, TRA-1-60, TRA-1-81, and Alkaline Phosphatase, but not SSEA-1. Examples of methods of generating and characterizing ESCs may be found in, for example, U.S. Pat. Nos. 7,029,913, 5,843,780, and 6,200, 806, the disclosures of which are incorporated herein by reference. Methods for proliferating hESCs in the undifferentiated form are described in WO 99/20741, WO 01/51616, and WO 03/020920.

By "embryonic germ stem cell" (EGSC) or "embryonic germ cell" or "EG cell" is meant a PSC that is derived from germ cells and/or germ cell progenitors, e.g. primordial germ cells, i.e. those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, the disclosures of which are incorporated herein by reference.

By "induced pluripotent stem cell" or "iPSC" it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs may be found in, for example, U.S. Patent Publication Nos. US20090047263, US20090068742, US20090191159, US20090227032, US20090246875, and US20090304646, the disclosures of which are incorporated herein by reference. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e. ectoderm, mesoderm and endoderm. For example, somatic cells would include both neurons and neural progenitors, the latter of which may be able to naturally give rise to all or some cell types of the central nervous system but cannot give rise to cells of the mesoderm or endoderm lineages.

By "mitotic cell" it is meant a cell undergoing mitosis. Mitosis is the process by which a eukaryotic cell separates the chromosomes in its nucleus into two identical sets in two separate nuclei. It is generally followed immediately by cytokinesis, which divides the nuclei, cytoplasm, organelles and cell membrane into two cells containing roughly equal shares of these cellular components.

By "post-mitotic cell" it is meant a cell that has exited from mitosis, i.e., it is "quiescent", i.e. it is no longer undergoing divisions. This quiescent state may be temporary, i.e. reversible, or it may be permanent.

By "meiotic cell" it is meant a cell that is undergoing meiosis. Meiosis is the process by which a cell divides its nuclear material for the purpose of producing gametes or spores. Unlike mitosis, in meiosis, the chromosomes undergo a recombination step which shuffles genetic material between chromosomes. Additionally, the outcome of meiosis is four (genetically unique) haploid cells, as compared with the two (genetically identical) diploid cells produced from mitosis.

In some instances, a component (e.g., a nucleic acid component (e.g., a GeoCas9 guide RNA); a protein component (e.g., wild-type GeoCas9; variant GeoCas9; variant GeoCas9 comprising a heterologous PI domain; fusion GeoCas9; etc.); and the like) includes a label moiety. The terms "label", "detectable label", or "label moiety" as used herein refer to any moiety that provides for signal detection and may vary widely depending on the particular nature of the assay. Label moieties of interest include both directly detectable labels (direct labels; e.g., a fluorescent label) and indirectly detectable labels (indirect labels; e.g., a binding pair member). A fluorescent label can be any fluorescent label (e.g., a fluorescent dye (e.g., fluorescein, Texas red, rhodamine, ALEXAFLUOR® labels, and the like), a fluorescent protein (e.g., green fluorescent protein (GFP), enhanced GFP (EGFP), yellow fluorescent protein (YFP), red fluorescent protein (RFP), cyan fluorescent protein (CFP), cherry, tomato, tangerine, and any fluorescent derivative thereof), etc.). Suitable detectable (directly or indirectly) label moieties for use in the methods include any moiety that is detectable by spectroscopic, photochemical, biochemical, immunochemical, electrical, optical, chemical, or other means. For example, suitable indirect labels include biotin (a binding pair member), which can be bound by streptavidin (which can itself be directly or indirectly labeled). Labels can also include: a radiolabel (a direct label)(e.g., $^3$H, $^{125}$I, $^{35}$S, $^{14}$C or $^{32}$P); an enzyme (an indirect label)(e.g., peroxidase, alkaline phosphatase, galactosidase, luciferase, glucose oxidase, and the like); a fluorescent protein (a direct label)(e.g., green fluorescent protein, red fluorescent protein, yellow fluorescent protein, and any convenient derivatives thereof); a metal label (a direct label); a colorimetric label; a binding pair member; and the like. By "partner of a binding pair" or "binding pair member" is meant one of a first and a second moiety, wherein the first and the second moiety have a specific binding affinity for each other. Suitable binding pairs include, but are not limited to: antigen/antibodies (for example, digoxigenin/anti-digoxigenin, dinitrophenyl (DNP)/anti-DNP, dansyl-X-anti-dansyl, fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Any binding pair member can be suitable for use as an indirectly detectable label moiety.

Any given component, or combination of components can be unlabeled, or can be detectably labeled with a label moiety. In some cases, when two or more components are labeled, they can be labeled with label moieties that are distinguishable from one another.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a thermostable RNA-guided endonuclease" includes a plurality of such thermostable RNA-guided endonuclease and reference to "the guide RNA" includes reference to one or more guide RNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides RNA-guided endonucleases, nucleic acids encoding same, and compositions comprising same. The present disclosure provides ribonucleoprotein complexes comprising: an RNA-guided endonuclease of the present disclosure; and a guide RNA. The present disclosure provides methods of modifying a target nucleic acid, using an RNA-guided endonuclease of the present disclosure and a guide RNA.

RNA-Guided Endonuclease

The present disclosure provides RNA-guided endonucleases that are thermostable, and that, when complexed with a guide RNA (e.g., a single-molecule guide RNA; a dual-molecule guide RNA), can modify a target nucleic acid, e.g., a target nucleic acid present in a cell. An RNA-guided endonuclease of the present disclosure is also referred to herein as a "GeoCas9 polypeptide" or as a "GeoCas polypeptide."

In some cases, an RNA-guided endonuclease of the present disclosure comprises: a) an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to amino acids 1-994 of the amino acid sequence depicted in FIG. 6 and set forth in SEQ ID NO: 1; and b) a heterologous protospacer adjacent motif (PAM) interacting domain ("PI domain").

In some cases, the heterologous PI domain comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence:

(LC300 PID; SEQ ID NO: 4)
IIKTAGGEEIKIKDLFAYYKTIHSGTAGLELVSHDCSFSLSGVGSRTLKR

FEKYQVDVLGNIYKVRGEKRVGLASSAHSKTGETIRPLQSTRD.

In some cases, the heterologous PI domain comprises an amino acid sequence having less than 83%, less than 80%, less than 75%, less than 70%, less than 65%, less than 60%, less than 55%, less than 50%, less than 45%, less than 40%, less than 35%, less than 30%, or less than 25%, amino acid sequence identity to the following amino acid sequence:

(GeoCas9 PID; SEQ ID NO: 5)
TVKTAAGEEINVKDVFVYYKTIDSANGGLELISHDHRFSLRGVGSRTLKR

FEKYQVDVLGNIYKVRGEKRVGLASSAHSKPGKTIRPLQSTRD.

In some cases, an RNA-guided endonuclease of the present disclosure comprises: a) an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to amino acids 1-994 of the amino acid sequence depicted in FIG. 6 and set forth in SEQ ID NO: 1; and b) a heterologous PI domain comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence:

(LC300 PID; SEQ ID NO: 4)
IIKTAGGEEIKIKDLFAYYKTIHSGTAGLELVSHDCSFSLSGVGSRTLKR

FEKYQVDVLGNIYKVRGEKRVGLASSAHSKTGETIRPLQSTRD.

In some cases, an RNA-guided endonuclease of the present disclosure comprises, in order from N-terminus to C-terminus: a RuvCI domain; an α-helical REC domain, a RuvCII domain; an HNH domain; a RuvCIII domain; and a PI domain, where the PI domain is heterologous to the portion of the RNA-guided endonuclease that comprises the RuvCI, REC, RuvCII, HNH, and RuvCIII domains.

In some cases, the RuvCI domain of an RNA-guided endonuclease of the present disclosure has a length of from about 45 amino acids to about 55 amino acids (e.g., 45 amino acids (aa), 46 aa, 47 aa, 48 aa, 49 aa, 50 aa, 51 aa, 52 aa, 53 aa, 54 aa, or 55 aa); and comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence (SEQ ID NO: 133)
MRYKIGLDIGITSVGWAVMNLDIPRIEDLGVRIFDRAENPQTGESLAL.

In some cases, the RuvCI domain of an RNA-guided endonuclease of the present disclosure has a length of 48 amino acids. In some cases, the RuvC1 domain of an RNA-guided endonuclease of the present disclosure has a length of 48 amino acids; and comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence (SEQ ID NO: 133)
MRYKIGLDIGITSVGWAVMNLDIPRIEDLGVRIFDRAENPQTGESLAL.

In some cases, the REC domain of an RNA-guided endonuclease of the present disclosure has a length of from about 350 amino acids to about 400 amino acids (e.g., 350 amino acids (aa), 351 aa, 352 aa, 353 aa, 354 aa, 355 aa, 356 aa, 357 aa, 358 aa, 359 aa, 360 aa, 361 aa, 363 aa, 363 aa, 364 aa, 365 aa, 366 aa, 367 aa, 368 aa, 369 aa, 370 aa, 371 aa, 372 aa, 373 aa, 374 aa, 375 aa, 376 aa, 377 aa, 378 aa, 379 aa, 380 aa, 381 aa, 382 aa, 383 aa, 384 aa, 385 aa, 386 aa, 387 aa, 388 aa, 389 aa, 390 aa, 391 aa, 392 aa, 393 aa, 394 aa, 395 aa, 396 aa, 397 aa, 398 aa, 399 aa, or 400 aa); and comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence (SEQ ID NO: 134)
KHRLERIRRLVIREGILTKEELDKLFEEKHEIDVWQLRVEALDRKLNNDE

LARVLLHLAKRRGFKSNRKSERSNKENSTMLKHIEENRAILSSYRTVGEM

IVKDPKFALHKRNKGENYTNTIARDDLEREIRLIFSKQREFGNMSCTEEF

ENEYITIWASQRPVASKDDIEKKVGFCTFEPKEKRAPKATYTFQSFIAWE

HINKLRLISPSGARGLTDEERRLLYEQAFQKNKITYHDIRTLLHLPDDTY

FKGIVYDRGESRKQNENIRFLELDAYHQIRKAVDKVYGKGKSSSFLPIDF

DTFGYALTLFKDDADIHSYLRNEYEQNGKRMPNLANKVYDNELIEELLNL

SFTKFGHLSLKALRSILPYMEQGEVYSSACERAGYTFTGPKKKQKT.

In some cases, the RuvC1 domain of an RNA-guided endonuclease of the present disclosure has a length of 396 amino acids; and comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence (SEQ ID NO: 134)
KHRLERIRRLVIREGILTKEELDKLFEEKHEIDVWQLRVEALDRKLNNDE

LARVLLHLAKRRGFKSNRKSERSNKENSTMLKHIEENRAILSSYRTVGEM

IVKDPKFALHKRNKGENYTNTIARDDLEREIRLIFSKQREFGNMSCTEEF

ENEYITIWASQRPVASKDDIEKKVGFCTFEPKEKRAPKATYTFQSFIAWE

HINKLRLISPSGARGLTDEERRLLYEQAFQKNKITYHDIRTLLHLPDDTY

FKGIVYDRGESRKQNENIRFLELDAYHQIRKAVDKVYGKGKSSSFLPIDF

DTFGYALTLFKDDADIHSYLRNEYEQNGKRMPNLANKVYDNELIEELLNL

SFTKFGHLSLKALRSILPYMEQGEVYSSACERAGYTFTGPKKKQKT.

In some cases, the RuvCII domain of an RNA-guided endonuclease of the present disclosure has a length of from about 45 amino acids to about 60 amino acids (e.g., 45 amino acids (aa), 46 aa, 47 aa, 48 aa, 49 aa, 50 aa, 51 aa, 52 aa, 53 aa, 54 aa, 55 aa, 56 aa, 57 aa, 58 aa, 59 aa, or 60 aa); and comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence (SEQ ID NO: 135)
MLLPNIPPIANPVVMRALTQARKVVNAIIKKYGSPVSIHIELARDLSQTF
DE.

In some cases, the RuvCII domain of an RNA-guided endonuclease of the present disclosure has a length of 52 amino acids; and comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence (SEQ ID NO: 135)
MLLPNIPPIANPVVMRALTQARKVVNAIIKKYGSPVSIHIELARDLSQTF
DE.

In some cases, the HNH domain an RNA-guided endonuclease of the present disclosure has a length of from about 140 amino acids to about 155 amino acids (e.g., 140 amino acids (aa), 141 aa, 142 aa, 143 aa, 144 aa, 145 aa, 146 aa, 147 aa, 148 aa, 149 aa, 150 aa, 151 aa, 152 aa, 153 aa, 154 aa, or 155 aa); and comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence (SEQ ID NO: 136)
RRKTKKEQDENRKKNETAIRQLMEYGLTLNPTGHDIVKFKLWSEQNGRCA
YSLQPIEIERLLEPGYVEVDHVIPYSRSLDDSYTNKVLVLTRENREKGNR
IPAEYLGVGTERWQQFETFVLTNKQFSKKKRDRLLRLHYDENEETEFKNR
N.

In some cases, the HNH domain of an RNA-guided endonuclease of the present disclosure has a length of 151 amino acids; and comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence (SEQ ID NO: 136)
RRKTKKEQDENRKKNETAIRQLMEYGLTLNPTGHDIVKFKLWSEQNGRCA
YSLQPIEIERLLEPGYVEVDHVIPYSRSLDDSYTNKVLVLTRENREKGNR
IPAEYLGVGTERWQQFETFVLTNKQFSKKKRDRLLRLHYDENEETEFKNR
N In some cases, the RuvCIII domain of an RNA-guided endonuclease of the present disclosure has a length of from about 160 to about 175 amino acids (e.g., 160 amino acids (aa), 161 aa, 162 aa, 163 aa, 164 aa, 165 aa, 166 aa, 167 aa, 168 aa, 169 aa, 170 aa, 171 aa, 172 aa, 173 aa, 174 aa, or 175 aa); and comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence (SEQ ID NO: 137)
LNDTRYISRFFANFIREHLKFAESDDKQKVYTVNGRVTAHLRSRWEFNKN
REESDLHHAVDAVIVACTTPSDIAKVTAFYQRREQNKELAKKTEPHFPQP
WPHFADELRARLSKHPKESIKALNLGNYDDQKLESLQPVFVSRMPKRSVT
GAAHQETLRRYVGIDERS.

In some cases, the RuvCIII domain of an RNA-guided endonuclease of the present disclosure has a length of 168 amino acids; and comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence (SEQ ID NO: 137)
LNDTRYISRFFANFIREHLKFAESDDKQKVYTVNGRVTAHLRSRWEFNKN
REESDLHHAVDAVIVACTTPSDIAKVTAFYQRREQNKELAKKTEPHFPQP
WPHFADELRARLSKHPKESIKALNLGNYDDQKLESLQPVFVSRMPKRSVT
GAAHQETLRRYVGIDERS.

The heterologous PI domain of an RNA-guided endoribonuclease of the present disclosure can have a length of from about 87 amino acids to about 99 amino acids (e.g., 87 amino acids (aa), 88 aa, 89 aa, 90 aa, 91 aa, 92 aa, 93 aa, 94 aa, 95 aa, 96 aa, 97 aa, 98 aa, or 99 aa; and can comprise an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence:

(LC300 PID; SEQ ID NO: 4)
IIKTAGGEEIKIKDLFAYYKTIHSGTAGLELVSHDCSFSLSGVGSRTLKR
FEKYQVDVLGNIYKVRGEKRVGLASSAHSKTGETIRPLQSTRD.

In some cases, the heterologous PI domain of an RNA-guided endoribonuclease of the present disclosure has a length of 93 amino acids; and comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence:

(LC300 PID; SEQ ID NO: 4)
IIKTAGGEEIKIKDLFAYYKTIHSGTAGLELVSHDCSFSLSGVGSRTLKR
FEKYQVDVLGNIYKVRGEKRVGLASSAHSKTGETIRPLQSTRD.

The heterologous PI domain of an RNA-guided endoribonuclease of the present disclosure can have a length of from 250 amino acids to 265 amino acids (e.g. 250 amino acids (aa), 251 aa, 252 aa, 253 aa, 254 aa, 255 aa, 256 aa, 257, 258 aa, 259 aa, 260 aa, 261 aa, 262 aa, 263 aa, 264 aa, or 265 aa), and can comprise an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence:

(SEQ ID NO: 138)
GKIQTVVKTKLSEIKLDASGHFPMYGKESDPRTYEAIRQRLLEHNNDPKK

AFQEPLYKPKKNGEPGPVIRTVKIIDTKNQVIPLNDGKTVAYNSNIVRVD

VFEKDGKYYCVPVYTMDIMKGILPNKAIEPNKPYSEWKEMTEDYTFRFSL

YPNDLIRIELPREKIIKTAGGEEIKIKDLFAYYKTIHSGTAGLELVSHDC

SFSLSGVGSRTLKRFEKYQVDVLGNIYKVRGEKRVGLASSAHSKTGETIR

PLQSTRD.

A PI domain of an RNA-guided endoribonuclease of the present disclosure can have a length of 257 amino acids and can comprise an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence:

(SEQ ID NO: 138)
GKIQTVVKIKLSEIKLDASGHFPMYGKESDPRIYEAIRQRLLEHNNDPKK

AFQEPLYKPKKNGEPGPVIRTVKIIDTKNQVIPLNDGKIVAYNSNIVRVD

VFEKDGKYYCVPVYTMDIMKGILPNKAIEPNKPYSEWKEMTEDYTFRFSL

YPNDLIRIELPREKIIKTAGGEEIKIKDLFAYYKTIHSGTAGLELVSHDC

SFSLSGVGSRILKRFEKYQVDVLGNIYKVRGEKRVGLASSAHSKTGETIR

PLQSTRD.

A PI domain of an RNA-guided endoribonuclease of the present disclosure can have a length of from 250 amino acids to 265 amino acids (e.g. 250 amino acids (aa), 251 aa, 252 aa, 253 aa, 254 aa, 255 aa, 256 aa, 257, 258 aa, 259 aa, 260 aa, 261 aa, 262 aa, 263 aa, 264 aa, or 265 aa), and can comprise an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence:

(SEQ ID NO: 139)
GKIQTVVKTKLSEIKLDASGHFPMYGKESDPRTYEAIRQRLLEHNNDPKK

AFQEPLYKPKKNGEPGPVIRTVKIIDTKNQVIPLNDGKTVAYNSNIVRVD

VFEKDGKYYCVPVYTMDIMKGILPNKAIEPNKPYSEWKEMTEDYTFRFSL

YPNDLIRIELPREKTVKTAAGEEINVKDVFVYYKTIDSANGGLELISHDH

RFSLRGVGSRTLKRFEKYQVDVLGNIYKVRGEKRVGLASSAHSKPGKTIR

PLQSTRD.

A PI domain of an RNA-guided endoribonuclease of the present disclosure can have a length of 257 amino acids and can comprise an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence:

(SEQ ID NO: 139)
GKIQTVVKTKLSEIKLDASGHFPMYGKESDPRTYEAIRQRLLEHNNDPKK

AFQEPLYKPKKNGEPGPVIRTVKIIDTKNQVIPLNDGKTVAYNSNIVRVD

VFEKDGKYYCVPVYTMDIMKGILPNKAIEPNKPYSEWKEMTEDYTFRFSL

YPNDLIRIELPREKTVKTAAGEEINVKDVFVYYKTIDSANGGLELISHDH

RFSLRGVGSRTLKRFEKYQVDVLGNIYKVRGEKRVGLASSAHSKPGKTIR

PLQSTRD.

An RNA-guided endonuclease of the present disclosure can have a length of from 1050 amino acids to 1120 amino acids. For example, in some cases, an RNA-guided endonuclease of the present disclosure has a length of from 1050 amino acids to 1055 amino acids, from 1055 amino acids to 1060 amino acids, from 1060 amino acids to 1065 amino acids, from 1065 amino acids to 1070 amino acids, from 1070 amino acids to 1075 amino acids, from 1075 amino acids to 1080 amino acids, from 1080 amino acids to 1085 amino acids, from 1085 amino acids to 1090 amino acids, from 1090 amino acids to 1095 amino acids, from 1095 amino acids to 1100 amino acids, from 1100 amino acids to 1105 amino acids, from 1105 amino acids to 1110 amino acids, from 1110 amino acids to 1115 amino acids, or from 1115 amino acids to 1120 amino acids. In some cases, an RNA-guided endonuclease of the present disclosure has a length of from 1080 amino acids to 1095 amino acids. In some cases, an RNA-guided endonuclease of the present disclosure has a length of from 1080 to 1090 amino acids. In some cases, an RNA-guided endonuclease of the present disclosure has a length of 1087 amino acids.

Amino acid His-582 (based on the amino acid numbering of the GeoCas9 amino acid sequence depicted in FIG. 6) of an RNA-guided endonuclease of the present disclosure can be substituted with an amino acid other than histidine. For example, in some cases, amino acid 582 (based on the amino acid numbering of the GeoCas9 amino acid sequence depicted in FIG. 6) of an RNA-guided endonuclease of the present disclosure is replaced with any amino acid other than His. In some cases, amino acid 582 (based on the amino acid numbering of the GeoCas9 amino acid sequence depicted in FIG. 6) of an RNA-guided endonuclease of the present disclosure is replaced with Ala, Ser, Thr, Val, Leu, Ile, or Gly. A variant GeoCas9 comprising a substitution of His-582 (based on the amino acid numbering of the GeoCas9 amino acid sequence depicted in FIG. 6) exhibits nickase activity, i.e., the variant GeoCas9 does not substantially cleave both strands of a target nucleic acid, but instead cleaves only one strand of a target nucleic acid.

Amino acid Asp-8 (based on the amino acid numbering of the GeoCas9 amino acid sequence depicted in FIG. 6) of an RNA-guided endonuclease of the present disclosure can be substituted with an amino acid other than aspartic acid. For example, in some cases, amino acid 8 (based on the amino acid numbering of the GeoCas9 amino acid sequence depicted in FIG. 6) of an RNA-guided endonuclease of the present disclosure is replaced with any amino acid other than Asp. In some cases, amino acid 8 (based on the amino acid numbering of the GeoCas9 amino acid sequence depicted in FIG. 6) of an RNA-guided endonuclease of the present disclosure is replaced with Ala, Ser, Thr, Val, Leu, Ile, or Gly. A variant GeoCas9 comprising a substitution of Asp-8 (based on the amino acid numbering of the GeoCas9 amino acid sequence depicted in FIG. 6) exhibits nickase activity, i.e., the variant GeoCas9 does not substantially cleave both strands of a target nucleic acid, but instead cleaves only one strand of a target nucleic acid. In some cases, Asp-8 is replaced with Ala.

In some cases, a variant GeoCas9 of the present disclosure comprises substitutions of both Asp-8 and His-582 (based on the amino acid numbering of the GeoCas9 amino acid sequence depicted in FIG. 6). In some cases, Asp-8 is replaced with any amino acid other than Asp; and His-582 is replaced with any amino acid other than His. In some cases, Asp-8 is replaced with Ala, Ser, Thr, Val, Leu, Ile, or Gly; and His-582 is replaced with Ala, Ser, Thr, Val, Leu, Ile, or Gly. In some cases, Asp-8 is replaced with Ala; and His-582 is replaced with Ala. A variant GeoCas9 comprising a substitution of Asp-8 and His-582 (based on the amino acid numbering of the GeoCas9 amino acid sequence depicted in FIG. 6) is enzymatically inactive, e.g., does not substantially cleave a target nucleic acid, but retains the ability to bind the target nucleic acid. Such a variant GeoCas9 is referred to herein as a "dead GeoCas9."

In some cases, a variant GeoCas9 of the present disclosure comprises: i) a wild-type PI domain; and ii) a substitution of His-582 (based on the amino acid numbering of the GeoCas9 amino acid sequence depicted in FIG. 6). In some cases, a variant GeoCas9 of the present disclosure comprises: i) a heterologous PI domain; and ii) a substitution of His-582 (based on the amino acid numbering of the GeoCas9 amino acid sequence depicted in FIG. 6).

In some cases, a variant GeoCas9 of the present disclosure comprises: i) a wild-type PI domain; and ii) a substitution of Asp-8 (based on the amino acid numbering of the GeoCas9 amino acid sequence depicted in FIG. 6). In some cases, a variant GeoCas9 of the present disclosure comprises: i) a heterologous PI domain; and ii) a substitution of Asp-8 (based on the amino acid numbering of the GeoCas9 amino acid sequence depicted in FIG. 6).

In some cases, a variant GeoCas9 of the present disclosure comprises: i) a wild-type PI domain; and ii) a substitution of Asp-8 and His-582 (based on the amino acid numbering of the GeoCas9 amino acid sequence depicted in FIG. 6). In some cases, a variant GeoCas9 of the present disclosure comprises: i) a heterologous PI domain; and ii) a substitution of Asp-8 and His-582 (based on the amino acid numbering of the GeoCas9 amino acid sequence depicted in FIG. 6).

Thermostability

An RNA-guided endonuclease of the present disclosure is enzymatically active in a temperature range of from 15° C. to 75° C. In some case, an RNA-guided endonuclease of the present disclosure is enzymatically active in a temperature range of from 20° C. to 75° C. In some case, an RNA-guided endonuclease of the present disclosure is enzymatically active in a temperature range of from 25° C. to 75° C. In some cases, an RNA-guided endonuclease of the present disclosure exhibits maximal enzymatic activity (as defined by cleavage rate of a target nucleic acid when complexed with a guide RNA) in a temperature range of from 50° C. to 70° C. In some cases, an RNA-guided endonuclease of the present disclosure, at a temperature of from 40° C. to 49° C., cleaves a target nucleic acid at a cleavage rate that is at least 30%, at least 35%, at least 40%, at least 45%, at least 50%, at least 60%, at least 70%, at least 80%, or at least 90%, of the maximal cleavage rate that is obtained in a temperature range of from 50° C. to 70° C. In some cases, an RNA-guided endonuclease of the present disclosure, at a temperature of from 30° C. to 40° C., cleaves a target nucleic acid at a cleavage rate that is at least at least 10%, at least 15%, at least 20%, at least 25%, at least 30%, at least 35%, at least 40%, at least 45%, at least 50%, at least 60%, at least 70%, at least 80%, or at least 90%, of the maximal cleavage rate that is obtained in a temperature range of from 50° C. to 70° C.

The terms "enzymatic activity" and "enzymatically active," as used herein with reference to an RNA-guided endonuclease of the present disclosure, refers to cleavage of one or both strands of a target nucleic acid by the RNA-guided endonuclease when the RNA-guided endonuclease is complexed with a guide RNA.

In some cases, an RNA-guided endonuclease of the present disclosure is stable, and retains enzymatic activity, in serum. For example, in some cases, an RNA-guided endonuclease of the present disclosure, when present in undiluted serum (e.g., undiluted human serum) in vitro at 37° C., retains at least 50%, at least 60%, at least 70%, at least 80%, at least 90%, at least 95%, at least 98%, or 100%, of the starting enzymatic activity (e.g., the enzymatic activity of the RNA-guided endonuclease before being added to the serum), for a period of time of at least 30 minutes, at least 1 hour, at least 2 hours, at least 4 hours, at least 8 hours, at least 12 hours, at least 24 hours, at least 36 hours, at least 3 days, at least 4 days, at least 5 days, at least 6 days, at least 7 days, at least 2 weeks, at least 4 weeks, at least 2 months, at least 4 months, at least 6 months, or more than 6 months. For example, in some cases, an RNA-guided endonuclease of the present disclosure, when present in undiluted serum (e.g., undiluted human serum) in vitro at 37° C., retains at least 50%, at least 60%, at least 70%, at least 80%, at least 90%, at least 95%, at least 98%, or 100%, of the starting enzymatic activity (e.g., the enzymatic activity of the RNA-guided endonuclease before being added to the serum), for a period of time of from about 30 minutes to longer than 6 months, e.g., from about 30 minutes to about 1 hour, from about 1 hour to about 2 hours, from about 2 hours to about 4 hours, from about 4 hours to about 8 hours, from about 8 hours to about 12 hours, from about 12 hours to about 24 hours, from about 24 hours to about 36 hours, from about 36 hours to about 2 days, from about 2 days to about 7 days, from about 1 week to about 4 weeks, from about 1 month to about 6 months, or more than 6 months.

In some cases, an RNA-guided endonuclease of the present disclosure, when present in serum (e.g., human serum) in vivo at 37° C., retains at least 50%, at least 60%, at least 70%, at least 80%, at least 90%, at least 95%, at least 98%, or 100%, of the starting enzymatic activity (e.g., the enzymatic activity of the RNA-guided endonuclease before being added to the serum), for a period of time of at least 30 minutes, at least 1 hour, at least 2 hours, at least 4 hours, at least 8 hours, at least 12 hours, at least 24 hours, at least 36 hours, at least 3 days, at least 4 days, at least 5 days, at least 6 days, at least 7 days, at least 2 weeks, at least 4 weeks, at least 2 months, at least 4 months, at least 6 months, or more than 6 months. In some cases, an RNA-guided endonuclease of the present disclosure, when present in serum (e.g., human serum) in vivo at 37° C., retains at least 50%, at least 60%, at least 70%, at least 80%, at least 90%, at least 95%, at least 98%, or 100%, of the starting enzymatic activity (e.g., the enzymatic activity of the RNA-guided endonuclease before being added to the serum), for a period of time of from about 30 minutes to longer than 6 months, e.g., from about 30 minutes to about 1 hour, from about 1 hour to about 2 hours, from about 2 hours to about 4 hours, from about 4 hours to about 8 hours, from about 8 hours to about 12 hours, from about 12 hours to about 24 hours, from about 24 hours to about 36 hours, from about 36 hours to about 2 days, from about 2 days to about 7 days, from about 1 week to about 4 weeks, from about 1 month to about 6 months, or more than 6 months.

Protospacer Adjacent Motif (PAM)

An RNA-guided endonuclease of the present disclosure binds to target DNA at a target sequence defined by the region of complementarity between the DNA-targeting RNA (guide RNA) and the target DNA. As is the case for many CRISPR endonucleases, site-specific binding (and/or cleavage) of a double stranded target DNA occurs at locations determined by both (i) base-pairing complementarity between the guide RNA and the target DNA; and (ii) a short motif [referred to as the protospacer adjacent motif (PAM)] in the target DNA.

In some embodiments, the PAM for an RNA-guided endonuclease of the present disclosure is immediately 5' of the target sequence of the non-complementary strand of the target DNA (the complementary strand hybridizes to the guide sequence of the guide RNA while the non-complementary strand does not directly hybridize with the guide RNA and is the reverse complement of the non-complementary strand). In some cases, an RNA-guided endonuclease of the present disclosure binds to a target nucleic acid comprising a PAM comprising a GMAA sequence, where M is A or C (amino) In some cases, an RNA-guided endonuclease binds to a target nucleic acid comprising a PAM comprising a CRAA sequence, where R is G or A (purine).

Guide RNAs

A nucleic acid that binds to an RNA-guided endonuclease of the present disclosure, forming a ribonucleoprotein complex (RNP), and targets the complex to a specific location within a target nucleic acid (e.g., a target DNA) is referred to herein as a "GeoCas9 guide RNA" or simply "guide RNA." It is to be understood that in some cases, a hybrid DNA/RNA can be made such that guide RNA suitable for use in a complex with an RNA-guided endonuclease of the present disclosure includes DNA bases in addition to RNA bases, but the term "guide RNA" is still used to encompass such a molecule herein.

A GeoCas guide RNA can be said to include two segments, a targeting segment and a protein-binding segment. The targeting segment of a GeoCas guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a GeoCas polypeptide. The protein-binding segment of a subject GeoCas guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the GeoCas guide RNA (the guide sequence of the GeoCas guide RNA) and the target nucleic acid.

A GeoCas guide RNA and an RNA-guided endonuclease of the present disclosure (e.g., a "GeoCas polypeptide"; a fusion GeoCas polypeptide comprising a GeoCas polypeptide and a heterologous fusion partner), form a complex (e.g., bind via non-covalent interactions). The GeoCas guide RNA provides target specificity to the complex by including a targeting segment, which includes a guide sequence (a nucleotide sequence that is complementary to a sequence of a target nucleic acid). The GeoCas protein (or fusion GeoCas protein) of the complex provides the site-specific activity (e.g., cleavage activity provided by the GeoCas protein and/or an activity provided by the fusion partner in the case of a fusion GeoCas protein). In other words, the GeoCas protein is guided to a target nucleic acid sequence (e.g. a target sequence) by virtue of its association with the GeoCas guide RNA.

The "guide sequence" also referred to as the "targeting sequence" of a GeoCas guide RNA can be modified so that the GeoCas guide RNA can target a GeoCas protein (e.g., a naturally occurring GeoCas protein, a GeoCas protein of the present disclosure a fusion GeoCas polypeptide, and the like) to any desired sequence of any desired target nucleic acid, with the exception (e.g., as described herein) that the PAM sequence can be taken into account. Thus, for example, a GeoCas guide RNA can have a guide sequence with complementarity to (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

A subject GeoCas guide RNA can also be said to include an "activator" and a "targeter" (e.g., an "activator-RNA" and a "targeter-RNA," respectively). When the "activator" and a "targeter" are two separate molecules the guide RNA is referred to herein as a "dual guide RNA", a "dgRNA," a "double-molecule guide RNA", or a "two-molecule guide RNA." (e.g., a "GeoCas dual guide RNA"). In some embodiments, the activator and targeter are covalently linked to one another (e.g., via intervening nucleotides) and the guide RNA is referred to herein as a "single guide RNA", an "sgRNA," a "single-molecule guide RNA," or a "one-molecule guide RNA" (e.g., a "GeoCas single guide RNA"). Thus, a subject GeoCas single guide RNA comprises a targeter (e.g., targeter-RNA) and an activator (e.g., activator-RNA) that are linked to one another (e.g., by intervening nucleotides), and hybridize to one another to form the double stranded RNA duplex (dsRNA duplex) of the protein-binding segment of the guide RNA, thus resulting in a stem-loop structure. Thus, the targeter and the activator each have a duplex-forming segment, where the duplex forming segment of the targeter and the duplex-forming segment of the activator have complementarity with one another and hybridize to one another.

In some embodiments, the linker of a GeoCas single guide RNA is a stretch of nucleotides. In some cases, the targeter and activator of a GeoCas single guide RNA are linked to one another by intervening nucleotides and the linker can have a length of from 3 to 20 nucleotides (nt) (e.g., from 3 to 15, 3 to 12, 3 to 10, 3 to 8, 3 to 6, 3 to 5, 3 to 4, 4 to 20, 4 to 15, 4 to 12, 4 to 10, 4 to 8, 4 to 6, or 4 to 5 nt). In some embodiments, the linker of a GeoCas single guide RNA can have a length of from 3 to 100 nucleotides (nt) (e.g., from 3 to 80, 3 to 50, 3 to 30, 3 to 25, 3 to 20, 3 to 15, 3 to 12, 3 to 10, 3 to 8, 3 to 6, 3 to 5, 3 to 4, 4 to 100, 4 to 80, 4 to 50, 4 to 30, 4 to 25, 4 to 20, 4 to 15, 4 to 12, 4 to 10, 4 to 8, 4 to 6, or 4 to 5 nt). In some embodiments, the linker of a GeoCas single guide RNA can have a length of from 3 to 10 nucleotides (nt) (e.g., from 3 to 9, 3 to 8, 3 to 7, 3 to 6, 3 to 5, 3 to 4, 4 to 10, 4 to 9, 4 to 8, 4 to 7, 4 to 6, or 4 to 5 nt).

Guide Sequence of a GeoCas Guide RNA

The targeting segment of a subject GeoCas guide RNA includes a guide sequence (i.e., a targeting sequence), which is a nucleotide sequence that is complementary to a sequence (a target site) in a target nucleic acid. In other words, the targeting segment of a GeoCas guide RNA can interact with a target nucleic acid (e.g., double stranded DNA (dsDNA), single stranded DNA (ssDNA), single stranded RNA (ssRNA), or double stranded RNA (dsRNA)) in a sequence-specific manner via hybridization (i.e., base pairing). The guide sequence of a GeoCas guide RNA can be modified (e.g., by genetic engineering)/designed to hybridize to any desired target sequence (e.g., while taking the PAM into account, e.g., when targeting a dsDNA target) within a target nucleic acid (e.g., a eukaryotic target nucleic acid such as genomic DNA).

In some embodiments, the percent complementarity between the guide sequence and the target site of the target nucleic acid is 60% or more (e.g., 65% or more, 70% or more, 75% or more, 80% or more, 85% or more, 90% or more, 95% or more, 97% or more, 98% or more, 99% or more, or 100%). In some cases, the percent complementarity between the guide sequence and the target site of the target nucleic acid is 80% or more (e.g., 85% or more, 90% or more, 95% or more, 97% or more, 98% or more, 99% or more, or 100%). In some cases, the percent complementarity between the guide sequence and the target site of the target nucleic acid is 90% or more (e.g., 95% or more, 97% or more, 98% or more, 99% or more, or 100%). In some cases, the percent complementarity between the guide sequence and the target site of the target nucleic acid is 100%.

In some cases, the percent complementarity between the guide sequence and the target site of the target nucleic acid is 100% over the seven contiguous 3'-most nucleotides of the target site of the target nucleic acid.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 100% over 19 or more (e.g., 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 90% or more (e.g., 95% or more, 97% or more, 98% or more, 99% or more, or 100%) over 19-25 contiguous nucleotides. In some cases, the percent complementarity between the guide sequence and the target site of the target nucleic acid is 100% over 19-25 contiguous nucleotides.

In some cases, the guide sequence has a length in a range of from 19-30 nucleotides (nt) (e.g., from 19-25, 19-22, 19-20, 20-30, 20-25, or 20-22 nt). In some cases, the guide sequence has a length in a range of from 19-25 nucleotides (nt) (e.g., from 19-22, 19-20, 20-25, 20-25, or 20-22 nt). In some cases, the guide sequence has a length of 19 or more nt (e.g., 20 or more, 21 or more, or 22 or more nt; 19 nt, 20 nt, 21 nt, 22 nt, 23 nt, 24 nt, 25 nt, etc.). In some cases the guide sequence has a length of 19 nt. In some cases the guide sequence has a length of 20 nt. In some cases the guide sequence has a length of 21 nt. In some cases the guide sequence has a length of 22 nt. In some cases the guide sequence has a length of 23 nt.

Protein-Binding Segment of a GeoCas Guide RNA

The protein-binding segment of a subject GeoCas guide RNA interacts with a GeoCas protein. The GeoCas guide RNA guides the bound GeoCas protein to a specific nucleotide sequence within target nucleic acid via the above mentioned guide sequence. The protein-binding segment of a GeoCas guide RNA comprises two stretches of nucleotides (the duplex-forming segment of the activator and the duplex-forming segment of the targeter) that are complementary to one another and hybridize to form a double stranded RNA duplex (dsRNA duplex). Thus, the protein-binding segment includes a dsRNA duplex.

In some cases, the dsRNA duplex region formed between the activator and targeter (i.e., the activator/targeter dsRNA duplex) (e.g., in dual or single guide RNA format) includes a range of from 8-25 base pairs (bp) (e.g., from 8-22, 8-18, 8-15, 8-12, 12-25, 12-22, 12-18, 12-15, 13-25, 13-22, 13-18, 13-15, 14-25, 14-22, 14-18, 14-15, 15-25, 15-22, 15-18, 17-25, 17-22, or 17-18 bp, e.g., 15 bp, 16 bp, 17 bp, 18 bp, 19 bp, 20 bp, 21 bp, etc.). In some cases, the duplex region (e.g., in dual or single guide RNA format) includes 8 or more bp (e.g., 10 or more, 12 or more, 15 or more, or 17 or more bp). In some cases, not all nucleotides of the duplex region are paired, and therefore the duplex forming region can include a bulge. The term "bulge" herein is used to mean a stretch of nucleotides (which can be one nucleotide) that do not contribute to a double stranded duplex, but which are surround 5' and 3' by nucleotides that do contribute, and as such a bulge is considered part of the duplex region. In some cases, the dsRNA duplex formed between the activator and targeter (i.e., the activator/targeter dsRNA duplex) includes 1 or more bulges (e.g., 2 or more, 3 or more, 4 or more bulges). In some cases, the dsRNA duplex formed between the activator and targeter (i.e., the activator/targeter dsRNA duplex) includes 2 or more bulges (e.g., 3 or more, 4 or more bulges). In some cases, the dsRNA duplex formed between the activator and targeter (i.e., the activator/targeter dsRNA duplex) includes 1-5 bulges (e.g., 1-4, 1-3, 2-5, 2-4, or 2-3 bulges).

Thus, in some cases, the duplex-forming segments of the activator and targeter have 70%-100% complementarity (e.g., 75%-100%, 80%-10%, 85%-100%, 90%-100%, 95%-100% complementarity) with one another. In some cases, the duplex-forming segments of the activator and targeter have 70%-100% complementarity (e.g., 75%-100%, 80%-10%, 85%-100%, 90%-100%, 95%-100% complementarity) with one another. In some cases, the duplex-forming segments of the activator and targeter have 85%-100% complementarity (e.g., 90%-100%, 95%-100% complementarity) with one another. In some cases, the duplex-forming segments of the activator and targeter have 70%-95% complementarity (e.g., 75%-95%, 80%-95%, 85%-95%, 90%-95% complementarity) with one another.

In other words, in some cases, the dsRNA duplex formed between the activator and targeter (i.e., the activator/targeter dsRNA duplex) includes two stretches of nucleotides that have 70%-100% complementarity (e.g., 75%-100%, 80%-10%, 85%-100%, 90%-100%, 95%-100% complementarity) with one another. In some cases, the activator/targeter dsRNA duplex includes two stretches of nucleotides that have 85%-100% complementarity (e.g., 90%-100%, 95%-100% complementarity) with one another. In some cases, the activator/targeter dsRNA duplex includes two stretches of nucleotides that have 70%-95% complementarity (e.g., 75%-95%, 80%-95%, 85%-95%, 90%-95% complementarity) with one another.

The duplex region of a subject GeoCas guide RNA (in dual guide or single guide RNA format) can include one or more (1, 2, 3, 4, 5, etc.) mutations relative to a naturally occurring duplex region. For example, in some cases a base pair can be maintained while the nucleotides contributing to the base pair from each segment (targeter and activator) can be different. In some cases, the duplex region of a subject GeoCas guide RNA includes more paired bases, less paired bases, a smaller bulge, a larger bulge, fewer bulges, more bulges, or any convenient combination thereof, as compared to a naturally occurring duplex region (of a naturally occurring GeoCas guide RNA).

In some cases, the activator (e.g., activator-RNA) of a subject GeoCas guide RNA (in dual or single guide RNA format) includes at least two internal RNA duplexes (i.e., two internal hairpins in addition to the activator/targeter dsRNA). The internal RNA duplexes (hairpins) of the activator can be positioned 5' of the activator/targeter dsRNA duplex. In some cases, the activator includes one hairpin positioned 5' of the activator/targeter dsRNA duplex. In some cases, the activator includes two hairpins positioned 5' of the activator/targeter dsRNA duplex. In some cases, the activator includes three hairpins positioned 5' of the activator/targeter dsRNA duplex. In some cases, the activator includes two or more hairpins (e.g., 3 or more or 4 or more hairpins) positioned 5' of the activator/targeter dsRNA duplex. In some cases, the activator includes 2 to 5 hairpins (e.g., 2 to 4, or 2 to 3 hairpins) positioned 5' of the activator/targeter dsRNA duplex.

In some cases, the activator-RNA (e.g., in dual or single guide RNA format) comprises at least 2 nucleotides (nt) (e.g., at least 3 or at least 4 nt) 5' of the 5'-most hairpin stem. In some cases, the activator-RNA (e.g., in dual or single guide RNA format) comprises at least 4 nt 5' of the 5'-most hairpin stem.

In some cases, the activator-RNA (e.g., in dual or single guide format) has a length of 65 nucleotides (nt) or more (e.g., 66 or more, 67 or more, 68 or more, 69 or more, 70 or more, or 75 or more nt). In some cases, the activator-RNA (e.g., in dual or single guide format) has a length of 66 nt or more (e.g., 67 or more, 68 or more, 69 or more, 70 or more, or 75 or more nt). In some cases, the activator-RNA (e.g., in dual or single guide format) has a length of 67 nt or more (e.g., 68 or more, 69 or more, 70 or more, or 75 or more nt). In some cases, the activator-RNA has a length of from 80 nt to 100 nt. In some cases, the activator-RNA has a length of 80 nt, 81 nt, 82 nt, 83 nt, 84 nt, 85 nt, 86 nt, 87 nt, 88 nt, 89 nt, 90 nt, 91 nt, 92 nt, 93 nt, 94 nt, 95 nt, 96 nt, 97 nt, 98 nt, 99 nt, or 100 nt (or more than 100 nt).

In some cases, the activator-RNA (e.g., in dual or single guide format) includes 45 or more nucleotides (nt) (e.g., 46 or more, 47 or more, 48 or more, 49 or more, 50 or more, 51 or more, 52 or more, 53 or more, 54 or more, or 55 or more nt) 5' of the dsRNA duplex formed between the activator and the targeter (the activator/targeter dsRNA duplex). In some cases, the activator is truncated at the 5' end relative to a naturally occurring GeoCas activator. In some cases, the activator is extended at the 5' end relative to a naturally occurring GeoCas activator.

In some cases, the tracrRNA (e.g., the portion of the activator-RNA that does not include the duplex-forming segments) has a length of at least 75 nucleotides (nt). In some cases, the tracrRNA has a length of from 75 nt to 100 nt. In some cases, the tracrRNA has a length of 75 nt. In some cases, the tracrRNA has a length of 75 nt, 76 nt, 77 nt, 78 nt, 79 nt, 80 nt, 81 nt, 82 nt, 83 nt, 84 nt, or 85 nt (or more than 85 nt). In a single-molecule guide RNA (sgRNA), the tracrRNA can be considered the nucleotide sequence that is 3' of the duplex-forming segment. For example, in some cases, a GeoCas9 sgRNA of the present disclosure comprises, in order from 5' to 3': i) a "spacer" nucleotide sequence (having a length of from 15 to 25 nt) that hybridizes with (has complementarity to) a target nucleotide sequence in a target nucleic acid); ii) a first duplex forming segment comprising a first stretch of complementary nucleotides (where the first duplex-forming segment has a length of from 10 nucleotides to 25 nucleotides, or more than 25 nucleotides); iii) a linker; iv) a second duplex-forming segment comprising a second stretch of complementary nucleotides (where the second duplex-forming segment has a length that is the same, or nearly the same, as the first duplex-forming segment), where the first duplex-forming segment and the second duplex-forming segment hybridize to one another via the first and second stretches of complementary nucleotides to form a double stranded RNA (dsRNA) duplex, where the two complementary stretches of nucleotides are covalently linked to one another via the linker; and v) a tracrRNA, where the tracrRNA has a length of from about 75 nt to 100 nt, or more than 100 nt.

Examples of various Cas9 guide RNAs can be found in the art, and in some cases variations similar to those introduced into Cas9 guide RNAs can also be introduced into GeoCas guide RNAs of the present disclosure. For example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al., Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et al., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889, 418; 8,889,356; 8,871,445; 8,865,406; 8,795,965; 8,771, 945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

The term "activator" or "activator RNA" is used herein to mean a tracrRNA-like molecule (tracrRNA: "trans-acting CRISPR RNA") of a GeoCas dual guide RNA (and therefore of a GeoCas single guide RNA when the "activator" and the "targeter" are linked together by, e.g., intervening nucleotides). Thus, for example, a GeoCas guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a GeoCas dual guide RNA. The term "activator" is used herein to encompass naturally existing tracrRNAs, but also to encompass tracrRNAs with modifications (e.g., truncations, extensions, sequence variations, base modifications, backbone modifications, linkage modifications, etc.) where the activator retains at least one function of a tracrRNA (e.g., contributes to the dsRNA duplex to which GeoCas protein binds). In some cases the activator provides one or more stem loops that can interact with GeoCas protein. An activator can be referred to as having a tracr sequence (tracrRNA sequence) and in some cases is a tracrRNA, but the term "activator" is not limited to naturally existing tracrRNAs.

The term "targeter" or "targeter RNA" is used herein to refer to a crRNA-like molecule (crRNA: "CRISPR RNA") of a GeoCas dual guide RNA (and therefore of a GeoCas single guide RNA when the "activator" and the "targeter" are linked together, e.g., by intervening nucleotides). Thus, for example, a GeoCas guide RNA (dgRNA or sgRNA) comprises a guide sequences and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, the duplex-forming segment of a targeter (described in more detail herein), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term "targeter" encompasses naturally occurring crRNAs.

As noted above, a targeter comprises both the guide sequence of the GeoCas guide RNA and a stretch (a "duplex-forming segment") of nucleotides that forms one half of the dsRNA duplex of the protein-binding segment of the GeoCas guide RNA. A corresponding tracrRNA-like molecule (activator) comprises a stretch of nucleotides (a duplex-forming segment) that forms the other half of the dsRNA duplex of the protein-binding segment of the GeoCas guide RNA. In other words, a stretch of nucleotides of the targeter is complementary to and hybridizes with a stretch of nucleotides of the activator to form the dsRNA duplex of the protein-binding segment of a GeoCas guide RNA. As such, each targeter can be said to have a corresponding activator (which has a region that hybridizes with the targeter). The targeter molecule additionally provides the guide sequence. Thus, a targeter and an activator (as a corresponding pair) hybridize to form a GeoCas guide RNA. The particular sequence of a given naturally existing crRNA or tracrRNA molecule can be characteristic of the species in which the RNA molecules are found. Examples of suitable activators and targeters are provided herein.

Example Guide RNA Sequences

The guide RNAs depicted in FIG. 11 are non-limiting examples of possible guide RNAs.

In some cases, a GeoCas9 single-guide RNA comprises, in order from 5' to 3': i) a spacer (e.g., a nucleotide sequence that hybridizes to (binds to) a target nucleotide sequence in a target nucleic acid) having a length of from 18 nt to 25 nt (e.g., 18 nt, 19 nt, 20 nt, 21 nt, 22 tt, 23 nt, 24 nt, or 25 nt); ii) a crRNA (duplex-forming RNA segment) comprising two complementary stretches of nucleotides that hybridize to form a double-stranded RNA duplex, where each of the two complementary stretches of nucleotides has a length of from about 19 nt to 25 nt (e.g., 19 nt, 20 nt, 21 nt, 22, nt, 23 nt, 24 nt, or 25 nt); and iii) a tracrRNA (e.g., RNA segment not including the duplex-forming crRNA) having a length of at least 75 nt, e.g., having a length of from 75 nt to 100 nt, e.g., 75 nt, 76 nt, 77 nt, 78 nt, 79 nt, 80 nt, 81 nt, 82 nt, 83 nt, 84 nt, 85 nt, 86 nt, 87 nt, 88 nt, 89 nt, 90 nt, 91 nt, 92 nt, 93 nt, 94 nt, 95 nt, 96 nt, 97 nt, 98 nt, 99 nt, or 100 nt. The crRNA can comprise two complementary stretches of nucleotides that hybridize to form a double-stranded RNA duplex, where the two complementary stretches of nucleotides are covalently linked by intervening nucleotides, e.g., are covalently linked by a linker having a length of from 4 nt to 50 nt (or more than 50 nt), e.g., having a length of 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, from 20 nt to 25 nt, from 25 nt to 30 nt, from 30 nt to 40 nt, from 40 nt to 50 nt, or more than 50 nt). In some cases, the linker has a length of 4 nt.

In some cases, a GeoCas9 single-guide RNA comprises a tracrRNA comprising a nucleotide sequence having at least 80%, at least 90%, at least 95%, at least 98%, at least 99%, or 100%, nucleotide sequence identity to the following nucleotide sequence:

(SEQ ID NO: 6)
UCAGGGUUACUAUGAUAAGGGCUUUCUGCCUAAGGCAGACUGACCCGCGG

CGUUGGGGAUCGCCUGUCGCCCGCUUUUGGCGGGCAUUCCCCAUCCUU.

In some cases, a GeoCas9 single-guide RNA comprises a tracrRNA comprising a nucleotide sequence having at least 80%, at least 90%, at least 95%, at least 98%, at least 99%, or 100%, nucleotide sequence identity to the following nucleotide sequence:

(SEQ ID NO: 140)
AAGGGCUUUCUGCCUAAGGCAGACUGACCCGCGGCGUUGGGGAUCGCCUGU

CGCCCGCUUUUGGCGGGCAUUCCCCAUCCUU.

In some cases, a GeoCas9 single-guide RNA comprises a tracrRNA comprising a nucleotide sequence having at least 80%, at least 90%, at least 95%, at least 98%, at least 99%, or 100%, nucleotide sequence identity to any one of the tracrRNAs provided in FIG. 11.

In some cases, a GeoCas9 single-guide RNA comprises a tracrRNA comprising a nucleotide sequence having no more than 1 nucleotide (nt), no more than 2 nt, no more than 3 nt, no more than 4 nt, no more than 5 nt, no more than 6 nt, no more than 7 nt, no more than 8 nt, no more than 9 nt, no more than 10 nt, no more than 11 nt, no more than 12 nt, no more than 13 nt, no more than 14 nt, no more than 15 nt, no more than 16 nt, no more than 17 nt, no more than 18 nt, no more than 19 nt, or no more than 20 nt, differences from the following nucleotide sequence:

(SEQ ID NO: 6)
UCAGGGUUACUAUGAUAAGGGCUUUCUGCCUAAGGCAGACUGACCCGCGGC

GUUGGGGAUCGCCUGUCGCCCGCUUUUGGCGGGCAUUCCCCAUCCUU.

In some cases, a GeoCas9 single-guide RNA comprises a tracrRNA comprising a nucleotide sequence having no more than 1 nucleotide (nt), no more than 2 nt, no more than 3 nt, no more than 4 nt, no more than 5 nt, no more than 6 nt, no more than 7 nt, no more than 8 nt, no more than 9 nt, no more than 10 nt, no more than 11 nt, no more than 12 nt, no more than 13 nt, no more than 14 nt, no more than 15 nt, no more than 16 nt, no more than 17 nt, no more than 18 nt, no more than 19 nt, or no more than 20 nt, differences from the following nucleotide sequence: nucleotide sequence identity to the following nucleotide sequence:

(SEQ ID NO: 140)
AAGGGCUUUCUGCCUAAGGCAGACUGACCCGCGGCGUUGGGGAUCGCCUGU

CGCCCGCUUUUGGCGGGCAUUCCCCAUCCUU.

As one non-limiting example, a GeoCas9 single-guide RNA comprises the following nucleotide sequence:

(SEQ ID NO: 7)
(spacer) GUCAUAGUUCCCCUGAgaaaUCAGGGUUACUAUGAUAAGGGCU

UUCUGCCUAAGGCAGACUGACCCGCGGCGUUGGGGAUCGCCUGUCGCCCGC

UUUUGGCGGGCAUUCCCCAUCCUU where: i) the "spacer" comprises a nucleotide sequence that hybridizes to a target nucleotide sequence in a target nucleic acid; ii) the double-underlined regions are the duplex-forming crRNA; iii) the underlined and bolded "gaaa" sequence is the linker (or "tetraloop" in this example); and iv) the bolded sequence (without underlining) is the tracrRNA.

Detectable Labels

In some cases, a variant GeoCas9 polypeptide of the present disclosure (e.g., a GeoCas9 polypeptide comprising a heterologous PI domain, as described above) comprises a detectable label.

Label moieties of interest include both directly detectable labels (direct labels; e.g., a fluorescent label) and indirectly detectable labels (indirect labels; e.g., a binding pair member). A fluorescent label can be any fluorescent label (e.g., a fluorescent dye (e.g., fluorescein, Texas red, rhodamine, ALEXAFLUOR® labels, and the like), a fluorescent protein (e.g., green fluorescent protein (GFP), enhanced GFP (EGFP), yellow fluorescent protein (YFP), red fluorescent protein (RFP), cyan fluorescent protein (CFP), cherry, tomato, tangerine, and any fluorescent derivative thereof), etc.). Suitable detectable (directly or indirectly) label moieties include any moiety that is detectable by spectroscopic, photochemical, biochemical, immunochemical, electrical, optical, chemical, or other means. For example, suitable indirect labels include biotin (a binding pair member), which can be bound by streptavidin (which can itself be directly or indirectly labeled). Labels can also include: a radiolabel (a direct label)(e.g., $^{3}$H, $^{125}$I, $^{35}$S, $^{14}$C or $^{32}$P); an enzyme (an indirect label)(e.g., peroxidase, alkaline phosphatase, galactosidase, luciferase, glucose oxidase, and the like); a fluorescent protein (a direct label)(e.g., green fluorescent protein, red fluorescent protein, yellow fluorescent protein, and any convenient derivatives thereof); a metal label (a direct label); a colorimetric label; a binding pair member; and the like. Suitable binding pairs include, but are not limited to: antigen/antibodies (for example, digoxigenin/anti-digoxigenin, dinitrophenyl (DNP)/anti-DNP, dansyl-X-anti-dansyl, fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Any binding pair member can be suitable for use as an indirectly detectable label moiety.

Fusion Polypeptides

The present disclosure provides a fusion polypeptide comprising: a) an RNA-guided endonuclease of the present disclosure (i.e., a GeoCas9 polypeptide; a variant GeoCas9 polypeptide; a variant GeoCas9 polypeptide comprising a heterologous PI domain; a variant GeoCas9 polypeptide comprising a substitution of Asp-8 and/or His-582); and b) a heterologous fusion partner, where the RNA-guided endonuclease and the heterologous fusion partner are fused so as to form a single polypeptide chain. In some cases, the heterologous fusion partner is fused to the amino terminus (N-terminus) of the RNA-guided endonuclease, such that the fusion polypeptide comprises, from N-terminus to C-terminus: a) the heterologous fusion partner polypeptide; and b) the RNA-guided endonuclease. In some cases, a fusion polypeptide of the present disclosure comprises two or more heterologous fusion polypeptides fused to the N-terminus of an RNA-guided endonuclease of the present disclosure. In some cases, the heterologous fusion partner is fused to the carboxyl terminus (C-terminus) of the RNA-guided endonuclease, such that the fusion polypeptide comprises, from N-terminus to C-terminus: a) the RNA-guided endonuclease; and b) the heterologous fusion partner polypeptide. In some cases, a fusion polypeptide of the present disclosure comprises two or more heterologous fusion polypeptides fused to the C-terminus of an RNA-guided endonuclease of the present disclosure. In some cases, a fusion polypeptide of the present disclosure comprises, from N-terminus to C-terminus: a) a first fusion partner polypeptide; b) an RNA-guided endonuclease of the present disclosure; and c) a second fusion partner polypeptide. In some cases, the first fusion partner polypeptide and the second fusion partner polypeptide are the same polypeptides, i.e., have the same amino acid sequence as one another. In some cases, the first fusion partner polypeptide and the second fusion partner polypeptide are two different polypeptides.

In some cases, an RNA-guided endonuclease present in a fusion polypeptide of the present disclosure is an RNA-guided endonuclease, as described above, which RNA-guided endonuclease comprises a heterologous PI domain.

For example, in some cases, a fusion polypeptide of the present disclosure comprises: a) an RNA-guided endonuclease of the present disclosure that comprises: i) an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to amino acids 1-994 of the amino acid sequence depicted in FIG. 6 and set forth in SEQ ID NO: 1; and ii) a heterologous PI domain comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence:

(LC300 PID; SEQ ID NO: 4)
IIKTAGGEEIKIKDLFAYYKTIHSGTAGLELVSHDCSFSLSGVGSRTLKRF

EKYQVDVLGNIYKVRGEKRVGLASSAHSKTGETIRPLQSTRD;

and b) a heterologous fusion partner polypeptide.

In other embodiments, a fusion polypeptide of the present disclosure comprises: a) an RNA-guided endonuclease comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 6; and b) a heterologous fusion partner polypeptide.

Fusion Partners

Any of a variety of fusion partner polypeptides can be used in fusion polypeptide of the present disclosure.

In some cases, the fusion partner can modulate transcription (e.g., inhibit transcription, increase transcription) of a target DNA. For example, in some cases the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, fusion GeoCas9 protein includes a heterologous polypeptide that has enzymatic activity that modifies a target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a fusion GeoCas9 protein includes a heterologous polypeptide that has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used in increase transcription include but are not limited to: transcriptional activators such as VP16, VP64, VP48, VP160, p65 subdomain (e.g., from NFkB), and activation domain of EDLL and/or TAL acitvation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

Examples of proteins (or fragments thereof) that can be used in decrease transcription include but are not limited to: transcriptional repressors such as the Krüppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like; and periphery recruitment elements such as Lamin A, Lamin B, and the like.

In some cases the fusion partner has enzymatic activity that modifies the target nucleic acid (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases the fusion partner has enzymatic activity that modifies a protein associated with the target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB1, and the like, SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragment of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

An additional examples of a suitable fusion partners are dihydrofolate reductase (DHFR) destabilization domain (e.g., to generate a chemically controllable fusion GeoCas protein), and a chloroplast transit peptide. Suitable chloroplast transit peptides include, but are not limited to:

```
                                          (SEQ ID NO: 8)
MASMISSSAVTTVSRASRGQSAAMAPFGGLKSMTGFPVRKVNTDITSITSN

GGRVKCMQVWPPIGKKKFETLSYLPPLTRDSRA;

(SEQ ID NO: 9)
MASMISSSAVTTVSRASRGQSAAMAPFGGLKSMTGFPVRKVNTDITSITSN

GGRVKS;

(SEQ ID NO: 10)
MASSMLSSATMVASPAQATMVAPFNGLKSSAAFPATRKANNDITSITSNGG

RVNCMQVWPPIEKKKFETLSYLPDLTDSGGRVNC;

(SEQ ID NO: 11)
MAQVSRICNGVQNPSLISNLSKSSQRKSPLSVSLKTQQHPRAYPISSSWGL

KKSGMTLIGSELRPLKVMSSVSTAC;

(SEQ ID NO: 12)
MAQVSRICNGVWNPSLISNLSKSSQRKSPLSVSLKTQQHPRAYPISSSWGL

KKSGMTLIGSELRPLKVMSSVSTAC;

(SEQ ID NO: 13)
MAQINNMAQGIQTLNPNSNFHKPQVPKSSSFLVFGSKKLKNSANSMLVLKK

DSIFMQLFCSFRISASVATAC;

(SEQ ID NO: 14)
MAALVTSQLATSGTVLSVTDRFRRPGFQGLRPRNPADAALGMRTVGASAAP

KQSRKPHRFDRRCLSMVV;

(SEQ ID NO: 15)
MAALTTSQLATSATGFGIADRSAPSSLLRHGFQGLKPRSPAGGDATSLSVT

TSARATPKQQRSVQRGSRRFPSVVVC;

(SEQ ID NO: 16)
MASSVLSSAAVATRSNVAQANMVAPFTGLKSAASFPVSRKQNLDITSIASN

GGRVQC;

(SEQ ID NO: 17)
MESLAATSVFAPSRVAVPAARALVRAGTVVPTRRTSSTSGTSGVKCSAAVT

PQASPVISRSAAAA;
and
                                          (SEQ ID NO: 18)
MGAAATSMQSLKFSNRLVPPSRRLSPVPNNVTCNNLPKSAAPVRTVKCCAS

SWNSTINGAAATTNGASAASS.
```

In some case, a GeoCas fusion polypeptide of the present disclosure comprises: a) a GeoCas polypeptide of the present disclosure; and b) a chloroplast transit peptide. Thus, for example, a GeoCas/guide RNA complex can be targeted to the chloroplast. In some cases, this targeting may be achieved by the presence of an N-terminal extension, called a chloroplast transit peptide (CTP) or plastid transit peptide. Chromosomal transgenes from bacterial sources must have a sequence encoding a CTP sequence fused to a sequence encoding an expressed polypeptide if the expressed polypeptide is to be compartmentalized in the plant plastid (e.g. chloroplast). Accordingly, localization of an exogenous polypeptide to a chloroplast is often 1 accomplished by means of operably linking a polynucleotide sequence encoding a CTP sequence to the 5' region of a polynucleotide encoding the exogenous polypeptide. The CTP is removed in a processing step during translocation into the plastid. Processing efficiency may, however, be affected by the amino acid sequence of the CTP and nearby sequences at the NH 2 terminus of the peptide. Other options for targeting to the chloroplast which have been described are the maize cab-m7 signal sequence (U.S. Pat. No. 7,022,896, WO 97/41228) a pea glutathione reductase signal sequence (WO 97/41228) and the CTP described in US2009029861.

In some cases, a GeoCas fusion polypeptide of the present disclosure can comprise: a) a GeoCas polypeptide (e.g., a wild-type GeoCas9 polypeptide; a variant of a wild-type GeoCas9 polypeptide; a variant GeoCas9 polypeptide comprising a heterologous PI domain; etc.); and b) an endosomal escape peptide. In some cases, an endosomal escape polypeptide comprises the amino acid sequence GLFX-ALLXLLXSLWXLLLXA (SEQ ID NO: 19), wherein each X is independently selected from lysine, histidine, and arginine. In some cases, an endosomal escape polypeptide comprises the amino acid sequence GLF-HALLHLLHSLWHLLLHA (SEQ ID NO: 20).

For examples of some of the above fusion partners (and more) used in the context of fusions with Cas9, Zinc Finger, and/or TALE proteins (for site specific target nucleic modification, modulation of transcription, and/or target protein modification, e.g., histone modification), see, e.g.: Nomura et al., J Am Chem Soc. 2007 Jul. 18; 129(28):8676-7; Rivenbark et al., Epigenetics. 2012 April; 7(4):350-60; Nucleic Acids Res. 2016 Jul. 8; 44(12):5615-28; Gilbert et al., Cell. 2013 Jul. 18; 154(2):442-51; Kearns et al., Nat Methods. 2015 May; 12(5):401-3; Mendenhall et al., Nat Biotechnol. 2013 December; 31(12):1133-6; Hilton et al., Nat Biotechnol. 2015 May; 33(5):510-7; Gordley et al., Proc Natl Acad Sci USA. 2009 Mar. 31; 106(13):5053-8; Akopian et al., Proc Natl Acad Sci USA. 2003 Jul. 22; 100(15):8688-91; Tan et al., J Virol. 2006 February; 80(4):1939-48; Tan et al., Proc Natl Acad Sci USA. 2003 Oct. 14; 100(21):11997-2002; Papworth et al., Proc Natl Acad Sci USA. 2003 Feb.

18; 100(4):1621-6; Sanjana et al., Nat Protoc. 2012 Jan. 5; 7(1):171-92; Beerli et al., Proc Natl Acad Sci USA. 1998 Dec. 8; 95(25):14628-33; Snowden et al., Curr Biol. 2002 Dec. 23; 12(24):2159-66; Xu et. al., Xu et al., Cell Discov. 2016 May 3; 2:16009; Komor et al., Nature. 2016 Apr. 20; 533(7603):420-4; Chaikind et al., Nucleic Acids Res. 2016 Aug. 11; Choudhury at. al., Oncotarget. 2016 Jun. 23; Du et al., Cold Spring Harb Protoc. 2016 Jan. 4; Pham et al., Methods Mol Biol. 2016; 1358:43-57; Balboa et al., Stem Cell Reports. 2015 Sep. 8; 5(3):448-59; Hara et al., Sci Rep. 2015 Jun. 9; 5:11221; Piatek et al., Plant Biotechnol J. 2015 May; 13(4):578-89; Hu et al., Nucleic Acids Res. 2014 April; 42(7):4375-90; Cheng et al., Cell Res. 2013 October; 23(10):1163-71; Cheng et al., Cell Res. 2013 October; 23(10):1163-71; and Maeder et al., Nat Methods. 2013 October; 10(10):977-9.

Additional suitable heterologous polypeptide include, but are not limited to, a polypeptide that directly and/or indirectly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.). Non-limiting examples of heterologous polypeptides to accomplish increased or decreased transcription include transcription activator and transcription repressor domains. In some such cases, a fusion GeoCas polypeptide is targeted by the guide nucleic acid (guide RNA) to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of heterologous polypeptides for use when targeting ssRNA target nucleic acids include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or in some cases can include a fragment of the protein (e.g., a functional domain).

The heterologous polypeptide of a subject fusion GeoCas polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP S1, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable heterologous polypeptide is a PUF RNA-binding domain, which is described in more detail in WO2012068627, which is hereby incorporated by reference in its entirety.

Some RNA splicing factors that can be used (in whole or as fragments thereof) as heterologous polypeptides for a fusion GeoCas polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal Glycine-rich domain Some splicing factors can regulate alternative use of splice site (ss) by binding to regulatory sequences between the two alternative sites. For example, ASF/SF2 can recognize ESEs and promote the use of intron proximal sites, whereas hnRNP Al can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cω-elements that are located in either the core exon region or the exon extension region (i.e., between the two alternative 5' splice sites). For more examples, see WO2010075303, which is hereby incorporated by reference in its entirety.

Further suitable fusion partners include, but are not limited to proteins (or fragments thereof) that are boundary elements (e.g., CTCF), proteins and fragments thereof that provide periphery recruitment (e.g., Lamin A, Lamin B, etc.), protein docking elements (e.g., FKBP/FRB, Pil1/Aby1, etc.).

Examples of various additional suitable heterologous polypeptide (or fragments thereof) for a subject fusion GeoCas polypeptide include, but are not limited to those described in the following applications (which publications are related to other CRISPR endonucleases such as Cas9, but the described fusion partners can also be used with GeoCas instead): PCT patent applications: WO2010075303, WO2012068627, and WO2013155555, and can be found, for example, in U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

In some cases, a heterologous polypeptide (a fusion partner) provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a GeoCas fusion polypeptide does not include a NLS so that the protein is not targeted to the nucleus (which can be advantageous, e.g., when the target nucleic acid is an RNA that is present in the cytosol). In some embodiments, the heterologous polypeptide can provide a tag (i.e., the heterologous polypeptide is a detectable label) for ease of tracking and/or purification (e.g., a fluorescent protein, e.g., green fluorescent protein (GFP), yellow fluorescent protein (YFP), red fluorescent protein (RFP), cyan fluorescent protein (CFP), mCherry, tdTomato, and the like; a histidine tag, e.g., a 6×His tag; a hemagglutinin (HA) tag; a FLAG tag; a Myc tag; and the like).

In some cases a GeoCas protein (e.g., a wild-type GeoCas9 polypeptide; a variant of a wild-type GeoCas9 polypeptide; a variant GeoCas9 polypeptide comprising a heterologous PI domain; etc.) includes (is fused to) a nuclear localization signal (NLS) (e.g., in some cases 2 or more, 3 or more, 4 or more, or 5 or more NLSs). Thus, in some cases, a fusion GeoCas polypeptide of the present disclosure includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus.

In some cases a GeoCas protein (e.g., a wild-type GeoCas9 polypeptide; a variant of a wild-type GeoCas9 polypeptide; a variant GeoCas9 polypeptide comprising a heterologous PI domain; etc.) includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases a GeoCas protein (e.g., a wild-type GeoCas9 polypeptide; a variant of a wild-type GeoCas9 polypeptide; a variant GeoCas9 polypeptide comprising a heterologous PI domain; etc.) includes (is fused to) between 2 and 5 NLSs (e.g., 2-4, or 2-3 NLSs).

Non-limiting examples of NLSs include an NLS sequence derived from: the NLS of the SV40 virus large T-antigen, having the amino acid sequence PKKKRKV (SEQ ID NO: 21); the NLS from nucleoplasmin (e.g., the nucleoplasmin bipartite NLS with the sequence KRPAATKKAGQAKKKK (SEQ ID NO: 22); the c-myc NLS having the amino acid sequence PAAKRVKLD (SEQ ID NO: 23) or RQRRNELKRSP (SEQ ID NO: 24); the hRNPA1 M9 NLS having the sequence NQSSNFGPMKGGNFGGRSSGPYGGGGQYFAKPRNQGGY (SEQ ID NO: 25); the sequence RMRIZFKNKGKDTAELRRRRVEVSVELRKAKKDEQILKRRNV (SEQ ID NO: 26) of the IBB domain from importin-alpha; the sequences VSRKRPRP (SEQ ID NO: 27) and PPKKARED (SEQ ID NO: 28) of the myoma T protein; the sequence PQPKKKPL (SEQ ID NO: 29) of human p53; the sequence SALIKKKKKMAP (SEQ ID NO: 30) of mouse c-abl IV; the sequences DRLRR (SEQ ID NO: 31) and PKQKKRK (SEQ ID NO: 32) of the influenza virus NS1; the sequence RKLKKKIKKL (SEQ ID NO: 33) of the Hepatitis virus delta antigen; the sequence REKKKFLKRR (SEQ ID NO: 34) of the mouse Mx1 protein; the sequence KRKGDEVDGVDEVAKKKSKK (SEQ ID NO: 35 of the human poly(ADP-ribose) polymerase; and the sequence RKCLQAGMNLEARKTKK (SEQ ID NO: 36) of the steroid hormone receptors (human) glucocorticoid. In general, NLS (or multiple NLSs) are of sufficient strength to drive accumulation of the GeoCas protein in a detectable amount in the nucleus of a eukaryotic cell. Detection of accumulation in the nucleus may be performed by any suitable technique. For example, a detectable marker may be fused to the GeoCas protein such that location within a cell may be visualized. Cell nuclei may also be isolated from cells, the contents of which may then be analyzed by any suitable process for detecting protein, such as immunohistochemistry, Western blot, or enzyme activity assay. Accumulation in the nucleus may also be determined indirectly.

In some cases, a GeoCas fusion polypeptide includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus a polypeptide (e.g., linked to a wild type GeoCas to generate a fusion protein, or linked to a variant GeoCas protein to generate a fusion protein). In some embodiments, a PTD is covalently linked to the carboxyl terminus of a polypeptide (e.g., linked to a wild type GeoCas to generate a fusion protein, or linked to a variant GeoCas protein to generate a fusion protein). In some cases, the PTD is inserted internally in the GeoCas fusion polypeptide (i.e., is not at the N- or C-terminus of the GeoCas fusion polypeptide) at a suitable insertion site. In some cases, a subject GeoCas fusion polypeptide includes (is conjugated to, is fused to) one or more PTDs (e.g., two or more, three or more, four or more PTDs). In some cases a PTD includes a nuclear localization signal (NLS) (e.g, in some cases 2 or more, 3 or more, 4 or more, or 5 or more NLSs). Thus, in some cases, a GeoCas fusion polypeptide includes one or more NLSs (e.g., 2 or more, 3 or more, 4 or more, or 5 or more NLSs). In some embodiments, a PTD is covalently linked to a nucleic acid (e.g., a GeoCas guide nucleic acid, a polynucleotide encoding a GeoCas guide nucleic acid, a polynucleotide encoding a GeoCas fusion polypeptide, a donor polynucleotide, etc.). Examples of PTDs include but are not limited to a minimal undecapeptide protein transduction domain (corresponding to residues 47-57 of HIV-1 TAT comprising YGRKKRRQRRR; SEQ ID NO: 37); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); a *Drosophila antennapedia* protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO: 38); Transportan GWTLNSAGYLLGKINLKALAALAKKIL (SEQ ID NO: 39); KALAWEAKLAKALAKALAKHLAKALAKALKCEA (SEQ ID NO: 40); and RQIKIWFQNRRMKWKK (SEQ ID NO: 41). Exemplary PTDs include but are not limited to, YGRKKRRQRRR (SEQ ID NO: 37), RKKRRQRRR (SEQ ID NO: 42); an arginine homopolymer of from 3 arginine residues to 50 arginine residues; Exemplary PTD domain amino acid sequences include, but are not limited to, any of the following: YGRKKRRQRRR (SEQ ID NO: 37); RKKRRQRR (SEQ ID NO: 43); YARAAARQARA (SEQ ID NO: 44); THRLPRRRRRR (SEQ ID NO: 45); and GGRRARRRRRR (SEQ ID NO: 46). In some embodiments, the PTD is an activatable CPP (ACPP) (Aguilera et al. (2009) *Integr Biol (Camb)* June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

In some cases, a GeoCas9 fusion polypeptide of the present disclosure comprises: a) a variant GeoCas9 polypeptide comprising amino acid substitutions of Asp-8 and His-582, as described above, where the variant GeoCas9 has reduced nuclease activity compared to wild-type GeoCas9; and b) a heterologous polypeptide that: i) has DNA modifying activity; ii) exhibits the ability to increase or decrease transcription; or iii) has enzymatic activity that modifies a polypeptide associated with DNA. The present disclosure provides a composition comprising: A) a GeoCas9 fusion polypeptide comprising: a) a variant GeoCas9 polypeptide comprising amino acid substitutions of Asp-8 and His-582, as described above, where the variant GeoCas9 has reduced nuclease activity compared to wild-type GeoCas9; and b) a heterologous polypeptide that: i) has DNA modifying activity; ii) exhibits the ability to increase or decrease transcription; or iii) has enzymatic activity that modifies a polypeptide associated with DNA; and B) a GeoCas9 guide RNA. In some cases, the GeoCas9 guide RNA is a single-molecule guide RNA. The present disclosure provides a composition comprising: A) a nucleic acid comprising a nucleotide sequence encoding a GeoCas9 fusion polypeptide comprising: a) a variant GeoCas9 polypeptide comprising amino acid substitutions of Asp-8 and His-582, as described above, where the variant GeoCas9 has reduced nuclease activity compared to wild-type GeoCas9; and b) a heterologous polypeptide that: i) has DNA modifying activity; ii) exhibits the ability to increase or decrease transcription; or iii) has enzymatic activity that modifies a polypeptide associated with DNA; and B) a nucleic acid comprising a nucleotide sequence encoding a GeoCas9 guide RNA. In some cases, the GeoCas9 guide RNA is a single-molecule guide RNA.

Linkers (e.g., for Fusion Partners)

In some cases, a GeoCas protein (e.g., a wild-type GeoCas9 polypeptide; a variant of a wild-type GeoCas9 polypeptide; a variant GeoCas9 polypeptide comprising a heterologous PI domain; etc.) can be fused to a fusion partner via a linker polypeptide (e.g., one or more linker polypeptides). The linker polypeptide may have any of a variety of amino acid sequences. Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers can be produced by using synthetic, linker-encoding oligonucleotides to couple the proteins, or can be encoded by a nucleic acid sequence encoding the fusion protein. Peptide linkers with a degree of flexibility can be used. The linking peptides may have virtually any amino acid sequence, bearing in mind that the linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

Examples of linker polypeptides include glycine polymers $(G)_n$, glycine-serine polymers (including, for example, (GS)$_n$, GSGGS$_n$ (SEQ ID NO: 47), GGSGGS$_n$ (SEQ ID NO: 48), and GGGS$_n$ (SEQ ID NO: 49), where n is an integer of at least one), glycine-alanine polymers, alanine-serine polymers. Exemplary linkers can comprise amino acid sequences including, but not limited to, GGSG (SEQ ID NO: 50), GGSGG (SEQ ID NO: 51), GSGSG (SEQ ID NO: 52), GSGGG (SEQ ID NO: 53), GGGSG (SEQ ID NO: 54), GSSSG (SEQ ID NO: 55) and the like. The ordinarily skilled artisan will recognize that design of a peptide conjugated to any desired element can include linkers that are all or partially flexible, such that the linker can include a flexible linker as well as one or more portions that confer less flexible structure.

Nucleic Acids and Expression Vectors

The present disclosure provides a nucleic acid comprising a nucleotide sequence encoding an RNA-guided endonuclease of the present disclosure (e.g., a GeoCas9 polypeptide comprising a heterologous PI domain; a variant GeoCas9 polypeptide comprising a substitution of Asp-8 and/or His-582). The present disclosure provides a nucleic acid comprising a nucleotide sequence encoding a GeoCas fusion polypeptide of the present disclosure. The present disclosure provides a nucleic acid comprising a nucleotide sequence encoding a variant GeoCas9 polypeptide. In some cases, the nucleic acid comprises a nucleotide sequence encoding one or more GeoCas9 guide RNAs. In some cases, the nucleic acid comprises a nucleotide sequence encoding a donor template nucleic acid.

The present disclosure provides one ore more nucleic acids comprising one or more of: a) a donor polynucleotide sequence; b) a nucleotide sequence encoding a GeoCas polypeptide (e.g., a wild type GeoCas protein; a fusion GeoCas polypeptide of the present disclosure; a variant GeoCas polypeptide of the present disclosure (e.g., a GeoCas polypeptide comprising a heterologous PI domain); and the like); c) a GeoCas guide RNA; and d) a nucleotide sequence encoding a GeoCas guide RNA (which can include two separate nucleotide sequences in the case of dual guide RNA format or which can include a singe nucleotide sequence in the case of single guide RNA format). The present disclosure provides a nucleic acid comprising a nucleotide sequence encoding a GeoCas fusion polypeptide. The present disclosure provides a recombinant expression vector that comprises a nucleotide sequence encoding a GeoCas polypeptide. The present disclosure provides a recombinant expression vector that comprises a nucleotide sequence encoding a GeoCas fusion polypeptide. The present disclosure provides a recombinant expression vector that comprises: a) a nucleotide sequence encoding a GeoCas polypeptide; and b) a nucleotide sequence encoding a GeoCas guide RNA(s). The present disclosure provides a recombinant expression vector that comprises: a) a nucleotide sequence encoding a GeoCas fusion polypeptide; and b) a nucleotide sequence encoding a GeoCas guide RNA(s). In some cases, the nucleotide sequence encoding the GeoCas protein and/or the nucleotide sequence encoding the GeoCas guide RNA is operably linked to a promoter that is operable in a cell type of choice (e.g., a prokaryotic cell, a eukaryotic cell, a plant cell, an animal cell, a mammalian cell, a primate cell, an invertebrate, a rodent cell, a human cell, etc.).

In some cases, a nucleotide sequence encoding a GeoCas polypeptide (e.g., a wild type GeoCas protein; a fusion GeoCas polypeptide of the present disclosure; a variant GeoCas polypeptide of the present disclosure (e.g., a GeoCas polypeptide comprising a heterologous PI domain; a variant GeoCas9 polypeptide comprising a substitution of Asp-8 and/or His-582); and the like) is codon optimized. This type of optimization can entail a mutation of a GeoCas-encoding nucleotide sequence to mimic the codon preferences of the intended host organism or cell while encoding the same protein. Thus, the codons can be changed, but the encoded protein remains unchanged. For example, if the intended target cell was a human cell, a human codon-optimized GeoCas-encoding nucleotide sequence could be used. As another non-limiting example, if the intended host cell were a mouse cell, then a mouse codon-optimized GeoCas-encoding nucleotide sequence could be generated. As another non-limiting example, if the intended host cell were a plant cell, then a plant codon-optimized GeoCas-encoding nucleotide sequence could be generated. As another non-limiting example, if the intended host cell were an insect cell, then an insect codon-optimized GeoCas-encoding nucleotide sequence could be generated.

The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); (ii) a nucleotide sequence that encodes a GeoCas guide RNA that hybridizes to a target sequence of the target locus of the targeted genome (e.g., a single or dual guide RNA) (e.g., operably linked to a promoter that is operable in a target cell such as a eukaryotic cell); and (iii) a nucleotide sequence encoding a GeoCas protein (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); and (ii) a nucleotide sequence that encodes a GeoCas guide RNA that hybridizes to a target sequence of the target locus of the targeted genome (e.g., a single or dual guide RNA) (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence that encodes a GeoCas guide RNA that hybridizes to a target sequence of the target locus of the targeted genome (e.g., a single or dual guide RNA) (e.g., operably linked to a promoter that is operable in a target cell such as a eukaryotic cell); and (ii) a nucleotide sequence encoding a GeoCas protein (e.g., operably linked to a promoter that is operable in a target cell such as a eukaryotic cell).

Suitable expression vectors include viral expression vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., Human Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166: 154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector.

Depending on the host/vector system utilized, any of a number of suitable transcription and translation control elements, including constitutive and inducible promoters, transcription enhancer elements, transcription terminators, etc. may be used in the expression vector.

In some embodiments, a nucleotide sequence encoding a GeoCas guide RNA is operably linked to a control element, e.g., a transcriptional control element, such as a promoter. In some embodiments, a nucleotide sequence encoding a GeoCas protein (e.g., a wild type GeoCas protein; a fusion GeoCas polypeptide of the present disclosure; a variant GeoCas polypeptide of the present disclosure (e.g., a GeoCas polypeptide comprising a heterologous PI domain; a variant GeoCas9 polypeptide comprising a substitution of Asp-8 and/or His-582); and the like) is operably linked to a control element, e.g., a transcriptional control element, such as a promoter.

The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells, e.g., hematopoietic stem cells (e.g., mobilized peripheral blood (mPB) CD34(+) cell, bone marrow (BM) CD34(+) cell, etc.).

Non-limiting examples of eukaryotic promoters (promoters functional in a eukaryotic cell) include EF1α, those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, fluorescent protein, etc.) that can be fused to the GeoCas protein, thus resulting in a fusion GeoCas polypeptide.

In some cases, a nucleotide sequence encoding a GeoCas guide RNA and/or a GeoCas polypeptide (e.g., a wild type GeoCas protein; a fusion GeoCas polypeptide of the present disclosure; a variant GeoCas polypeptide of the present disclosure (e.g., a GeoCas polypeptide comprising a heterologous PI domain; a variant GeoCas9 polypeptide comprising a substitution of Asp-8 and/or His-582); and the like) is operably linked to an inducible promoter. In some cases, a nucleotide sequence encoding a GeoCas guide RNA and/or a GeoCas protein (e.g., a wild type GeoCas protein; a fusion GeoCas polypeptide of the present disclosure; a variant GeoCas polypeptide of the present disclosure (e.g., a GeoCas polypeptide comprising a heterologous PI domain); and the like) is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

In some cases, a nucleotide sequence encoding a GeoCas guide RNA is operably linked to (under the control of) a promoter operable in a eukaryotic cell (e.g., a U6 promoter, an enhanced U6 promoter, an H1 promoter, and the like). As would be understood by one of ordinary skill in the art, when expressing an RNA (e.g., a guide RNA) from a nucleic acid (e.g., an expression vector) using a U6 promoter (e.g., in a eukaryotic cell), or another PolIII promoter, the RNA may need to be mutated if there are several Ts in a row (coding for Us in the RNA). This is because a string of Ts (e.g., 5 Ts) in DNA can act as a terminator for polymerase III (PolIII). Thus, in order to ensure transcription of a guide RNA (e.g., the activator portion and/or targeter portion, in dual guide or single guide format) in a eukaryotic cell it may sometimes be necessary to modify the sequence encoding the guide RNA to eliminate runs of Ts. In some cases, a nucleotide sequence encoding a GeoCas protein (e.g., a wild type GeoCas protein, a variant GeoCas polypeptide, a fusion GeoCas polypeptide, and the like) is operably linked to a promoter operable in a eukaryotic cell (e.g., a CMV promoter, an EF1α promoter, an estrogen receptor-regulated promoter, and the like).

Examples of inducible promoters include, but are not limited to T7 RNA polymerase promoter, T3 RNA polymerase promoter, isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; estrogen and/or an estrogen analog; IPTG; etc.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

The present disclosure provides a recombinant expression vector comprising: i) an insertion site for insertion of a nucleotide sequence encoding a targeting sequence (a nucleotide sequence that hybridizes to a target sequence in a target nucleic acid); and ii) a nucleotide sequence encoding a GeoCas9 guide RNA as described above. For example, a nucleotide sequence encoding a GeoCas9 guide RNA can encode the following nucleotide sequence:

(SEQ ID NO: 7)
GUCAUAGUUCCCCUGAgaaaUCAGGGUUACUAUGAUAAGGGCUUUCUGCCU

AAGGCAGACUGACCCGCGGCGUUGGGGAUCGCCUGUCGCCCGCUUUUGGCG

GGCAUUCCCCAUCCUU.

In some cases, the recombinant expression vector further comprises a nucleotide sequence encoding a GeoCas9 polypeptide of the present disclosure (e.g., wild-type GeoCas9; a variant GeoCas9 polypeptide of the present disclosure; a fusion GeoCas9 polypeptide of the present disclosure).

Methods of introducing a nucleic acid (e.g., a nucleic acid comprising a donor polynucleotide sequence, one or more nucleic acids encoding a GeoCas protein and/or a GeoCas guide RNA, and the like) into a host cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

Introducing the recombinant expression vector into cells can occur in any culture media and under any culture conditions that promote the survival of the cells. Introducing the recombinant expression vector into a target cell can be carried out in vivo or ex vivo. Introducing the recombinant expression vector into a target cell can be carried out in vitro.

In some embodiments, a GeoCas protein can be provided as RNA. The RNA can be provided by direct chemical synthesis or may be transcribed in vitro from a DNA (e.g., encoding the GeoCas protein). Once synthesized, the RNA may be introduced into a cell by any of the well-known techniques for introducing nucleic acids into cells (e.g., microinjection, electroporation, transfection, etc.).

Nucleic acids may be provided to the cells using well-developed transfection techniques; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Minis Bio LLC. See also Beumer et al. (2008) PNAS 105(50):19821-19826.

Vectors may be provided directly to a target host cell. In other words, the cells are contacted with vectors comprising the subject nucleic acids (e.g., recombinant expression vectors having the donor template sequence and encoding the GeoCas guide RNA; recombinant expression vectors encoding the GeoCas protein; etc.) such that the vectors are taken up by the cells. Methods for contacting cells with nucleic acid vectors that are plasmids, include electroporation, calcium chloride transfection, microinjection, and lipofection are well known in the art. For viral vector delivery, cells can be contacted with viral particles comprising the subject viral expression vectors.

Retroviruses, for example, lentiviruses, are suitable for use in methods of the present disclosure. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art. Nucleic acids can also introduced by direct micro-injection (e.g., injection of RNA).

Vectors used for providing the nucleic acids encoding GeoCas guide RNA and/or a GeoCas polypeptide to a target host cell can include suitable promoters for driving the expression, that is, transcriptional activation, of the nucleic acid of interest. In other words, in some cases, the nucleic acid of interest will be operably linked to a promoter. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a nucleic acid encoding a GeoCas guide RNA and/or a GeoCas protein to a cell may include nucleic acid sequences that encode for selectable markers in the target cells, so as to identify cells that have taken up the GeoCas guide RNA and/or GeoCas protein.

A nucleic acid comprising a nucleotide sequence encoding a GeoCas polypeptide, or a GeoCas fusion polypeptide, is in some cases an RNA. Thus, a GeoCas fusion protein can be introduced into cells as RNA. Methods of introducing RNA into cells are known in the art and may include, for example, direct injection, transfection, or any other method used for the introduction of DNA. A GeoCas protein may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, a GeoCas polypeptide (e.g., a wild type GeoCas protein; a fusion GeoCas polypeptide of the present disclosure; a variant GeoCas polypeptide of the present disclosure (e.g., a GeoCas polypeptide comprising a heterologous PI domain); and the like) may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of Drosophila melanogaster transcription factor Antennapaedia, referred to as penetratin, which comprises the amino acid sequence RQIKIWFQNRRMKWKK (SEQ ID NO: 41). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

A GeoCas polypeptide (e.g., a wild type GeoCas protein; a fusion GeoCas polypeptide of the present disclosure; a variant GeoCas polypeptide of the present disclosure (e.g., a GeoCas polypeptide comprising a heterologous PI domain); and the like) may be produced in vitro or by eukaryotic cells or by prokaryotic cells, and it may be further processed by unfolding, e.g. heat denaturation, dithiothreitol reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also suitable for inclusion in embodiments of the present disclosure are nucleic acids (e.g., encoding a GeoCas guide RNA, encoding a GeoCas protein, etc.) and proteins (e.g., a wild type GeoCas protein; a fusion GeoCas polypeptide of the present disclosure; a variant GeoCas polypeptide of the present disclosure (e.g., a GeoCas polypeptide comprising a heterologous PI domain); and the like) that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc.) or to render them more suitable. Analogs of such polypeptides include those containing residues other than naturally occurring L-amino acids, e.g. D-amino acids or non-naturally occurring synthetic amino acids. D-amino acids may be substituted for some or all of the amino acid residues.

A GeoCas polypeptide (e.g., a wild type GeoCas protein; a fusion GeoCas polypeptide of the present disclosure; a variant GeoCas polypeptide of the present disclosure (e.g., a GeoCas polypeptide comprising a heterologous PI domain); and the like) may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

A GeoCas polypeptide (e.g., a wild type GeoCas protein; a fusion GeoCas polypeptide of the present disclosure; a variant GeoCas polypeptide of the present disclosure (e.g., a GeoCas polypeptide comprising a heterologous PI domain); and the like) may also be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein. Thus, in some cases, a GeoCas polypeptide, or a GeoCas fusion polypeptide, of the present disclosure is at least 80% pure, at least 85% pure, at least 90% pure, at least 95% pure, at least 98% pure, or at least 99% pure (e.g., free of contaminants, non-GeoCas proteins or other macromolecules, etc.).

To induce cleavage or any desired modification to a target nucleic acid (e.g., genomic DNA), or any desired modification to a polypeptide associated with target nucleic acid, the GeoCas guide RNA and/or the GeoCas polypeptide of the present disclosure and/or the donor template sequence, whether they be introduced as nucleic acids or polypeptides, are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different targeting complexes are provided to the cell (e.g., two different GeoCas guide RNAs that are complementary to different sequences within the same or different target nucleic acid), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

To improve the delivery of a DNA vector into a target cell, the DNA can be protected from damage and its entry into the cell facilitated, for example, by using lipoplexes and polyplexes. Thus, in some cases, a nucleic acid of the present disclosure (e.g., a recombinant expression vector of the present disclosure) can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA. Also as a result of their charge, they interact with the cell membrane. Endocytosis of the lipoplex then occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Dendrimers, a highly branched macromolecule with a spherical shape, may be also be used to genetically modify stem cells. The surface of the dendrimer particle may be functionalized to alter its properties. In particular, it is possible to construct a cationic dendrimer (i.e., one with a positive surface charge). When in the presence of genetic material such as a DNA plasmid, charge complementarity leads to a temporary association of the nucleic acid with the cationic dendrimer. On reaching its destination, the dendrimer-nucleic acid complex can be taken up into a cell by endocytosis.

In some cases, a nucleic acid of the disclosure (e.g., an expression vector) includes an insertion site for a guide sequence of interest. For example, a nucleic acid can include an insertion site for a guide sequence of interest, where the insertion site is immediately adjacent to a nucleotide sequence encoding the portion of a GeoCas guide RNA that does not change when the guide sequence is changed to hybrized to a desired target sequence (e.g., sequences that contribute to the GeoCas binding aspect of the guide RNA, e.g, the sequences that contribute to the dsRNA duplex(es) of the GeoCas guide RNA—this portion of the guide RNA can also be referred to as the 'scaffold' or 'constant region' of the guide RNA). Thus, in some cases, a subject nucleic acid (e.g., an expression vector) includes a nucleotide sequence encoding a GeoCas9 guide RNA, except that the portion encoding the guide sequence portion of the guide RNA is an insertion sequence (an insertion site). An insertion site is any nucleotide sequence used for the insertion of a the desired sequence. "Insertion sites" for use with various technologies are known to those of ordinary skill in the art and any convenient insertion site can be used. An insertion site can be for any method for manipulating nucleic acid sequences. For example, in some cases the insertion site is a multiple cloning site (MCS) (e.g., a site including one or more restriction enzyme recognition sequences), a site for ligation independent cloning, a site for recombination based cloning (e.g., recombination based on att sites), a nucleotide sequence recognized by a CRISPR/Cas (e.g. Cas9) based technology, and the like.

An insertion site can be any desirable length, and can depend on the type of insertion site (e.g., can depend on whether (and how many) the site includes one or more restriction enzyme recognition sequences, whether the site includes a target site for a GeoCas9 protein, etc.). In some cases, an insertion site of a subject nucleic acid is 3 or more nucleotides (nt) in length (e.g., 5 or more, 8 or more, 10 or more, 15 or more, 17 or more, 18 or more, 19 or more, 20 or more or 25 or more, or 30 or more nt in length). In some cases, the length of an insertion site of a subject nucleic acid has a length in a range of from 2 to 50 nucleotides (nt) (e.g., from 2 to 40 nt, from 2 to 30 nt, from 2 to 25 nt, from 2 to 20 nt, from 5 to 50 nt, from 5 to 40 nt, from 5 to 30 nt, from 5 to 25 nt, from 5 to 20 nt, from 10 to 50 nt, from 10 to 40 nt, from 10 to 30 nt, from 10 to 25 nt, from 10 to 20 nt, from 17 to 50 nt, from 17 to 40 nt, from 17 to 30 nt, from 17 to 25 nt). In some cases, the length of an insertion site of a subject nucleic acid has a length in a range of from 5 to 40 nt.

Nucleic Acid Modifications

In some embodiments, a subject nucleic acid (e.g., a GeoCas guide RNA) has one or more modifications, e.g., a base modification, a backbone modification, etc., to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound; however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2'Omethyl modified nucleotides, 2' fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stabile with respect to attack by single-stranded ribonucleases and is typically 5 to 10-fold less susceptible to DNases than DNA. It is commonly used in antisense oligos as a means to increase stability and binding affinity to the target message.

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siRNAs to improve stability in serum or other biological fluids.

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In some cases, the number of LNAs incorporated into a single oligo is 10 bases or less.

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

In some embodiments, a subject nucleic acid has one or more nucleotides that are 2'-O-Methyl modified nucleotides. In some embodiments, a subject nucleic acid (e.g., a GeoCas guide RNA etc.) has one or more 2' Fluoro modified nucleotides. In some embodiments, a subject nucleic acid (e.g., GeoCas guide RNA, etc.) has one or more LNA bases. In some embodiments, a subject nucleic acid (e.g., GeoCas guide RNA, etc.) has one or more nucleotides that are linked by a phosphorothioate bond (i.e., the subject nucleic acid has one or more phosphorothioate linkages). In some embodiments, a subject nucleic acid (e.g., a GeoCas guide RNA, etc.) has a 5' cap (e.g., a 7-methylguanylate cap (m7G)). In some embodiments, a subject nucleic acid (e.g., a GeoCas guide RNA, etc.) has a combination of modified nucleotides. For example, a subject nucleic acid (e.g., a GeoCas guide RNA, etc.) can have a 5' cap (e.g., a 7-methylguanylate cap (m7G)) in addition to having one or more nucleotides with other modifications (e.g., a 2'-O-Methyl nucleotide and/or a 2' fluoro modified nucleotide and/or a LNA base and/or a phosphorothioate linkage).

Modified Backbones and Modified Internucleoside Linkages

Examples of suitable nucleic acids (e.g., a GeoCas guide RNA) containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular —$CH_2$—NH—O—$CH_2$—, —$CH_2$—N($CH_3$)—O—$CH_2$-(known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). MMI type internucleoside linkages are disclosed in the above referenced U.S. Pat. No. 5,489,677, the disclosure of which is incorporated herein by reference in its entirety. Suitable amide internucleoside linkages are disclosed in U.S. Pat. No. 5,602,240, the disclosure of which is incorporated herein by reference in its entirety.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Mimetics

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262, the disclosures of which are incorporated herein by reference in their entirety.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, *Biochemistry*, 2002, 41(14), 4503-4510). Morpholino-based polynucleotides are disclosed in U.S. Pat. No. 5,034,506, the disclosure of which is incorporated herein by reference in its entirety. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.*, 2000, 122, 8595-8602, the disclosure of which is incorporated herein by reference in its entirety). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—$CH_2$—), group bridging the 2' oxygen atom and the 4' carbon atom wherein n is 1 or 2 (Singh et al., *Chem. Commun.*, 1998, 4, 455-456, the disclosure of which is incorporated herein by reference in its entirety). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., *Proc. Natl. Acad. Sci. U.S.A.*, 2000, 97, 5633-5638, the disclosure of which is incorporated herein by reference in its entirety).

The synthesis and preparation of the LNA monomers adenine, cytosine, guanine, 5-methylcytosine, thymine and uracil, along with their oligomerization, and nucleic acid recognition properties have been described (e.g., Koshkin et al., *Tetrahedron*, 1998, 54, 3607-3630, the disclosure of which is incorporated herein by reference in its entirety). LNAs and preparation thereof are also described in WO 98/39352 and WO 99/14226, as well as U.S. applications 20120165514, 20100216983, 20090041809, 20060117410, 20040014959, 20020094555, and 20020086998, the disclosures of which are incorporated herein by reference in their entirety.

Modified Sugar Moieties

A subject nucleic acid can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504, the disclosure of which is incorporated herein by reference in its entirety) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy (—$OCH_2CH_2CH_2NH_2$), allyl (—$CH_2$—CH=$CH_2$), —O-allyl $CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid (e.g., a GeoCas guide RNA) may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289-302, Crooke, S. T. and Lebleu, B., ed., CRC Press, 1993; the disclosures of which are incorporated herein by reference in their entirety. Certain of these nucleobases are useful for increasing the binding affinity of an oligomeric compound. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., *Antisense Research and Applications*, CRC Press, Boca Raton, 1993, pp. 276-278; the disclosure of which is incorporated herein by reference in its entirety) and are suitable base substitutions, e.g., when combined with 2'-O-methoxyethyl sugar modifications.

Conjugates

Another possible modification of a subject nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., *Proc. Natl. Acad. Sci. USA*, 1989, 86, 6553-6556), cholic acid (Manoharan et al., *Bioorg. Med. Chem. Let.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Let.*, 1993, 3, 2765-2770), a thiocholesterol (Oberhauser et al., *Nucl. Acids Res.*, 1992, 20, 533-538), an aliphatic chain, e.g., dodecandiol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid (Manoharan et al., *Tetrahedron Lett.*, 1995, 36, 3651-3654), a palmityl moiety (Mishra et al., *Biochim. Biophys. Acta*, 1995, 1264, 229-237), or an octadecylamine or hexylamino-carbonyl-oxycholesterol moiety (Crooke et al., *J. Pharmacol. Exp. Ther.*, 1996, 277, 923-937).

A conjugate may include a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle (e.g., the nucleus). In some embodiments, a PTD is covalently linked to the 3' end of an exogenous polynucleotide. In some embodiments, a PTD is covalently linked to the 5' end of an exogenous polynucleotide. Exemplary PTDs include but are not limited to a minimal undecapeptide protein transduction domain (corresponding to residues 47-57 of HIV-1 TAT comprising YGRKKRRQRRR; SEQ ID NO: 37); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) Proc. Natl. Acad. Sci. USA 97:13003-13008); RRQRRTSKLMKR (SEQ ID NO: 38); Transportan GWTLNSAGYLLGKINLKALAALAKKIL (SEQ ID NO: 39); KALAWEAKLAKALAKA-LAKHLAKALAKALKCEA (SEQ ID NO: 40); and RQIKIWFQNRRMKWKK (SEQ ID; NO: 41). Exemplary PTDs include but are not limited to, YGRKKRRQRRR (SEQ ID NO: 37), RKKRRQRRR (SEQ ID NO: 42); an arginine homopolymer of from 3 arginine residues to 50 arginine residues; Exemplary PTD domain amino acid sequences include, but are not limited to, any of the following: YGRKKRRQRRR (SEQ ID NO: 37); RKKRRQRR (SEQ ID NO: 43); YARAAARQARA (SEQ ID NO: 44); THRLPRRRRRR (SEQ ID NO: 45); and GGRRARRRRRR (SEQ ID NO: 46). In some embodiments, the PTD is an activatable CPP (ACPP) (Aguilera et al. (2009) *Integr Biol (Camb)* June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Introducing Components into a Target Cell

A GeoCas guide RNA (or a nucleic acid comprising a nucleotide sequence encoding same) and/or a GeoCas polypeptide of the present disclosure (or a nucleic acid comprising a nucleotide sequence encoding same) and/or a GeoCas fusion polypeptide of the present disclosure (or a nucleic acid that includes a nucleotide sequence encoding a GeoCas fusion polypeptide of the present disclosure) and/or a donor polynucleotide (donor template) can be introduced into a host cell by any of a variety of well-known methods.

Any of a variety of compounds and methods can be used to deliver to a target cell a GeoCas system of the present disclosure (e.g., where a GeoCas9 system comprises: a) a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.) and a GeoCas guide RNA; b) a GeoCas polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), a GeoCas guide RNA, and a donor template nucleic acid; c) a GeoCas fusion polypeptide of the present disclosure and a GeoCas guide RNA; d) a GeoCas9 fusion polypeptide of the present disclosure, a GeoCas guide RNA, and a donor template nucleic acid; e) an mRNA encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.); and a GeoCas9 guide RNA; f) an mRNA encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), a GeoCas9 guide RNA, and a donor template nucleic acid; g) an mRNA encoding a GeoCas9 fusion polypeptide of the present disclosure; and a GeoCas9 guide RNA; h) an mRNA encoding a GeoCas9 fusion polypeptide of the present disclosure, a GeoCas9 guide RNA, and a donor template nucleic acid; i) a recombinant expression vector comprising a nucleotide sequence encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.) and a nucleotide sequence encoding a GeoCas9 guide RNA; j) a recombinant expression vector comprising a nucleotide sequence encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), a nucleotide sequence encoding a GeoCas9 guide RNA, and a nucleotide sequence encoding a donor template nucleic acid; k) a recombinant expression vector comprising a nucleotide sequence encoding a GeoCas9 fusion polypeptide of the present disclosure and a nucleotide sequence encoding a GeoCas9 guide RNA; 1) a recombinant expression vector comprising a nucleotide sequence encoding a GeoCas9 fusion polypeptide of the present disclosure, a nucleotide sequence encoding a GeoCas9 guide RNA, and a nucleotide sequence encoding a donor template nucleic acid; m) a first recombinant expression vector comprising a nucleotide sequence encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), and a second recombinant expression vector comprising a nucleotide sequence encoding a GeoCas9 guide RNA; n) a first recombinant expression vector comprising a nucleotide sequence encoding a Geo-Cas9 polypeptide of the present disclosure, and a second recombinant expression vector comprising a nucleotide sequence encoding a GeoCas9 guide RNA; and a donor template nucleic acid; o) a first recombinant expression vector comprising a nucleotide sequence encoding a Geo-Cas9 fusion polypeptide of the present disclosure, and a second recombinant expression vector comprising a nucleotide sequence encoding a GeoCas9 guide RNA; p) a first recombinant expression vector comprising a nucleotide sequence encoding a GeoCas9 fusion polypeptide of the present disclosure, and a second recombinant expression vector comprising a nucleotide sequence encoding a Geo-Cas9 guide RNA; and a donor template nucleic acid; q) a recombinant expression vector comprising a nucleotide sequence encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), a nucleotide sequence encoding a first GeoCas9 guide RNA, and a nucleotide sequence encoding a second GeoCas9 guide RNA; or r) a recombinant expression vector comprising a nucleotide sequence encoding a GeoCas9 fusion polypeptide of the present disclosure, a nucleotide sequence encoding a first GeoCas9 guide RNA, and a nucleotide sequence encoding a second GeoCas9 guide RNA; or some variation of one of (a) through (r). As a non-limiting example, a GeoCas9 system of the present disclosure can be combined with a lipid. As another non-limiting example, a GeoCas9 system of the present disclosure can be combined with a particle, or formulated into a particle.

Methods of introducing a nucleic acid into a host cell are known in the art, and any convenient method can be used to introduce a subject nucleic acid (e.g., an expression construct/vector) into a target cell (e.g., prokaryotic cell, eukaryotic cell, plant cell, animal cell, mammalian cell, human cell, and the like). Suitable methods include, e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like.

In some cases, a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.) is provided as a nucleic acid (e.g., an mRNA, a DNA, a plasmid, an expression vector, a viral vector, etc.) that encodes the GeoCas9 polypeptide. In some cases, the GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.) is provided directly as a protein (e.g., without an associated guide RNA or with an associate guide RNA, i.e., as a ribonucleoprotein complex). A GeoCas9 polypeptide of the present disclosure (e.g., a wild-type GeoCas9 polypeptide; a variant GeoCas9 polypeptide; a variant GeoCas9 polypeptide comprising a heterologous PI domain; a fusion GeoCas9 polypeptide; etc.) can be introduced into a cell (provided to the cell) by any convenient method; such methods are known to those of ordinary skill in the art. As an illustrative example, a GeoCas9 polypeptide of the present disclosure (e.g., a wild-type GeoCas9 polypeptide; a variant GeoCas9 polypeptide; a variant GeoCas9 polypeptide comprising a heterologous PI domain; a fusion GeoCas9 polypeptide; etc.) can be injected directly into a cell (e.g., with or without a GeoCas9 guide RNA or nucleic acid encoding a GeoCas9 guide RNA, and with or without a donor polynucleotide). As another example, a preformed complex of a GeoCas9 polypeptide of the present disclosure and a GeoCas9 guide RNA (an RNP) can be introduced into a cell (e.g., eukaryotic cell) (e.g., via injection, via nucleofection; via a protein transduction domain (PTD) conjugated to one or more components, e.g., conjugated to the GeoCas9 protein, conjugated to a guide RNA, conjugated to a Geo-Cas9 polypeptide of the present disclosure and a guide RNA; etc.).

In some cases, a GeoCas9 fusion polypeptide of the present disclosure is provided as a nucleic acid (e.g., an mRNA, a DNA, a plasmid, an expression vector, a viral vector, etc.) that encodes the GeoCas9 fusion polypeptide. In some cases, the GeoCas9 fusion polypeptide of the present disclosure is provided directly as a protein (e.g., without an associated guide RNA or with an associate guide RNA, i.e., as a ribonucleoprotein complex). A GeoCas9 fusion polypeptide of the present disclosure can be introduced into a cell (provided to the cell) by any convenient method; such methods are known to those of ordinary skill in the art. As an illustrative example, a GeoCas9 fusion polypeptide of the present disclosure can be injected directly into a cell (e.g., with or without nucleic acid encoding a GeoCas9 guide RNA and with or without a donor polynucleotide). As another example, a preformed complex of a GeoCas9 fusion polypeptide of the present disclosure and a GeoCas9 guide RNA (an RNP) can be introduced into a cell (e.g., via injection, via nucleofection; via a protein transduction domain (PTD) conjugated to one or more components, e.g., conjugated to the GeoCas9 fusion protein, conjugated to a guide RNA, conjugated to a GeoCas9 fusion polypeptide of the present disclosure and a guide RNA; etc.).

In some cases, a nucleic acid (e.g., a GeoCas9 guide RNA; a nucleic acid comprising a nucleotide sequence encoding a GeoCas9 polypeptide (e.g., a wild-type GeoCas9 polypeptide; a variant GeoCas9 polypeptide; a variant Geo-Cas9 polypeptide comprising a heterologous PI domain; a fusion GeoCas9 polypeptide; etc.); etc.) is delivered to a cell (e.g., a target host cell) and/or a polypeptide (e.g., a Geo-Cas9 polypeptide; a GeoCas9 fusion polypeptide) in a particle, or associated with a particle. In some cases, a GeoCas9 system of the present disclosure is delivered to a cell in a particle, or associated with a particle. The terms "particle" and nanoparticle" can be used interchangeable, as appropriate. A recombinant expression vector comprising a nucleotide sequence encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.) and/or a GeoCas9 guide RNA, an mRNA comprising a nucleotide sequence encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), and guide RNA may be delivered simultaneously using particles or lipid envelopes; for instance, a GeoCas9 polypeptide and a GeoCas9 guide RNA, e.g., as a complex (e.g., a ribonucleoprotein (RNP) complex), can be delivered via a particle, e.g., a delivery particle comprising lipid or lipidoid and hydrophilic polymer, e.g., a cationic lipid and a hydrophilic polymer, for instance wherein the cationic lipid comprises 1,2-dioleoyl-3-trimethylammonium-propane (DO- TAP) or 1,2-ditetradecanoyl-sn-glycero-3-phosphocholine (DMPC) and/or wherein the hydrophilic polymer comprises ethylene glycol or poly(ethylene glycol) (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5). For example, a particle can be formed using a multistep process in which a GeoCas9 polypeptide and a GeoCas9 guideRNA are mixed together, e.g., at a 1:1 molar ratio, e.g., at room temperature, e.g., for 30 minutes, e.g., in sterile, nuclease free 1× phosphate-buffered saline (PBS); and separately, DOTAP, DMPC, PEG, and cholesterol as applicable for the formulation are dissolved in alcohol, e.g., 100% ethanol; and, the two solutions are mixed together to form particles containing the complexes).

The present disclosure thus provides a nanoparticle comprising: a) a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.); and b) a GeoCas9 guide RNA.

The present disclosure provides a composition comprising: a) a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.); b) a GeoCas9 guide RNA; and c) one or more of a solvent, an aqueous solvent, a non-aqueous solvent, a dispersion medium, a diluent, a suspension aid, a surface active agent, an isotonic agent, a thickening or emulsifying agent, a preservative, a lipid, a liposome, a lipid nanoparticle, a core-shell nanoparticle, a synthetic polymer, and a lipoplex.

A GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.) (or an mRNA comprising a nucleotide sequence encoding a GeoCas9 polypeptide; or a recombinant expression vector comprising a nucleotide sequence encoding a GeoCas9 polypeptide) and/or GeoCas9 guide RNA (or a nucleic acid such as one or more expression vectors encoding the GeoCas9 guide RNA) may be delivered simultaneously using particles or lipid envelopes. For example, a biodegradable core-shell structured nanoparticle with a poly (β-amino ester) (PBAE) core enveloped by a phospholipid bilayer shell can be used. In some cases, particles/nanoparticles based on self assembling bioadhesive polymers are used; such particles/nanoparticles may be applied to oral delivery of peptides, intravenous delivery of peptides and nasal delivery of peptides, e.g., to the brain. Other embodiments, such as oral absorption and ocular delivery of hydrophobic drugs are also contemplated. A molecular envelope technology, which involves an engineered polymer envelope which is protected and delivered to the site of the disease, can be used. Doses of about 5 mg/kg can be used, with single or multiple doses, depending on various factors, e.g., the target tissue.

Lipidoid compounds (e.g., as described in US patent application 20110293703) are also useful in the administration of polynucleotides, and can be used to deliver a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), an RNP of the present disclosure, a nucleic acid of the present disclosure, or a GeoCas9 system of the present disclosure (e.g., where a GeoCas9 system comprises: a) a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.) and a GeoCas9 guide RNA; b) a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), a GeoCas9 guide RNA, and a donor template nucleic acid; c) a GeoCas9 fusion polypeptide of the present disclosure and a GeoCas9 guide RNA; d) a GeoCas9 fusion polypeptide of the present disclosure, a GeoCas9 guide RNA, and a donor template nucleic acid; e) an mRNA encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.); and a GeoCas9 guide RNA; f) an mRNA encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), a GeoCas9 guide RNA, and a donor template nucleic acid; g) an mRNA encoding a GeoCas9 fusion polypeptide of the present disclosure; and a GeoCas9 guide RNA; h) an mRNA encoding a GeoCas9 fusion polypeptide of the present disclosure, a GeoCas9 guide RNA, and a donor template nucleic acid; i) a recombinant expression vector comprising a nucleotide sequence encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.) and a nucleotide sequence encoding a GeoCas9 guide RNA; j) a recombinant expression vector comprising a nucleotide sequence encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), a nucleotide sequence encoding a GeoCas9 guide RNA, and a nucleotide sequence encoding a donor template nucleic acid; k) a recombinant expression vector comprising a nucleotide sequence encoding a GeoCas9 fusion polypeptide of the present disclosure and a nucleotide sequence encoding a GeoCas9 guide RNA; l) a recombinant expression vector comprising a nucleotide sequence encoding a GeoCas9 fusion polypeptide of the present disclosure, a nucleotide sequence encoding a GeoCas9 guide RNA, and a nucleotide sequence encoding a donor template nucleic acid; m) a first recombinant expression vector comprising a nucleotide sequence encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), and a second recombinant expression vector comprising a nucleotide sequence encoding a GeoCas9 guide RNA; n) a first recombinant expression vector comprising a nucleotide sequence encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), and a second recombinant expression vector comprising a nucleotide sequence encoding a GeoCas9 guide RNA; and a donor template nucleic acid; o) a first recombinant expression vector comprising a nucleotide sequence encoding a GeoCas9 fusion polypeptide of the present disclosure, and a second recombinant expression vector comprising a nucleotide sequence encoding a GeoCas9 guide RNA; p) a first recombinant expression vector comprising a nucleotide sequence encoding a GeoCas9 fusion polypeptide of the present disclosure, and a second recombinant expression vector comprising a nucleotide sequence encoding a GeoCas9 guide RNA; and a donor template nucleic acid; q) a recombinant expression vector comprising a nucleotide sequence encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), a nucleotide sequence encoding a first GeoCas9 guide RNA, and a nucleotide sequence encoding a second GeoCas9 guide RNA; or r) a recombinant expression vector comprising a nucleotide sequence encoding a GeoCas9 fusion polypeptide of the present disclosure, a nucleotide sequence encoding a first GeoCas9 guide RNA, and a nucleotide sequence encoding a second GeoCas9 guide RNA; or some variation of one of (a) through (r). In one aspect, the aminoalcohol lipidoid compounds are combined with an agent to be delivered to a cell or a subject to form microparticles, nanoparticles, liposomes, or micelles. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A poly(beta-amino alcohol) (PBAA) can be used to deliver a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), an RNP of the present disclosure, a nucleic acid of the present disclosure, or a GeoCas9 system of the present disclosure, to a target cell. US Patent Publication No. 20130302401 relates to a class of poly(beta-amino alcohols) (PBAAs) that has been prepared using combinatorial polymerization.

Sugar-based particles may be used, for example GalNAc, as described with reference to WO2014118272 (incorporated herein by reference) and Nair, J K et al., 2014, Journal of the American Chemical Society 136 (49), 16958-16961) can be used to deliver a GeoCas9 polypeptide of the present disclosure, a GeoCas9 fusion polypeptide of the present disclosure, an RNP of the present disclosure, a nucleic acid of the present disclosure, or a GeoCas9 system of the present disclosure, to a target cell.

In some cases, lipid nanoparticles (LNPs) are used to deliver a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), an RNP of the present disclosure, a nucleic acid of the present disclosure, or a GeoCas9 system of the present disclosure, to a target cell. Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)[1,3]-dioxolane (DLinKC2-DMA). Preparation of LNPs and is described in, e.g., Rosin et al. (2011) Molecular Therapy 19:1286-2200). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(.omega.-methoxy-poly(ethylene glycol)2000) carbamoyl]-1,2-dimyristyloxlpropyl-3-amine (PEG-C-DOMG) may be used. A nucleic acid (e.g., a GeoCas9 guide RNA; a nucleic acid of the present disclosure; etc.) may be encapsulated in LNPs containing DLinDAP, DLinDMA, DLinK-DMA, and DLinKC2-DMA (cationic lipid:DSPC:CHOL:PEGS-DMG or PEG-C-DOMG at 40:10:40:10 molar ratios). In some cases, 0.2% SP-DiOC18 is incorporated.

Spherical Nucleic Acid (SNA™) constructs and other nanoparticles (particularly gold nanoparticles) can be used to deliver a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), an RNP of the present disclosure, a nucleic acid of the present disclosure, or a GeoCas9 system of the present disclosure, to a target cell. See, e.g., Cutler et al., J. Am. Chem. Soc. 2011 133:9254-9257, Hao et al., Small 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19): 7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG).

In general, a "nanoparticle" refers to any particle having a diameter of less than 1000 nm. In some cases, nanoparticles suitable for use in delivering a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), an RNP of the present disclosure, a nucleic acid of the present disclosure, or a GeoCas9 system of the present disclosure, to a target cell have a diameter of 500 nm or less, e.g., from 25 nm to 35 nm, from 35 nm to 50 nm, from 50 nm to 75 nm, from 75 nm to 100 nm, from 100 nm to 150 nm, from 150 nm to 200 nm, from 200 nm to 300 nm, from 300 nm to 400 nm, or from 400 nm to 500 nm. In some cases, nanoparticles suitable for use in delivering a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), an RNP of the present disclosure, a nucleic acid of the present disclosure, or a GeoCas9 system of the present disclosure, to a target cell have a diameter of from 25 nm to 200 nm. In some cases, nanoparticles suitable for use in delivering a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), an RNP of the present disclosure, a nucleic acid of the present disclosure, or a GeoCas9 system of the present disclosure, to a target cell have a diameter of 100 nm or less In some cases, nanoparticles suitable for use in delivering a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), an RNP of the present disclosure, a nucleic acid of the present disclosure, or a GeoCas9 system of the present disclosure, to a target cell have a diameter of from 35 nm to 60 nm.

Nanoparticles suitable for use in delivering a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), an RNP of the present disclosure, a nucleic acid of the present disclosure, or a GeoCas9 system of the present disclosure, to a target cell may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically below 10 nm) that quantization of electronic energy levels occurs. Such nanoscale particles are used in biomedical applications as drug carriers or imaging agents and may be adapted for similar purposes in the present disclosure.

Semi-solid and soft nanoparticles are also suitable for use in delivering a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), an RNP of the present disclosure, a nucleic acid of the present disclosure, or a GeoCas9 system of the present disclosure, to a target cell. A prototype nanoparticle of semi-solid nature is the liposome.

In some cases, an exosome is used to deliver a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.) an RNP of the present disclosure, a nucleic acid of the present disclosure, or a GeoCas9 system of the present disclosure, to a target cell. Exosomes are endogenous nano-vesicles that transport RNAs and proteins, and which can deliver RNA to the brain and other target organs.

In some cases, a liposome is used to deliver a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), an RNP of the present disclosure, a nucleic acid of the present disclosure, or a GeoCas9 system of the present disclosure, to a target cell. Liposomes are spherical vesicle structures composed of a uni- or multilamellar lipid bilayer surrounding internal aqueous compartments and a relatively impermeable outer lipophilic phospholipid bilayer. Liposomes can be made from several different types of lipids; however, phospholipids are most commonly used to generate liposomes. Although liposome formation is spontaneous when a lipid film is mixed with an aqueous solution, it can also be expedited by applying force in the form of shaking by using a homogenizer, sonicator, or an extrusion apparatus. Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside.

A stable nucleic-acid-lipid particle (SNALP) can be used to deliver a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), an RNP of the present disclosure, a nucleic acid of the present disclosure, or a GeoCas9 system of the present disclosure, to a target cell. The SNALP formulation may contain the lipids 3-N-[(methoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio. The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulting SNALP liposomes can be about 80-100 nm in size. A SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol)2000) carbamoyl]-1,2-dimyrestyloxypropylamine, and cationic 1,2-dilinoleyloxy-3-N,Ndimethylaminopropane. A SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N;N-dimethyl)aminopropane (DLinDMA).

Other cationic lipids, such as amino lipid 2,2-dilinoleyl-4-dimethylaminoethyl-[1,3]-dioxolane (DLin-KC2-DMA) can be used to deliver a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), an RNP of the present disclosure, a nucleic acid of the present disclosure, or a GeoCas9 system of the present disclosure, to a target cell. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11.+−.0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Lipids may be formulated with a GeoCas9 system of the present disclosure or component(s) thereof or nucleic acids encoding the same to form lipid nanoparticles (LNPs). Suitable lipids include, but are not limited to, DLin-KC2-DMA4, C12-200 and colipids disteroylphosphatidyl choline, cholesterol, and PEG-DMG may be formulated with a GeoCas9 system, or component thereof, of the present disclosure, using a spontaneous vesicle formation procedure. The component molar ratio may be about 50/10/38.5/1.5 (DLin-KC2-DMA or C12-200/disteroylphosphatidyl choline/cholesterol/PEG-DMG).

A GeoCas9 system of the present disclosure, or a component thereof, may be delivered encapsulated in PLGA microspheres such as that further described in US published applications 20130252281 and 20130245107 and 20130244279.

Supercharged proteins can be used to deliver a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), an RNP of the present disclosure, a nucleic acid of the present disclosure, or a GeoCas9 system of the present disclosure, to a target cell. Supercharged proteins are a class of engineered or naturally occurring proteins with unusually high positive or negative net theoretical charge. Both supernegatively and superpositively charged proteins exhibit the ability to withstand thermally or chemically induced aggregation. Superpositively charged proteins are also able to penetrate mammalian cells. Associating cargo with these proteins, such as plasmid DNA, RNA, or other proteins, can facilitate the functional delivery of these macromolecules into mammalian cells both in vitro and in vivo.

Cell Penetrating Peptides (CPPs) can be used to deliver a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), an RNP of the present disclosure, a nucleic acid of the present disclosure, or a GeoCas9 system of the present disclosure, to a target cell. CPPs typically have an amino acid composition that either contains a high relative abundance of positively charged amino acids such as lysine or arginine or has sequences that contain an alternating pattern of polar/charged amino acids and non-polar, hydrophobic amino acids.

An implantable device can be used to deliver a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), an RNP of the present disclosure, a nucleic acid of the present disclosure (e.g., a GeoCas9 guide RNA, a nucleic acid encoding a GeoCas9 guide RNA, a nucleic acid encoding GeoCas9 polypeptide, a donor template, and the like), or a GeoCas9 system of the present disclosure, to a target cell (e.g., a target cell in vivo, where the target cell is a target cell in circulation, a target cell in a tissue, a target cell in an organ, etc.). An implantable device suitable for use in delivering a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), an RNP of the present disclosure, a nucleic acid of the present disclosure, or a GeoCas9 system of the present disclosure, to a target cell (e.g., a target cell in vivo, where the target cell is a target cell in circulation, a target cell in a tissue, a target cell in an organ, etc.) can include a container (e.g., a reservoir, a matrix, etc.) that comprises the GeoCas9 polypeptide, the GeoCas9 fusion polypeptide, the RNP, or the GeoCas9 system (or component thereof, e.g., a nucleic acid of the present disclosure).

A suitable implantable device can comprise a polymeric substrate, such as a matrix for example, that is used as the device body, and in some cases additional scaffolding materials, such as metals or additional polymers, and materials to enhance visibility and imaging. An implantable delivery device can be advantageous in providing release locally and over a prolonged period, where the polypeptide and/or nucleic acid to be delivered is released directly to a target site, e.g., the extracellular matrix (ECM), the vasculature surrounding a tumor, a diseased tissue, etc. Suitable implantable delivery devices include devices suitable for use in delivering to a cavity such as the abdominal cavity and/or any other type of administration in which the drug delivery system is not anchored or attached, comprising a biostable and/or degradable and/or bioabsorbable polymeric substrate, which may for example optionally be a matrix. In some cases, a suitable implantable drug delivery device comprises degradable polymers, wherein the main release mechanism is bulk erosion. In some cases, a suitable implantable drug delivery device comprises non degradable, or slowly degraded polymers, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the can be maintained effectively constant during a significant period of the total releasing period, and therefore the diffusion rate is effectively constant (termed "zero mode" diffusion). By the term "constant" it is meant a diffusion rate that is maintained above the lower threshold of therapeutic effectiveness, but which may still optionally feature an initial burst and/or may fluctuate, for example increasing and decreasing to a certain degree. The diffusion rate can be so maintained for a prolonged period, and it can be considered constant to a certain level to optimize the therapeutically effective period, for example the effective silencing period.

In some cases, the implantable delivery system is designed to shield the nucleotide based therapeutic agent from degradation, whether chemical in nature or due to attack from enzymes and other factors in the body of the subject.

The site for implantation of the device, or target site, can be selected for maximum therapeutic efficacy. For example, a delivery device can be implanted within or in the proximity of a tumor environment, or the blood supply associated with a tumor. The target location can be, e.g.: 1) the brain at degenerative sites like in Parkinson or Alzheimer disease at the basal ganglia, white and gray matter; 2) the spine, as in the case of amyotrophic lateral sclerosis (ALS); 3) uterine cervix; 4) active and chronic inflammatory joints; 5) dermis as in the case of psoriasis; 7) sympathetic and sensory nervous sites; 7) a bone; 8) a site of acute or chronic infection; 9) intra vaginal; 10) inner ear-auditory system, labyrinth of the inner ear, vestibular system; 11) intra tracheal; 12) intra-cardiac; coronary, epicardiac; 13) urinary tract or bladder; 14) biliary system; 15) parenchymal tissue including and not limited to the kidney, liver, spleen; 16) lymph nodes; 17) salivary glands; 18) dental gums; 19) intra-articular (into joints); 20) intra-ocular; 21) brain tissue; 22) brain ventricles; 23) cavities, including abdominal cavity (for example but without limitation, for ovarian cancer); 24) Intra esophageal; and 25) intra rectal; and 26) into the vasculature.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as stereotactic methods into the brain tissue, laparoscopy, including implantation with a laparoscope into joints, abdominal organs, the bladder wall and body cavities.

Compositions

The present disclosure provides compositions, including pharmaceutical compositions, comprising a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), a nucleic acid of the present disclosure, a GeoCas9 RNP of the present disclosure, or a GeoCas9 system of the present disclosure.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, phosphate buffered saline (PBS), Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The components used to formulate the pharmaceutical compositions are generally of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Cells

The present disclosure provides a modified cell comprising a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.) and/or a nucleic acid comprising a nucleotide sequence encoding a GeoCas9 polypeptide. The present disclosure provides a modified cell comprising a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.), where the modified cell is a cell that does not normally comprise a GeoCas9. The present disclosure provides a modified cell (e.g., a genetically modified cell) comprising nucleic acid comprising a nucleotide sequence encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.). The present disclosure provides a genetically modified cell that is genetically modified with an mRNA comprising a nucleotide sequence encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.). The present disclosure provides a genetically modified cell that is genetically modified with a recombinant expression vector comprising a nucleotide sequence encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.). The present disclosure provides a genetically modified cell that is genetically modified with a recombinant expression vector comprising: a) a nucleotide sequence encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.); and b) a nucleotide sequence encoding a GeoCas9 guide RNA of the present disclosure. The present disclosure provides a genetically modified cell that is genetically modified with a recombinant expression vector comprising: a) a nucleotide sequence encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.); b) a nucleotide sequence encoding a GeoCas9 guide RNA of the present disclosure; and c) a nucleotide sequence encoding a donor template.

A cell that serves as a recipient for a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.) and/or a nucleic acid comprising a nucleotide sequence encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.) and/or a GeoCas9 guide RNA of the present disclosure, can be any of a variety of cells, including, e.g., in vitro cells; in vivo cells; ex vivo cells; primary cells; cancer cells; animal cells; plant cells; algal cells; fungal cells; etc. A cell that serves as a recipient for a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.) and/or a nucleic acid comprising a nucleotide sequence encoding a GeoCas9 polypeptide (e.g., a wild-type GeoCas9 polypeptide; a variant GeoCas9 polypeptide; a variant GeoCas9 polypeptide comprising a heterologous PI domain; a fusion GeoCas9 polypeptide; etc.) and/or a GeoCas9 guide RNA of the present disclosure is referred to as a "host cell" or a "target cell." A host cell or a target cell can be a recipient of a GeoCas9 system of the present disclosure. A host cell or a target cell can be a recipient of a GeoCas9 RNP of the present disclosure. A host cell or a target cell can be a recipient of a single component of a GeoCas9 system of the present disclosure.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatos, rice, cassava, sugarcane, pumpkin, hay, potatos, cotton, cannabis, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., an insect, an arachnid, a fruit fly, a cnidarian, an echinoderm, a nematode, etc.), a cell from a vertebrate animal (e.g., fish, amphibian, reptile, bird, mammal), a cell from a mammal (e.g., an ungulate (e.g., a pig, a cow, a goat, a sheep, a camel); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell. A cell can be an insect cell. A cell can be an arachnid cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera, or Lepidoptera.

A cell is in some cases an insect cell. For example, in some cases, the cell is a cell of a mosquito, a grasshopper, a true bug, a fly, a flea, a bee, a wasp, an ant, a louse, a moth, or a beetle.

In some cases, a suitable cell is a prokaryotic cell. In some cases, the cell is a thermophilic prokaryotic cell. In some cases, the cell is an obligate thermophile (e.g., an obligate thermophilic prokaryotic cell). In some cases, the cell is a microorganism selected from a *Cupriavidus* sp., *Ralstonia* sp, *Xanthobacter* sp., *Rhodococcus* sp., *Hydrogenovibrio* sp., *Rhodopseudomonas* sp., *Rhodobacter* sp., *Hydrogenobacter* sp., *Arthrobacter* sp., *Paracoccus* sp., *Mycobacterium* sp., *Streptomyces* sp., and *Bacillus* sp.

In some cases, the host cell is a microorganism. In some cases, the microorganism is *Rhodococcus opacus* or *Rhodococcus jostii* or *Rhodococcus* sp. In some cases, the microorganism is *Hydrogenovibrio marinus*. In some cases, the microorganism is *Rhodopseudomonas capsulata*, *Rhodopseudomonas palustris*, or *Rhodobacter sphaeroides*. In some cases, the microorganism is an oxyhydrogen or knallgas strain. In some cases, the microorganism is selected from: *Aquifex pyrophilus* and *Aquifex aeolicus* or other *Aquifex* sp.; *Cupriavidus necator* or *Cupriavidus metallidurans* or other *Cupriavidus* sp.; *Corynebacterium autotrophicum* or other *Corynebacterium* sp.; *Nocardia autotrophica* and *Nocardia opaca* and other *Nocardia* sp.; purple non-sulfur photosynthetic bacteria including but not limited to *Rhodopseudomonas palustris*, *Rhodopseudomonas capsulata*, *Rhodopseudomonas viridis*, *Rhodopseudomonas sulfoviridis*, *Rhodopseudomonas blastica*, *Rhodopseudomonas spheroides*, *Rhodopseudomonas acidophila* and other *Rhodopseudomonas* sp., *Rhodospirillum rubrum*, and other *Rhodospirillum* sp.; *Rhodococcus opacus* and other *Rhodococcus* sp.; *Rhizobium japonicum* and other *Rhizobium* sp.; *Thiocapsa roseopersicina* and other *Thiocapsa* sp.; *Pseudomonas facilis* and *Pseudomonas flava* and *Pseudomonas putida* and *Pseudomonas hydrogenovora*, *Pseudomonas hydrogenothermophila*, *Pseudomonas palleronii* and *Pseudomonas pseudoflava* and *Pseudomonas saccharophila* and *Pseudomonas thermophila* and other *Pseudomonas* sp.; *Hydrogenomonas pantotropha*, *Hydrogenomonas eutropha*, *Hydrogenomonas facilis*, and other *Hydrogenomonas* sp.; *Hydrogenobacter thermophilus* and *Hydrogenobacter halophilus* and *Hydrogenobacter hydrogenophilus* and other *Hydrogenobacter* sp.; *Hydrogenophilus islandicus* and other *Hydrogenophilus* sp.; *Hydrogenovibrio marinus* and other *Hydrogenovibrio* sp.; *Hydrogenothermus marinus* and other *Hydrogenothermus* sp.; *Helicobacter pylori* and other *Helicobacter* sp.; *Xanthobacter autotrophicus* and *Xanthobacter flavus* other *Xanthobacter* sp.; *Hydrogenophaga flava* and *Hydrogenophaga palleronii* and *Hydrogenophaga pseudoflava* and other *Hydrogenophaga* sp.; *Bradyrhizobium japonicum* and other *Bradyrhizobium* sp.; *Ralstonia eutropha* and other *Ralstonia* sp.; *Alcaligenes eutrophus* and *Alcaligenes facilis* and *Alcaligenes hydrogenophilus* and *Alcaligenes latus* and *Alcaligenes paradoxus* and *Alcaligenes ruhlandii* and other *Alcaligenes* sp.; *Amycolata* sp.; *Aquaspirillum autotrophicum* and other *Aquaspirillum* sp.; *Arthrobacter* strain 11/X and other *Arthrobacter* sp.; *Azospirillum lipoferum* and other *Azospirillum* sp.; *Variovorax paradoxus*, and other *Variovorax* sp.; *Acidovorax facilis*, and other *Acidovorax* sp.; *Bacillus schlegelii* and *Bacillus tusciae* and other *Bacillus* sp.; *Calderobacterium hydrogenophilum* and other *Calderobac-* terium sp.; *Derxia gummosa* and other *Derxia* sp.; *Flavobacterium autothermophilum* and other *Flavobacterium* sp.; *Microcyclus aquaticus* and other *Microcyclus*; *Mycobacterium gordoniae* and other *Mycobacterium* sp.; *Paracoccus denitrificans* and other *Paracoccus* sp.; *Persephonella marina* and *Persephonella guaymasensis* and other *Persephonella* sp.; *Renobacter vacuolatum* and other *Renobacter* sp.; *Thermocrinis ruber* and other *Thermocrinis* sp.; *Wautersia* sp.; cyanobacteria including but not limited to *Anabaena oscillarioides, Anabaena spiroides, Anabaena cylindrica*, and other *Anabaena* sp.; green algae including but not limited to *Scenedesmus obliquus* and other *Scenedesmus* sp., *Chlamydomonas reinhardtii* and other *Chlamydomonas* sp., *Ankistrodesmus* sp., *Rhaphidium polymorphium* and other *Rhaphidium* sp; as well as a consortiums of microorganisms that include oxyhydrogen microorganisms.

In some cases, the host cell is an obligate and/or facultative chemoautotrophic microorganism selected from: *Acetoanaerobium* sp.; *Acetobacterium* sp.; *Acetogenium* sp.; *Achromobacter* sp.; *Acidianus* sp.; *Acinetobacter* sp.; *Actinomadura* sp.; *Aeromonas* sp.; *Alcaligenes* sp.; *Alcaligenes* sp.; *Arcobacter* sp.; *Aureobacterium* sp.; *Bacillus* sp.; *Beggiatoa* sp.; *Butyribacterium* sp.; *Carboxydothermus* sp.; *Clostridium* sp.; *Comamonas* sp.; *Dehalobacter* sp.; *Dehalococcoide* sp.; *Dehalospirillum* sp.; *Desulfobacterium* sp.; *Desulfomonile* sp.; *Desulfotomaculum* sp.; *Desulfovibrio* sp.; *Desulfurosarcina* sp.; *Ectothiorhodospira* sp.; *Enterobacter* sp.; *Eubacterium* sp.; *Ferroplasma* sp.; *Halothibacillus* sp.; *Hydrogenobacter* sp.; *Hydrogenomonas* sp.; *Leptospirillum* sp.; *Metallosphaera* sp.; *Methanobacterium* sp.; *Methanobrevibacter* sp.; *Methanococcus* sp.; *Methanosarcina* sp.; *Micrococcus* sp.; *Nitrobacter* sp.; *Nitrosococcus* sp.; *Nitrosolobus* sp.; *Nitrosomonas* sp.; *Nitrosospira* sp.; *Nitrosovibrio* sp.; *Nitrospina* sp.; *Oleomonas* sp.; *Paracoccus* sp.; *Peptostreptococcus* sp.; *Planctomycetes* sp.; *Pseudomonas* sp.; *Ralstonia* sp.; *Rhodobacter* sp.; *Rhodococcus* sp.; *Rhodocyclus* sp.; *Rhodomicrobium* sp.; *Rhodopseudomonas* sp.; *Rhodospirillum* sp.; *Shewanella* sp.; *Streptomyces* sp.; *Sulfobacillus* sp.; *Sulfolobus* sp.; *Thiobacillus* sp.; *Thiomicrospira* sp.; *Thioploca* sp.; *Thiosphaera* sp.; *Thiothrix* sp.; sulfur-oxidizers; hydrogen-oxidizers; iron-oxidizers; acetogens; and methanogens; consortiums of microorganisms that include chemoautotrophs; chemoautotrophs native to at least one of hydrothermal vents, geothermal vents, hot springs, cold seeps, underground aquifers, salt lakes, saline formations, mines, acid mine drainage, mine tailings, oil wells, refinery wastewater, coal seams, deep sub-surface; waste water and sewage treatment plants; geothermal power plants, sulfatara fields, and soils; and extremophiles selected from one or more of thermophiles, hyperthermophiles, acidophiles, halophiles, and psychrophiles.

Geocas9 Systems and Geocas9 Ribonucleoprotein Complexes

The present disclosure provides systems and ribonucleoprotein (RNP) complexes comprising a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure).

The present disclosure provides a GeoCas system. A GeoCas system of the present disclosure can comprise: a) a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure) and a GeoCas guide RNA; b) a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure), a GeoCas guide RNA, and a donor template nucleic acid; c) a GeoCas fusion polypeptide of the present disclosure and a GeoCas guide RNA; d) a GeoCas fusion polypeptide of the present disclosure, a GeoCas guide RNA, and a donor template nucleic acid; e) an mRNA encoding a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure); and a GeoCas guide RNA; f) an mRNA encoding a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure), a GeoCas guide RNA, and a donor template nucleic acid; g) an mRNA encoding a GeoCas fusion polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure); and a GeoCas guide RNA; h) an mRNA encoding a GeoCas fusion polypeptide of the present disclosure, a GeoCas guide RNA, and a donor template nucleic acid; i) a recombinant expression vector comprising a nucleotide sequence encoding a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure) and a nucleotide sequence encoding a GeoCas guide RNA; j) a recombinant expression vector comprising a nucleotide sequence encoding a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure), a nucleotide sequence encoding a GeoCas guide RNA, and a nucleotide sequence encoding a donor template nucleic acid; k) a recombinant expression vector comprising a nucleotide sequence encoding a GeoCas fusion polypeptide of the present disclosure and a nucleotide sequence encoding a GeoCas guide RNA; 1) a recombinant expression vector comprising a nucleotide sequence encoding a GeoCas fusion polypeptide of the present disclosure, a nucleotide sequence encoding a GeoCas guide RNA, and a nucleotide sequence encoding a donor template nucleic acid; m) a first recombinant expression vector comprising a nucleotide sequence encoding a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure), and a second recombinant expression vector comprising a nucleotide sequence encoding a GeoCas guide RNA; n) a first recombinant expression vector comprising a nucleotide sequence encoding a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure), and a second recombinant expression vector comprising a nucleotide sequence encoding a GeoCas guide RNA; and a donor template nucleic acid; o) a first recombinant expression vector comprising a nucleotide sequence encoding a GeoCas fusion polypeptide of the present disclosure, and a second recombinant expression vector comprising a nucleotide sequence encoding a GeoCas guide RNA; p) a first recombinant expression vector comprising a nucleotide sequence encoding a GeoCas fusion polypeptide of the present disclosure, and a second recombinant expression vector comprising a nucleotide sequence encoding a GeoCas guide RNA; and a donor template nucleic acid; q) a recombinant expression vector comprising a nucleotide sequence encoding a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure), a nucleotide sequence encoding a first GeoCas guide RNA, and a nucleotide sequence encoding a second GeoCas guide RNA; or r) a recombinant expression vector comprising a nucleotide sequence encoding a GeoCas fusion polypeptide of the present disclosure, a nucleotide sequence encoding a first GeoCas guide RNA, and a nucleotide sequence encoding a second GeoCas9 guide RNA; or some variation of one of (a) through (r).

Multicellular Non-Human Organisms

The present disclosure provides a multicellular non-human organism comprising one or more of: a) a nucleic acid comprising a nucleotide sequence encoding a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure); b) a GeoCas9 guide RNA; c) a nucleic acid comprising a nucleotide sequence encoding a GeoCas9 guide RNA; d) a donor template; and e) a nucleic acid comprising a nucleotide sequence encoding a donor template. The nucleic acid(s) can be integrated into the genome of the host organism. The nucleic acid(s) can be integrated into the genome of all cells of the host organism. The nucleic acid(s) can be integrated into the genome of a subset of the cells of the host organism. The nucleic acid(s) can be extrachromosomal.

In some cases, a nucleic acid (e.g., a recombinant expression vector) of the present disclosure (e.g., a nucleic acid comprising a nucleotide sequence encoding a GeoCas9 polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure) is used as a transgene to generate a transgenic non-human organism that produces a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure). The present disclosure provides a transgenic-non-human organism comprising a nucleotide sequence encoding a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure).

Transgenic, Non-Human Animals

The present disclosure provides a transgenic non-human animal, which animal comprises a transgene comprising a nucleic acid comprising a nucleotide sequence encoding a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure). In some embodiments, the genome of the transgenic non-human animal comprises a nucleotide sequence encoding a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure). In some cases, the transgenic non-human animal is homozygous for the genetic modification. In some cases, the transgenic non-human animal is heterozygous for the genetic modification. In some embodiments, the transgenic non-human animal is a vertebrate, for example, a fish (e.g., salmon, trout, zebra fish, gold fish, puffer fish, cave fish, etc.), an amphibian (frog, newt, salamander, etc.), a bird (e.g., chicken, turkey, etc.), a reptile (e.g., snake, lizard, etc.), a non-human mammal (e.g., an ungulate, e.g., a pig, a cow, a goat, a sheep, etc.; a lagomorph (e.g., a rabbit); a rodent (e.g., a rat, a mouse); a non-human primate; etc.), etc. In some cases, the transgenic non-human animal is an invertebrate. In some cases, the transgenic non-human animal is an insect (e.g., a mosquito; an agricultural pest; etc.). In some cases, the transgenic non-human animal is an arachnid.

Nucleotide sequences encoding a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure) can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., cytomegalovirus promoter), inducible promoters (e.g., heat shock promoter, tetracycline-regulated promoter, steroid-regulated promoter, metal-regulated promoter, estrogen receptor-regulated promoter, etc.), spatially restricted and/or temporally restricted promoters (e.g., a tissue specific promoter, a cell type specific promoter, etc.), etc.

Transgenic Plants

As described above, in some cases, a nucleic acid (e.g., a recombinant expression vector) of the present disclosure (e.g., a nucleic acid comprising a nucleotide sequence encoding a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure)), is used as a transgene to generate a transgenic plant that produces a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure). The present disclosure provides a transgenic plant comprising a nucleotide sequence encoding a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure). In some embodiments, the genome of the transgenic plant comprises a subject nucleic acid. In some embodiments, the transgenic plant is homozygous for the genetic modification. In some embodiments, the transgenic plant is heterozygous for the genetic modification.

Methods of introducing exogenous nucleic acids into plant cells are well known in the art. Such plant cells are considered "transformed," as defined above. Suitable methods include viral infection (such as double stranded DNA viruses), transfection, conjugation, protoplast fusion, electroporation, particle gun technology, calcium phosphate precipitation, direct microinjection, silicon carbide whiskers technology, Agrobacterium-mediated transformation and the like. The choice of method is generally dependent on the type of cell being transformed and the circumstances under which the transformation is taking place (i.e. in vitro, ex vivo, or in vivo).

Transformation methods based upon the soil bacterium Agrobacterium tumefaciens are particularly useful for introducing an exogenous nucleic acid molecule into a vascular plant. The wild type form of Agrobacterium contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An Agrobacterium-based vector is a modified form of a Ti plasmid, in which the tumor inducing functions are replaced by the nucleic acid sequence of interest to be introduced into the plant host.

Agrobacterium-mediated transformation generally employs cointegrate vectors or binary vector systems, in which the components of the Ti plasmid are divided between a helper vector, which resides permanently in the Agrobacterium host and carries the virulence genes, and a shuttle vector, which contains the gene of interest bounded by T-DNA sequences. A variety of binary vectors is well known in the art and are commercially available, for example, from Clontech (Palo Alto, Calif.). Methods of coculturing Agrobacterium with cultured plant cells or wounded tissue such as leaf tissue, root explants, hypocotyledons, stem pieces or tubers, for example, also are well known in the art. See, e.g., Glick and Thompson, (eds.), Methods in Plant Molecular Biology and Biotechnology, Boca Raton, Fla.: CRC Press (1993).

Microprojectile-mediated transformation also can be used to produce a subject transgenic plant. This method, first described by Klein et al. (Nature 327:70-73 (1987)), relies on microprojectiles such as gold or tungsten that are coated with the desired nucleic acid molecule by precipitation with calcium chloride, spermidine or polyethylene glycol. The microprojectile particles are accelerated at high speed into an angiosperm tissue using a device such as the BIOLISTIC PD-1000 (Biorad; Hercules Calif.).

A nucleic acid of the present disclosure (e.g., a nucleic acid (e.g., a recombinant expression vector) comprising a nucleotide sequence encoding a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure)) may be introduced into a plant in a manner such that the nucleic acid is able to enter a plant cell(s), e.g., via an in vivo or ex vivo protocol. By "in vivo," it is meant in the nucleic acid is administered to a living body of a plant e.g. infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of Agrobacterium tumefaciens, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9:957-9 and 4462) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for Agrobacterium-mediated DNA transfer (Ishida et al. (1996) Nature Biotech 14: 745-750). Exemplary methods for introduction of DNA into chloroplasts are biolistic bombardment, polyethylene glycol transformation of protoplasts, and microinjection (Danieli et al Nat. Biotechnol 16:345-348, 1998; Staub et al Nat. Biotechnol 18: 333-338, 2000; O'Neill et al Plant J. 3:729-738, 1993; Knoblauch et al Nat. Biotechnol 17: 906-909; U.S. Pat. Nos. 5,451,513, 5,545,817, 5,545,818, and 5,576, 198; in Intl. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Natl. Acad. Sci. USA 91: 7301-7305 (1994)). Any vector suitable for the methods of biolistic bombardment, polyethylene glycol transformation of protoplasts and microinjection will be suitable as a targeting vector for chloroplast transformation. Any double stranded DNA vector may be used as a transformation vector, especially when the method of introduction does not utilize Agrobacterium.

Plants which can be genetically modified include grains, forage crops, fruits, vegetables, oil seed crops, palms, forestry, and vines. Specific examples of plants which can be modified follow: maize, banana, peanut, field peas, sunflower, tomato, canola, tobacco, wheat, barley, oats, potato, soybeans, cotton, carnations, sorghum, lupin and rice.

The present disclosure provides transformed plant cells, tissues, plants and products that contain the transformed plant cells. A feature of the subject transformed cells, and tissues and products that include the same is the presence of a subject nucleic acid integrated into the genome, and production by plant cells of a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure). Recombinant plant cells of the present invention are useful as populations of recombinant cells, or as a tissue, seed, whole plant, stem, fruit, leaf, root, flower, stem, tuber, grain, animal feed, a field of plants, and the like.

Nucleotide sequences encoding a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure) can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters, inducible promoters, spatially restricted and/or temporally restricted promoters, etc.

Utility

The above-described RNA-guided endonucleases, GeoCas fusion polypeptides, nucleic acids, RNPs, and expression vectors, find use in a variety of methods. For example, the above-described RNA-guided endonucleases, GeoCas fusion polypeptides, nucleic acids, RNPs, and expression vectors, find use in modifying a target nucleic acid.

Methods of Modifying a Target Nucleic Acid

A GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure), finds use in a variety of methods (e.g., in combination with a GeoCas9 guide RNA and in some cases further in combination with a donor template). For example, a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure) can be used to (i) modify (e.g., cleave, e.g., nick; methylate; etc.) target nucleic acid (DNA or RNA; single stranded or double stranded); (ii) modulate transcription of a target nucleic acid; (iii) label a target nucleic acid; (iv) bind a target nucleic acid (e.g., for purposes of isolation, labeling, imaging, tracking, etc.); (v) modify a polypeptide (e.g., a histone) associated with a target nucleic acid; and the like. Thus, the present disclosure provides a method of modifying a target nucleic acid. In some cases, a method of the present disclosure for modifying a target nucleic acid comprises contacting the target nucleic acid with: a) a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure); and b) one or more (e.g., two) GeoCas9 guide RNAs. In some cases, a method of the present disclosure for modifying a target nucleic acid comprises contacting the target nucleic acid with: a) a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure); b) a GeoCas9 guide RNA; and c) a donor nucleic acid (e.g., a donor template). In some cases, the contacting step is carried out in a cell in vitro. In some cases, the contacting step is carried out in a cell in vivo. In some cases, the contacting step is carried out in a cell ex vivo.

Because a method that uses a GeoCas9 polypeptide includes binding of the GeoCas9 polypeptide to a particular region in a target nucleic acid (by virtue of being targeted there by an associated GeoCas9 guide RNA), the methods are generally referred to herein as methods of binding (e.g., a method of binding a target nucleic acid). However, it is to be understood that in some cases, while a method of binding may result in nothing more than binding of the target nucleic acid, in other cases, the method can have different final results (e.g., the method can result in modification of the target nucleic acid, e.g., cleavage/methylation/etc., modulation of transcription from the target nucleic acid; modulation of translation of the target nucleic acid; genome editing; modulation of a protein associated with the target nucleic acid; isolation of the target nucleic acid; etc.).

For examples of suitable methods, see, for example, Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al, Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et. at., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; each of which is hereby incorporated by reference in its entirety.

For example, the present disclosure provides (but is not limited to) methods of cleaving a target nucleic acid; methods of editing a target nucleic acid; methods of modulating transcription from a target nucleic acid; methods of isolating a target nucleic acid, methods of binding a target nucleic acid, methods of imaging a target nucleic acid, methods of modifying a target nucleic acid, and the like.

As used herein, the terms/phrases "contact a target nucleic acid" and "contacting a target nucleic acid", for example, with a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure), etc., encompass all methods for contacting the target nucleic acid. For example, a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure) can be provided to a cell as protein, RNA (encoding the GeoCas9 polypeptide), or DNA (encoding the GeoCas9 polypeptide); while a GeoCas9 guide RNA can be provided as a guide RNA or as a nucleic acid encoding the guide RNA. As such, when, for example, performing a method in a cell (e.g., inside of a cell in vitro, inside of a cell in vivo, inside of a cell ex vivo), a method that includes contacting the target nucleic acid encompasses the introduction into the cell of any or all of the components in their active/final state (e.g., in the form of a protein(s) for a GeoCas9 polypeptide; in the form of a protein for a GeoCas9 fusion polypeptide; in the form of an RNA in some cases for a GeoCas9 guide RNA), and also encompasses the introduction into the cell of one or more nucleic acids encoding one or more of the components (e.g., nucleic acid(s) comprising nucleotide sequence(s) encoding a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure), nucleic acid(s) comprising nucleotide sequence(s) encoding guide RNA(s), nucleic acid comprising a nucleotide sequence encoding a donor template, and the like). Because the methods can also be performed in vitro outside of a cell, a method that includes contacting a target nucleic acid, (unless otherwise specified) encompasses contacting outside of a cell in vitro, inside of a cell in vitro, inside of a cell in vivo, inside of a cell ex vivo, etc.

In some cases, a method of the present disclosure for modifying a target nucleic acid comprises contacting a target nucleic acid with a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure). In some cases, a method of the present disclosure for modifying a target nucleic acid comprises contacting a target nucleic acid with a GeoCas9 polypeptide and a GeoCas9 guide RNA. In some cases, a method of the present disclosure for modifying a target nucleic acid comprises contacting a target nucleic acid with a GeoCas polypeptide (e.g., a wild-type GeoCas polypeptide; a GeoCas9 variant; a GeoCas9 polypeptide of the present disclosure (e.g., a GeoCas9 polypeptide comprising a heterologous PI domain); or a GeoCas9 fusion polypeptide of the present disclosure), a first GeoCas9 guide RNA, and a second GeoCas9 guide RNA In some cases, a method of the present disclosure for modifying a target nucleic acid comprises contacting a target nucleic acid with a GeoCas polypeptide (e.g., a wild-type GeoCas polypeptide; a GeoCas9 variant; a GeoCas polypeptide of the present disclosure (e.g., a GeoCas9 polypeptide comprising a heterologous PI domain); or a GeoCas fusion polypeptide of the present disclosure) and a GeoCas9 guide RNA and a donor DNA template.

Target Nucleic Acids and Target Cells of Interest

A GeoCas polypeptide (e.g., a wild-type GeoCas polypeptide; a GeoCas9 variant; a GeoCas9 polypeptide of the present disclosure (e.g., a GeoCas9 polypeptide comprising a heterologous PI domain); or a GeoCas9 fusion polypeptide of the present disclosure), when bound to a GeoCas9 guide RNA, can bind to a target nucleic acid, and in some cases, can bind to and modify a target nucleic acid. A target nucleic acid can be any nucleic acid (e.g., DNA, RNA), can be double stranded or single stranded, can be any type of nucleic acid (e.g., a chromosome (genomic DNA), derived from a chromosome, chromosomal DNA, plasmid, viral, extracellular, intracellular, mitochondrial, chloroplast, linear, circular, etc.) and can be from any organism (e.g., as long as the GeoCas9 guide RNA comprises a nucleotide sequence that hybridizes to a target sequence in a target nucleic acid, such that the target nucleic acid can be targeted).

A target nucleic acid can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro, inside of a cell in vivo, inside of a cell ex vivo. Suitable target cells (which can comprise target nucleic acids such as genomic DNA) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell from an invertebrate animal (e.g. fruit fly, a cnidarian, an echinoderm, a nematode, etc.); a cell of an insect (e.g., a mosquito; a bee; an agricultural pest; etc.); a cell of an arachnid (e.g., a spider; a tick; etc.); a cell from a vertebrate animal (e.g., a fish, an amphibian, a reptile, a bird, a mammal); a cell from a mammal (e.g., a cell from a rodent; a cell from a human; a cell of a non-human mammal; a cell of a rodent (e.g., a mouse, a rat); a cell of a lagomorph (e.g., a rabbit); a cell of an ungulate (e.g., a cow, a horse, a camel, a llama, a vicuna, a sheep, a goat, etc.); a cell of a marine mammal (e.g., a whale, a seal, an elephant seal, a dolphin, a sea lion; etc.) and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), an adult stem cell, a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.).

Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA, to cleave or otherwise modify target DNA, to genetically modify a target cell, and the like). Because the guide RNA provides specificity by hybridizing to target nucleic acid, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens, C. agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.). In some cases, a GeoCas9 protein (and/or nucleic acid encoding the protein such as DNA and/or RNA), and/or GeoCas9 guide RNA (and/or a DNA encoding the guide RNA), and/or donor template, and/or RNP can be introduced into an individual (i.e., the target cell can be in vivo) (e.g., a mammal, a rat, a mouse, a pig, a primate, a non-human primate, a human, etc.). In some case, such an administration can be for the purpose of treating and/or preventing a disease, e.g., by editing the genome of targeted cells.

Plant cells include cells of a monocotyledon, and cells of a dicotyledon. The cells can be root cells, leaf cells, cells of the xylem, cells of the phloem, cells of the cambium, apical meristem cells, parenchyma cells, collenchyma cells, sclerenchyma cells, and the like. Plant cells include cells of agricultural crops such as wheat, corn, rice, sorghum, millet, soybean, etc. Plant cells include cells of agricultural fruit and nut plants, e.g., plant that produce apricots, oranges, lemons, apples, plums, pears, almonds, etc.

Additional examples of target cells are listed above in the section titled "Modified cells." Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatos, rice, cassava, sugarcane, pumpkin, hay, potatos, cotton, *cannabis*, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (*rappini*), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, *chrysanthemum* leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera, or Lepidoptera.

A cell is in some cases an insect cell. For example, in some cases, the cell is a cell of a mosquito, a grasshopper, a true bug, a fly, a flea, a bee, a wasp, an ant, a louse, a moth, or a beetle.

In some cases, a suitable cell is a prokaryotic cell. In some cases, the cell is a thermophilic prokaryotic cell. In some cases, the cell is an obligate thermophile (e.g., an obligate thermophilic prokaryotic cell). In some cases, the cell is a microorganism selected from a *Cupriavidus* sp., *Ralstonia* sp, *Xanthobacter* sp., *Rhodococcus* sp., *Hydrogenovibrio* sp., *Rhodopseudomonas* sp., *Rhodobacter* sp., *Hydrogenobacter* sp., *Arthrobacter* sp., *Paracoccus* sp., *Mycobacterium* sp., *Streptomyces* sp., and *Bacillus* sp.

In some cases, the host cell is a microorganism. In some cases, the microorganism is *Rhodococcus opacus* or *Rhodococcus jostii* or *Rhodococcus* sp. In some cases, the microorganism is *Hydrogenovibrio marinus*. In some cases, the microorganism is *Rhodopseudomonas capsulata*, *Rhodopseudomonas palustris*, or *Rhodobacter sphaeroides*. In some cases, the microorganism is an oxyhydrogen or knallgas strain. In some cases, the microorganism is selected from: *Aquifex pyrophilus* and *Aquifex aeolicus* or other *Aquifex* sp.; *Cupriavidus necator* or *Cupriavidus metallidurans* or other *Cupriavidus* sp.; *Corynebacterium autotrophicum* or other *Corynebacterium* sp.; *Nocardia autotrophica* and *Nocardia opaca* and other *Nocardia* sp.; purple non-sulfur photosynthetic bacteria including but not limited to *Rhodopseudomonas palustris*, *Rhodopseudomonas capsulata*, *Rhodopseudomonas viridis*, *Rhodopseudomonas sulfoviridis*, *Rhodopseudomonas blastica*, *Rhodopseudomonas spheroides*, *Rhodopseudomonas acidophila* and other *Rhodopseudomonas* sp., *Rhodospirillum rubrum*, and other *Rhodospirillum* sp.; *Rhodococcus opacus* and other *Rhodococcus* sp.; *Rhizobium japonicum* and other *Rhizobium* sp.; *Thiocapsa roseopersicina* and other *Thiocapsa* sp.; *Pseudomonas facilis* and *Pseudomonas flava* and *Pseudomonas putida* and *Pseudomonas hydrogenovora*, *Pseudomonas hydrogenothermophila*, *Pseudomonas palleronii* and *Pseudomonas pseudoflava* and *Pseudomonas saccharophila* and *Pseudomonas thermophila* and other *Pseudomonas* sp.; *Hydrogenomonas pantotropha*, *Hydrogenomonas eutropha*, *Hydrogenomonas facilis*, and other *Hydrogenomonas* sp.; *Hydrogenobacter thermophilus* and *Hydrogenobacter halophilus* and *Hydrogenobacter hydrogenophilus* and other *Hydrogenobacter* sp.; *Hydrogenophilus islandicus* and other *Hydrogenophilus* sp.; *Hydrogenovibrio marinus* and other *Hydrogenovibrio* sp.; *Hydrogenothermus marinus* and other *Hydrogenothermus* sp.; *Helicobacter pylori* and other *Helicobacter* sp.; *Xanthobacter autotrophicus* and *Xanthobacter flavus* other *Xanthobacter* sp.; *Hydrogenophaga flava* and *Hydrogenophaga palleronii* and

*Hydrogenophaga pseudoflava* and other *Hydrogenophaga* sp.; *Bradyrhizobium japonicum* and other *Bradyrhizobium* sp.; *Ralstonia eutropha* and other *Ralstonia* sp.; *Alcaligenes eutrophus* and *Alcaligenes facilis* and *Alcaligenes hydrogenophilus* and *Alcaligenes latus* and *Alcaligenes paradoxus* and *Alcaligenes ruhlandii* and other *Alcaligenes* sp.; *Amycolata* sp.; *Aquaspirillum autotrophicum* and other *Aquaspirillum* sp.; *Arthrobacter* strain 11/X and other *Arthrobacter* sp.; *Azospirillum lipoferum* and other *Azospirillum* sp.; *Variovorax paradoxus*, and other *Variovorax* sp.; *Acidovorax facilis*, and other *Acidovorax* sp.; *Bacillus schlegelii* and *Bacillus tusciae* and other *Bacillus* sp.; *Calderobacterium hydrogenophilum* and other *Calderobacterium* sp.; *Derxia gummosa* and other *Derxia* sp.; *Flavobacterium autothermophilum* and other *Flavobacterium* sp.; *Microcyclus aquaticus* and other *Microcyclus; Mycobacterium gordoniae* and other *Mycobacterium* sp.; *Paracoccus denitrificans* and other *Paracoccus* sp.; *Persephonella marina* and *Persephonella guaymasensis* and other *Persephonella* sp.; *Renobacter vacuolatum* and other *Renobacter* sp.; *Thermocrinis ruber* and other *Thermocrinis* sp.; *Wautersia* sp.; cyanobacteria including but not limited to *Anabaena oscillarioides, Anabaena spiroides, Anabaena cylindrica*, and other *Anabaena* sp.; green algae including but not limited to *Scenedesmus obliquus* and other *Scenedesmus* sp., *Chlamydomonas reinhardtii* and other *Chlamydomonas* sp., *Ankistrodesmus* sp., *Rhaphidium polymorphium* and other *Rhaphidium* sp; as well as a consortiums of microorganisms that include oxyhydrogen microorganisms.

In some cases, the host cell is an obligate and/or facultative chemoautotrophic microorganism selected from: *Acetoanaerobium* sp.; *Acetobacterium* sp.; *Acetogenium* sp.; *Achromobacter* sp.; *Acidianus* sp.; *Acinetobacter* sp.; *Actinomadura* sp.; *Aeromonas* sp.; *Alcaligenes* sp.; *Alcaligenes* sp.; *Arcobacter* sp.; *Aureobacterium* sp.; *Bacillus* sp.; *Beggiatoa* sp.; *Butyribacterium* sp.; *Carboxydothermus* sp.; *Clostridium* sp.; *Comamonas* sp.; *Dehalobacter* sp.; *Dehalococcoide* sp.; *Dehalospirillum* sp.; *Desulfobacterium* sp.; *Desulfomonile* sp.; *Desulfotomaculum* sp.; *Desulfovibrio* sp.; *Desulfurosarcina* sp.; *Ectothiorhodospira* sp.; *Enterobacter* sp.; *Eubacterium* sp.; *Ferroplasma* sp.; *Halothibacillus* sp.; *Hydrogenobacter* sp.; *Hydrogenomonas* sp.; *Leptospirillum* sp.; *Metallosphaera* sp.; *Methanobacterium* sp.; *Methanobrevibacter* sp.; *Methanococcus* sp.; *Methanosarcina* sp.; *Micrococcus* sp.; *Nitrobacter* sp.; *Nitrosococcus* sp.; *Nitrosolobus* sp.; *Nitrosomonas* sp.; *Nitrosospira* sp.; *Nitrosovibrio* sp.; *Nitrospina* sp.; *Oleomonas* sp.; *Paracoccus* sp.; *Peptostreptococcus* sp.; *Planctomycetes* sp.; *Pseudomonas* sp.; *Ralstonia* sp.; *Rhodobacter* sp.; *Rhodococcus* sp.; *Rhodocyclus* sp.; *Rhodomicrobium* sp.; *Rhodopseudomonas* sp.; *Rhodospirillum* sp.; *Shewanella* sp.; *Streptomyces* sp.; *Sulfobacillus* sp.; *Sulfolobus* sp.; *Thiobacillus* sp.; *Thiomicrospira* sp.; *Thioploca* sp.; *Thiosphaera* sp.; *Thiothrix* sp.; sulfur-oxidizers; hydrogen-oxidizers; iron-oxidizers; acetogens; and methanogens; consortiums of microorganisms that include chemoautotrophs; chemoautotrophs native to at least one of hydrothermal vents, geothermal vents, hot springs, cold seeps, underground aquifers, salt lakes, saline formations, mines, acid mine drainage, mine tailings, oil wells, refinery wastewater, coal seams, deep sub-surface; waste water and sewage treatment plants; geothermal power plants, sulfatara fields, and soils; and extremophiles selected from one or more of thermophiles, hyperthermophiles, acidophiles, halophiles, and psychrophiles.

Introducing Components into a Target Cell

A GeoCas9 guide RNA (or a nucleic acid comprising a nucleotide sequence encoding same), and/or a GeoCas polypeptide (e.g., a wild-type GeoCas polypeptide; a GeoCas9 variant; a GeoCas9 polypeptide of the present disclosure (e.g., a GeoCas9 polypeptide comprising a heterologous PI domain); or a GeoCas9 fusion polypeptide of the present disclosure) (or a nucleic acid comprising a nucleotide sequence encoding same) and/or a donor polynucleotide can be introduced into a host cell by any of a variety of well-known methods.

Methods of introducing a nucleic acid into a cell are known in the art, and any convenient method can be used to introduce a nucleic acid (e.g., an expression construct) into a target cell (e.g., eukaryotic cell, human cell, stem cell, progenitor cell, a prokaryotic cell, and the like). Suitable methods are described in more detail elsewhere herein and include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like. Any or all of the components can be introduced into a cell as a composition (e.g., including any convenient combination of: a GeoCas polypeptide (e.g., a wild-type GeoCas polypeptide; a GeoCas9 variant; a GeoCas9 polypeptide of the present disclosure (e.g., a GeoCas9 polypeptide comprising a heterologous PI domain); or a GeoCas9 fusion polypeptide of the present disclosure), a GeoCas9 guide RNA, a donor polynucleotide, etc.) using known methods, e.g., such as nucleofection.

Donor Polynucleotide (Donor Template)

Guided by a GeoCas9 dual or single guide RNA, a GeoCas9 protein in some cases generates site-specific double strand breaks (DSBs) or single strand breaks (SSBs) (e.g., when the GeoCas9 protein is a nickase variant) within double-stranded DNA (dsDNA) target nucleic acids, which are repaired either by non-homologous end joining (NHEJ) or homology-directed recombination (HDR).

In some cases, contacting a target DNA (with a GeoCas9 protein and a GeoCas9 guide RNA) occurs under conditions that are permissive for nonhomologous end joining or homology-directed repair. Thus, in some cases, a subject method includes contacting the target DNA with a donor polynucleotide (e.g., by introducing the donor polynucleotide into a cell), wherein the donor polynucleotide, a portion of the donor polynucleotide, a copy of the donor polynucleotide, or a portion of a copy of the donor polynucleotide integrates into the target DNA. In some cases, the method does not comprise contacting a cell with a donor polynucleotide, and the target DNA is modified such that nucleotides within the target DNA are deleted.

In some cases, GeoCas9 guide RNA (or DNA encoding same) and a GeoCas9 protein (or a nucleic acid encoding same, such as an RNA or a DNA, e.g, one or more expression vectors) are coadministered (e.g., contacted with a target nucleic acid, administered to cells, etc.) with a donor polynucleotide sequence that includes at least a segment with homology to the target DNA sequence, the subject methods may be used to add, i.e. insert or replace, nucleic acid material to a target DNA sequence (e.g. to "knock in" a nucleic acid, e.g., one that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g., introduce a mutation, remove a disease causing mutation by introducing a correct sequence), and the like. As such, a complex comprising a GeoCas9 guide RNA and GeoCas9 protein is useful in any in vitro or in vivo application in which it is desirable to modify DNA in a site-specific, i.e. "targeted", way, for example gene knock-out, gene knock-in, gene editing, gene tagging, etc., as used in, for example, gene therapy, e.g. to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In applications in which it is desirable to insert a polynucleotide sequence into the genome where a target sequence is cleaved, a donor polynucleotide (a nucleic acid comprising a donor sequence) can also be provided to the cell. By a "donor sequence" or "donor polynucleotide" or "donor template" it is meant a nucleic acid sequence to be inserted at the site cleaved by the GeoCas9 protein (e.g., after dsDNA cleavage, after nicking a target DNA, after dual nicking a target DNA, and the like). The donor polynucleotide can contain sufficient homology to a genomic sequence at the target site, e.g. 70%, 80%, 85%, 90%, 95%, or 100% homology with the nucleotide sequences flanking the target site, e.g. within about 50 bases or less of the target site, e.g. within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) can support homology-directed repair. Donor polynucleotides can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair (e.g., for gene correction, e.g., to convert a disease-causing base pair of a non disease-causing base pair). In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

In some cases, the donor sequence is provided to the cell as single-stranded DNA. In some cases, the donor sequence is provided to the cell as double-stranded DNA. It may be introduced into a cell in linear or circular form. If introduced in linear form, the ends of the donor sequence may be protected (e.g., from exonucleolytic degradation) by any convenient method and such methods are known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked nucleic acid, as nucleic acid complexed with an agent such as a liposome or poloxamer, or can be delivered by viruses (e.g., adenovirus, AAV), as described elsewhere herein for nucleic acids encoding a GeoCas9 guide RNA and/or a GeoCas9 fusion polypeptide and/or donor polynucleotide.

Kits

The present disclosure provides a kit comprising a GeoCas9 system of the present disclosure, or a component of a GeoCas9 system of the present disclosure.

A kit of the present disclosure can comprise: a) a GeoCas polypeptide (e.g., a wild-type GeoCas polypeptide; a GeoCas9 variant; a GeoCas9 polypeptide of the present disclosure (e.g., a GeoCas9 polypeptide comprising a heterologous PI domain; a GeoCas9 polypeptide comprising a substitution of Asp-8 and/or His-582); or a GeoCas9 fusion polypeptide of the present disclosure) and a GeoCas9 guide RNA; b) a GeoCas polypeptide (e.g., a wild-type GeoCas polypeptide; a GeoCas9 variant; a GeoCas9 polypeptide of the present disclosure (e.g., a GeoCas9 polypeptide comprising a heterologous PI domain; a GeoCas9 polypeptide comprising a substitution of Asp-8 and/or His-582); or a GeoCas9 fusion polypeptide of the present disclosure), a GeoCas9 guide RNA, and a donor template nucleic acid; c)

a GeoCas9 fusion polypeptide of the present disclosure and a GeoCas9 guide RNA; d) a GeoCas9 fusion polypeptide of the present disclosure, a GeoCas9 guide RNA, and a donor template nucleic acid; e) an mRNA encoding a GeoCas polypeptide (e.g., a wild-type GeoCas polypeptide; a GeoCas9 variant; a GeoCas9 polypeptide of the present disclosure (e.g., a GeoCas9 polypeptide comprising a heterologous PI domain; a GeoCas9 polypeptide comprising a substitution of Asp-8 and/or His-582); or a GeoCas9 fusion polypeptide of the present disclosure); and a GeoCas9 guide RNA; f) an mRNA encoding a GeoCas polypeptide (e.g., a wild-type GeoCas polypeptide; a GeoCas9 variant; a GeoCas9 polypeptide of the present disclosure (e.g., a GeoCas9 polypeptide comprising a heterologous PI domain; a GeoCas9 polypeptide comprising a substitution of Asp-8 and/or His-582); or a GeoCas9 fusion polypeptide of the present disclosure), a GeoCas9 guide RNA, and a donor template nucleic acid; g) an mRNA encoding a GeoCas9 fusion polypeptide of the present disclosure; and a GeoCas9 guide RNA; h) an mRNA encoding a GeoCas9 fusion polypeptide of the present disclosure, a GeoCas9 guide RNA, and a donor template nucleic acid; i) a recombinant expression vector comprising a nucleotide sequence encoding a GeoCas polypeptide (e.g., a wild-type GeoCas polypeptide; a GeoCas9 variant; a GeoCas9 polypeptide of the present disclosure (e.g., a GeoCas9 polypeptide comprising a heterologous PI domain; a GeoCas9 polypeptide comprising a substitution of Asp-8 and/or His-582); or a GeoCas9 fusion polypeptide of the present disclosure) and a nucleotide sequence encoding a GeoCas9 guide RNA; j) a recombinant expression vector comprising a nucleotide sequence encoding a GeoCas polypeptide (e.g., a wild-type GeoCas polypeptide; a GeoCas9 variant; a GeoCas9 polypeptide of the present disclosure (e.g., a GeoCas9 polypeptide comprising a heterologous PI domain; a GeoCas9 polypeptide comprising a substitution of Asp-8 and/or His-582); or a GeoCas9 fusion polypeptide of the present disclosure), a nucleotide sequence encoding a GeoCas9 guide RNA, and a nucleotide sequence encoding a donor template nucleic acid; k) a recombinant expression vector comprising a nucleotide sequence encoding a GeoCas9 fusion polypeptide of the present disclosure and a nucleotide sequence encoding a GeoCas9 guide RNA; l) a recombinant expression vector comprising a nucleotide sequence encoding a GeoCas9 fusion polypeptide of the present disclosure, a nucleotide sequence encoding a GeoCas9 guide RNA, and a nucleotide sequence encoding a donor template nucleic acid; m) a first recombinant expression vector comprising a nucleotide sequence encoding a GeoCas polypeptide (e.g., a wild-type GeoCas polypeptide; a GeoCas9 variant; a GeoCas9 polypeptide of the present disclosure (e.g., a GeoCas9 polypeptide comprising a heterologous PI domain; a GeoCas9 polypeptide comprising a substitution of Asp-8 and/or His-582); or a GeoCas9 fusion polypeptide of the present disclosure), and a second recombinant expression vector comprising a nucleotide sequence encoding a GeoCas9 guide RNA; n) a first recombinant expression vector comprising a nucleotide sequence encoding a GeoCas polypeptide (e.g., a wild-type GeoCas polypeptide; a GeoCas9 variant; a GeoCas9 polypeptide of the present disclosure (e.g., a GeoCas9 polypeptide comprising a heterologous PI domain; a GeoCas9 polypeptide comprising a substitution of Asp-8 and/or His-582); or a GeoCas9 fusion polypeptide of the present disclosure), and a second recombinant expression vector comprising a nucleotide sequence encoding a GeoCas9 guide RNA; and a donor template nucleic acid; o) a first recombinant expression vector comprising a nucleotide sequence encoding a GeoCas9 fusion polypeptide of the present disclosure, and a second recombinant expression vector comprising a nucleotide sequence encoding a GeoCas9 guide RNA; p) a first recombinant expression vector comprising a nucleotide sequence encoding a GeoCas9 fusion polypeptide of the present disclosure, and a second recombinant expression vector comprising a nucleotide sequence encoding a GeoCas9 guide RNA; and a donor template nucleic acid; q) a recombinant expression vector comprising a nucleotide sequence encoding a GeoCas polypeptide (e.g., a wild-type GeoCas polypeptide; a GeoCas9 variant; a GeoCas9 polypeptide of the present disclosure (e.g., a GeoCas9 polypeptide comprising a heterologous PI domain; a GeoCas9 polypeptide comprising a substitution of Asp-8 and/or His-582); or a GeoCas9 fusion polypeptide of the present disclosure), a nucleotide sequence encoding a first GeoCas9 guide RNA, and a nucleotide sequence encoding a second GeoCas9 guide RNA; or r) a recombinant expression vector comprising a nucleotide sequence encoding a GeoCas9 fusion polypeptide of the present disclosure, a nucleotide sequence encoding a first GeoCas9 guide RNA, and a nucleotide sequence encoding a second GeoCas9 guide RNA; or some variation of one of (a) through (r).

A kit of the present disclosure can comprise: a) a component, as described above, of a GeoCas9 system of the present disclosure, or can comprise a GeoCas9 system of the present disclosure; and b) one or more additional reagents, e.g., i) a buffer; ii) a protease inhibitor; iii) a nuclease inhibitor; iv) a reagent required to develop or visualize a detectable label; v) a positive and/or negative control target DNA; vi) a positive and/or negative control guide RNA; and the like. A kit of the present disclosure can comprise: a) a component, as described above, of a GeoCas9 system of the present disclosure, or can comprise a GeoCas9 system of the present disclosure; and b) a therapeutic agent.

A kit of the present disclosure can comprise a recombinant expression vector comprising: a) an insertion site for inserting a nucleic acid comprising a nucleotide sequence encoding a portion of a GeoCas9 guide RNA that hybridizes to a target nucleotide sequence in a target nucleic acid; and b) a nucleotide sequence encoding the GeoCas9-binding portion of a GeoCas9 guide RNA. A kit of the present disclosure can comprise a recombinant expression vector comprising: a) an insertion site for inserting a nucleic acid comprising a nucleotide sequence encoding a portion of a GeoCas9 guide RNA that hybridizes to a target nucleotide sequence in a target nucleic acid; b) a nucleotide sequence encoding the GeoCas9-binding portion of a GeoCas9 guide RNA; and c) a nucleotide sequence encoding a GeoCas polypeptide (e.g., a wild-type GeoCas polypeptide; a GeoCas9 variant; a GeoCas9 polypeptide of the present disclosure (e.g., a GeoCas9 polypeptide comprising a heterologous PI domain; a GeoCas9 polypeptide comprising a substitution of Asp-8 and/or His-582); or a GeoCas9 fusion polypeptide of the present disclosure).

The present disclosure provides a transdermal patch comprising a GeoCas9 polypeptide (e.g., a wild-type GeoCas polypeptide; a GeoCas9 variant; a GeoCas9 polypeptide of the present disclosure (e.g., a GeoCas9 polypeptide comprising a heterologous PI domain; a GeoCas9 polypeptide comprising a substitution of Asp-8 and/or His-582); or a GeoCas9 fusion polypeptide of the present disclosure). The present disclosure provides a transdermal patch comprising: a) a GeoCas9 polypeptide (e.g., a wild-type GeoCas polypeptide; a GeoCas9 variant; a GeoCas9 polypeptide of the present disclosure (e.g., a GeoCas9 polypeptide comprising a heterologous PI domain; a GeoCas9 polypeptide comprising a substitution of Asp-8 and/or His-582); or a GeoCas9 fusion polypeptide of the present disclosure); and b) a GeoCas9 guide RNA (e.g., a GeoCas9 sgRNA). The present disclosure provides a transdermal patch comprising one or more nucleic acids comprising nucleotide sequences encoding a) a GeoCas9 polypeptide (e.g., a wild-type GeoCas polypeptide; a GeoCas9 variant; a GeoCas9 polypeptide of the present disclosure (e.g., a GeoCas9 polypeptide comprising a heterologous PI domain; a GeoCas9 polypeptide comprising a substitution of Asp-8 and/or His-582); or a GeoCas9 fusion polypeptide of the present disclosure); and b) a GeoCas9 guide RNA (e.g., a GeoCas9 sgRNA). In some cases, the transdermal patch includes a donor template nucleic acid.

The present disclosure provides a transdermal or subcutaneous delivery device comprising a GeoCas9 polypeptide (e.g., a wild-type GeoCas polypeptide; a GeoCas9 variant; a GeoCas9 polypeptide of the present disclosure (e.g., a GeoCas9 polypeptide comprising a heterologous PI domain; a GeoCas9 polypeptide comprising a substitution of Asp-8 and/or His-582); or a GeoCas9 fusion polypeptide of the present disclosure). The present disclosure provides a transdermal or subcutaneous delivery device comprising: a) a GeoCas9 polypeptide (e.g., a wild-type GeoCas polypeptide; a GeoCas9 variant; a GeoCas9 polypeptide of the present disclosure (e.g., a GeoCas9 polypeptide comprising a heterologous PI domain; a GeoCas9 polypeptide comprising a substitution of Asp-8 and/or His-582); or a GeoCas9 fusion polypeptide of the present disclosure); and b) a GeoCas9 guide RNA (e.g., a GeoCas9 sgRNA). The present disclosure provides a transdermal or subcutaneous delivery device comprising one or more nucleic acids comprising nucleotide sequences encoding a) a GeoCas9 polypeptide (e.g., a wild-type GeoCas polypeptide; a GeoCas9 variant; a GeoCas9 polypeptide of the present disclosure (e.g., a GeoCas9 polypeptide comprising a heterologous PI domain; a GeoCas9 polypeptide comprising a substitution of Asp-8 and/or His-582); or a GeoCas9 fusion polypeptide of the present disclosure); and b) a GeoCas9 guide RNA (e.g., a GeoCas9 sgRNA). In some cases, the transdermal or subcutaneous delivery device includes a donor template nucleic acid.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-123 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. An RNA-guided endonuclease that comprises:
a) an amino acid sequence having at least 50% amino acid sequence identity to amino acids 1-994 of the amino acid sequence set forth in SEQ ID NO: 1; and
b) a heterologous protospacer adjacent motif (PAM) interacting domain.

Aspect 2. The RNA-guided endonuclease of aspect 1, wherein the RNA-guided endonuclease is enzymatically active in a temperature range of from 15° C. to 75° C.

Aspect 3. The RNA-guided endonuclease of aspect 1, wherein the RNA-guided endonuclease binds to a target nucleic acid comprising a PAM comprising a GMAA sequence.

Aspect 4. The RNA-guided endonuclease of aspect 1, wherein the heterologous PI domain comprises an amino acid sequence having at least 50% amino acid sequence identity to the following amino acid sequence:

(SEQ ID NO: 4)
IIKTAGGEEIKIKDLFAYYKTIHSGTAGLELVSHDCSFSLSGVGSRTLKRF

EKYQVDVLGNIYKVRGEKRVGLASSAHSKTGETIRPLQSTRD.

Aspect 5. The RNA-guided endonuclease of aspect 1, wherein the heterologous PI domain comprises an amino acid sequence having less than 83% amino acid sequence identity to the following amino acid sequence:

(SEQ ID NO: 5)
TVKTAAGEEINVKDVFVYYKTIDSANGGLELISHDHRFSLRGVGSRTLKRF

EKYQVDVLGNIYKVRGEKRVGLASSAHSKPGKTIRPLQSTRD.

Aspect 6. The RNA-guided endonuclease of aspect 1, wherein the RNA-guided endonuclease has a length of from 1050 amino acids to 1120 amino acids.

Aspect 7. The RNA-guided endonuclease of aspect 1, wherein the RNA-guided endonuclease has a length of from 1080 amino acids to 1095 amino acids.

Aspect 8. The RNA-guided endonuclease of aspect 1, wherein the RNA-guided endonuclease comprises an amino acid sequence having at least 60% amino acid sequence identity to amino acids 1-994 of the amino acid sequence set forth in SEQ ID NO: 1.

Aspect 9. The RNA-guided endonuclease of aspect 1, wherein the RNA-guided endonuclease comprises an amino acid sequence having at least 70% amino acid sequence identity to amino acids 1-994 of the amino acid sequence set forth in SEQ ID NO: 1.

Aspect 10. The RNA-guided endonuclease of aspect 1, wherein the RNA-guided endonuclease comprises an amino acid sequence having at least 80% amino acid sequence identity to amino acids 1-994 of the amino acid sequence set forth in SEQ ID NO: 1.

Aspect 11. The RNA-guided endonuclease of aspect 1, wherein the RNA-guided endonuclease comprises an amino acid sequence having at least 90% amino acid sequence identity to amino acids 1-994 of the amino acid sequence set forth in SEQ ID NO: 1.

Aspect 12. The RNA-guided endonuclease of aspect 1, wherein the RNA-guided endonuclease comprises an amino acid sequence having at least 95% amino acid sequence identity to amino acids 1-994 of the amino acid sequence set forth in SEQ ID NO: 1.

Aspect 13. The RNA-guided endonuclease of aspect 1, wherein the RNA-guided endonuclease comprises: a) a substitution of amino acid Asp-8; b) a substitution of amino acid His-582; or c) substitution of both Asp-8 and His-582, based on the amino acid numbering of the amino acid sequence depicted in FIG. 6.

Aspect 14. A nucleic acid comprising a nucleotide sequence encoding the RNA-guided endonuclease of any one of aspects 1-13.

Aspect 15. The nucleic acid of aspect 14, wherein the nucleotide sequence encoding the RNA-guided endonuclease is codon optimized for expression in a eukaryotic cell.

Aspect 16. The nucleic acid of aspect 14, wherein the nucleotide sequence encoding the RNA-guided endonuclease is codon optimized for expression in a mammalian cell.

Aspect 17. The nucleic acid of aspect 14, wherein the nucleotide sequence encoding the RNA-guided endonuclease is codon optimized for expression in prokaryotic cell.

Aspect 18. The nucleic acid of any one of aspects 14-17, wherein the nucleotide sequence encoding the RNA-guided endonuclease is operably linked to one or more transcriptional control elements.

Aspect 19. The nucleic acid of aspect 18, wherein the one or more transcriptional control elements comprises a promoter.

Aspect 20. The nucleic acid of aspect 19, wherein the promoter is a regulatable promoter.

Aspect 21. The nucleic acid of aspect 19, wherein the promoter is a constitutive promoter.

Aspect 22. The nucleic acid of any one of aspects 19-21, wherein the promoter is functional in a eukaryotic cell.

Aspect 23. The nucleic acid of any one of aspects 19-21, wherein the promoter is functional in a prokaryotic cell.

Aspect 24. The nucleic acid of any one of aspects 19-21, wherein the promoter is functional in a thermophilic prokaryotic or archaeal cell.

Aspect 25. A recombinant expression vector comprising the nucleic acid of any one of aspects 14-24.

Aspect 26. The recombinant expression vector of aspect 25, wherein the recombinant expression vector is a recombinant viral vector, a recombinant plasmid, or a recombinant artificial chromosome.

Aspect 27. A composition comprising the RNA-guided endonuclease of any one of aspects 1-13, the nucleic acid of any one of aspects 14-24, or the recombinant expression vector of aspect 25 or aspect 26.

Aspect 28. The composition of aspect 27, comprising one or more of: i) a buffer; ii) a nuclease inhibitor; iii) a protease inhibitor; and iv) a lipid.

Aspect 29. A fusion polypeptide comprising:
a) an RNA-guided endonuclease comprising an amino acid sequence having at least 50% amino acid sequence identity to the amino acid sequence set forth in SEQ ID NO: 1 or SEQ ID NO:2; and
b) a heterologous fusion partner polypeptide.

Aspect 30. The fusion polypeptide of aspect 29, wherein the heterologous fusion partner polypeptide comprises a protein transduction domain that facilitates traversal of the RNA-guided endonuclease from the cytosol of a cell to within an organelle in the cell.

Aspect 31. The fusion polypeptide of aspect 29, wherein the heterologous fusion partner polypeptide is a nuclear localization signal (NLS).

Aspect 32. The fusion polypeptide of aspect 31, wherein the fusion polypeptide comprises two or more NLS.

Aspect 33. The fusion polypeptide of aspect 31, wherein the fusion polypeptide comprises an NLS fused to the N-terminus of the RNA-guided endonuclease.

Aspect 34. The fusion polypeptide of aspect 33, wherein the fusion polypeptide comprises two or more NLSs fused to the N-terminus of the RNA-guided endonuclease.

Aspect 35. The fusion polypeptide of aspect 31, wherein the fusion polypeptide comprises an NLS fused at or within 50 amino acids of the C-terminus of the RNA-guided endonuclease.

Aspect 36. The fusion polypeptide of aspect 35, wherein the fusion polypeptide comprises two or more NLSs fused at or within 50 amino acids of the C-terminus of the RNA-guided endonuclease.

Aspect 37. The fusion polypeptide of aspect 31, wherein the fusion polypeptide comprises one or more NLSs fused to the N-terminus of the RNA-guided endonuclease and one or more NLSs fused at or within 50 amino acids of the C-terminus of the RNA-guided endonuclease.

Aspect 38. The fusion polypeptide of aspect 29, wherein the fusion partner polypeptide is an enzyme.

Aspect 39. The fusion polypeptide of aspect 38, wherein the enzyme has DNA modifying activity, increases transcription, decreases transcription, or modifies a polypeptide associated with a nucleic acid.

Aspect 40. The fusion polypeptide of any one of aspects 29-39, wherein the RNA-guided endonuclease comprises: a) a substitution of amino acid Asp-8; b) a substitution of amino acid His-582; or c) substitution of both Asp-8 and His-582, based on the amino acid numbering of the amino acid sequence depicted in FIG. 6.

Aspect 41. A fusion polypeptide comprising:
a) an RNA-guided endonuclease that comprises:
i) an amino acid sequence having at least 50% amino acid sequence identity to amino acids 1-994 of the amino acid sequence set forth in SEQ ID NO: 1; and
ii) a heterologous protospacer adjacent motif (PAM) interacting domain; and
b) a heterologous fusion partner polypeptide.

Aspect 42. The fusion polypeptide of aspect 41, wherein the heterologous fusion partner polypeptide comprises a protein transduction domain that facilitates traversal of the RNA-guided endonuclease from the cytosol of a cell to within an organelle in the cell.

Aspect 43. The fusion polypeptide of aspect 41, wherein the heterologous fusion partner polypeptide is a nuclear localization signal (NLS).

Aspect 44. The fusion polypeptide of aspect 43, wherein the fusion polypeptide comprises two or more NLS.

Aspect 45. The fusion polypeptide of aspect 43, wherein the fusion polypeptide comprises an NLS fused to the N-terminus of the RNA-guided endonuclease.

Aspect 46. The fusion polypeptide of aspect 45, wherein the fusion polypeptide comprises two or more NLSs fused to the N-terminus of the RNA-guided endonuclease.

Aspect 47. The fusion polypeptide of aspect 43, wherein the fusion polypeptide comprises an NLS fused at or within 50 amino acids of the C-terminus of the RNA-guided endonuclease.

Aspect 48. The fusion polypeptide of aspect 47, wherein the fusion polypeptide comprises two or more NLSs fused at or within 50 amino acids of the C-terminus of the RNA-guided endonuclease.

Aspect 49. The fusion polypeptide of aspect 43, wherein the fusion polypeptide comprises one or more NLSs fused to the N-terminus of the RNA-guided endonuclease and one or more NLSs fused at or within 50 amino acids of the C-terminus of the RNA-guided endonuclease.

Aspect 50. The fusion polypeptide of aspect 41, wherein the fusion partner polypeptide is an enzyme.

Aspect 51. The fusion polypeptide of aspect 50, wherein the enzyme has DNA modifying activity, increases transcription, decreases transcription, or modifies a polypeptide associated with a nucleic acid.

Aspect 52. The fusion polypeptide of any one of aspects 41-51, wherein the RNA-guided endonuclease comprises: a) a substitution of amino acid Asp-8; b) a substitution of amino acid His-582; or c) substitution of both Asp-8 and His-582, based on the amino acid numbering of the amino acid sequence depicted in FIG. 6.

Aspect 53. A nucleic acid comprising a nucleotide sequence encoding the fusion polypeptide of any one of aspects 29-52.

Aspect 54. The nucleic acid of aspect 53, wherein the nucleotide sequence encoding the fusion polypeptide is codon optimized for expression in a eukaryotic cell.

Aspect 55. The nucleic acid of aspect 53, wherein the nucleotide sequence encoding the fusion polypeptide is codon optimized for expression in a mammalian cell.

Aspect 56. The nucleic acid of aspect 53, wherein the nucleotide sequence encoding the fusion polypeptide is codon optimized for expression in prokaryotic cell.

Aspect 57. The nucleic acid of any one of aspects 53-56, wherein the nucleotide sequence encoding the fusion polypeptide is operably linked to one or more transcriptional control elements.

Aspect 58. The nucleic acid of aspect 57, wherein the one or more transcriptional control elements comprises a promoter.

Aspect 59. The nucleic acid of aspect 58, wherein the promoter is a regulatable promoter.

Aspect 60. The nucleic acid of aspect 58, wherein the promoter is a constitutive promoter.

Aspect 61. The nucleic acid of any one of aspects 58-60, wherein the promoter is functional in a eukaryotic cell.

Aspect 62. The nucleic acid of any one of aspects 58-60, wherein the promoter is functional in a prokaryotic cell.

Aspect 63. The nucleic acid of any one of aspects 58-60, wherein the promoter is functional in a thermophilic prokaryotic or archaeal cell.

Aspect 64. A recombinant expression vector comprising the nucleic acid of any one of aspects 53-63.

Aspect 65. The recombinant expression vector of aspect 64, wherein the recombinant expression vector is a recombinant viral vector, a recombinant plasmid, or a recombinant artificial chromosome.

Aspect 66. A composition comprising the fusion polypeptide of any one of aspects 29-51, the nucleic acid of any one of aspects 53-63, or the recombinant expression vector of aspect 64 or aspect 65.

Aspect 67. The composition of aspect 66, comprising one or more of: i) a buffer; ii) a nuclease inhibitor; iii) a protease inhibitor; iv) a lipid.

Aspect 68. A cell comprising:
a) the RNA-guided endonuclease of any one of aspects 1-13; or
b) the nucleic acid of any one of aspects 14-24; or
c) the expression vector of aspect 25 or aspect 26; or
d) the fusion polypeptide of any one of aspects 29-51; or
e) the nucleic acid of any one of aspects 53-63; or
f) the expression vector of aspect 64 or aspect 65.

Aspect 69. The cell of aspect 66, wherein the cell is a eukaryotic cell.

Aspect 70. The cell of aspect 68, wherein the cell is a prokaryotic cell.

Aspect 71. The cell of aspect 68, wherein the cell is a thermophile.

Aspect 72. The cell of aspect 68, wherein the cell is an obligate thermophile.

Aspect 73. The cell of aspect 68, wherein the cell is a stem cell.

Aspect 74. The cell of aspect 68, wherein the cell is a mammalian cell, a fish cell, a invertebrate animal cell, a vertebrate cell, a plant cell, an algal cell, a bird cell, an insect cell, an arachnid cell, an ungulate cell, a non-human primate cell, or a human cell.

Aspect 75. The cell of any one of aspects 68-74, wherein the cell is in vitro.

Aspect 76. The cell of any one of aspects 68-74, wherein the cell is in vivo.

Aspect 77. The cell of any one of aspects 68-74, wherein the nucleotide sequence encoding the RNA-guided endonuclease or the nucleotide sequence encoding the fusion polypeptide is integrated into the genome of the cell.

Aspect 78. The cell of any one of aspects 68-74, wherein the nucleotide sequence encoding the RNA-guided endonuclease or the nucleotide sequence encoding the fusion polypeptide is not integrated into the genome of the cell.

Aspect 79. A ribonucleoprotein (RNP) complex comprising:
a1) the RNA-guided endonuclease of any one of aspects 1-13; and
b1) a guide RNA comprising:
i) a DNA-targeting segment comprising a nucleotide sequence that is complementary to a target nucleotide sequence in a target nucleic acid; and
ii) an protein-binding segment that binds to and activates the thermostable RNA-guided endonuclease, wherein the protein-binding segment comprises a duplex-forming linker segment and a tracrRNA; or
a2) the fusion polypeptide of any one of aspects 29-51; and
b2) a guide RNA comprising:
i) a DNA-targeting segment comprising a nucleotide sequence that is complementary to a target nucleotide sequence in a target nucleic acid; and
ii) an protein-binding segment that binds to and activates the thermostable RNA-guided endonuclease, wherein the protein-binding segment comprises a duplex-forming linker segment and a tracrRNA.

Aspect 80. The RNP complex of aspect 79, wherein the guide RNA is a dual-guide RNA comprising:
i) a first RNA comprising the DNA-targeting segment; and
ii) a second RNA comprising the protein-binding segment, wherein the first RNA and the second RNA are not contiguous with one another and are not covalently linked to one another.

Aspect 81. The RNP complex of aspect 79, wherein the guide RNA is a single-molecule guide RNA, wherein the DNA-targeting segment and the protein-binding segment are present in a single RNA molecule.

Aspect 82. The RNP complex of any one of aspects 79-81, wherein the nucleotide sequence that is complementary to the target nucleotide sequence has a length of from 18 nucleotides to 24 nucleotides.

Aspect 83. The RNP complex of any one of aspects 79-81, wherein the nucleotide sequence that is complementary to the target nucleotide sequence has a length of from 20 nucleotides to 22 nucleotides.

Aspect 84. The RNP complex of any one of aspects 79-81, wherein the tracrRNA has a length of at least 75 nucleotides.

Aspect 85. The RNP complex of any one of aspects 79-83, wherein the tracrRNA has a length of from 75 nucleotides to 150 nucleotides.

Aspect 86. The RNP complex of any one of aspects 79-83, wherein the tracrRNA has a length of from 75 nucleotides to 100 nucleotides.

Aspect 87. The RNP complex of any one of aspects 79-83, wherein the tracrRNA comprises a nucleotide sequence having at least 80% nucleotide sequence identity to the following nucleotide sequence (SEQ ID NO: 6)
UCAGGGUUACUAUGAUAAGGGCUUUCUGCCUAAGGCAGACUGACCCGCGGC

GUUGGGGAUCGCCUGUCGCCCGCUUUUGGCGGGCAUUCCCCAUCCUU or to the following nucleotide sequence:

(SEQ ID NO: 140)
AAGGGCUUUCUGCCUAAGGCAGACUGACCCGCGGCGUUGGGGAUCGCCUGU

CGCCCGCUUUUGGCGGGCAUUCCCCAUCCUU.

Aspect 88. The RNP complex of any one of aspects 79-87, wherein the guide RNA comprises one or more of a modified nucleobase, a modified backbone, a non-natural internucleoside linkage, a modified sugar moiety, a Locked Nucleic Acid, and a Peptide Nucleic Acid.

Aspect 89. The RNP complex of any one of aspects 79-88, comprising a cationic lipid.

Aspect 90. The RNP complex of any one of aspects 79-89, comprising a polyamine moiety.

Aspect 91. The RNP complex of any one of aspects 79-90, comprising two or more guide RNAs.

Aspect 92. The RNP complex of any one of aspects 79-91, comprising a donor template nucleic acid.

Aspect 93. A ribonucleoprotein (RNP) complex comprising:
 a) a thermostable RNA-guided endonuclease comprising an amino acid sequence having at least 90% amino acid sequence identity to the amino acid sequence set forth in SEQ ID NO: 1; and
 b) a single-molecule guide RNA comprising:
  i) a targeter segment comprising a nucleotide sequence that is complementary to a target nucleotide sequence in a target nucleic acid; and
  ii) an protein-binding segment that binds to and activates the thermostable RNA-guided endonuclease,
 wherein the DNA-targeting segment and the protein-binding segment are present in a single RNA molecule.

Aspect 94. The RNP complex of aspect 93, wherein the nucleotide sequence that is complementary to the target nucleotide sequence has a length of from 18 nucleotides to 24 nucleotides.

Aspect 95. The RNP complex of aspect 93 or aspect 94, wherein the nucleotide sequence that is complementary to the target nucleotide sequence has a length of from 20 nucleotides to 22 nucleotides.

Aspect 96. The RNP complex of any one of aspects 91-93, wherein the tracrRNA has a length of at least 75 nucleotides.

Aspect 97. The RNP complex of any one of aspects 93-95, wherein the tracrRNA has a length of from 75 nucleotides to 150 nucleotides.

Aspect 98. The RNP complex of any one of aspects 93-95, wherein the tracrRNA has a length of from 75 nucleotides to 100 nucleotides.

Aspect 99. The RNP complex of any one of aspects 93-98, wherein the tracrRNA comprises a nucleotide sequence having at least 80% nucleotide sequence identity to the following nucleotide sequence (SEQ ID NO: 6)
UCAGGGUUACUAUGAUAAGGGCUUUCUGCCUAAGGCAGACUGACCCGCGGC

GUUGGGGAUCGCCUGUCGCCCGCUUUUGGCGGGCAUUCCCCAUCCUU or to the following nucleotide sequence:

(SEQ ID NO: 140)
AAGGGCUUUCUGCCUAAGGCAGACUGACCCGCGGCGUUGGGGAUCGCCUGU

CGCCCGCUUUUGGCGGGCAUUCCCCAUCCUU.

Aspect 100. The RNP complex of any one of aspects 93-99, wherein the guide RNA comprises one or more of a modified nucleobase, a modified backbone, a non-natural internucleoside linkage, a modified sugar moiety, a Locked Nucleic Acid, and a Peptide Nucleic Acid.

Aspect 101. The RNP complex of any one of aspects 93-100, comprising a cationic lipid.

Aspect 102. The RNP complex of any one of aspects 93-101, comprising a polyamine moiety.

Aspect 103. The RNP complex of any one of aspects 93-102, comprising two or more guide RNAs.

Aspect 104. The RNP complex of any one of aspects 93-102, comprising a donor template nucleic acid.

Aspect 105. A multicellular, non-human organism comprising:
 a) the RNA-guided endonuclease of any one of aspects 1-13; or
 b) the nucleic acid of any one of aspects 14-24; or
 c) the expression vector of aspect 25 or aspect 26; or
 d) the fusion polypeptide of any one of aspects 29-51; or
 e) the nucleic acid of any one of aspects 53-63; or
 f) the expression vector of aspect 64 or aspect 65.

Aspect 106. The multicellular, non-human organism of aspect 105, wherein the organism is an animal.

Aspect 107. The multicellular, non-human organism of aspect 105, wherein the organism is a plant.

Aspect 108. A method of modifying a target DNA, the method comprising contacting the target DNA with the RNP complex of any one of aspects 79-104.

Aspect 109. The method of aspect 108, wherein said modifying comprises non-homologous end joining.

Aspect 110. The method of aspect 108, wherein said modifying comprises homology-directed repair.

Aspect 111. The method of any one of aspects 108-110, wherein said contacting occurs in a cell in vitro.

Aspect 112. The method of any one of aspects 108-110, wherein said contacting occurs in a cell in vivo.

Aspect 113. The method of any one of aspects 108-112, wherein the target DNA is present in a prokaryotic cell.

Aspect 114. The method of aspect 113, wherein the prokaryotic cell is a thermophile.

Aspect 115. The method of any one of aspects 108-112, wherein the target DNA is present in a eukaryotic cell.

Aspect 116. The method of aspect 115, wherein the target DNA is chromosomal DNA.

Aspect 117. The method of aspect 115, wherein the target DNA is mitochondrial DNA.

Aspect 118. The method of any one of aspects 108-117, wherein said modifying comprises cleavage of the target DNA.

Aspect 120. A nucleic acid comprising a nucleotide sequence encoding the RNA-guided endonuclease of aspect 119.

Aspect 121. A recombinant expression vector comprising the nucleic acid of aspect 120.

Aspect 122. An RNP complex comprising:
 a) the RNA-guided endonuclease of aspect 119; and
 b) a guide RNA.

Aspect 123. A cell comprising the RNA-guided endonuclease of aspect 119, the nucleic acid of aspect 120, the recombinant expression vector of aspect 121, or the RNP complex of aspect 122.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: Characterization of GeoCas9

Methods:

Identification of Thermophilic Cas9 Homologs and Generation of Heterologous Expression Plasmids.

All isolate genomes were mined from the public Integrated Microbial genomes (IMG) database[17] using the "Genome Search by Metadata Category tool." All of the genomes annotated as "thermophile" (336) or "hyperthermophile" (94) were selected. The selected genomes were searched for the presence of Cas9-like candidates (hits to a TIGRfam model 01865 for Csn-like or 03031 for a Csx12-like) contained within a full CRISPR-Cas system (presence of Cas1, Cas2, and a Repeat-Spacers array). The GeoCas9 variant was initially selected due to its completeness, smaller gene size (shorter than the widely used SpyCas9), and growth in a large temperature range from 30-75° C. (optimal at 55° C.). The Cas9 from *Geobacillus stearothermophilus* was codon optimized for *E. coli*, ordered as Gblocks (IDT), and assembled using Gibson Assembly. For protein expression, a pET based plasmid containing an N terminal 10×His-tag and MBP was used. For PAM depletion assays, a p15A plasmid was generated with the sgRNA constitutively expressed.

Cas9 Purification.

Cas9 was purified as previously described[6] with modification. After induction, Cas9 was grown in Terrific Broth overnight at 18° C. Cells were harvested and resuspended in Lysis Buffer (50 mM Tris-HCl, pH 7.5, 20 mM imidazol, 0.5 mM TCEP, 500 mM NaCl, 1 mM PMSF), broken by sonication, and purified on Ni-NTA resin. TEV was added to the elution and allowed to cleave overnight at 4° C. The resulting protein was loaded over an MBP affinity column onto a heparin column and eluted with a linear gradient from 300 mM to 1250 mM NaCl. The resulting fractions containing Cas9 were purified by gel filtration chromatography and flash frozen in Storage Buffer (20 mM HEPES-NaOH pH 7.5, 5% Glycerol, 150 mM NaCl, 1 mM TCEP).

Differential Scanning Calorimetry.

Cas9 proteins were dialyzed into degassed DSC Buffer (0.5 mM TCEP, 50 mM $KH_2PO_4$ (pH 7.5), 150 mM NaCl) overnight at 4° C. Samples were diluted to 0.3 mg/ml and were loaded into sample cell of a NanoDSC (TA instruments) and buffer in the reference cell. The cell was pressurized to 3 atm and the sample was heated from 20 to 90° C. Measurements made for buffer in both the sample and reference cells were subtracted from the sample measurements.

PAM Depletion Assays.

PAM depletion assays were conducted as previously described[16]. Plasmids expressing Cas9 under the control of a tetracycline inducible promoter and constrictively expressing a targeting or non-targeting sgRNA were transformed with target plasmid containing a randomized PAM sequence. *E. coli* was plated and the surviving colonies were pooled. The PAM containing region was amplified and deep sequenced.

Biochemical Cleavage Assays.

Radioactive cleavage assays were conducted as previously described[38]. Reactions were carried out in 1× Reaction Buffer (20 mM Tris-HCl, pH 7.5, 100 mM KCl, 5 mM $MgCl_2$, 1 mM DTT and 5% glycerol (v/v)). 100 nM Cas9 and 125 nM sgRNA were allowed to complex for 5 min at 37° C. ~1 nM radiolabeled probe was added to the RNP to initiate the reaction. Finally, the reaction was quenched with 2× Loading Buffer (90% formamide, 20 mM EDTA, 0.02% bromophenol blue, 0.02% xylene cyanol and products were analyzed on 10% urea-PAGE gel containing 7M urea.

For thermostability measurements (FIG. 4a), 100 nM Cas9 was complexed with 150 nM sgRNA in 1× Reaction Buffer for 5 min at 37° C. 100 nM of a polymerase chain reaction (PCR) product containing the targeted sequence was cleaved using dilutions of the estimated 100 nM RNP complex to accurately determine a 1:1 ratio of Cas9 to target. Next, samples were challenged at the indicated temperature (40° C.-75° C.) for 10 min and then returned to 37° C. 100 nM PCR product containing the targeted sequence was added to the reaction and it was allowed to react for 30 min at 37° C. The reaction was quenched with 6× Quench Buffer (15% glycerol (v/v), 1 mg/ml Orange G, 100 mM EDTA) and products were analyzed on a 1.25% agarose gel stained with ethidium bromide.

For thermophilicity measurements (FIG. 4b), 500 nM Cas9 was complexed with 750 nM sgRNA in 1× Reaction Buffer for 5 min at 37° C. The samples were placed at the assayed temperature (20° C.-80° C.) and 100 nM of PCR product was added to the reaction. Timepoints were quenched using 6× Quench Buffer and analyzed on a 1.25% agarose gel stained with SYBR Safe (Thermo Fisher Scientific).

To study the effect of human plasma on the stability of Cas9 proteins, preassembled Cas9-RNP was incubated for 8 hours either at 37° C. or 4° C. in Reaction Buffer with the specified amount of normal human plasma. Substrate was then added and cleavage products were analyzed as described for thermostability measurements.

Small RNA Sequencing.

*Geobacillus stearothermophilus* was obtained from ATCC and cultured at 55° C. in Nutrient Broth (3 g beef extract and 5 g peptone per liter water, pH 6.8) to saturation. Cells were pelleted and RNA was extracted using a hot phenol extraction as previously described[39]. Total RNA was treated with TURBO DNase (Thermo Fisher Scientific), rSAP (NEB) and T4 PNK (NEB) according to manufactures instructions. Adapters were ligated onto the 3' and 5' ends of the small RNA, followed by reverse transcription with Superscript III. The library was amplified with limited cycles of PCR, gel-extracted on an 8% native polyacrylamide gel electrophoresis (PAGE) gel and sequenced on an Illumina MiSeq. Adapters were trimmed using Cutadapt and sequences >10 nt were mapped to the G. st. CRISPR locus using Bowtie 240.

HEK293T EGFP Disruption Assay and Indel Analysis.

HEK293T cells expressing a destabilized GFP were grown in Dulbecco's Modification of Eagle's Medium (MEM) with 4.5 g/L glucose L-glutamine and sodium pyruvate (Corning Cellgro), supplemented with 10% fetal bovine serum, penicillin and streptomycin at 37° C. with 5% $CO_2$. ~24 hrs before transfection, ~3×10$^4$ cells were seeded into each well of a 96-well plate. The next day, 20 pmol (unless otherwise specified) of RNP was assembled as previously described[41] and mixed with 10 μLOMEM. The RNP was added to 10 μl of 1:10 dilution of Lipofectamine 2000 (Life Technologies) in OMEM and allowed to incubate at room temperature for 10 min and added to the cells. Cells were analyzed for GFP fluorescence 48 h later using Guava EasyCyte 6HT. Experiments were conducted in triplicate and the mean±S.D. is shown. For analysis of indels, genomic DNA was extracted using Quick Extraction Solution (Epicentre), and the DNMT1 and AAVS1 loci were amplified by PCR. T7E1 reaction was conducted according to the manufacturer's instructions and products were analyzed on a 1.5% agarose gel stained with SYBR gold (Thermo Fisher Scientific).

Results

GeoCas9 is a Thermostable Cas9 Homolog

Figure 9:
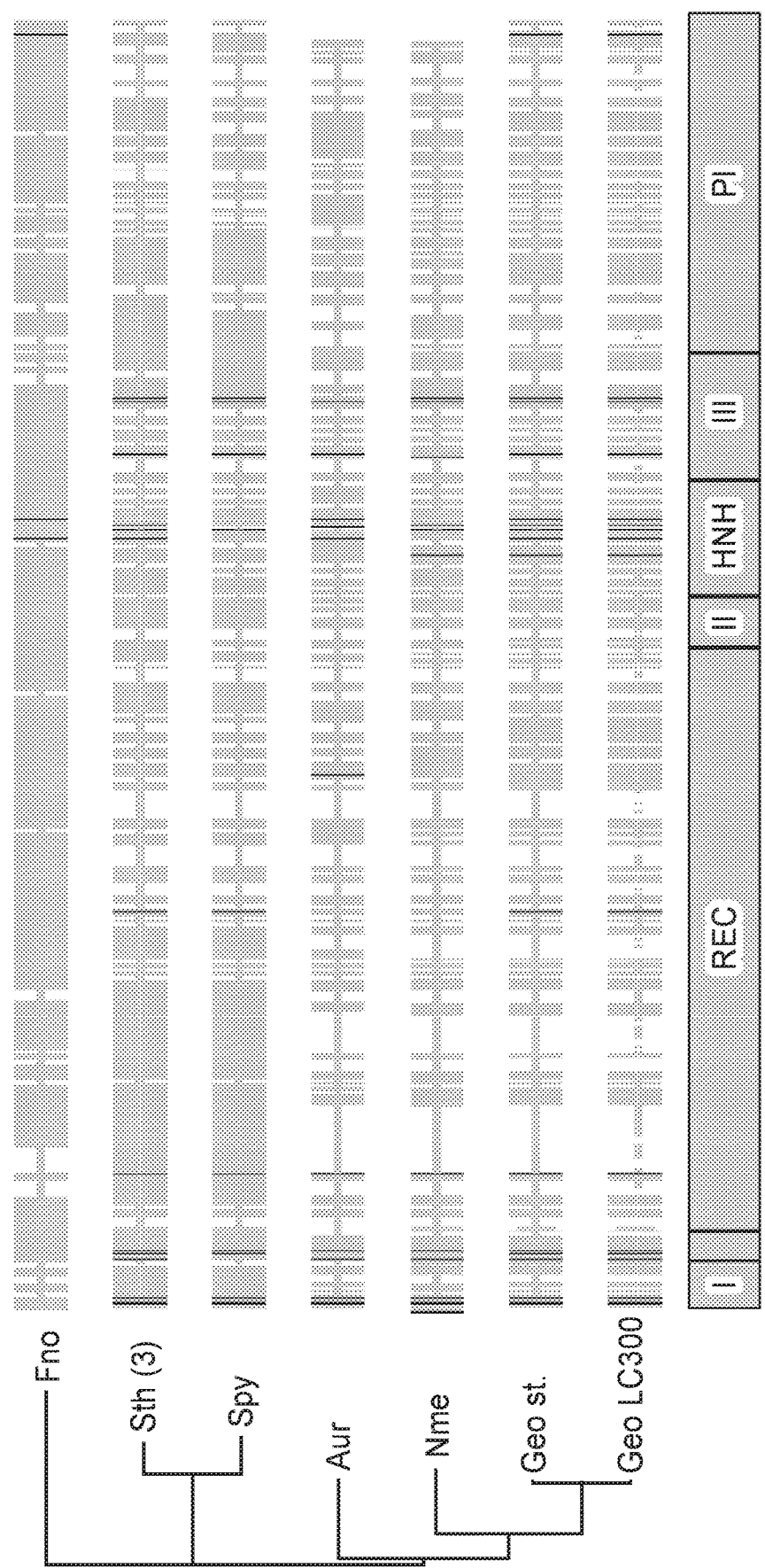
FIG. 9 provides an alignment of selected Cas9 homologs.

Although thousands of cas9 homologs have been sequenced, there have been no functionally validated Cas9 from archaea[16], restricting our search for a thermophilic Cas9 to thermophilic bacteria. All the isolates in Integral Microbial Genomes database (IMG) from a thermophilic environment that contained a Cas9-like protein[17] (hits to a TIGRfam model 01865 for Csn1-like or 03031 for a Csx12-like) were searched. From them, the Cas9 from *Geobacillus stearothermophilus* (G. st.; formerly *Bacillus stearothermophilus*)[18] stood out because it was full-length and its sequence is shorter than the average Cas9. Most importantly, this candidate is from the organism that can grow in a reported temperature range from 30° C.-75° C. (optimal at 55° C.). A BLASTn of GeoCas9 revealed several nearly identical homologs (from 93.19-99.91% identity over the full length) in 6 other *Geobacillus* species (Table 2; FIG. 12) and 92.55% Identity over the full length in *Effusibacillus pohliae* DSM22757. G. st. has been a proven source of enzymes for thermophilic molecular cloning applications[19], thermostable proteases[20] and enzymes for metabolic engineering[21]. Moreover, the wide temperature range that G. st. occupies[22] holds promise that the Cas9 from this species (GeoCas9) may be able to maintain activity at both mesophilic and thermophilic temperatures (FIG. 1a). Notably, GeoCas9 is considerably smaller than SpyCas9 (GeoCas9, 1,087 amino acids; SpyCas9, 1,368 amino acids). A homology model of GeoCas9 based on available Cas9 crystal structures along with sequence alignments revealed that the small size of GeoCas9 is largely the result of a reduced REC lobe, as is the case with other compact Cas9 homologs from *Streptococcus aureus* Cas9 (SauCas9) and *Actinomyces naeslundii* Cas9 (AnaCas9) (FIG. 1b; FIG. 9).

Figure 1E:
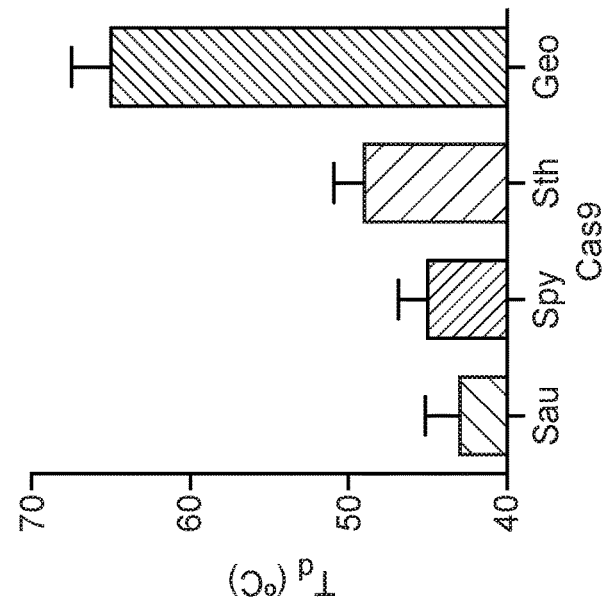
Figure 1D:
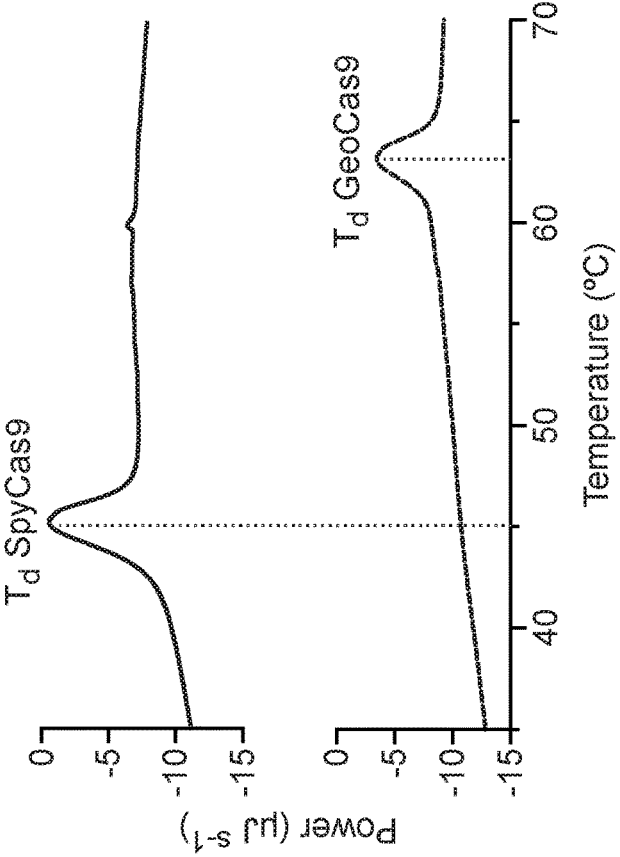

Initial thermostability tests were performed on purified GeoCas9 using differential scanning calorimetry (DSC), which showed that in the absence of RNA or DNA, GeoCas9 has a denaturation temperature about 20° C. higher than SpyCas9 (FIG. 1d). Moreover, GeoCas9 denatures at 15° C. higher than the slightly thermophilic *Streptococcus thermophilus* CRISPR III Cas9 (SthCas9) (FIG. 1e). Given these results, GeoCas9 was selected as a candidate for further development and optimization.

FIG. 1A-1E. GeoCas9 is a Small, Thermostable Cas9 Homolog.

a, Phylogeny of Cas9 proteins used for genome editing with their length (amino acids) and the maximum temperatures that supports growth of the host indicated to the right[22] (Nme, *Neisseria meningitidis*; Geo, *Geobacillus stearothermophilus*; Geo LC300, *Geobacillus* LC300; Spy, *Streptococcus pyogenes*; Sau, *Streptococcus aureus*; Fno, *Francisella novicida*; Sth (3), *Streptococcus thermophilus* CRISPR III). b, Homology model of GeoCas9 generated using Phyre 2[42] with the DNA from PDB 5CZZ docked in. c, Schematic illustration of the domains of Spy Cas9 (blue) and GeoCas9 (orange) with active site residues indicated below with asterisks. d, Representative traces for Differential Scanning calorimetry (DSC) of GeoCas9 and SpyCas9, $T_d$; Denaturation temperature. e, Denaturation temperature of various Cas9 proteins as measured by DSC, mean±S.D. is shown.

FIG. 9. Alignment of Selected Cas9 Homologs.

Alignment was generated using MAFFT and the approximate domain boundaries are shown below. Black lines indicate conserved residues.

GeoCas9 PAM identification and Engineering

Figure 2A:
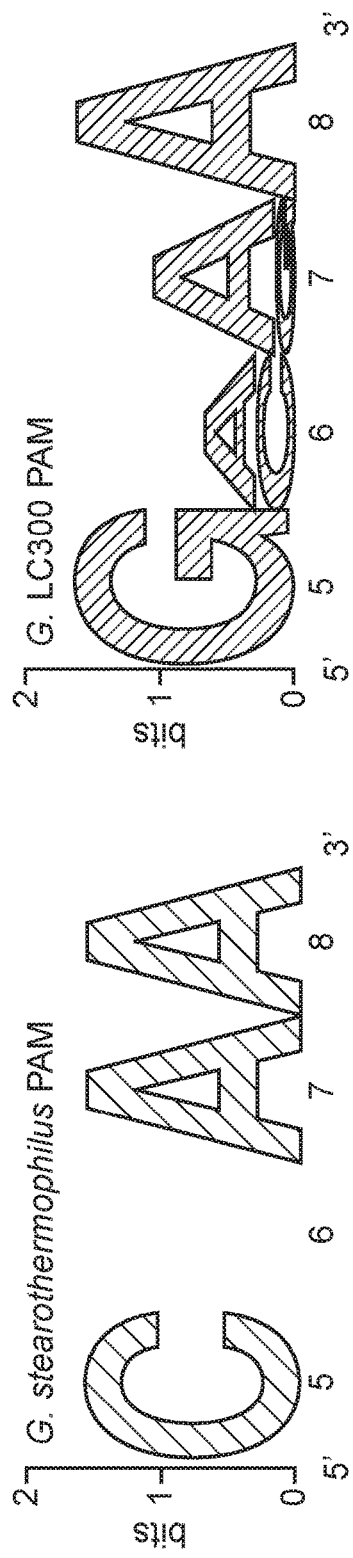
FIG. 2A-2D depict PAM identification and engineering of GeoCas9.
Figure 2B:
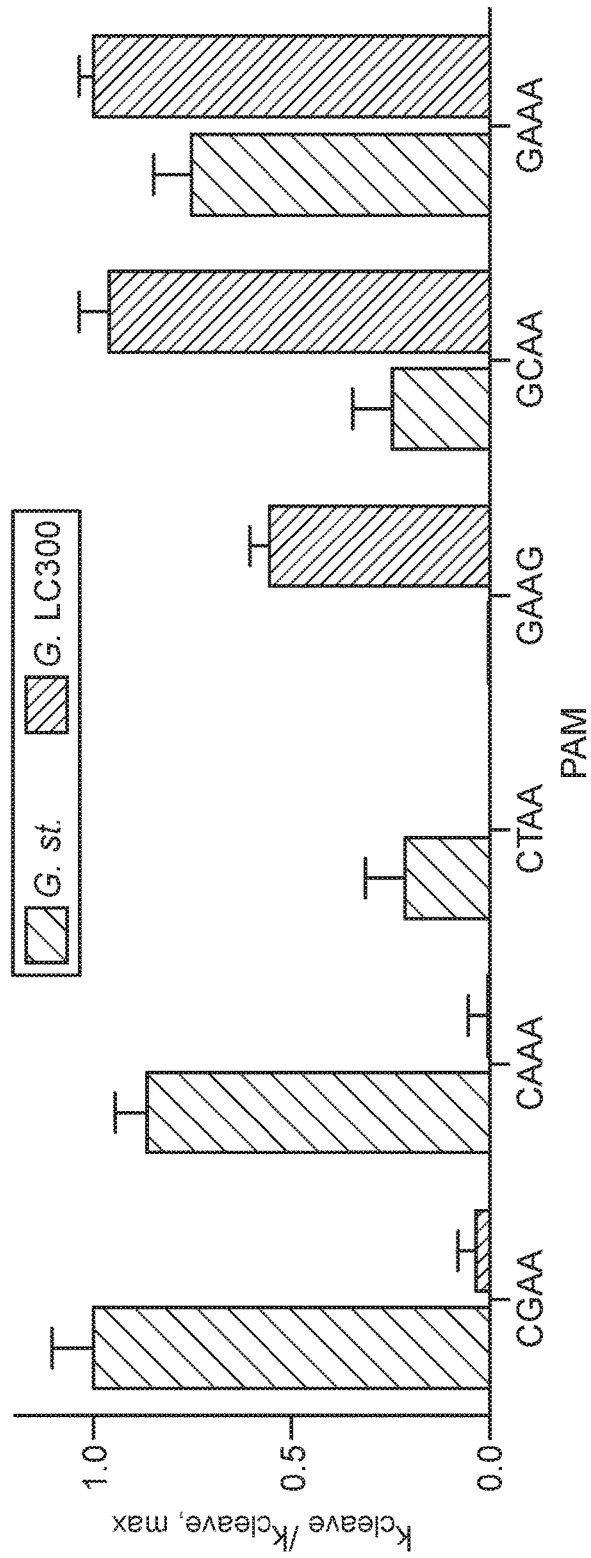

CRISPR systems have evolved a preference for a protospacer adjacent motif (PAM) to avoid self-targeting of the host genome[23,24]. These PAM sequences are divergent among Cas9 homologs and DNA targets are often mutated in this region to escape cleavage by Cas9[25]. To identify the PAM for GeoCas9, naturally targeted viral and plasmid sequences were searched for, using CRISPRtarget[26]. The three sequenced strains of G. st. provided 77 spacer sequences, and 3 of them had high-confidence viral and plasmid targets (FIG. 10; Table 3, FIG. 13). Extracting the sequences 3' of the targeted sequence revealed a consensus of 5'-NNNNCNAA-3' (FIG. 2a, ED FIG. 2). Given the low number of viral targets, cleavage assays were performed on substrates containing various PAM sequences, revealing a complete PAM sequence of 5'-NNNNCRAA-3' (FIG. 2b).

Figure 2C:
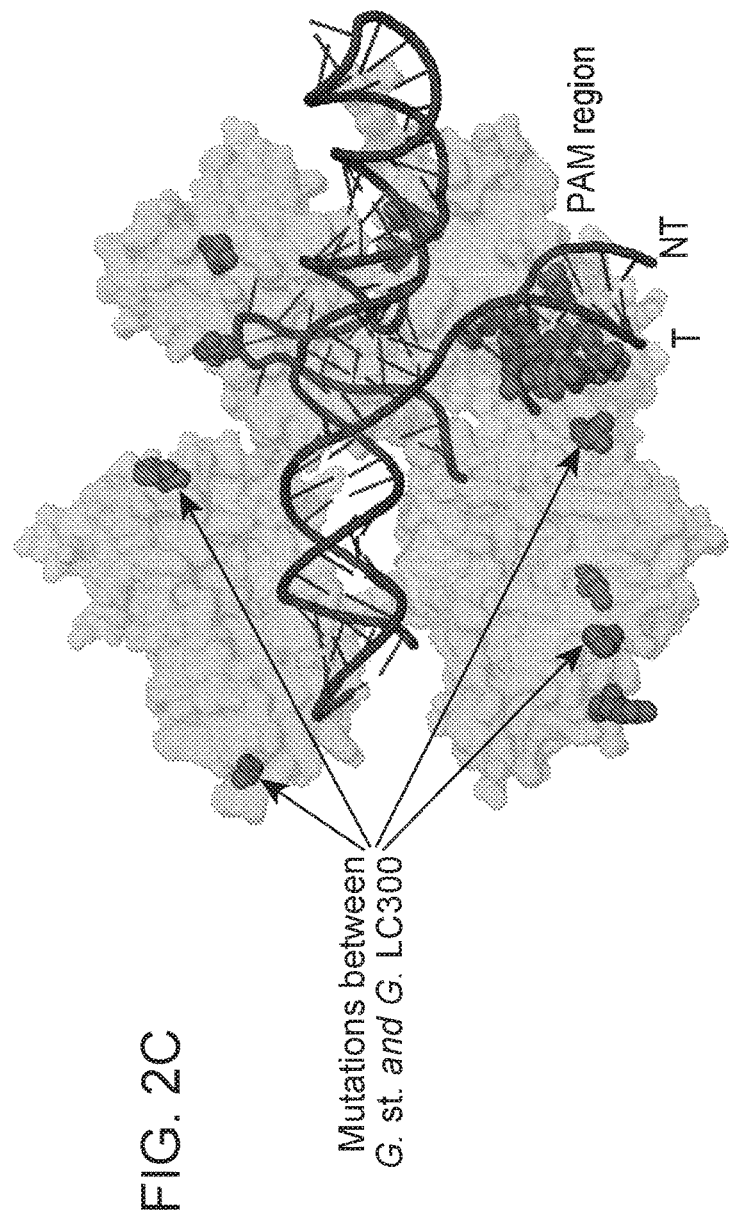
Figure 2D:
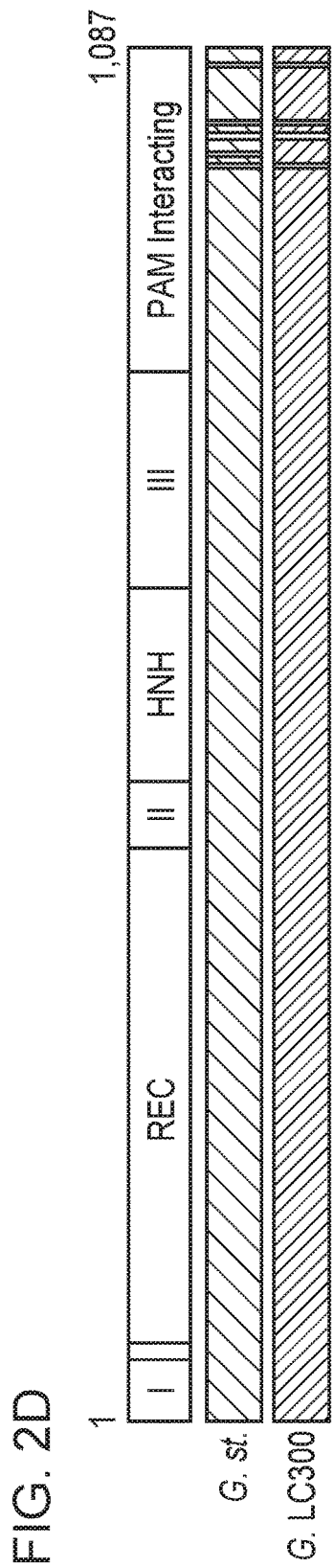

In addition to the CRISPR loci found in G. st. strains, a type II CRISPR locus was found in *Geobacillus* LC300, the locus containing a Cas9 with ~97% amino acid identity to the G. st. Cas9. Despite having nearly identical sequences, alignment of these two homologs of GeoCas9 revealed a tight cluster of mutations in the PAM interacting domain (PI) (FIG. 2d). Furthermore, mapping these mutations onto the homology model of GeoCas9 showed that they are located near the PAM region of the target DNA (FIG. 2c). It was hypothesized that this GeoCas9 variant might have evolved altered PAM specificity. By searching for viral targets using the spacers in the G. LC300 array, a preference for GMAA in place of the CRAA PAM of G. st. was identified, lending support to the hypothesis. A hybrid Cas9 protein was constructed and purified, in which the PI domain of the G. LC300 Cas9 was substituted for the PI domain of G. st. Cas9. Cleavage activity of the hybrid Cas9 protein was tested on targets containing various PAM sequences (FIG. 2b). It was found that, as predicted by protospacer sequences, the hybrid Cas9 preferred a GMAA PAM rather than the CRAA PAM utilized by GeoCas9. Moreover, G. LC300 appears to be more specific for its optimal PAM, which may result in lower off-target cleavage for genome editing applications[27]. By creating a hybrid Cas9 with this naturally occurring PAM-recognition variant, the sequence space that can be targeted by GeoCas9 is doubled without resorting to structure based protein engineering as has been done for other Cas9 homologs[27].

FIG. 2A-2D. PAM Identification and Engineering of GeoCas9.

a, WebLogo for sequences found at the 3' end of protospacer targets identified with CRISPRTarget for *Geobacillus stearothermophilus* (left panel) and *Geobacillus* LC300 (right panel). b, Cleavage assays conducted with the two homologs of GeoCas9. Substrates with various PAM sequences were P32-labelled and mean±S.D. is shown. c, Mapping of mutated residues (orange spheres) between G. st. and G. LC300 onto the homology model of GeoCas9 showing high density in the PAM interacting domain near the PAM region of the target DNA. d, Alignment of the Cas9 proteins from G. st. and G. LC300 with the domain boundaries shown above. Solid colors represent identical residues and grey lines indicate residues that are mutated between the two Cas9 homologs.

FIG. 10A-10D. Targets Used to Generate Logos in FIG. 2b and FIG. 2c. FIGS. 10A and 10C.

Phage and plasmid targets matching the *G. stearothermophilus* and G. LC300 spacer sequences. PAM region is highlighted in yellow. FIGS. 10B and 10D. Logo of the sequences 3' of the protospacer target identified in FIGS. 10A and 10C.

Identification of Both crRNA and tracrRNA and Engineering of GeoCas9 sgRNA

Figure 3A:
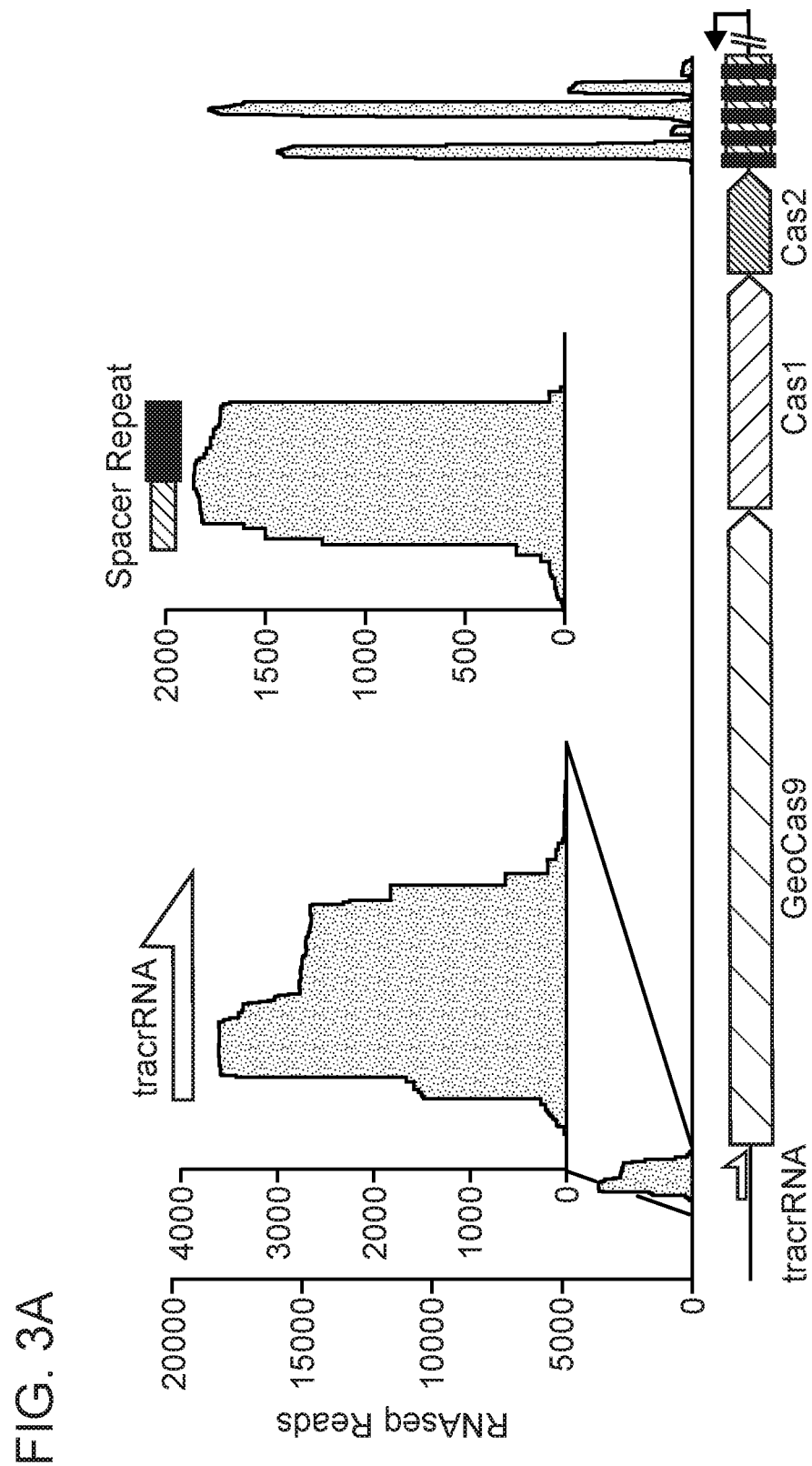

CRISPR-Cas9 systems use a trans-activating crRNA (tracrRNA), which is required for maturation of the crRNA and activation of Cas9[6,28]. To identify the tracrRNA for GeoCas9, G. st. was cultured, and the small RNA it produced was deep sequenced. It was found that the CRISPR array was transcribed despite a lack of phage or plasmid challenge, and that the array was transcribed in the opposite direction of the Cas proteins (FIG. 3a). The crRNA was processed to 23 nt (FIG. 3b) of the spacer sequence and 18 nt of the repeat sequence in vivo, similar to other small type IIC Cas9 proteins[8,29]. Mapping of the RNAseq reads to the CRISPR array also revealed a putative tracrRNA upstream of the Cas9 open reading frame (ORF).

This putative tracrRNA was joined to the processed crRNA using a GAAA-tetraloop to generate a single-guide RNA (sgRNA)[30]. Variations of this sgRNA were in vitro transcribed and tested for their ability to direct GeoCas9 to cleave a radiolabeled double-stranded DNA target at 37° C. The length of the crRNA:tracrRNA duplex was varied; it was found that this modification had little impact on the DNA cleavage rate (left panel, FIG. 3c), making it a valuable place for further sgRNA modifications[31]. Next, the length of the tracrRNA was tested; stopping points near predicted rho-independent terminators were chosen. In contrast to the crRNA:tracrRNA duplex length, the length of the tracrRNA had a dramatic effect on the cleavage rate, with sequences shorter than 91 nt supporting only a small amount of cleavage (middle panel, FIG. 3c). Finally, the length of the spacer sequence was varied; it was found that 21-22 nt resulted in a more than 5-fold increase in cleavage rate, compared to the 20 nt spacer preferred by SpyCas9 (right panel, FIG. 3c). This finding contrasts with the most abundant spacer length of 23 nt found in RNAseq. This difference may be due to inter- or intramolecular guide interactions in the in vitro transcribed sgRNA[32].

FIG. 3A-3C. Small RNA-Seq and sgRNA Engineering for GeoCas9.

a, Small RNA sequenced from *G. stearothermophilus* mapped to the CRISPR locus. Inset shows enlargement of the region corresponding to the tracrRNA and the most highly transcribed repeat and spacer sequence. b, Distribution of the length of the spacer sequences extracted from the small RNA sequencing results. c, Length optimization of the tracrRNA and crRNA for GeoCas9 and the optimal guide RNA design (right panel). The length of the tracrRNA, crRNA:tracrRNA duplex and spacer was optimized sequentially by transcribing variations of the sgRNA and testing their ability to guide GeoCas9-mediated cleavage of a radiolabeled substrate. The mean $k_{cleave}$±S.D. is shown and experiments were conducted in triplicate.

Genome Editing by GeoCas9 RNP in Mammalian Cells

Figure 4B:
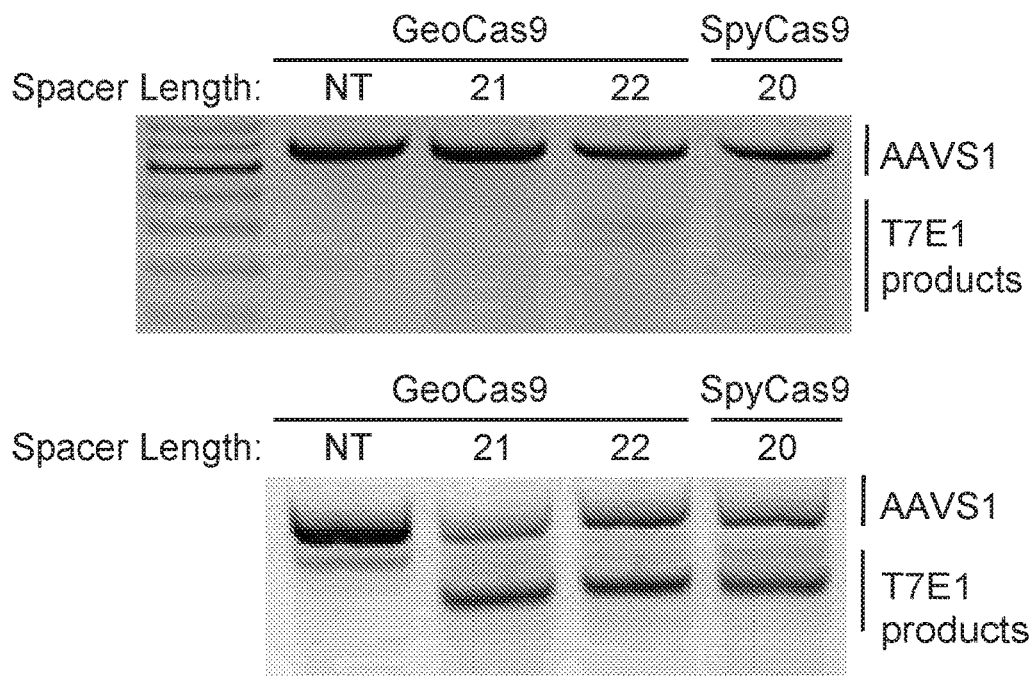
Figure 4C:
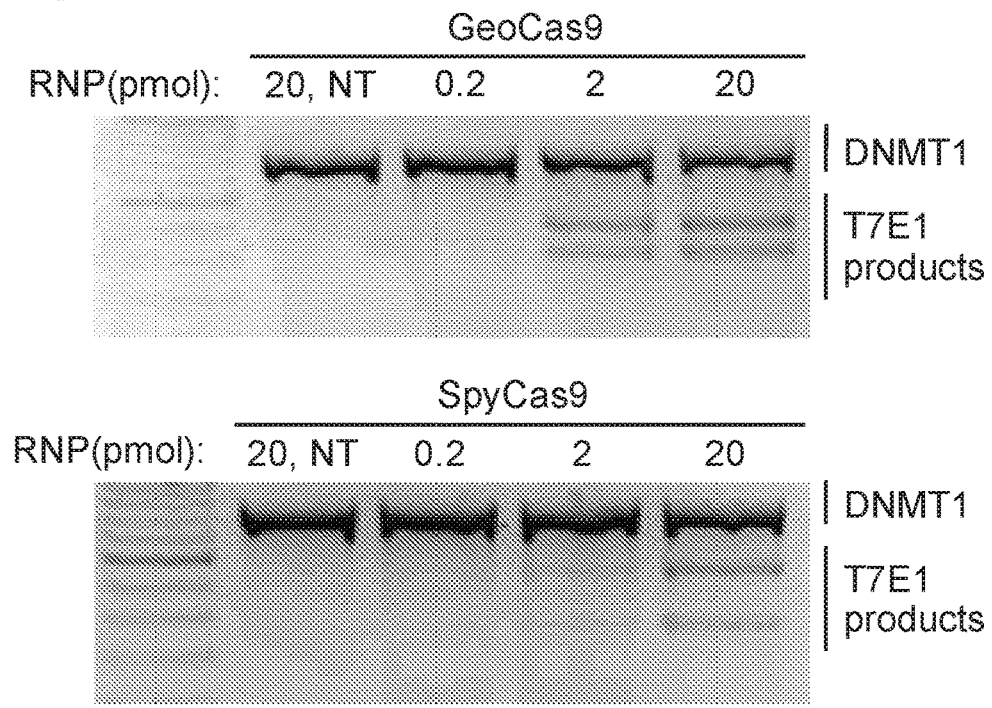

With evidence that GeoCas9 maintains cleavage activity at mesophilic temperatures, the ability of GeoCas9 to edit mammalian genomes was assessed. GeoCas9 and SpyCas9 editing efficiency were tested by delivering preassembled ribonucleoprotein complexes (RNPs) into cultured cells, circumventing differences between SpyCas9 and GeoCas9 protein expression. First, GeoCas9 RNPs targeting regions adjacent to various PAM sequences were delivered into HEK293T cells expressing a destabilized GFP (FIG. 4a). It was found that when targeted to sequences adjacent to the preferred CRAA PAM, GeoCas9 decreased GFP fluorescence at levels comparable to those observed for SpyCas9 (FIG. 4a). Next, GeoCas9 was targeted to cleave the native genomic loci DNMT1 and AAVS1 (FIG. 4b,c). The length of the targeting spacer sequence was varied; it was found that at one site 21 nt was a sufficient length to efficiently induce indels while at another site a 22 nt spacer length was necessary. Given this variability and that extending the spacer length to 22 nt had no detrimental effects, it was concluded that a 22 nt guide segment length is preferred for use in genome editing applications. Moreover, when editing efficiency at a site containing an overlapping PAM for both GeoCas9 and SpyCas9 was tested, similar editing efficiencies by both proteins were observed (FIG. 4b). At the DNMT1 locus, amounts of GeoCas9 and SpyCas9 RNPs were titrated to assess the effect on genome editing efficiency (FIG. 4c). Products analyzed by T7E1 assay again showed efficient production of indels by both GeoCas9 and SpyCas9. These results demonstrate that GeoCas9 is an effective alternative to SpyCas9 for genome editing in mammalian cells.

FIG. 4A-4V. Genome Editing Activity of GeoCas9 in Mammalian Cells.

a, EGFP disruption in HEK293T cells by GeoCas9. HEK293FT cells expressing a destabilized GFP were transfected with GeoCas9 RNP preassembled with a targeting or non-targeting guide RNA. Cells were analyzed by flow cytometry and targets adjacent to the CRAA PAM resulted in efficient GFP disruption (NT; non-targeting). b, T7E1 analysis of indels produced at the AAVS1 locus when the guide length was varied from 21 to 22 nt. c, T7E1 analysis of indels produced using a titration of GeoCas9 and SpyCas9 RNP targeting the DNMT1 locus in HEK293T cells.

Figure 5A:
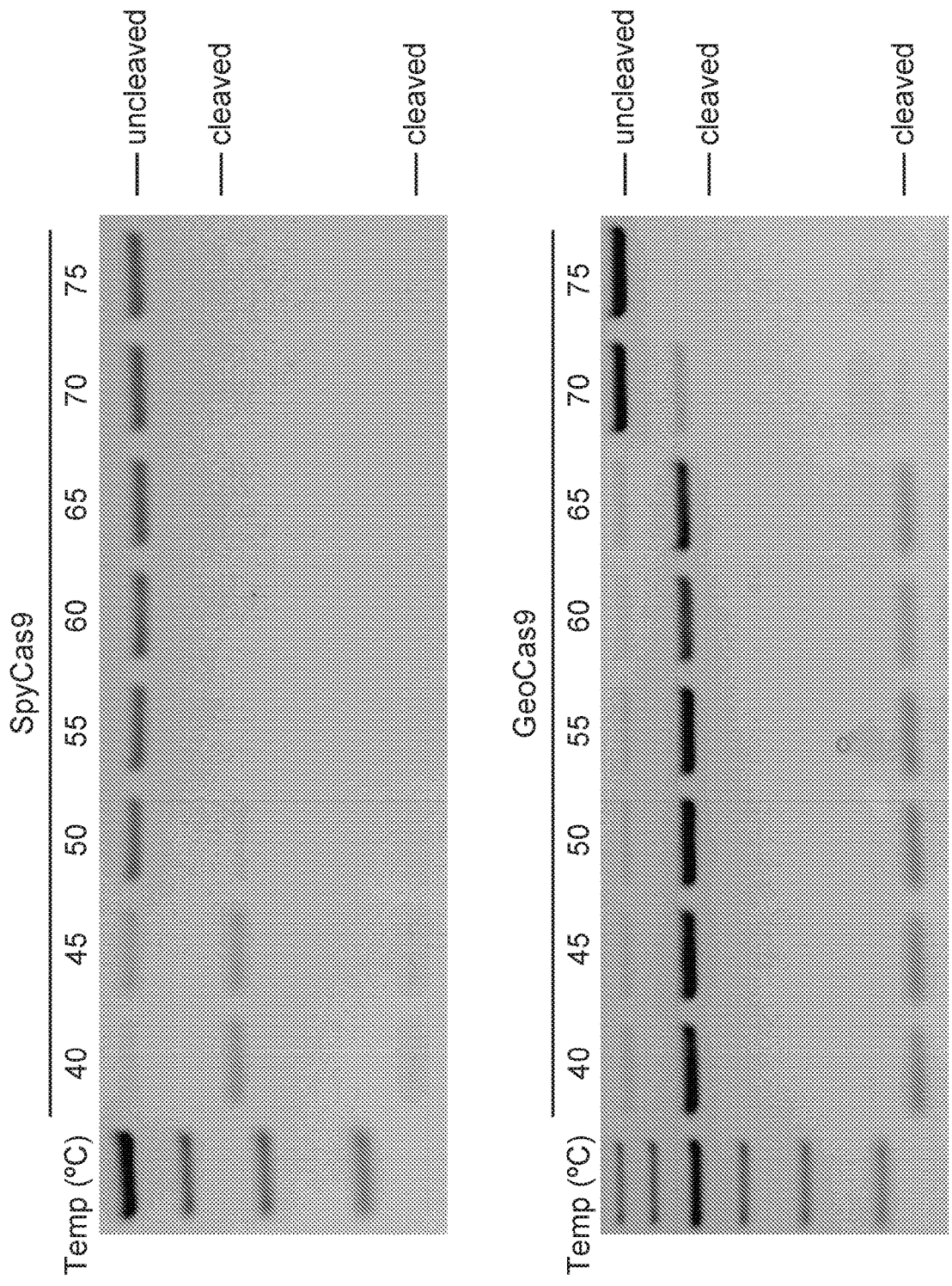
FIG. 5A-5C depict GeoCas9 activity at various temperatures.

GeoCas9 Functions Over a Wide Temperature Range and has Extended Lifetime in Human Plasma Based on initial observations showing that GeoCas9 protein remains folded at elevated temperatures (FIG. 1d, e), it was tested whether the GeoCas9 RNP maintains activity after exposure to high temperatures. SpyCas9 and GeoCas9 were incubated at a challenge temperature and equimolar substrate was added to test the fraction of RNP that remained functional. After incubation for 10 min at 45° C., the fraction of active SpyCas9 was greatly reduced (FIG. 5a). In contrast, the fraction of GeoCas9 after incubation at 45° C. remained at 100% and not until challenge at 70° C. was a decrease in activity detected (FIG. 5a).

Figure 5B:
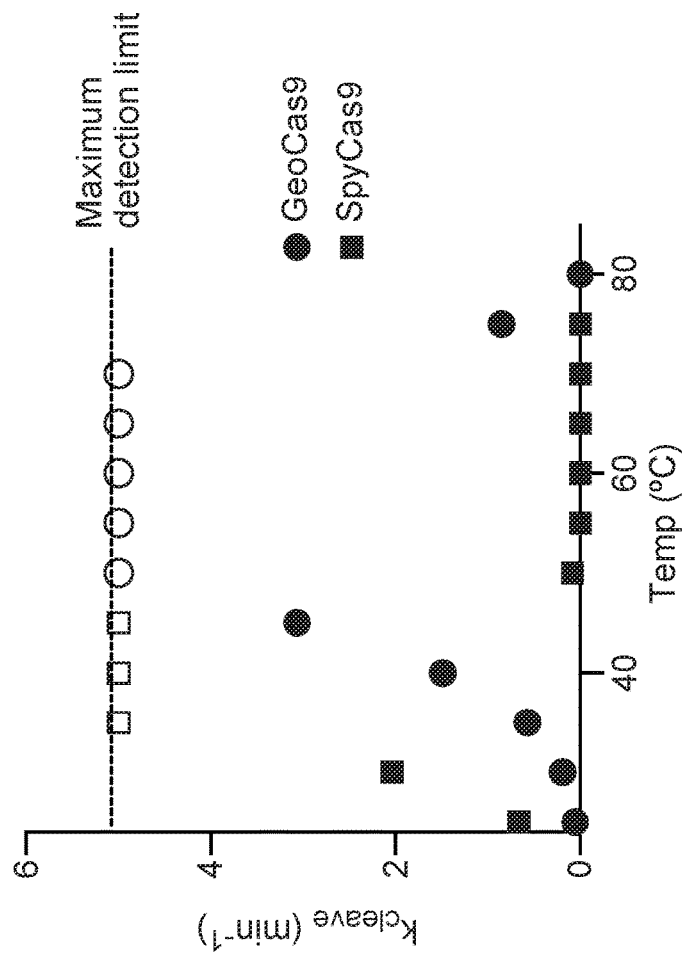

Often thermostability comes at the cost of reduced activity at lower temperatures[33]. However, the wide range of natural growth temperatures for G. st. suggested that Geo-Cas9 might maintain activity at mesophilic temperatures. To examine this hypothesis, the cleavage rates of SpyCas9 and GeoCas9 were measured at various temperatures (FIG. 5b). SpyCas9 DNA cleavage rates increased between 20-35° C., reaching maximum levels from 35-45° C. Above these temperatures, SpyCas9 activity dropped sharply to undetectable levels, as predicted by thermostability measurements. In contrast, GeoCas9 activity increased to the maximum detection limit at 50° C. and maintained maximum detectable activity up to 70° C., dropping to low levels at 75° C. These results make GeoCas9 a valuable candidate for editing obligate thermophilic organisms and for biochemical cleavage applications requiring Cas9 to operate at elevated temperatures.

Figure 5C:
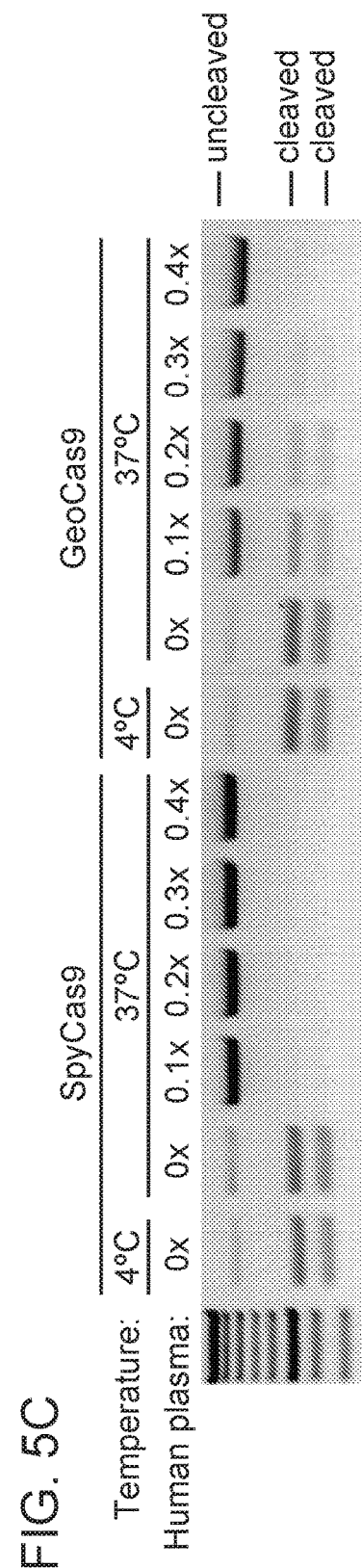

It was shown previously that thermostable proteins have longer lifetime in blood[34]. To test if this is the case for GeoCas9, SpyCas9 and GeoCas9 were incubated in diluted human plasma at 37° C. for 8 hrs and measured the amount of Cas9 activity remaining (FIG. 5c). Although SpyCas9 maintained activity when incubated in reaction buffer at 37° C., its activity was abolished even at the lowest concentration of plasma. In contrast, GeoCas9 maintained robust activity after incubation with human plasma, making it a promising candidate for in vivo RNP delivery.

FIG. 5A-5C. Thermostability of GeoCas9 and Longevity in Human Plasma.

a, Activity of SpyCas9 and GeoCas9 after incubation at the indicated temperature. After challenging at the higher temperature, reactions were conducted at 37° C. using a 1:1 ratio of substrate to RNP. b, Cleavage rate of SpyCas9 and GeoCas9 RNPs at various temperatures. Maximum detection limit is shown by the dashed line at $k_{cleave}=5$, indicating that the reaction completed in 30 s. c, Effect of incubating GeoCas9 and SpyCas9 in human plasma. After incubation in varying concentrations of human plasma for 8 hrs at 37° C., the reaction was carried out with 1:1 ratio of DNA substrate to RNP.

FIGS. 11-14 provide guide RNAs, primers, and DNA substrates used in various figures; candidate thermophiles; and spacer sequences in Geobacillus sp. LC300 (complete genome).

REFERENCES

1. Wang, H., Russa, M. La & Qi, L. S. CRISPR/Cas9 in Genome Editing and Beyond. (2016). doi:10.1146/annurev-biochem-060815-014607
2. Chylinski, K., Makarova, K. S., Charpentier, E. & Koonin, E. V. Classification and evolution of type II CRISPR-Cas systems. Nucleic Acids Res. 42, 6091-6105 (2014).
3. Chylinski, K., Makarova, K. S., Charpentier, E. & Koonin, E. V. Classification and evolution of type II CRISPR-Cas systems. Nucleic Acids Res. 42, 6091-6105 (2014).
4. Ma, E., Harrington, L. B., O'Connell, M. R., Zhou, K. & Doudna, J. A. Single-Stranded DNA Cleavage by Divergent CRISPR-Cas9 Enzymes. Mol. Cell 60, 398-407 (2015).
5. Ran, F. A. et al. In vivo genome editing using Staphylococcus aureus Cas9. Nature 520, 186-191 (2015).
6. Jinek, M. et al. A Programmable Dual-RNA-Guided. 337, 816-822 (2012).
7. Esvelt, K. M. et al. Orthogonal Cas9 proteins for RNA-guided gene regulation and editing. Nat. Methods 10, 1116-21 (2013).
8. Hou, Z. et al. Efficient genome engineering in human pluripotent stem cells using Cas9 from Neisseria meningitidis. Proc. Natl. Acad. Sci. 110, 15644-15649 (2013).
9. Hirano, H. et al. Structure and Engineering of Francisella novicida Cas9. Cell 1-12 (2016). doi:10.1016/j.cell.2016.01.039
10. Cong, L., Ran, F., Cox, D., Lin, S. & Barretto, R. Multiplex Genome Engineering Using CRISPR/Cas Systems. Science (80-.). (2013). doi:10.1038/nbt1319
11. Xiang, G., Zhang, X., An, C., Cheng, C. & Wang, H. Temperature effect on CRISPR-Cas9 mediated genome editing. J. Genet. Genomics 3-9 (2017). doi:10.1016/j.jgg.2017.03.004
12. Mougiakos, I. et al. Efficient genome editing of a facultative thermophile using the mesophilic spCas9. ACS Synth. Biol. acssynbio.6b00339 (2017). doi:10.1021/acssynbio.6b00339
13. Zeldes, B. M. et al. Extremely thermophilic microorganisms as metabolic engineering platforms for production of fuels and industrial chemicals. Front. Microbiol. 6, 1-17 (2015).
14. Porteus, M. Genome Editing: A New Approach to Human Therapeutics. Annu. Rev. Pharmacol. Toxicol. 56, 163-190 (2016).
15. Staahl, B. T. et al. Efficient genome editing in the mouse brain by local delivery of engineered Cas9 ribonucleoprotein complexes. Nat. Biotechnol. (2017). doi:10.1038/nbt.3806
16. Burstein, D., Harrington, L. B., Strutt, S. C. & Probst, A. J. New CRISPR-Cas systems from uncultivated microbes. Nat. Publ. Gr. 542, 237-241 (2017).
17. Markowitz, V. M. et al. IMG: The integrated microbial genomes database and comparative analysis system. Nucleic Acids Res. 40, 115-122 (2012).
18. Donk, P. J. & Name, B. N. S. A HIGHLY RESISTANT THERMOPHILIC ORGANISM An examination of spoilage samples of 'Standard Maine Style' corn which had been packed in the usual manner and processed at 118° C. for 75 minutes showed the presence of a thermophile. The same organism was I. 373-374 (1920).
19. Notomi, T. et al. Loop-mediated isothermal amplification of DNA. Nucleic Acids Res. 28, E63 (2000).
20. Fujii, M., Takagi, M., Imanaka, T. & Aiba, S. Molecular Cloning of a Thermostable Neutral Protease Gene from Bacillus stearothermophilus in a Vector Plasmid and Its Expression in Bacillus stearothermophilus and Bacillus subtilis. Microbiology 154, 831-837 (1983).
21. Ingram, L. O. et al. Metabolic engineering for production of biorenewable fuels and chemicals: Contributions of synthetic biology. J. Biomed. Biotechnol. 2010, (2010).
22. Cordova, L. T., Long, C. P., Venkataramanan, K. P. & Antoniewicz, M. R. Complete genome sequence, metabolic model construction and phenotypic characterization of Geobacillus LC300, an extremely thermophilic, fast growing, xylose-utilizing bacterium. Metab. Eng. 32, 74-81 (2015).
23. Mojica, F. J. M. et al. Short motif sequences determine the targets of the prokaryotic CRISPR defence system. Microbiology 155, 733-740 (2009).
24. Bolotin, A., Quinquis, B., Sorokin, A. & Dusko Ehrlich, S. Clustered regularly interspaced short palindrome repeats (CRISPRs) have spacers of extrachromosomal origin. Microbiology 151, 2551-2561 (2005).
25. Paez-Espino, D. et al. CRISPR immunity drives rapid phage genome evolution in Streptococcus thermophilus. MBio 6, 1-9 (2015).

26. Biswas, A., Gagnon, J. N., Brouns, S. J. J., Fineran, P. C. & Brown, C. M. CRISPRTarget. *RNA Biol.* 10, 817-827 (2013).
27. Kleinstiver, B. P. et al. Engineered CRISPR-Cas9 nucleases with altered PAM specificities. *Nature* (2015). doi: 10.1038/nature14592
28. Deltcheva, E. et al. CRISPR RNA maturation by trans-encoded small RNA and host factor RNase III. *Nature* 471, 602-607 (2011).
29. Fonfara, I. et al. Phylogeny of Cas9 determines functional exchangeability of dual-RNA and Cas9 among orthologous type II CRISPR-Cas systems. *Nucleic Acids Res.* 42, 2577-2590 (2014).
30. Jinek, M. et al. A Programmable Dual-RNA-Guided DNA Endonuclease in Adaptive Bacterial Immunity. *Science (80-.).* 337, 816-822 (2012).
31. Konermann, S. et al. Genome-scale transcriptional activation by an engineered CRISPR-Cas9 complex. *Nature* 517, 583-8 (2014).
32. Thyme, S. B., Akhmetova, L., Montague, T. G., Valen, E. & Schier, A. F. Internal guide RNA interactions interfere with Cas9-mediated cleavage. *Nat. Commun.* 7, 11750 (2016).
33. Sawle, L. & Ghosh, K. How do thermophilic proteins and proteomes withstand high temperature? *Biophys. J.* 101, 217-227 (2011).
34. Narasimhan, D. et al. Structural analysis of thermostabilizing mutations of cocaine esterase. *Protein Eng. Des. Sel.* 23, 537-547 (2010).
35. Li, Y. et al. Harnessing Type i and Type III CRISPR-Cas systems for genome editing. *Nucleic Acids Res.* 44, (2015).
36. Weinberger, A. D., Wolf, Y. I., Lobkovsky, A. E., Gilmore, M. S. & Koonin, E. V. Viral diversity threshold for adaptive immunity in prokaryotes. *MBio* 3, 1-10 (2012).
37. Shmakov, S. et al. Diversity and evolution of class 2 CRISPR-Cas systems. *Nat. Rev. Microbiol.* 15, 169-182 (2017).
38. Wright, A. V et al. Rational design of a split-Cas9 enzyme complex. *Proc. Natl. Acad. Sci. U.S.A* 112, 2984-9 (2015).
39. Zhang, Y. et al. Processing-Independent CRISPR RNAs Limit Natural Transformation in *Neisseria meningitidis*. *Mol. Cell* 50, 488-503 (2013).
40. Langmead, B. & Salzberg, S. L. Fast gapped-read alignment with Bowtie 2. *Nat Methods* 9, 357-359 (2012).
41. Lin, S., Staahl, B., Alla, R. K. & Doudna, J. a. Enhanced homology-directed human genome engineering by controlled timing of CRISPR/Cas9 delivery. *Elife* 3, 1-13 (2014).
42. Kelly, L. A., Mezulis, S., Yates, C., Wass, M. & Sternberg, M. The Phyre2 web portal for protein modelling, prediction, and analysis. *Nat. Protoc.* 10, 845-858 (2015).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An RNA-guided endonuclease that comprises:
   a) an amino acid sequence having at least 95% amino acid sequence identity to amino acids 1-994 of the amino acid sequence set forth in SEQ ID NO: 1; and
   b) a heterologous protospacer adjacent motif (PAM) interacting (PI) domain comprising an amino acid sequence having at least 95% amino acid sequence identity to the following amino acid sequence: IIKTAGGEEIKIKDLFAYYKTIHSGTA-GLELVSHDCSFSLSGVGSRTLKR-FEKYQVDVLGNIYKVRGEKRVGLASSAHSKTGETIRPLQSTRD (SEQ ID NO: 4), wherein the PI domain is heterologous to the amino acid sequence of part a).

2. The RNA-guided endonuclease of claim 1, wherein the RNA-guided endonuclease is enzymatically active in a temperature range of from 15° C. to 75° C.

3. The RNA-guided endonuclease of claim 1, wherein the RNA-guided endonuclease binds to a target nucleic acid comprising a PAM comprising a GMAA sequence, wherein M is A or C.

4. The RNA-guided endonuclease of claim 1, wherein the heterologous PI domain comprises an amino acid sequence having at least 99% amino acid sequence identity to the following amino acid sequence:

(SEQ ID NO: 4)
IIKTAGGEEIKIKDLFAYYKTIHSGTAGLELVSHDCSFSLSGVGSRTLKRF

EKYQVDVLGNIYKVRGEKRVGLASSAHSKTGETIRPLQSTRD.

5. The RNA-guided endonuclease of claim 1, wherein the heterologous PI domain comprises an amino acid sequence having less than 83% amino acid sequence identity to the following amino acid sequence:

(SEQ ID NO: 5)
TVKTAAGEEINVKDVFVYYKTIDSANGGLELISHDHRFSLRGVGSRTLKRF

EKYQVDVLGNIYKVRGEKRVGLASSAHSKPGKTIRPLQSTRD.

6. The RNA-guided endonuclease of claim 1, wherein the RNA-guided endonuclease has a length of from 1050 amino acids to 1120 amino acids.

7. The RNA-guided endonuclease of claim 1, wherein the RNA-guided endonuclease has a length of from 1080 amino acids to 1095 amino acids.

8. The RNA-guided endonuclease of claim 1, wherein the RNA-guided endonuclease comprises an amino acid sequence having at least 99% amino acid sequence identity to amino acids 1-994 of the amino acid sequence set forth in SEQ ID NO: 1.

9. The RNA-guided endonuclease of claim 1, wherein the RNA-guided endonuclease comprises: a) a substitution of amino acid Asp-8; b) a substitution of amino acid His-582; or c) substitution of both Asp-8 and His-582, based on the amino acid numbering of the amino acid sequence of SEQ ID NO:1.

10. A fusion polypeptide comprising:
    a) an RNA-guided endonuclease that comprises:
       i) an amino acid sequence having at least 95% amino acid sequence identity to amino acids 1-994 of the amino acid sequence set forth in SEQ ID NO: 1; and
       ii) a heterologous protospacer adjacent motif (PAM) interacting (PI) domain comprising an amino acid sequence having at least 95% amino acid sequence identity to the following amino acid sequence: IIKTAGGEEIKIKDLFAYYKTIHSGTA-GLELVSHDCSFSLSGVGSRTLKR-FEKYQVDVLGNIYKVRGEKRVGLASSAHSKTGETIRPLQSTRD (SEQ ID NO: 4), wherein the PI domain is heterologous to the amino acid sequence of part i); and
    b) a heterologous fusion partner polypeptide.

11. A cell comprising the RNA-guided endonuclease of claim 1.

12. A ribonucleoprotein (RNP) complex comprising:
    a1) the RNA-guided endonuclease of claim 1; and
    b1) a guide RNA comprising:
       i) a DNA-targeting segment comprising a nucleotide sequence that is complementary to a target nucleotide sequence in a target nucleic acid; and
       ii) a protein-binding segment that binds to and activates the thermostable RNA-guided endonuclease, wherein the protein-binding segment comprises a duplex-forming linker segment and a tracrRNA.

13. A method of modifying a target DNA, the method comprising contacting the target DNA with the RNP complex of claim 12.

14. The RNA-guided endonuclease of claim 1, wherein the RNA-guided endonuclease comprises:
  a) an amino acid sequence having amino acids 1-994 of the sequence set forth in SEQ ID NO: 1; and
  b) a heterologous PI domain comprising the amino acid sequence of SEQ ID NO: 4.

15. The fusion polypeptide of claim 10, wherein the RNA-guided endonuclease comprises an amino acid sequence having at least 99% amino acid sequence identity to amino acids 1-994 of the amino acid sequence set forth in SEQ ID NO: 1.

16. The fusion polypeptide of claim 10, wherein the heterologous PI domain comprises an amino acid sequence having at least 99% amino acid sequence identity to the amino acid sequence set forth in SEQ ID NO: 4.

* * * * *

SEQUENCE LISTING

```
<160> NUMBER OF SEQ ID NOS: 140

<210> SEQ ID NO 1
<211> LENGTH: 1087
<212> TYPE: PRT
<213> ORGANISM: Geobacillus stearothermophilus

<400> SEQUENCE: 1

Met Arg Tyr Lys Ile Gly Leu Asp Ile Gly Ile Thr Ser Val Gly Trp
1               5                   10                  15

Ala Val Met Asn Leu Asp Ile Pro Arg Ile Glu Asp Leu Gly Val Arg
            20                  25                  30

Ile Phe Asp Arg Ala Glu Asn Pro Gln Thr Gly Glu Ser Leu Ala Leu
        35                  40                  45

Pro Arg Arg Leu Ala Arg Ser Ala Arg Arg Arg Leu Arg Arg Arg Lys
    50                  55                  60

His Arg Leu Glu Arg Ile Arg Arg Leu Val Ile Arg Glu Gly Ile Leu
65                  70                  75                  80

Thr Lys Glu Glu Leu Asp Lys Leu Phe Glu Glu Lys His Glu Ile Asp
                85                  90                  95

Val Trp Gln Leu Arg Val Glu Ala Leu Asp Arg Lys Leu Asn Asn Asp
            100                 105                 110

Glu Leu Ala Arg Val Leu Leu His Leu Ala Lys Arg Arg Gly Phe Lys
        115                 120                 125

Ser Asn Arg Lys Ser Glu Arg Ser Asn Lys Glu Asn Ser Thr Met Leu
    130                 135                 140

Lys His Ile Glu Glu Asn Arg Ala Ile Leu Ser Ser Tyr Arg Thr Val
```

```
            145                 150                 155                 160
Gly Glu Met Ile Val Lys Asp Pro Lys Phe Ala Leu His Lys Arg Asn
                    165                 170                 175

Lys Gly Glu Asn Tyr Thr Asn Thr Ile Ala Arg Asp Asp Leu Glu Arg
                    180                 185                 190

Glu Ile Arg Leu Ile Phe Ser Lys Gln Arg Glu Phe Gly Asn Met Ser
                    195                 200                 205

Cys Thr Glu Glu Phe Glu Asn Glu Tyr Ile Thr Ile Trp Ala Ser Gln
                    210                 215                 220

Arg Pro Val Ala Ser Lys Asp Ile Glu Lys Lys Val Gly Phe Cys
225                 230                 235                 240

Thr Phe Glu Pro Lys Glu Lys Arg Ala Pro Lys Ala Thr Tyr Thr Phe
                    245                 250                 255

Gln Ser Phe Ile Ala Trp Glu His Ile Asn Lys Leu Arg Leu Ile Ser
                    260                 265                 270

Pro Ser Gly Ala Arg Gly Leu Thr Asp Glu Arg Arg Leu Leu Tyr
                    275                 280                 285

Glu Gln Ala Phe Gln Lys Asn Lys Ile Thr Tyr His Asp Ile Arg Thr
                    290                 295                 300

Leu Leu His Leu Pro Asp Asp Thr Tyr Phe Lys Gly Ile Val Tyr Asp
305                 310                 315                 320

Arg Gly Glu Ser Arg Lys Gln Asn Glu Asn Ile Arg Phe Leu Glu Leu
                    325                 330                 335

Asp Ala Tyr His Gln Ile Arg Lys Ala Val Asp Lys Val Tyr Gly Lys
                    340                 345                 350

Gly Lys Ser Ser Ser Phe Leu Pro Ile Asp Phe Asp Thr Phe Gly Tyr
                    355                 360                 365

Ala Leu Thr Leu Phe Lys Asp Asp Ala Asp Ile His Ser Tyr Leu Arg
                    370                 375                 380

Asn Glu Tyr Glu Gln Asn Gly Lys Arg Met Pro Asn Leu Ala Asn Lys
385                 390                 395                 400

Val Tyr Asp Asn Glu Leu Ile Glu Glu Leu Leu Asn Leu Ser Phe Thr
                    405                 410                 415

Lys Phe Gly His Leu Ser Leu Lys Ala Leu Arg Ser Ile Leu Pro Tyr
                    420                 425                 430

Met Glu Gln Gly Glu Val Tyr Ser Ser Ala Cys Glu Arg Ala Gly Tyr
                    435                 440                 445

Thr Phe Thr Gly Pro Lys Lys Lys Gln Lys Thr Met Leu Leu Pro Asn
                    450                 455                 460

Ile Pro Pro Ile Ala Asn Pro Val Val Met Arg Ala Leu Thr Gln Ala
465                 470                 475                 480

Arg Lys Val Val Asn Ala Ile Ile Lys Lys Tyr Gly Ser Pro Val Ser
                    485                 490                 495

Ile His Ile Glu Leu Ala Arg Asp Leu Ser Gln Thr Phe Asp Glu Arg
                    500                 505                 510

Arg Lys Thr Lys Lys Glu Gln Asp Glu Asn Arg Lys Lys Asn Glu Thr
                    515                 520                 525

Ala Ile Arg Gln Leu Met Glu Tyr Gly Leu Thr Leu Asn Pro Thr Gly
                    530                 535                 540

His Asp Ile Val Lys Phe Lys Leu Trp Ser Glu Gln Asn Gly Arg Cys
545                 550                 555                 560

Ala Tyr Ser Leu Gln Pro Ile Glu Ile Glu Arg Leu Leu Glu Pro Gly
                    565                 570                 575
```

```
Tyr Val Glu Val Asp His Val Ile Pro Tyr Ser Arg Ser Leu Asp Asp
            580                 585                 590

Ser Tyr Thr Asn Lys Val Leu Val Leu Thr Arg Glu Asn Arg Glu Lys
            595                 600                 605

Gly Asn Arg Ile Pro Ala Glu Tyr Leu Gly Val Gly Thr Glu Arg Trp
610                 615                 620

Gln Gln Phe Glu Thr Phe Val Leu Thr Asn Lys Gln Phe Ser Lys Lys
625                 630                 635                 640

Lys Arg Asp Arg Leu Leu Arg Leu His Tyr Asp Glu Asn Glu Glu Thr
            645                 650                 655

Glu Phe Lys Asn Arg Asn Leu Asn Asp Thr Arg Tyr Ile Ser Arg Phe
            660                 665                 670

Phe Ala Asn Phe Ile Arg Glu His Leu Lys Phe Ala Glu Ser Asp Asp
            675                 680                 685

Lys Gln Lys Val Tyr Thr Val Asn Gly Arg Val Thr Ala His Leu Arg
            690                 695                 700

Ser Arg Trp Glu Phe Asn Lys Asn Arg Glu Glu Ser Asp Leu His His
705                 710                 715                 720

Ala Val Asp Ala Val Ile Val Ala Cys Thr Thr Pro Ser Asp Ile Ala
            725                 730                 735

Lys Val Thr Ala Phe Tyr Gln Arg Arg Glu Gln Asn Lys Glu Leu Ala
            740                 745                 750

Lys Lys Thr Glu Pro His Phe Pro Gln Pro Trp Pro His Phe Ala Asp
            755                 760                 765

Glu Leu Arg Ala Arg Leu Ser Lys His Pro Lys Glu Ser Ile Lys Ala
            770                 775                 780

Leu Asn Leu Gly Asn Tyr Asp Asp Gln Lys Leu Glu Ser Leu Gln Pro
785                 790                 795                 800

Val Phe Val Ser Arg Met Pro Lys Arg Ser Val Thr Gly Ala Ala His
            805                 810                 815

Gln Glu Thr Leu Arg Arg Tyr Val Gly Ile Asp Glu Arg Ser Gly Lys
            820                 825                 830

Ile Gln Thr Val Val Lys Thr Lys Leu Ser Glu Ile Lys Leu Asp Ala
            835                 840                 845

Ser Gly His Phe Pro Met Tyr Gly Lys Glu Ser Asp Pro Arg Thr Tyr
            850                 855                 860

Glu Ala Ile Arg Gln Arg Leu Leu Glu His Asn Asn Asp Pro Lys Lys
865                 870                 875                 880

Ala Phe Gln Glu Pro Leu Tyr Lys Pro Lys Lys Asn Gly Glu Pro Gly
            885                 890                 895

Pro Val Ile Arg Thr Val Lys Ile Ile Asp Thr Lys Asn Gln Val Ile
            900                 905                 910

Pro Leu Asn Asp Gly Lys Thr Val Ala Tyr Asn Ser Asn Ile Val Arg
            915                 920                 925

Val Asp Val Phe Glu Lys Asp Gly Lys Tyr Tyr Cys Val Pro Val Tyr
            930                 935                 940

Thr Met Asp Ile Met Lys Gly Ile Leu Pro Asn Lys Ala Ile Glu Pro
945                 950                 955                 960

Asn Lys Pro Tyr Ser Glu Trp Lys Glu Met Thr Glu Asp Tyr Thr Phe
            965                 970                 975

Arg Phe Ser Leu Tyr Pro Asn Asp Leu Ile Arg Ile Glu Leu Pro Arg
            980                 985                 990
```

Glu Lys Thr Val Lys Thr Ala Ala Gly Glu Glu Ile Asn Val Lys Asp
                995                 1000                1005

Val Phe Val Tyr Tyr Lys Thr Ile Asp Ser Ala Asn Gly Gly Leu
    1010                1015                1020

Glu Leu Ile Ser His Asp His Arg Phe Ser Leu Arg Gly Val Gly
    1025                1030                1035

Ser Arg Thr Leu Lys Arg Phe Glu Lys Tyr Gln Val Asp Val Leu
    1040                1045                1050

Gly Asn Ile Tyr Lys Val Arg Gly Glu Lys Arg Val Gly Leu Ala
    1055                1060                1065

Ser Ser Ala His Ser Lys Pro Gly Lys Thr Ile Arg Pro Leu Gln
    1070                1075                1080

Ser Thr Arg Asp
    1085

<210> SEQ ID NO 2
<211> LENGTH: 1087
<212> TYPE: PRT
<213> ORGANISM: Artificial sequence
<220> FEATURE:
<223> OTHER INFORMATION: Synthetic sequence

<400> SEQUENCE: 2

Met Arg Tyr Lys Ile Gly Leu Asp Ile Gly Ile Thr Ser Val Gly Trp
1               5                   10                  15

Ala Val Met Asn Leu Asp Ile Pro Arg Ile Glu Asp Leu Gly Val Arg
            20                  25                  30

Ile Phe Asp Arg Ala Glu Asn Pro Gln Thr Gly Glu Ser Leu Ala Leu
        35                  40                  45

Pro Arg Arg Leu Ala Arg Ser Ala Arg Arg Leu Arg Arg Arg Lys
    50                  55                  60

His Arg Leu Glu Arg Ile Arg Arg Leu Val Ile Arg Glu Gly Ile Leu
65                  70                  75                  80

Thr Lys Glu Glu Leu Asp Lys Leu Phe Glu Glu Lys His Glu Ile Asp
                85                  90                  95

Val Trp Gln Leu Arg Val Glu Ala Leu Asp Arg Lys Leu Asn Asn Asp
            100                 105                 110

Glu Leu Ala Arg Val Leu Leu His Leu Ala Lys Arg Arg Gly Phe Lys
        115                 120                 125

Ser Asn Arg Lys Ser Glu Arg Ser Asn Lys Gly Asn Ser Thr Met Leu
    130                 135                 140

Lys His Ile Glu Glu Asn Arg Ala Ile Leu Ser Ser Tyr Arg Thr Val
145                 150                 155                 160

Gly Glu Met Ile Val Lys Asp Pro Lys Phe Ala Leu His Lys Arg Asn
                165                 170                 175

Lys Gly Glu Asn Tyr Thr Asn Thr Ile Ala Arg Asp Asp Leu Glu Arg
            180                 185                 190

Glu Ile Arg Leu Ile Phe Ser Lys Gln Arg Glu Phe Gly Asn Met Ser
        195                 200                 205

Cys Thr Glu Glu Phe Glu Asn Glu Tyr Ile Thr Ile Trp Ala Ser Gln
    210                 215                 220

Arg Pro Val Ala Ser Lys Asp Asp Ile Glu Lys Lys Val Gly Phe Cys
225                 230                 235                 240

Thr Phe Glu Pro Lys Glu Lys Arg Ala Pro Lys Ala Thr Tyr Thr Phe
                245                 250                 255

```
Gln Ser Phe Ile Ala Trp Glu His Ile Asn Lys Leu Arg Leu Ile Ser
            260                 265                 270

Pro Ser Gly Ala Arg Gly Leu Thr Asp Glu Arg Arg Leu Leu Tyr
        275                 280                 285

Glu Gln Ala Phe Gln Lys Asn Lys Ile Thr Tyr His Asp Ile Arg Thr
290                 295                 300

Leu Leu His Leu Pro Asp Asp Thr Tyr Phe Lys Gly Ile Val Tyr Asp
305                 310                 315                 320

Arg Gly Glu Ser Arg Lys Gln Asn Glu Asn Ile Arg Phe Leu Glu Leu
                325                 330                 335

Asp Ala Tyr His Gln Ile Arg Lys Ala Val Asp Lys Val Tyr Gly Lys
            340                 345                 350

Gly Lys Ser Ser Ser Phe Leu Pro Ile Asp Phe Asp Thr Phe Gly Tyr
        355                 360                 365

Ala Leu Thr Leu Phe Lys Asp Asp Ala Asp Ile His Ser Tyr Leu Arg
370                 375                 380

Asn Glu Tyr Glu Gln Asn Gly Lys Arg Met Pro Asn Leu Ala Asn Lys
385                 390                 395                 400

Val Tyr Asp Asn Glu Leu Ile Glu Glu Leu Leu Asn Leu Ser Phe Thr
                405                 410                 415

Lys Phe Gly His Leu Ser Leu Lys Ala Leu Arg Ser Ile Leu Pro Tyr
            420                 425                 430

Met Glu Gln Gly Glu Val Tyr Ser Ser Ala Cys Glu Arg Ala Gly Tyr
        435                 440                 445

Thr Phe Thr Gly Pro Lys Lys Lys Gln Lys Thr Met Leu Leu Pro Asn
450                 455                 460

Ile Pro Pro Ile Ala Asn Pro Val Val Met Arg Ala Leu Thr Gln Ala
465                 470                 475                 480

Arg Lys Val Val Asn Ala Ile Ile Lys Lys Tyr Gly Ser Pro Val Ser
                485                 490                 495

Ile His Ile Glu Leu Ala Arg Asp Leu Ser Gln Thr Phe Asp Glu Arg
            500                 505                 510

Arg Lys Thr Lys Lys Glu Gln Asp Glu Asn Arg Lys Lys Asn Glu Thr
        515                 520                 525

Ala Ile Arg Gln Leu Met Glu Tyr Gly Leu Thr Leu Asn Pro Thr Gly
530                 535                 540

His Asp Ile Val Lys Phe Lys Leu Trp Ser Glu Gln Asn Gly Arg Cys
545                 550                 555                 560

Ala Tyr Ser Leu Gln Pro Ile Glu Ile Glu Arg Leu Leu Glu Pro Gly
                565                 570                 575

Tyr Val Glu Val Asp His Val Ile Pro Tyr Ser Arg Ser Leu Asp Asp
            580                 585                 590

Ser Tyr Thr Asn Lys Val Leu Val Leu Thr Arg Glu Asn Arg Glu Lys
        595                 600                 605

Gly Asn Arg Ile Pro Ala Glu Tyr Leu Gly Val Gly Thr Glu Arg Trp
610                 615                 620

Gln Gln Phe Glu Thr Phe Val Leu Thr Asn Lys Gln Phe Ser Lys Lys
625                 630                 635                 640

Lys Arg Asp Arg Leu Leu Arg Leu His Tyr Asp Glu Asn Glu Glu Thr
                645                 650                 655

Glu Phe Lys Asn Arg Asn Leu Asn Asp Thr Arg Tyr Ile Ser Arg Phe
            660                 665                 670

Phe Ala Asn Phe Ile Arg Glu His Leu Lys Phe Ala Glu Ser Asp Asp
```

```
              675                 680                 685
Lys Gln Lys Val Tyr Thr Val Asn Gly Arg Val Thr Ala His Leu Arg
        690                 695                 700
Ser Arg Trp Glu Phe Asn Lys Asn Arg Glu Glu Ser Asp Leu His His
705                 710                 715                 720
Ala Val Asp Ala Val Ile Val Ala Cys Thr Thr Pro Ser Asp Ile Ala
                725                 730                 735
Lys Val Thr Ala Phe Tyr Gln Arg Arg Glu Gln Asn Lys Glu Leu Ala
                740                 745                 750
Lys Lys Thr Glu Pro His Phe Pro Gln Pro Trp Pro His Phe Ala Asp
                755                 760                 765
Glu Leu Arg Ala Arg Leu Ser Lys His Pro Lys Glu Ser Ile Lys Ala
                770                 775                 780
Leu Asn Leu Gly Asn Tyr Asp Asp Gln Lys Leu Glu Ser Leu Gln Pro
785                 790                 795                 800
Val Phe Val Ser Arg Met Pro Lys Arg Ser Val Thr Gly Ala Ala His
                805                 810                 815
Gln Glu Thr Leu Arg Arg Tyr Val Gly Ile Asp Glu Arg Ser Gly Lys
                820                 825                 830
Ile Gln Thr Val Val Lys Thr Lys Leu Ser Glu Ile Lys Leu Asp Ala
                835                 840                 845
Ser Gly His Phe Pro Met Tyr Gly Lys Glu Ser Asp Pro Arg Thr Tyr
                850                 855                 860
Glu Ala Ile Arg Gln Arg Leu Leu Glu His Asn Asn Asp Pro Lys Lys
865                 870                 875                 880
Ala Phe Gln Glu Pro Leu Tyr Lys Pro Lys Lys Asn Gly Glu Pro Gly
                885                 890                 895
Pro Val Ile Arg Thr Val Lys Ile Ile Asp Thr Lys Asn Gln Val Ile
                900                 905                 910
Pro Leu Asn Asp Gly Lys Thr Val Ala Tyr Asn Ser Asn Ile Val Arg
                915                 920                 925
Val Asp Val Phe Glu Lys Asp Gly Lys Tyr Tyr Cys Val Pro Val Tyr
                930                 935                 940
Thr Met Asp Ile Met Lys Gly Ile Leu Pro Asn Lys Ala Ile Glu Pro
945                 950                 955                 960
Asn Lys Pro Tyr Ser Glu Trp Lys Glu Met Thr Glu Asp Tyr Thr Phe
                965                 970                 975
Arg Phe Ser Leu Tyr Pro Asn Asp Leu Ile Arg Ile Glu Leu Pro Arg
                980                 985                 990
Glu Lys Ile Ile Lys Thr Ala Gly Gly Glu Glu Ile Lys Ile Lys Asp
                995                1000                1005
Leu Phe Ala Tyr Tyr Lys Thr Ile His Ser Gly Thr Ala Gly Leu
        1010                1015                1020
Glu Leu Val Ser His Asp Cys Ser Phe Ser Leu Ser Gly Val Gly
        1025                1030                1035
Ser Arg Thr Leu Lys Arg Phe Glu Lys Tyr Gln Val Asp Val Leu
        1040                1045                1050
Gly Asn Ile Tyr Lys Val Arg Gly Glu Lys Arg Val Gly Leu Ala
        1055                1060                1065
Ser Ser Ala His Ser Lys Gly Glu Thr Ile Arg Pro Leu Gln
        1070                1075                1080
Ser Thr Arg Asp
        1085
```

<210> SEQ ID NO 3
<211> LENGTH: 1087
<212> TYPE: PRT
<213> ORGANISM: Geobacillus LC300

<400> SEQUENCE: 3

```
Met Arg Tyr Lys Ile Gly Leu Asp Ile Gly Ile Thr Ser Val Gly Trp
1               5                   10                  15

Ala Val Ile Asn Leu Asp Ile Pro Arg Ile Glu Asp Leu Gly Val Arg
            20                  25                  30

Ile Phe Asp Arg Ala Glu Asn Pro Gln Thr Gly Glu Ser Leu Ala Leu
        35                  40                  45

Pro Arg Arg Leu Ala Arg Ser Ala Arg Arg Leu Arg Arg Arg Lys
50                  55                  60

His Arg Leu Glu Arg Ile Arg Arg Leu Ile Arg Glu Gly Ile Leu
65                  70                  75                  80

Thr Lys Glu Glu Leu Asp Lys Leu Phe Glu Lys His Glu Ile Asp
                85                  90                  95

Val Trp Gln Leu Arg Val Glu Ala Leu Asp Arg Lys Leu Asn Asn Asp
            100                 105                 110

Glu Leu Ala Arg Val Leu Leu His Leu Ala Lys Arg Arg Gly Phe Lys
        115                 120                 125

Ser Asn Arg Lys Ser Glu Arg Ser Asn Lys Glu Asn Ser Thr Met Leu
130                 135                 140

Lys His Ile Glu Glu Asn Arg Ala Ile Leu Ser Ser Tyr Arg Thr Val
145                 150                 155                 160

Gly Glu Met Ile Val Lys Asp Pro Lys Phe Ala Leu His Lys Arg Asn
                165                 170                 175

Lys Gly Glu Asn Tyr Thr Asn Thr Ile Ala Arg Asp Asp Leu Glu Arg
            180                 185                 190

Glu Ile Arg Leu Ile Phe Ser Lys Gln Arg Glu Phe Gly Asn Met Ser
        195                 200                 205

Cys Thr Glu Glu Phe Glu Asn Glu Tyr Ile Ala Ile Trp Ala Ser Gln
210                 215                 220

Arg Pro Val Ala Ser Lys Asp Asp Ile Glu Lys Lys Val Gly Phe Cys
225                 230                 235                 240

Thr Phe Glu Pro Lys Glu Lys Arg Ala Pro Lys Ala Thr Tyr Thr Phe
                245                 250                 255

Gln Ser Phe Ile Ala Trp Glu His Ile Asn Lys Leu Arg Leu Ile Ser
            260                 265                 270

Pro Ser Gly Thr Arg Gly Leu Thr Asp Glu Glu Arg Arg Leu Leu Tyr
        275                 280                 285

Glu Gln Ala Phe Gln Lys Asn Lys Ile Thr Tyr His Asp Ile Arg Thr
290                 295                 300

Leu Leu His Leu Pro Asp Asp Thr Tyr Phe Lys Gly Ile Val Tyr Asp
305                 310                 315                 320

Arg Gly Glu Ser Arg Lys Gln Asn Glu Asn Ile Arg Phe Leu Glu Leu
                325                 330                 335

Asp Ala Tyr His Gln Ile Arg Lys Ala Val Asp Lys Val Tyr Gly Lys
            340                 345                 350

Gly Lys Ser Ser Ser Phe Leu Pro Ile Asp Phe Asp Thr Phe Gly Tyr
        355                 360                 365

Ala Leu Thr Leu Phe Lys Asp Asp Ala Asp Ile Arg Ser Tyr Leu Arg
```

```
                370             375             380
Asn Glu Tyr Glu Gln Asn Gly Lys Arg Met Pro Asn Leu Ala Asn Lys
385                 390                 395                 400

Val Tyr Asp Asn Glu Leu Ile Glu Glu Leu Leu Asn Leu Ser Phe Thr
            405                 410                 415

Lys Phe Gly His Leu Ser Leu Lys Ala Leu Arg Ser Ile Leu Pro Tyr
                420                 425                 430

Met Glu Gln Gly Glu Val Tyr Ser Ser Ala Cys Glu Arg Ala Gly Tyr
        435                 440                 445

Thr Phe Thr Gly Pro Lys Lys Gln Lys Thr Met Leu Leu Pro Asn
    450                 455                 460

Ile Pro Pro Ile Ala Asn Pro Val Val Met Arg Ala Leu Thr Gln Ala
465                 470                 475                 480

Arg Lys Val Val Asn Ala Ile Ile Lys Lys Tyr Gly Ser Pro Val Ser
                485                 490                 495

Ile His Ile Glu Leu Ala Arg Asp Leu Ser Gln Thr Phe Asp Glu Arg
            500                 505                 510

Arg Lys Thr Lys Lys Glu Gln Asp Glu Asn Arg Lys Lys Asn Glu Thr
        515                 520                 525

Ala Ile Arg Gln Leu Met Glu Tyr Gly Leu Thr Leu Asn Pro Thr Gly
    530                 535                 540

His Asp Ile Val Lys Phe Lys Leu Trp Ser Glu Gln Asn Gly Arg Cys
545                 550                 555                 560

Ala Tyr Ser Leu Gln Pro Ile Glu Ile Glu Arg Leu Leu Glu Pro Gly
                565                 570                 575

Tyr Thr Glu Val Asp His Val Ile Pro Tyr Ser Arg Ser Leu Asp Asp
            580                 585                 590

Ser Tyr Thr Asn Lys Val Leu Val Leu Thr Lys Glu Asn Arg Glu Lys
        595                 600                 605

Gly Asn Arg Ile Pro Ala Glu Tyr Leu Gly Val Gly Thr Glu Arg Trp
    610                 615                 620

Gln Gln Phe Glu Thr Phe Val Leu Thr Asn Lys Gln Phe Ser Lys Lys
625                 630                 635                 640

Lys Arg Asp Arg Leu Leu Arg Leu His Tyr Asp Glu Asn Glu Glu Thr
                645                 650                 655

Glu Phe Lys Asn Arg Asn Leu Asn Asp Thr Arg Tyr Ile Ser Arg Phe
            660                 665                 670

Phe Ala Asn Phe Ile Arg Glu His Leu Lys Phe Ala Glu Ser Asp Asp
        675                 680                 685

Lys Gln Lys Val Tyr Thr Val Asn Gly Arg Val Thr Ala His Leu Arg
    690                 695                 700

Ser Arg Trp Glu Phe Asn Lys Asn Arg Glu Glu Ser Asp Leu His His
705                 710                 715                 720

Ala Val Asp Ala Val Ile Val Ala Cys Thr Thr Pro Ser Asp Ile Ala
                725                 730                 735

Lys Val Thr Ala Phe Tyr Gln Arg Arg Glu Gln Asn Lys Glu Leu Ala
            740                 745                 750

Lys Lys Thr Glu Pro His Phe Pro Gln Pro Trp Pro His Phe Ala Asp
        755                 760                 765

Glu Leu Arg Ala Arg Leu Ser Lys His Pro Lys Glu Ser Ile Lys Ala
    770                 775                 780

Leu Asn Leu Gly Asn Tyr Asp Asp Gln Lys Leu Glu Ser Leu Gln Pro
785                 790                 795                 800
```

```
Val Phe Val Ser Arg Met Pro Lys Arg Ser Val Thr Gly Ala Ala His
                805                 810                 815

Gln Glu Thr Leu Arg Arg Tyr Val Gly Ile Asp Glu Arg Ser Gly Lys
            820                 825                 830

Ile Gln Thr Val Val Lys Thr Lys Leu Ser Glu Ile Lys Leu Asp Ala
        835                 840                 845

Ser Gly His Phe Pro Met Tyr Gly Lys Glu Ser Asp Pro Arg Thr Tyr
    850                 855                 860

Glu Ala Ile Arg Gln Arg Leu Leu Glu His Asn Asn Asp Pro Lys Lys
865                 870                 875                 880

Ala Phe Gln Glu Pro Leu Tyr Lys Pro Lys Asn Gly Glu Pro Gly
                885                 890                 895

Pro Val Ile Arg Thr Val Lys Ile Ile Asp Thr Lys Asn Gln Val Ile
                900                 905                 910

Pro Leu Asn Asp Gly Lys Thr Val Ala Tyr Asn Ser Asn Ile Val Arg
            915                 920                 925

Val Asp Val Phe Glu Lys Asp Gly Lys Tyr Tyr Cys Val Pro Val Tyr
        930                 935                 940

Thr Met Asp Ile Met Lys Gly Ile Leu Pro Asn Lys Ala Ile Glu Pro
945                 950                 955                 960

Asn Lys Pro Tyr Ser Glu Trp Lys Glu Met Thr Glu Asp Tyr Thr Phe
                965                 970                 975

Arg Phe Ser Leu Tyr Pro Asn Asp Leu Ile Arg Ile Glu Leu Pro Arg
            980                 985                 990

Glu Lys Ile Ile Lys Thr Ala Gly Gly Glu Glu Ile Lys Ile Lys Asp
        995                 1000                1005

Leu Phe Ala Tyr Tyr Lys Thr Ile His Ser Gly Thr Ala Gly Leu
    1010                1015                1020

Glu Leu Val Ser His Asp Cys Ser Phe Ser Leu Ser Gly Val Gly
    1025                1030                1035

Ser Arg Thr Leu Lys Arg Phe Glu Lys Tyr Gln Val Asp Val Leu
    1040                1045                1050

Gly Asn Ile Tyr Lys Val Arg Gly Glu Lys Arg Val Gly Leu Ala
    1055                1060                1065

Ser Ser Ala His Ser Lys Gly Glu Thr Ile Arg Pro Leu Gln
    1070                1075                1080

Ser Thr Arg Asp
    1085

<210> SEQ ID NO 4
<211> LENGTH: 93
<212> TYPE: PRT
<213> ORGANISM: Artificial sequence
<220> FEATURE:
<223> OTHER INFORMATION: Synthetic sequence

<400> SEQUENCE: 4

Ile Ile Lys Thr Ala Gly Gly Glu Glu Ile Lys Ile Lys Asp Leu Phe
1               5                   10                  15

Ala Tyr Tyr Lys Thr Ile His Ser Gly Thr Ala Gly Leu Glu Leu Val
            20                  25                  30

Ser His Asp Cys Ser Phe Ser Leu Ser Gly Val Gly Ser Arg Thr Leu
        35                  40                  45

Lys Arg Phe Glu Lys Tyr Gln Val Asp Val Leu Gly Asn Ile Tyr Lys
    50                  55                  60
```

```
Val Arg Gly Glu Lys Arg Val Gly Leu Ala Ser Ser Ala His Ser Lys
 65                  70                  75                  80

Thr Gly Glu Thr Ile Arg Pro Leu Gln Ser Thr Arg Asp
                 85                  90
```

<210> SEQ ID NO 5
<211> LENGTH: 93
<212> TYPE: PRT
<213> ORGANISM: Artificial sequence
<220> FEATURE:
<223> OTHER INFORMATION: Synthetic sequence

<400> SEQUENCE: 5

```
Thr Val Lys Thr Ala Ala Gly Glu Glu Ile Asn Val Lys Asp Val Phe
  1               5                  10                  15

Val Tyr Tyr Lys Thr Ile Asp Ser Ala Asn Gly Gly Leu Glu Leu Ile
             20                  25                  30

Ser His Asp His Arg Phe Ser Leu Arg Gly Val Gly Ser Arg Thr Leu
         35                  40                  45

Lys Arg Phe Glu Lys Tyr Gln Val Asp Val Leu Gly Asn Ile Tyr Lys
     50                  55                  60

Val Arg Gly Glu Lys Arg Val Gly Leu Ala Ser Ser Ala His Ser Lys
 65                  70                  75                  80

Pro Gly Lys Thr Ile Arg Pro Leu Gln Ser Thr Arg Asp
                 85                  90
```

<210> SEQ ID NO 6
<211> LENGTH: 98
<212> TYPE: RNA
<213> ORGANISM: Artificial sequence
<220> FEATURE:
<223> OTHER INFORMATION: Synthetic sequence

<400> SEQUENCE: 6

```
ucaggguuac uaugauaagg gcuuucugcc uaaggcagac ugacccgcgg cguuggggau    60
cgccugucgc ccgcuuuugg cgggcauucc ccauccuu                            98
```

<210> SEQ ID NO 7
<211> LENGTH: 138
<212> TYPE: RNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(20)
<223> OTHER INFORMATION: n is a, c, g, or u

<400> SEQUENCE: 7

```
nnnnnnnnnn nnnnnnnnnn gucauaguuc cccugagaaa ucaggguuac uaugauaagg    60
gcuuucugcc uaaggcagac ugacccgcgg cguuggggau cgccugucgc ccgcuuuugg   120
cgggcauucc ccauccuu                                                 138
```

<210> SEQ ID NO 8
<211> LENGTH: 84
<212> TYPE: PRT
<213> ORGANISM: Artificial sequence
<220> FEATURE:
<223> OTHER INFORMATION: Synthetic sequence

<400> SEQUENCE: 8

```
Met Ala Ser Met Ile Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Cys Met Gln Val Trp Pro Pro Ile
    50                  55                  60

Gly Lys Lys Lys Phe Glu Thr Leu Ser Tyr Leu Pro Pro Leu Thr Arg
65                  70                  75                  80

Asp Ser Arg Ala

<210> SEQ ID NO 9
<211> LENGTH: 57
<212> TYPE: PRT
<213> ORGANISM: Artificial sequence
<220> FEATURE:
<223> OTHER INFORMATION: Synthetic sequence

<400> SEQUENCE: 9

Met Ala Ser Met Ile Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Ser
    50                  55

<210> SEQ ID NO 10
<211> LENGTH: 85
<212> TYPE: PRT
<213> ORGANISM: Artificial sequence
<220> FEATURE:
<223> OTHER INFORMATION: Synthetic sequence

<400> SEQUENCE: 10

Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys Met Gln Val Trp Pro Pro Ile Glu Lys
    50                  55                  60

Lys Lys Phe Glu Thr Leu Ser Tyr Leu Pro Asp Leu Thr Asp Ser Gly
65                  70                  75                  80

Gly Arg Val Asn Cys
                85

<210> SEQ ID NO 11
<211> LENGTH: 76
<212> TYPE: PRT
<213> ORGANISM: Artificial sequence
<220> FEATURE:
<223> OTHER INFORMATION: Synthetic sequence

<400> SEQUENCE: 11

Met Ala Gln Val Ser Arg Ile Cys Asn Gly Val Gln Asn Pro Ser Leu
1               5                   10                  15
```

```
Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75

<210> SEQ ID NO 12
<211> LENGTH: 76
<212> TYPE: PRT
<213> ORGANISM: Artificial sequence
<220> FEATURE:
<223> OTHER INFORMATION: Synthetic sequence

<400> SEQUENCE: 12

Met Ala Gln Val Ser Arg Ile Cys Asn Gly Val Trp Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75

<210> SEQ ID NO 13
<211> LENGTH: 72
<212> TYPE: PRT
<213> ORGANISM: Artificial sequence
<220> FEATURE:
<223> OTHER INFORMATION: Synthetic sequence

<400> SEQUENCE: 13

Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Ser Phe Leu
            20                  25                  30

Val Phe Gly Ser Lys Lys Leu Lys Asn Ser Ala Asn Ser Met Leu Val
        35                  40                  45

Leu Lys Lys Asp Ser Ile Phe Met Gln Leu Phe Cys Ser Phe Arg Ile
    50                  55                  60

Ser Ala Ser Val Ala Thr Ala Cys
65                  70

<210> SEQ ID NO 14
<211> LENGTH: 69
<212> TYPE: PRT
<213> ORGANISM: Artificial sequence
<220> FEATURE:
<223> OTHER INFORMATION: Synthetic sequence

<400> SEQUENCE: 14

Met Ala Ala Leu Val Thr Ser Gln Leu Ala Thr Ser Gly Thr Val Leu
1               5                   10                  15

Ser Val Thr Asp Arg Phe Arg Arg Pro Gly Phe Gln Gly Leu Arg Pro
            20                  25                  30
```

```
Arg Asn Pro Ala Asp Ala Ala Leu Gly Met Arg Thr Val Gly Ala Ser
         35                  40                  45

Ala Ala Pro Lys Gln Ser Arg Lys Pro His Arg Phe Asp Arg Arg Cys
 50                  55                  60

Leu Ser Met Val Val
 65
```

<210> SEQ ID NO 15
<211> LENGTH: 77
<212> TYPE: PRT
<213> ORGANISM: Artificial sequence
<220> FEATURE:
<223> OTHER INFORMATION: Synthetic sequence

<400> SEQUENCE: 15

```
Met Ala Ala Leu Thr Thr Ser Gln Leu Ala Thr Ser Ala Thr Gly Phe
 1               5                  10                  15

Gly Ile Ala Asp Arg Ser Ala Pro Ser Ser Leu Leu Arg His Gly Phe
                 20                  25                  30

Gln Gly Leu Lys Pro Arg Ser Pro Ala Gly Gly Asp Ala Thr Ser Leu
         35                  40                  45

Ser Val Thr Thr Ser Ala Arg Ala Thr Pro Lys Gln Gln Arg Ser Val
 50                  55                  60

Gln Arg Gly Ser Arg Arg Phe Pro Ser Val Val Val Cys
 65                  70                  75
```

<210> SEQ ID NO 16
<211> LENGTH: 57
<212> TYPE: PRT
<213> ORGANISM: Artificial sequence
<220> FEATURE:
<223> OTHER INFORMATION: Synthetic sequence

<400> SEQUENCE: 16

```
Met Ala Ser Ser Val Leu Ser Ser Ala Ala Val Ala Thr Arg Ser Asn
 1               5                  10                  15

Val Ala Gln Ala Asn Met Val Ala Pro Phe Thr Gly Leu Lys Ser Ala
                 20                  25                  30

Ala Ser Phe Pro Val Ser Arg Lys Gln Asn Leu Asp Ile Thr Ser Ile
         35                  40                  45

Ala Ser Asn Gly Gly Arg Val Gln Cys
 50                  55
```

<210> SEQ ID NO 17
<211> LENGTH: 65
<212> TYPE: PRT
<213> ORGANISM: Artificial sequence
<220> FEATURE:
<223> OTHER INFORMATION: Synthetic sequence

<400> SEQUENCE: 17

```
Met Glu Ser Leu Ala Ala Thr Ser Val Phe Ala Pro Ser Arg Val Ala
 1               5                  10                  15

Val Pro Ala Ala Arg Ala Leu Val Arg Ala Gly Thr Val Val Pro Thr
                 20                  25                  30

Arg Arg Thr Ser Ser Thr Ser Gly Thr Ser Gly Val Lys Cys Ser Ala
         35                  40                  45

Ala Val Thr Pro Gln Ala Ser Pro Val Ile Ser Arg Ser Ala Ala Ala
 50                  55                  60

Ala
```

<210> SEQ ID NO 18
<211> LENGTH: 72
<212> TYPE: PRT
<213> ORGANISM: Artificial sequence
<220> FEATURE:
<223> OTHER INFORMATION: Synthetic sequence

<400> SEQUENCE: 18

Met Gly Ala Ala Ala Thr Ser Met Gln Ser Leu Lys Phe Ser Asn Arg
1               5                   10                  15

Leu Val Pro Pro Ser Arg Arg Leu Ser Pro Val Pro Asn Asn Val Thr
            20                  25                  30

Cys Asn Asn Leu Pro Lys Ser Ala Ala Pro Val Arg Thr Val Lys Cys
        35                  40                  45

Cys Ala Ser Ser Trp Asn Ser Thr Ile Asn Gly Ala Ala Ala Thr Thr
    50                  55                  60

Asn Gly Ala Ser Ala Ala Ser Ser
65                  70

<210> SEQ ID NO 19
<211> LENGTH: 20
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 19

Gly Leu Phe Xaa Ala Leu Leu Xaa Leu Leu Xaa Ser Leu Trp Xaa Leu
1               5                   10                  15

Leu Leu Xaa Ala
            20

<210> SEQ ID NO 20
<211> LENGTH: 20
<212> TYPE: PRT
<213> ORGANISM: Artificial sequence
<220> FEATURE:
<223> OTHER INFORMATION: Synthetic sequence

<400> SEQUENCE: 20

Gly Leu Phe His Ala Leu Leu His Leu Leu His Ser Leu Trp His Leu
1               5                   10                  15

Leu Leu His Ala
            20

<210> SEQ ID NO 21
<211> LENGTH: 7
<212> TYPE: PRT
<213> ORGANISM: Artificial sequence
<220> FEATURE:
<223> OTHER INFORMATION: Synthetic sequence

<400> SEQUENCE: 21

Pro Lys Lys Lys Arg Lys Val
1               5

<210> SEQ ID NO 22
<211> LENGTH: 16
<212> TYPE: PRT
<213> ORGANISM: Artificial sequence
<220> FEATURE:
<223> OTHER INFORMATION: Synthetic sequence

<400> SEQUENCE: 22

Lys Arg Pro Ala Ala Thr Lys Lys Ala Gly Gln Ala Lys Lys Lys Lys
1               5                   10                  15

<210> SEQ ID NO 23
<211> LENGTH: 9
<212> TYPE: PRT
<213> ORGANISM: Artificial sequence
<220> FEATURE:
<223> OTHER INFORMATION: Synthetic sequence

<400> SEQUENCE: 23

Pro Ala Ala Lys Arg Val Lys Leu Asp
1               5

<210> SEQ ID NO 24
<211> LENGTH: 11
<212> TYPE: PRT
<213> ORGANISM: Artificial sequence
<220> FEATURE:
<223> OTHER INFORMATION: Synthetic sequence

<400> SEQUENCE: 24

Arg Gln Arg Arg Asn Glu Leu Lys Arg Ser Pro
1               5                   10

<210> SEQ ID NO 25
<211> LENGTH: 38
<212> TYPE: PRT
<213> ORGANISM: Artificial sequence
<220> FEATURE:
<223> OTHER INFORMATION: Synthetic sequence

<400> SEQUENCE: 25

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
            35

<210> SEQ ID NO 26
<211> LENGTH: 42
<212> TYPE: PRT
<213> ORGANISM: Artificial sequence
<220> FEATURE:
<223> OTHER INFORMATION: Synthetic sequence

```
<400> SEQUENCE: 26

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
                20                  25                  30

Asp Glu Gln Ile Leu Lys Arg Arg Asn Val
            35                  40

<210> SEQ ID NO 27
<211> LENGTH: 8
<212> TYPE: PRT
<213> ORGANISM: Artificial sequence
<220> FEATURE:
<223> OTHER INFORMATION: Synthetic sequence

<400> SEQUENCE: 27

Val Ser Arg Lys Arg Pro Arg Pro
1               5

<210> SEQ ID NO 28
<211> LENGTH: 8
<212> TYPE: PRT
<213> ORGANISM: Artificial sequence
<220> FEATURE:
<223> OTHER INFORMATION: Synthetic sequence

<400> SEQUENCE: 28

Pro Pro Lys Lys Ala Arg Glu Asp
1               5

<210> SEQ ID NO 29
<211> LENGTH: 8
<212> TYPE: PRT
<213> ORGANISM: Artificial sequence
<220> FEATURE:
<223> OTHER INFORMATION: Synthetic sequence

<400> SEQUENCE: 29

Pro Gln Pro Lys Lys Lys Pro Leu
1               5

<210> SEQ ID NO 30
<211> LENGTH: 12
<212> TYPE: PRT
<213> ORGANISM: Artificial sequence
<220> FEATURE:
<223> OTHER INFORMATION: Synthetic sequence

<400> SEQUENCE: 30

Ser Ala Leu Ile Lys Lys Lys Lys Lys Met Ala Pro
1               5                   10

<210> SEQ ID NO 31
<211> LENGTH: 5
<212> TYPE: PRT
<213> ORGANISM: Artificial sequence
<220> FEATURE:
<223> OTHER INFORMATION: Synthetic sequence

<400> SEQUENCE: 31

Asp Arg Leu Arg Arg
1               5

<210> SEQ ID NO 32
<211> LENGTH: 7
```

```
<212> TYPE: PRT
<213> ORGANISM: Artificial sequence
<220> FEATURE:
<223> OTHER INFORMATION: Synthetic sequence

<400> SEQUENCE: 32

Pro Lys Gln Lys Lys Arg Lys
1               5

<210> SEQ ID NO 33
<211> LENGTH: 10
<212> TYPE: PRT
<213> ORGANISM: Artificial sequence
<220> FEATURE:
<223> OTHER INFORMATION: Synthetic sequence

<400> SEQUENCE: 33

Arg Lys Leu Lys Lys Lys Ile Lys Lys Leu
1               5                   10

<210> SEQ ID NO 34
<211> LENGTH: 10
<212> TYPE: PRT
<213> ORGANISM: Artificial sequence
<220> FEATURE:
<223> OTHER INFORMATION: Synthetic sequence

<400> SEQUENCE: 34

Arg Glu Lys Lys Lys Phe Leu Lys Arg Arg
1               5                   10

<210> SEQ ID NO 35
<211> LENGTH: 20
<212> TYPE: PRT
<213> ORGANISM: Artificial sequence
<220> FEATURE:
<223> OTHER INFORMATION: Synthetic sequence

<400> SEQUENCE: 35

Lys Arg Lys Gly Asp Glu Val Asp Gly Val Asp Glu Val Ala Lys Lys
1               5                   10                  15

Lys Ser Lys Lys
            20

<210> SEQ ID NO 36
<211> LENGTH: 17
<212> TYPE: PRT
<213> ORGANISM: Artificial sequence
<220> FEATURE:
<223> OTHER INFORMATION: Synthetic sequence

<400> SEQUENCE: 36

Arg Lys Cys Leu Gln Ala Gly Met Asn Leu Glu Ala Arg Lys Thr Lys
1               5                   10                  15

Lys

<210> SEQ ID NO 37
<211> LENGTH: 11
<212> TYPE: PRT
<213> ORGANISM: Artificial sequence
<220> FEATURE:
<223> OTHER INFORMATION: Synthetic sequence

<400> SEQUENCE: 37

Tyr Gly Arg Lys Lys Arg Arg Gln Arg Arg
1               5                   10
```

```
<210> SEQ ID NO 38
<211> LENGTH: 12
<212> TYPE: PRT
<213> ORGANISM: Artificial sequence
<220> FEATURE:
<223> OTHER INFORMATION: Synthetic sequence

<400> SEQUENCE: 38

Arg Arg Gln Arg Arg Thr Ser Lys Leu Met Lys Arg
1               5                   10

<210> SEQ ID NO 39
<211> LENGTH: 27
<212> TYPE: PRT
<213> ORGANISM: Artificial sequence
<220> FEATURE:
<223> OTHER INFORMATION: Synthetic sequence

<400> SEQUENCE: 39

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 40
<211> LENGTH: 33
<212> TYPE: PRT
<213> ORGANISM: Artificial sequence
<220> FEATURE:
<223> OTHER INFORMATION: Synthetic sequence

<400> SEQUENCE: 40

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 41
<211> LENGTH: 16
<212> TYPE: PRT
<213> ORGANISM: Artificial sequence
<220> FEATURE:
<223> OTHER INFORMATION: Synthetic sequence

<400> SEQUENCE: 41

Arg Gln Ile Lys Ile Trp Phe Gln Asn Arg Arg Met Lys Trp Lys Lys
1               5                   10                  15

<210> SEQ ID NO 42
<211> LENGTH: 9
<212> TYPE: PRT
<213> ORGANISM: Artificial sequence
<220> FEATURE:
<223> OTHER INFORMATION: Synthetic sequence

<400> SEQUENCE: 42

Arg Lys Lys Arg Arg Gln Arg Arg Arg
1               5

<210> SEQ ID NO 43
<211> LENGTH: 8
<212> TYPE: PRT
<213> ORGANISM: Artificial sequence
```

```
<220> FEATURE:
<223> OTHER INFORMATION: Synthetic sequence

<400> SEQUENCE: 43

Arg Lys Lys Arg Arg Gln Arg Arg
1               5

<210> SEQ ID NO 44
<211> LENGTH: 11
<212> TYPE: PRT
<213> ORGANISM: Artificial sequence
<220> FEATURE:
<223> OTHER INFORMATION: Synthetic sequence

<400> SEQUENCE: 44

Tyr Ala Arg Ala Ala Ala Arg Gln Ala Arg Ala
1               5                   10

<210> SEQ ID NO 45
<211> LENGTH: 11
<212> TYPE: PRT
<213> ORGANISM: Artificial sequence
<220> FEATURE:
<223> OTHER INFORMATION: Synthetic sequence

<400> SEQUENCE: 45

Thr His Arg Leu Pro Arg Arg Arg Arg Arg Arg
1               5                   10

<210> SEQ ID NO 46
<211> LENGTH: 11
<212> TYPE: PRT
<213> ORGANISM: Artificial sequence
<220> FEATURE:
<223> OTHER INFORMATION: Synthetic sequence

<400> SEQUENCE: 46

Gly Gly Arg Arg Ala Arg Arg Arg Arg Arg Arg
1               5                   10

<210> SEQ ID NO 47
<211> LENGTH: 5
<212> TYPE: PRT
<213> ORGANISM: Artificial sequence
<220> FEATURE:
<223> OTHER INFORMATION: Synthetic sequence

<400> SEQUENCE: 47

Gly Ser Gly Gly Ser
1               5

<210> SEQ ID NO 48
<211> LENGTH: 6
<212> TYPE: PRT
<213> ORGANISM: Artificial sequence
<220> FEATURE:
<223> OTHER INFORMATION: Synthetic sequence

<400> SEQUENCE: 48

Gly Gly Ser Gly Gly Ser
1               5

<210> SEQ ID NO 49
<211> LENGTH: 4
<212> TYPE: PRT
<213> ORGANISM: Artificial sequence
<220> FEATURE:
```

```
<223> OTHER INFORMATION: Synthetic sequence

<400> SEQUENCE: 49

Gly Gly Gly Ser
1

<210> SEQ ID NO 50
<211> LENGTH: 4
<212> TYPE: PRT
<213> ORGANISM: Artificial sequence
<220> FEATURE:
<223> OTHER INFORMATION: Synthetic sequence

<400> SEQUENCE: 50

Gly Gly Ser Gly
1

<210> SEQ ID NO 51
<211> LENGTH: 5
<212> TYPE: PRT
<213> ORGANISM: Artificial sequence
<220> FEATURE:
<223> OTHER INFORMATION: Synthetic sequence

<400> SEQUENCE: 51

Gly Gly Ser Gly Gly
1               5

<210> SEQ ID NO 52
<211> LENGTH: 5
<212> TYPE: PRT
<213> ORGANISM: Artificial sequence
<220> FEATURE:
<223> OTHER INFORMATION: Synthetic sequence

<400> SEQUENCE: 52

Gly Ser Gly Ser Gly
1               5

<210> SEQ ID NO 53
<211> LENGTH: 5
<212> TYPE: PRT
<213> ORGANISM: Artificial sequence
<220> FEATURE:
<223> OTHER INFORMATION: Synthetic sequence

<400> SEQUENCE: 53

Gly Ser Gly Gly Gly
1               5

<210> SEQ ID NO 54
<211> LENGTH: 5
<212> TYPE: PRT
<213> ORGANISM: Artificial sequence
<220> FEATURE:
<223> OTHER INFORMATION: Synthetic sequence

<400> SEQUENCE: 54

Gly Gly Gly Ser Gly
1               5

<210> SEQ ID NO 55
<211> LENGTH: 5
<212> TYPE: PRT
<213> ORGANISM: Artificial sequence
<220> FEATURE:
<223> OTHER INFORMATION: Synthetic sequence
```

<400> SEQUENCE: 55

Gly Ser Ser Ser Gly
1               5

<210> SEQ ID NO 56
<211> LENGTH: 140
<212> TYPE: DNA
<213> ORGANISM: Artificial sequence
<220> FEATURE:
<223> OTHER INFORMATION: Synthetic sequence

<400> SEQUENCE: 56
ggctgtaagc ggatgccata tggtcatagt tcccctgaga aatcagggtt actatgataa      60
gggctttctg cctaaggcag actgacccgc ggcgttgggg atcgcctgtc gcccgctttt     120
ggcgggcatt ccccatcctt                                                 140

<210> SEQ ID NO 57
<211> LENGTH: 155
<212> TYPE: DNA
<213> ORGANISM: Artificial sequence
<220> FEATURE:
<223> OTHER INFORMATION: Synthetic sequence

<400> SEQUENCE: 57
ggctgtaagc ggatgccata tggtcatagt tcccctgaga ttatcgcgaa aatgatctca      60
gggttactat gataagggct ttctgcctaa ggcagactga cccgcggcgt tggggatcgc     120
ctgtcgcccg cttttggcgg gcattcccca tcctt                                155

<210> SEQ ID NO 58
<211> LENGTH: 177
<212> TYPE: DNA
<213> ORGANISM: Artificial sequence
<220> FEATURE:
<223> OTHER INFORMATION: Synthetic sequence

<400> SEQUENCE: 58
ggctgtaagc ggatgccata tggtcatagt tcccctgaga ttatcgctgt ggtataatga      60
aaataccaca gcaatgatct cagggttact atgataaggg ctttctgcct aaggcagact     120
gacccgcggc gttggggatc gcctgtcgcc cgcttttggc gggcattccc catcctt        177

<210> SEQ ID NO 59
<211> LENGTH: 105
<212> TYPE: DNA
<213> ORGANISM: Artificial sequence
<220> FEATURE:
<223> OTHER INFORMATION: Synthetic sequence

<400> SEQUENCE: 59
ggctgtaagc ggatgccata tggtcatagt tcccctgaga aatcagggtt actatgataa      60
gggctttctg cctaaggcag actgacccgc ggcgttgggg atcgc                     105

<210> SEQ ID NO 60
<211> LENGTH: 133
<212> TYPE: DNA
<213> ORGANISM: Artificial sequence
<220> FEATURE:
<223> OTHER INFORMATION: Synthetic sequence

<400> SEQUENCE: 60
ggctgtaagc ggatgccata tggtcatagt tcccctgaga aatcagggtt actatgataa      60

```
gggctttctg cctaaggcag actgacccgc ggcgttgggg atcgcctgtc gcccgctttt    120
ggcgggcatt ccc                                                       133

<210> SEQ ID NO 61
<211> LENGTH: 140
<212> TYPE: DNA
<213> ORGANISM: Artificial sequence
<220> FEATURE:
<223> OTHER INFORMATION: Synthetic sequence

<400> SEQUENCE: 61
ggctgtaagc ggatgccata tggtcatagt tcccctgaga aatcagggtt actatgataa    60
gggctttctg cctaaggcag actgacccgc ggcgttgggg atcgcctgtc gcccgctttt    120
ggcgggcatt cccatccctt                                                140

<210> SEQ ID NO 62
<211> LENGTH: 182
<212> TYPE: DNA
<213> ORGANISM: Artificial sequence
<220> FEATURE:
<223> OTHER INFORMATION: Synthetic sequence

<400> SEQUENCE: 62
ggctgtaagc ggatgccata tggtcatagt tcccctgaga aatcagggtt actatgataa    60
gggctttctg cctaaggcag actgacccgc ggcgttgggg atcgcctgtc gcccgctttt    120
ggcgggcatt cccatccctt gcgcaaactc agaccttggc ggaaaacgct aaggtctttt    180
tt                                                                   182

<210> SEQ ID NO 63
<211> LENGTH: 139
<212> TYPE: DNA
<213> ORGANISM: Artificial sequence
<220> FEATURE:
<223> OTHER INFORMATION: Synthetic sequence

<400> SEQUENCE: 63
ggtgtaagcg gatgccatat ggtcatagtt ccccctgagaa atcagggtta ctatgataag    60
ggctttctgc ctaaggcaga ctgacccgcg gcgttgggga tcgcctgtcg cccgcttttg    120
gcgggcattc ccatccctt                                                 139

<210> SEQ ID NO 64
<211> LENGTH: 140
<212> TYPE: DNA
<213> ORGANISM: Artificial sequence
<220> FEATURE:
<223> OTHER INFORMATION: Synthetic sequence

<400> SEQUENCE: 64
ggctgtaagc ggatgccata tggtcatagt tcccctgaga aatcagggtt actatgataa    60
gggctttctg cctaaggcag actgacccgc ggcgttgggg atcgcctgtc gcccgctttt    120
ggcgggcatt cccatccctt                                                140

<210> SEQ ID NO 65
<211> LENGTH: 141
<212> TYPE: DNA
<213> ORGANISM: Artificial sequence
<220> FEATURE:
<223> OTHER INFORMATION: Synthetic sequence
```

<400> SEQUENCE: 65
ggtctgtaag cggatgccat atggtcatag ttccctgag aaatcagggt tactatgata      60
agggctttct gcctaaggca gactgacccg cggcgttggg gatcgcctgt cgcccgcttt    120
tggcgggcat tccccatcct t                                              141

<210> SEQ ID NO 66
<211> LENGTH: 142
<212> TYPE: DNA
<213> ORGANISM: Artificial sequence
<220> FEATURE:
<223> OTHER INFORMATION: Synthetic sequence

<400> SEQUENCE: 66
gggtctgtaa gcggatgcca tatggtcata gttcccctga gaaatcaggg ttactatgat     60
aagggctttc tgcctaaggc agactgaccc gcggcgttgg gatcgcctg tcgcccgctt    120 ttggcgggca ttccccatcc tt                                             142

<210> SEQ ID NO 67
<211> LENGTH: 141
<212> TYPE: DNA
<213> ORGANISM: Artificial sequence
<220> FEATURE:
<223> OTHER INFORMATION: Synthetic sequence

<400> SEQUENCE: 67
ggtctgtaag cggatgccat atggtcatag ttccctgag aaatcagggt tactatgata      60
agggctttct gcctaaggca gactgacccg cggcgttggg gatcgcctgt cgcccgcttt    120
tggcgggcat tccccatcct t                                              141

<210> SEQ ID NO 68
<211> LENGTH: 139
<212> TYPE: DNA
<213> ORGANISM: Artificial sequence
<220> FEATURE:
<223> OTHER INFORMATION: Synthetic sequence

<400> SEQUENCE: 68
ggagctggac ggcgacgtaa agtcatagtt ccctgagaa atcagggtta ctatgataag     60
ggctttctgc ctaaggcaga ctgacccgcg gcgttgggga tcgcctgtcg cccgcttttg    120
gcgggcattc cccatcctt                                                 139

<210> SEQ ID NO 69
<211> LENGTH: 138
<212> TYPE: DNA
<213> ORGANISM: Artificial sequence
<220> FEATURE:
<223> OTHER INFORMATION: Synthetic sequence

<400> SEQUENCE: 69
ggagcgcacc atcttcttca gtcatagttc cctgagaaa tcagggttac tatgataagg      60
gctttctgcc taaggcagac tgacccgcgg cgttggggat cgcctgtcgc cgcttttgg    120 cgggcattcc ccatcctt                                                  138

<210> SEQ ID NO 70
<211> LENGTH: 140
<212> TYPE: DNA
<213> ORGANISM: Artificial sequence
<220> FEATURE:
<223> OTHER INFORMATION: Synthetic sequence

<400> SEQUENCE: 70

```
ggcctgagca cccagtccgc ccgtcatagt tcccctgaga aatcagggtt actatgataa      60
gggctttctg cctaaggcag actgacccgc ggcgttgggg atcgcctgtc gcccgctttt     120
ggcgggcatt ccccatcctt                                                 140
```

<210> SEQ ID NO 71
<211> LENGTH: 140
<212> TYPE: DNA
<213> ORGANISM: Artificial sequence
<220> FEATURE:
<223> OTHER INFORMATION: Synthetic sequence

<400> SEQUENCE: 71

```
ggtgcggttc accagggtgt cggtcatagt tcccctgaga aatcagggtt actatgataa      60
gggctttctg cctaaggcag actgacccgc ggcgttgggg atcgcctgtc gcccgctttt     120
ggcgggcatt ccccatcctt                                                 140
```

<210> SEQ ID NO 72
<211> LENGTH: 139
<212> TYPE: DNA
<213> ORGANISM: Artificial sequence
<220> FEATURE:
<223> OTHER INFORMATION: Synthetic sequence

<400> SEQUENCE: 72

```
caaatgaaag gagtgagagg tgtcatagtt cccctgagaa atcagggtta ctatgataag      60
ggctttctgc ctaaggcaga ctgacccgcg gcgttgggga tcgcctgtcg cccgcttttg     120
gcgggcattc cccatcctt                                                  139
```

<210> SEQ ID NO 73
<211> LENGTH: 140
<212> TYPE: DNA
<213> ORGANISM: Artificial sequence
<220> FEATURE:
<223> OTHER INFORMATION: Synthetic sequence

<400> SEQUENCE: 73

```
ccaaatgaaa ggagtgagag gtgtcatagt tcccctgaga aatcagggtt actatgataa      60
gggctttctg cctaaggcag actgacccgc ggcgttgggg atcgcctgtc gcccgctttt     120
ggcgggcatt ccccatcctt                                                 140
```

<210> SEQ ID NO 74
<211> LENGTH: 103
<212> TYPE: DNA
<213> ORGANISM: Artificial sequence
<220> FEATURE:
<223> OTHER INFORMATION: Synthetic sequence

<400> SEQUENCE: 74

```
gtggctaaag ccagggagac gttttagagc tagaaatagc aagttaaaat aaggctagtc      60
cgttatcaac ttgaaaaagt ggcaccgagt cggtgctttt ttt                       103
```

<210> SEQ ID NO 75
<211> LENGTH: 139
<212> TYPE: DNA
<213> ORGANISM: Artificial sequence
<220> FEATURE:
<223> OTHER INFORMATION: Synthetic sequence
```

```
<400> SEQUENCE: 75
gactccaatg cggaagagag tgtcatagtt ccccctgagaa atcagggtta ctatgataag      60
ggctttctgc ctaaggcaga ctgacccgcg gcgttgggga tcgcctgtcg cccgcttttg     120
gcgggcattc cccatcctt                                                   139

<210> SEQ ID NO 76
<211> LENGTH: 141
<212> TYPE: DNA
<213> ORGANISM: Artificial sequence
<220> FEATURE:
<223> OTHER INFORMATION: Synthetic sequence

<400> SEQUENCE: 76
gcgactccaa tgcggaagag agtgtcatag ttcccctgag aaatcagggt tactatgata      60
agggctttct gcctaaggca gactgacccg cggcgttggg gatcgcctgt cgcccgcttt     120
tggcgggcat tccccatcct t                                                141

<210> SEQ ID NO 77
<211> LENGTH: 104
<212> TYPE: DNA
<213> ORGANISM: Artificial sequence
<220> FEATURE:
<223> OTHER INFORMATION: Synthetic sequence

<400> SEQUENCE: 77
gactccaatg cggaagagag tgttttagag ctagaaatag caagttaaaa taaggctagt      60
ccgttatcaa cttgaaaaag tggcaccgag tcggtgcttt tttt                      104

<210> SEQ ID NO 78
<211> LENGTH: 141
<212> TYPE: DNA
<213> ORGANISM: Artificial sequence
<220> FEATURE:
<223> OTHER INFORMATION: Synthetic sequence

<400> SEQUENCE: 78
ggcagctgag gcaggtgcct gctgtcatag ttcccctgag aaatcagggt tactatgata      60
agggctttct gcctaaggca gactgacccg cggcgttggg gatcgcctgt cgcccgcttt     120
tggcgggcat tccccatcct t                                                141

<210> SEQ ID NO 79
<211> LENGTH: 105
<212> TYPE: DNA
<213> ORGANISM: Artificial sequence
<220> FEATURE:
<223> OTHER INFORMATION: Synthetic sequence

<400> SEQUENCE: 79
ggctgtaagc ggatgccata tggttttaga gctagaaata gcaagttaaa ataaggctag      60
tccgttatca acttgaaaaa gtggcaccga gtcggtgctt ttttt                     105

<210> SEQ ID NO 80
<211> LENGTH: 104
<212> TYPE: DNA
<213> ORGANISM: Artificial sequence
<220> FEATURE:
<223> OTHER INFORMATION: Synthetic sequence

<400> SEQUENCE: 80
gagtacgtta atgtttcctg agttttagag ctagaaatag caagttaaaa taaggctagt      60
```
ccgttatcaa cttgaaaaag tggcaccgag tcggtgcttt tttt    104

<210> SEQ ID NO 81
<211> LENGTH: 25
<212> TYPE: DNA
<213> ORGANISM: Artificial sequence
<220> FEATURE:
<223> OTHER INFORMATION: Synthetic sequence

<400> SEQUENCE: 81
gggtggaggg gacagataaa agtac    25

<210> SEQ ID NO 82
<211> LENGTH: 23
<212> TYPE: DNA
<213> ORGANISM: Artificial sequence
<220> FEATURE:
<223> OTHER INFORMATION: Synthetic sequence

<400> SEQUENCE: 82
acgtgatgtc ctctgagcgg atc    23

<210> SEQ ID NO 83
<211> LENGTH: 23
<212> TYPE: DNA
<213> ORGANISM: Artificial sequence
<220> FEATURE:
<223> OTHER INFORMATION: Synthetic sequence

<400> SEQUENCE: 83
tccaccaacg ccgacggtat cag    23

<210> SEQ ID NO 84
<211> LENGTH: 28
<212> TYPE: DNA
<213> ORGANISM: Artificial sequence
<220> FEATURE:
<223> OTHER INFORMATION: Synthetic sequence

<400> SEQUENCE: 84
gcagaagcca gtagagctca aagtggtc    28

<210> SEQ ID NO 85
<211> LENGTH: 25
<212> TYPE: DNA
<213> ORGANISM: Artificial sequence
<220> FEATURE:
<223> OTHER INFORMATION: Synthetic sequence

<400> SEQUENCE: 85
cctcacacaa cagcttcatg tcagc    25

<210> SEQ ID NO 86
<211> LENGTH: 21
<212> TYPE: DNA
<213> ORGANISM: Artificial sequence
<220> FEATURE:
<223> OTHER INFORMATION: Synthetic sequence

<400> SEQUENCE: 86
gccaaagccc gagagagtgc c    21

<210> SEQ ID NO 87
<211> LENGTH: 56
<212> TYPE: DNA

```
<213> ORGANISM: Artificial sequence
<220> FEATURE:
<223> OTHER INFORMATION: Synthetic sequence

<400> SEQUENCE: 87
tcacggtcac agctgatggt gtaagcggat gccatatgtg ggcaaactgc cgctt        56

<210> SEQ ID NO 88
<211> LENGTH: 56
<212> TYPE: DNA
<213> ORGANISM: Artificial sequence
<220> FEATURE:
<223> OTHER INFORMATION: Synthetic sequence

<400> SEQUENCE: 88
aagcgggcag tttgcccaca tatggcatcc gcttacacca tcagctgtga ccgtga        56

<210> SEQ ID NO 89
<211> LENGTH: 56
<212> TYPE: DNA
<213> ORGANISM: Artificial sequence
<220> FEATURE:
<223> OTHER INFORMATION: Synthetic sequence

<400> SEQUENCE: 89
tcacggtcac agctgatggt gtaagcggat gccatatgtg gggaaactgc cgctt        56

<210> SEQ ID NO 90
<211> LENGTH: 56
<212> TYPE: DNA
<213> ORGANISM: Artificial sequence
<220> FEATURE:
<223> OTHER INFORMATION: Synthetic sequence

<400> SEQUENCE: 90
aagcgggcag tttccccaca tatggcatcc gcttacacca tcagctgtga ccgtga        56

<210> SEQ ID NO 91
<211> LENGTH: 56
<212> TYPE: DNA
<213> ORGANISM: Artificial sequence
<220> FEATURE:
<223> OTHER INFORMATION: Synthetic sequence

<400> SEQUENCE: 91
tcacggtcac agctgatggt gtaagcggat gccatatgtg ggcgaactgc cgctt        56

<210> SEQ ID NO 92
<211> LENGTH: 56
<212> TYPE: DNA
<213> ORGANISM: Artificial sequence
<220> FEATURE:
<223> OTHER INFORMATION: Synthetic sequence

<400> SEQUENCE: 92
aagcgggcag ttcgcccaca tatggcatcc gcttacacca tcagctgtga ccgtga        56

<210> SEQ ID NO 93
<211> LENGTH: 56
<212> TYPE: DNA
<213> ORGANISM: Artificial sequence
<220> FEATURE:
<223> OTHER INFORMATION: Synthetic sequence

<400> SEQUENCE: 93
tcacggtcac agctgatggt gtaagcggat gccatatgtg gggcaactgc cgctt        56
```

<210> SEQ ID NO 94
<211> LENGTH: 56
<212> TYPE: DNA
<213> ORGANISM: Artificial sequence
<220> FEATURE:
<223> OTHER INFORMATION: Synthetic sequence

<400> SEQUENCE: 94
aagcgggcag ttgccccaca tatggcatcc gcttacacca tcagctgtga ccgtga        56

<210> SEQ ID NO 95
<211> LENGTH: 56
<212> TYPE: DNA
<213> ORGANISM: Artificial sequence
<220> FEATURE:
<223> OTHER INFORMATION: Synthetic sequence

<400> SEQUENCE: 95
tcacggtcac agctgatggt gtaagcggat gccatatgtg ggctaactgc ccgctt        56

<210> SEQ ID NO 96
<211> LENGTH: 56
<212> TYPE: DNA
<213> ORGANISM: Artificial sequence
<220> FEATURE:
<223> OTHER INFORMATION: Synthetic sequence

<400> SEQUENCE: 96
aagcgggcag ttagcccaca tatggcatcc gcttacacca tcagctgtga ccgtga        56

<210> SEQ ID NO 97
<211> LENGTH: 56
<212> TYPE: DNA
<213> ORGANISM: Artificial sequence
<220> FEATURE:
<223> OTHER INFORMATION: Synthetic sequence

<400> SEQUENCE: 97
tcacggtcac agctgatggt gtaagcggat gccatatgtg gggaagctgc ccgctt        56

<210> SEQ ID NO 98
<211> LENGTH: 56
<212> TYPE: DNA
<213> ORGANISM: Artificial sequence
<220> FEATURE:
<223> OTHER INFORMATION: Synthetic sequence

<400> SEQUENCE: 98
aagcgggcag cttccccaca tatggcatcc gcttacacca tcagctgtga ccgtga        56

<210> SEQ ID NO 99
<211> LENGTH: 55
<212> TYPE: DNA
<213> ORGANISM: Artificial sequence
<220> FEATURE:
<223> OTHER INFORMATION: Synthetic sequence

<400> SEQUENCE: 99
tcacggtcac agctggtctg taagcggatg ccatatgtgg gcaaactgcc cgctt         55

<210> SEQ ID NO 100
<211> LENGTH: 55
<212> TYPE: DNA
<213> ORGANISM: Artificial sequence
<220> FEATURE:

<223> OTHER INFORMATION: Synthetic sequence

<400> SEQUENCE: 100
aagcgggcag tttgcccaca tatggcatcc gcttacagac cagctgtgac cgtga        55

<210> SEQ ID NO 101
<211> LENGTH: 29
<212> TYPE: DNA
<213> ORGANISM: Artificial sequence
<220> FEATURE:
<223> OTHER INFORMATION: Synthetic sequence

<400> SEQUENCE: 101
cctcactcgc aacagtttcc accatgtcc                                    29

<210> SEQ ID NO 102
<211> LENGTH: 30
<212> TYPE: DNA
<213> ORGANISM: Artificial sequence
<220> FEATURE:
<223> OTHER INFORMATION: Synthetic sequence

<400> SEQUENCE: 102
aaggcttatg attacttagt tgatttatgg                                   30

<210> SEQ ID NO 103
<211> LENGTH: 30
<212> TYPE: DNA
<213> ORGANISM: Artificial sequence
<220> FEATURE:
<223> OTHER INFORMATION: Synthetic sequence

<400> SEQUENCE: 103
cgcagtatgc atttacacga aaaccagaag                                   30

<210> SEQ ID NO 104
<211> LENGTH: 30
<212> TYPE: DNA
<213> ORGANISM: Artificial sequence
<220> FEATURE:
<223> OTHER INFORMATION: Synthetic sequence

<400> SEQUENCE: 104
atcgataatc gccaataacg caaatcccta                                   30

<210> SEQ ID NO 105
<211> LENGTH: 30
<212> TYPE: DNA
<213> ORGANISM: Artificial sequence
<220> FEATURE:
<223> OTHER INFORMATION: Synthetic sequence

<400> SEQUENCE: 105
cagcgataaa gctataattc atcagttagt                                   30

<210> SEQ ID NO 106
<211> LENGTH: 29
<212> TYPE: DNA
<213> ORGANISM: Artificial sequence
<220> FEATURE:
<223> OTHER INFORMATION: Synthetic sequence

<400> SEQUENCE: 106
cgttggtgag ggacataacc gaagcgctg                                    29

```
<210> SEQ ID NO 107
<211> LENGTH: 30
<212> TYPE: DNA
<213> ORGANISM: Artificial sequence
<220> FEATURE:
<223> OTHER INFORMATION: Synthetic sequence

<400> SEQUENCE: 107
caaagacatg agaatgctgg cgcaggtgat                              30

<210> SEQ ID NO 108
<211> LENGTH: 30
<212> TYPE: DNA
<213> ORGANISM: Artificial sequence
<220> FEATURE:
<223> OTHER INFORMATION: Synthetic sequence

<400> SEQUENCE: 108
acaaatgata gacggggact acagacataa                              30

<210> SEQ ID NO 109
<211> LENGTH: 29
<212> TYPE: DNA
<213> ORGANISM: Artificial sequence
<220> FEATURE:
<223> OTHER INFORMATION: Synthetic sequence

<400> SEQUENCE: 109
aacaatgatt ttccctacgc cggtggtaa                               29

<210> SEQ ID NO 110
<211> LENGTH: 30
<212> TYPE: DNA
<213> ORGANISM: Artificial sequence
<220> FEATURE:
<223> OTHER INFORMATION: Synthetic sequence

<400> SEQUENCE: 110
aaatatgaaa ctctgacatc ttcaaatcag                              30

<210> SEQ ID NO 111
<211> LENGTH: 30
<212> TYPE: DNA
<213> ORGANISM: Artificial sequence
<220> FEATURE:
<223> OTHER INFORMATION: Synthetic sequence

<400> SEQUENCE: 111
tgcccatgcg acggcatgct ccttcatttc                              30

<210> SEQ ID NO 112
<211> LENGTH: 30
<212> TYPE: DNA
<213> ORGANISM: Artificial sequence
<220> FEATURE:
<223> OTHER INFORMATION: Synthetic sequence

<400> SEQUENCE: 112
gcttttttat ccaccttggc cggctgtggg                              30

<210> SEQ ID NO 113
<211> LENGTH: 29
<212> TYPE: DNA
<213> ORGANISM: Artificial sequence
<220> FEATURE:
<223> OTHER INFORMATION: Synthetic sequence
```

```
<400> SEQUENCE: 113
atttccagca gtcttttgac gacaaactg                                    29

<210> SEQ ID NO 114
<211> LENGTH: 30
<212> TYPE: DNA
<213> ORGANISM: Artificial sequence
<220> FEATURE:
<223> OTHER INFORMATION: Synthetic sequence

<400> SEQUENCE: 114
agtttttagg ccgtagcggc tcgaatacgg                                   30

<210> SEQ ID NO 115
<211> LENGTH: 30
<212> TYPE: DNA
<213> ORGANISM: Artificial sequence
<220> FEATURE:
<223> OTHER INFORMATION: Synthetic sequence

<400> SEQUENCE: 115
atgtctttag tctcattggt gccgtatggt                                   30

<210> SEQ ID NO 116
<211> LENGTH: 30
<212> TYPE: DNA
<213> ORGANISM: Artificial sequence
<220> FEATURE:
<223> OTHER INFORMATION: Synthetic sequence

<400> SEQUENCE: 116
tgttcttgac ttctacagtc aacaaataaa                                   30

<210> SEQ ID NO 117
<211> LENGTH: 29
<212> TYPE: DNA
<213> ORGANISM: Artificial sequence
<220> FEATURE:
<223> OTHER INFORMATION: Synthetic sequence

<400> SEQUENCE: 117
actgttcccc ttgaactgag tgacgcctt                                    29

<210> SEQ ID NO 118
<211> LENGTH: 30
<212> TYPE: DNA
<213> ORGANISM: Artificial sequence
<220> FEATURE:
<223> OTHER INFORMATION: Synthetic sequence

<400> SEQUENCE: 118
ggtcggccag ccgatcagca cgcacacgga                                   30

<210> SEQ ID NO 119
<211> LENGTH: 29
<212> TYPE: DNA
<213> ORGANISM: Artificial sequence
<220> FEATURE:
<223> OTHER INFORMATION: Synthetic sequence

<400> SEQUENCE: 119
gttgagcaag tagaaaggcg atggaggtt                                    29

<210> SEQ ID NO 120
<211> LENGTH: 30
```

```
<212> TYPE: DNA
<213> ORGANISM: Artificial sequence
<220> FEATURE:
<223> OTHER INFORMATION: Synthetic sequence

<400> SEQUENCE: 120
tcacacccct tttttgtctg tcgccgctca                                30

<210> SEQ ID NO 121
<211> LENGTH: 30
<212> TYPE: DNA
<213> ORGANISM: Artificial sequence
<220> FEATURE:
<223> OTHER INFORMATION: Synthetic sequence

<400> SEQUENCE: 121
catgaatcga aaggccgttt ttatacataa                                30

<210> SEQ ID NO 122
<211> LENGTH: 31
<212> TYPE: DNA
<213> ORGANISM: Artificial sequence
<220> FEATURE:
<223> OTHER INFORMATION: Synthetic sequence

<400> SEQUENCE: 122
ttccctcgct gatttctccg cgtgcgaatt g                              31

<210> SEQ ID NO 123
<211> LENGTH: 31
<212> TYPE: DNA
<213> ORGANISM: Artificial sequence
<220> FEATURE:
<223> OTHER INFORMATION: Synthetic sequence

<400> SEQUENCE: 123
taaatacgtc aacatctacg tggatatgga a                              31

<210> SEQ ID NO 124
<211> LENGTH: 30
<212> TYPE: DNA
<213> ORGANISM: Artificial sequence
<220> FEATURE:
<223> OTHER INFORMATION: Synthetic sequence

<400> SEQUENCE: 124
ccggggcctt tttgttatgg ccgatggtat                                30

<210> SEQ ID NO 125
<211> LENGTH: 31
<212> TYPE: DNA
<213> ORGANISM: Artificial sequence
<220> FEATURE:
<223> OTHER INFORMATION: Synthetic sequence

<400> SEQUENCE: 125
tcagtctcga cccagagggg acagtcaagg a                              31

<210> SEQ ID NO 126
<211> LENGTH: 30
<212> TYPE: DNA
<213> ORGANISM: Artificial sequence
<220> FEATURE:
<223> OTHER INFORMATION: Synthetic sequence

<400> SEQUENCE: 126
```
cggactgata cccaacacaa caaaggaggc                                              30

<210> SEQ ID NO 127
<211> LENGTH: 30
<212> TYPE: DNA
<213> ORGANISM: Artificial sequence
<220> FEATURE:
<223> OTHER INFORMATION: Synthetic sequence

<400> SEQUENCE: 127
tcggagtgac gttgttcggc ctgcgacgag                                              30

<210> SEQ ID NO 128
<211> LENGTH: 30
<212> TYPE: DNA
<213> ORGANISM: Artificial sequence
<220> FEATURE:
<223> OTHER INFORMATION: Synthetic sequence

<400> SEQUENCE: 128
tccgcctgaa gctccgtatg tagcggatag                                              30

<210> SEQ ID NO 129
<211> LENGTH: 30
<212> TYPE: DNA
<213> ORGANISM: Artificial sequence
<220> FEATURE:
<223> OTHER INFORMATION: Synthetic sequence

<400> SEQUENCE: 129
ttgaacaggc atagggaggg gactaaatga                                              30

<210> SEQ ID NO 130
<211> LENGTH: 29
<212> TYPE: DNA
<213> ORGANISM: Artificial sequence
<220> FEATURE:
<223> OTHER INFORMATION: Synthetic sequence

<400> SEQUENCE: 130
aagtgacgta agataaagac cgaaatcag                                               29

<210> SEQ ID NO 131
<211> LENGTH: 30
<212> TYPE: DNA
<213> ORGANISM: Artificial sequence
<220> FEATURE:
<223> OTHER INFORMATION: Synthetic sequence

<400> SEQUENCE: 131
cgcatccagg gctcgcccta tatcccaagg                                              30

<210> SEQ ID NO 132
<211> LENGTH: 30
<212> TYPE: DNA
<213> ORGANISM: Artificial sequence
<220> FEATURE:
<223> OTHER INFORMATION: Synthetic sequence

<400> SEQUENCE: 132
ttgctccgac tatccgaaat caagcgatac                                              30

<210> SEQ ID NO 133
<211> LENGTH: 48
<212> TYPE: PRT
<213> ORGANISM: Artificial sequence

```
<220> FEATURE:
<223> OTHER INFORMATION: Synthetic sequence

<400> SEQUENCE: 133

Met Arg Tyr Lys Ile Gly Leu Asp Ile Gly Ile Thr Ser Val Gly Trp
1               5                   10                  15

Ala Val Met Asn Leu Asp Ile Pro Arg Ile Glu Asp Leu Gly Val Arg
            20                  25                  30

Ile Phe Asp Arg Ala Glu Asn Pro Gln Thr Gly Glu Ser Leu Ala Leu
        35                  40                  45

<210> SEQ ID NO 134
<211> LENGTH: 396
<212> TYPE: PRT
<213> ORGANISM: Artificial sequence
<220> FEATURE:
<223> OTHER INFORMATION: Synthetic sequence

<400> SEQUENCE: 134

Lys His Arg Leu Glu Arg Ile Arg Arg Leu Val Ile Arg Glu Gly Ile
1               5                   10                  15

Leu Thr Lys Glu Glu Leu Asp Lys Leu Phe Glu Glu Lys His Glu Ile
            20                  25                  30

Asp Val Trp Gln Leu Arg Val Glu Ala Leu Asp Arg Lys Leu Asn Asn
        35                  40                  45

Asp Glu Leu Ala Arg Val Leu Leu His Leu Ala Lys Arg Arg Gly Phe
    50                  55                  60

Lys Ser Asn Arg Lys Ser Glu Arg Ser Asn Lys Glu Asn Ser Thr Met
65                  70                  75                  80

Leu Lys His Ile Glu Glu Asn Arg Ala Ile Leu Ser Ser Tyr Arg Thr
                85                  90                  95

Val Gly Glu Met Ile Val Lys Asp Pro Lys Phe Ala Leu His Lys Arg
            100                 105                 110

Asn Lys Gly Glu Asn Tyr Thr Asn Thr Ile Ala Arg Asp Asp Leu Glu
        115                 120                 125

Arg Glu Ile Arg Leu Ile Phe Ser Lys Gln Arg Glu Phe Gly Asn Met
    130                 135                 140

Ser Cys Thr Glu Glu Phe Glu Asn Glu Tyr Ile Thr Ile Trp Ala Ser
145                 150                 155                 160

Gln Arg Pro Val Ala Ser Lys Asp Asp Ile Glu Lys Lys Val Gly Phe
                165                 170                 175

Cys Thr Phe Glu Pro Lys Glu Lys Arg Ala Pro Lys Ala Thr Tyr Thr
            180                 185                 190

Phe Gln Ser Phe Ile Ala Trp Glu His Ile Asn Lys Leu Arg Leu Ile
        195                 200                 205

Ser Pro Ser Gly Ala Arg Gly Leu Thr Asp Glu Glu Arg Arg Leu Leu
    210                 215                 220

Tyr Glu Gln Ala Phe Gln Lys Asn Lys Ile Thr Tyr His Asp Ile Arg
225                 230                 235                 240

Thr Leu Leu His Leu Pro Asp Asp Thr Tyr Phe Lys Gly Ile Val Tyr
                245                 250                 255

Asp Arg Gly Glu Ser Arg Lys Gln Asn Glu Asn Ile Arg Phe Leu Glu
            260                 265                 270

Leu Asp Ala Tyr His Gln Ile Arg Lys Ala Val Asp Lys Val Tyr Gly
        275                 280                 285

Lys Gly Lys Ser Ser Ser Phe Leu Pro Ile Asp Phe Asp Thr Phe Gly
```

```
                290                 295                 300
Tyr Ala Leu Thr Leu Phe Lys Asp Asp Ala Asp Ile His Ser Tyr Leu
305                 310                 315                 320

Arg Asn Glu Tyr Glu Gln Asn Gly Lys Arg Met Pro Asn Leu Ala Asn
                325                 330                 335

Lys Val Tyr Asp Asn Glu Leu Ile Glu Leu Leu Asn Leu Ser Phe
                340                 345                 350

Thr Lys Phe Gly His Leu Ser Leu Lys Ala Leu Arg Ser Ile Leu Pro
                355                 360                 365

Tyr Met Glu Gln Gly Glu Val Tyr Ser Ser Ala Cys Glu Arg Ala Gly
                370                 375                 380

Tyr Thr Phe Thr Gly Pro Lys Lys Gln Lys Thr
385                 390                 395

<210> SEQ ID NO 135
<211> LENGTH: 52
<212> TYPE: PRT
<213> ORGANISM: Artificial sequence
<220> FEATURE:
<223> OTHER INFORMATION: Synthetic sequence

<400> SEQUENCE: 135

Met Leu Leu Pro Asn Ile Pro Pro Ile Ala Asn Pro Val Val Met Arg
1               5                   10                  15

Ala Leu Thr Gln Ala Arg Lys Val Val Asn Ala Ile Ile Lys Lys Tyr
                20                  25                  30

Gly Ser Pro Val Ser Ile His Ile Glu Leu Ala Arg Asp Leu Ser Gln
                35                  40                  45

Thr Phe Asp Glu
    50

<210> SEQ ID NO 136
<211> LENGTH: 151
<212> TYPE: PRT
<213> ORGANISM: Artificial sequence
<220> FEATURE:
<223> OTHER INFORMATION: Synthetic sequence

<400> SEQUENCE: 136

Arg Arg Lys Thr Lys Lys Glu Gln Asp Glu Asn Arg Lys Lys Asn Glu
1               5                   10                  15

Thr Ala Ile Arg Gln Leu Met Glu Tyr Gly Leu Thr Leu Asn Pro Thr
                20                  25                  30

Gly His Asp Ile Val Lys Phe Lys Leu Trp Ser Glu Gln Asn Gly Arg
                35                  40                  45

Cys Ala Tyr Ser Leu Gln Pro Ile Glu Ile Glu Arg Leu Leu Glu Pro
50                  55                  60

Gly Tyr Val Glu Val Asp His Val Ile Pro Tyr Ser Arg Ser Leu Asp
65                  70                  75                  80

Asp Ser Tyr Thr Asn Lys Val Leu Val Leu Thr Arg Glu Asn Arg Glu
                85                  90                  95

Lys Gly Asn Arg Ile Pro Ala Glu Tyr Leu Gly Val Gly Thr Glu Arg
                100                 105                 110

Trp Gln Gln Phe Glu Thr Phe Val Leu Thr Asn Lys Gln Phe Ser Lys
                115                 120                 125

Lys Lys Arg Asp Arg Leu Leu Arg Leu His Tyr Asp Glu Asn Glu Glu
                130                 135                 140
```

```
Thr Glu Phe Lys Asn Arg Asn
145                 150

<210> SEQ ID NO 137
<211> LENGTH: 168
<212> TYPE: PRT
<213> ORGANISM: Artificial sequence
<220> FEATURE:
<223> OTHER INFORMATION: Synthetic sequence

<400> SEQUENCE: 137

Leu Asn Asp Thr Arg Tyr Ile Ser Arg Phe Phe Ala Asn Phe Ile Arg
1               5                   10                  15

Glu His Leu Lys Phe Ala Glu Ser Asp Asp Lys Gln Lys Val Tyr Thr
            20                  25                  30

Val Asn Gly Arg Val Thr Ala His Leu Arg Ser Arg Trp Glu Phe Asn
        35                  40                  45

Lys Asn Arg Glu Glu Ser Asp Leu His His Ala Val Asp Ala Val Ile
    50                  55                  60

Val Ala Cys Thr Thr Pro Ser Asp Ile Ala Lys Val Thr Ala Phe Tyr
65                  70                  75                  80

Gln Arg Arg Glu Gln Asn Lys Glu Leu Ala Lys Lys Thr Glu Pro His
                85                  90                  95

Phe Pro Gln Pro Trp Pro His Phe Ala Asp Glu Leu Arg Ala Arg Leu
            100                 105                 110

Ser Lys His Pro Lys Glu Ser Ile Lys Ala Leu Asn Leu Gly Asn Tyr
        115                 120                 125

Asp Asp Gln Lys Leu Glu Ser Leu Gln Pro Val Phe Val Ser Arg Met
    130                 135                 140

Pro Lys Arg Ser Val Thr Gly Ala Ala His Gln Glu Thr Leu Arg Arg
145                 150                 155                 160

Tyr Val Gly Ile Asp Glu Arg Ser
                165

<210> SEQ ID NO 138
<211> LENGTH: 257
<212> TYPE: PRT
<213> ORGANISM: Artificial sequence
<220> FEATURE:
<223> OTHER INFORMATION: Synthetic sequence

<400> SEQUENCE: 138

Gly Lys Ile Gln Thr Val Val Lys Thr Lys Leu Ser Glu Ile Lys Leu
1               5                   10                  15

Asp Ala Ser Gly His Phe Pro Met Tyr Gly Lys Glu Ser Asp Pro Arg
            20                  25                  30

Thr Tyr Glu Ala Ile Arg Gln Arg Leu Leu Glu His Asn Asn Asp Pro
        35                  40                  45

Lys Lys Ala Phe Gln Glu Pro Leu Tyr Lys Pro Lys Lys Asn Gly Glu
    50                  55                  60

Pro Gly Pro Val Ile Arg Thr Val Lys Ile Ile Asp Thr Lys Asn Gln
65                  70                  75                  80

Val Ile Pro Leu Asn Asp Gly Lys Thr Val Ala Tyr Asn Ser Asn Ile
                85                  90                  95

Val Arg Val Asp Val Phe Glu Lys Asp Gly Lys Tyr Tyr Cys Val Pro
            100                 105                 110

Val Tyr Thr Met Asp Ile Met Lys Gly Ile Leu Pro Asn Lys Ala Ile
        115                 120                 125
```

```
Glu Pro Asn Lys Pro Tyr Ser Glu Trp Lys Glu Met Thr Glu Asp Tyr
        130                 135                 140

Thr Phe Arg Phe Ser Leu Tyr Pro Asn Asp Leu Ile Arg Ile Glu Leu
145                 150                 155                 160

Pro Arg Glu Lys Ile Ile Lys Thr Ala Gly Gly Glu Glu Ile Lys Ile
                165                 170                 175

Lys Asp Leu Phe Ala Tyr Tyr Lys Thr Ile His Ser Gly Thr Ala Gly
                180                 185                 190

Leu Glu Leu Val Ser His Asp Cys Ser Phe Ser Leu Ser Gly Val Gly
            195                 200                 205

Ser Arg Thr Leu Lys Arg Phe Glu Lys Tyr Gln Val Asp Val Leu Gly
        210                 215                 220

Asn Ile Tyr Lys Val Arg Gly Glu Lys Arg Val Gly Leu Ala Ser Ser
225                 230                 235                 240

Ala His Ser Lys Thr Gly Glu Thr Ile Arg Pro Leu Gln Ser Thr Arg
                245                 250                 255

Asp

<210> SEQ ID NO 139
<211> LENGTH: 257
<212> TYPE: PRT
<213> ORGANISM: Artificial sequence
<220> FEATURE:
<223> OTHER INFORMATION: Synthetic sequence

<400> SEQUENCE: 139

Gly Lys Ile Gln Thr Val Val Lys Thr Lys Leu Ser Glu Ile Lys Leu
1               5                   10                  15

Asp Ala Ser Gly His Phe Pro Met Tyr Gly Lys Glu Ser Asp Pro Arg
                20                  25                  30

Thr Tyr Glu Ala Ile Arg Gln Arg Leu Leu Glu His Asn Asn Asp Pro
            35                  40                  45

Lys Lys Ala Phe Gln Glu Pro Leu Tyr Lys Pro Lys Lys Asn Gly Glu
    50                  55                  60

Pro Gly Pro Val Ile Arg Thr Val Lys Ile Ile Asp Thr Lys Asn Gln
65                  70                  75                  80

Val Ile Pro Leu Asn Asp Gly Lys Thr Val Ala Tyr Asn Ser Asn Ile
                85                  90                  95

Val Arg Val Asp Val Phe Glu Lys Asp Gly Lys Tyr Tyr Cys Val Pro
                100                 105                 110

Val Tyr Thr Met Asp Ile Met Lys Gly Ile Leu Pro Asn Lys Ala Ile
            115                 120                 125

Glu Pro Asn Lys Pro Tyr Ser Glu Trp Lys Glu Met Thr Glu Asp Tyr
        130                 135                 140

Thr Phe Arg Phe Ser Leu Tyr Pro Asn Asp Leu Ile Arg Ile Glu Leu
145                 150                 155                 160

Pro Arg Glu Lys Thr Val Lys Thr Ala Ala Gly Glu Glu Ile Asn Val
                165                 170                 175

Lys Asp Val Phe Val Tyr Tyr Lys Thr Ile Asp Ser Ala Asn Gly Gly
                180                 185                 190

Leu Glu Leu Ile Ser His Asp His Arg Phe Ser Leu Arg Gly Val Gly
            195                 200                 205

Ser Arg Thr Leu Lys Arg Phe Glu Lys Tyr Gln Val Asp Val Leu Gly
        210                 215                 220
```

-continued

```
Asn Ile Tyr Lys Val Arg Gly Glu Lys Arg Val Gly Leu Ala Ser Ser
225                 230                 235                 240

Ala His Ser Lys Pro Gly Lys Thr Ile Arg Pro Leu Gln Ser Thr Arg
            245                 250                 255

Asp

<210> SEQ ID NO 140
<211> LENGTH: 82
<212> TYPE: RNA
<213> ORGANISM: Artificial sequence
<220> FEATURE:
<223> OTHER INFORMATION: Synthetic sequence

<400> SEQUENCE: 140
aagggcuuuc ugccuaaggc agacugaccc gcggcguugg ggaucgccug ucgcccgcuu    60
uuggcgggca uuccccaucc uu                                            82
```